US007510852B2

(12) United States Patent
Royer et al.

(10) Patent No.: US 7,510,852 B2
(45) Date of Patent: Mar. 31, 2009

(54) BIOSYNTHETIC GENES AND HOST CELLS FOR THE SYNTHESIS OF POLYKETIDE ANTIBIOTICS AND METHOD OF USE

(75) Inventors: Monique Royer, Montpellier (FR); Dean W. Gabriel, Gainesville, FL (US); Roger Frutos, Saint Georges d'Orques (FR); Philippe Rott, Clapiers (FR)

(73) Assignees: Centre de Cooperation Internationale en Recherche Agronomique pour le Developpement (CIRAD), Paris (FR); University of Florida Research Foundation, Inc., Gainesville, FL (US)

( * ) Notice: Subject to any disclaimer, the term of this patent is extended or adjusted under 35 U.S.C. 154(b) by 400 days.

(21) Appl. No.: 10/531,351

(22) PCT Filed: Oct. 17, 2003

(86) PCT No.: PCT/US03/33142

§ 371 (c)(1),
(2), (4) Date: Oct. 3, 2005

(87) PCT Pub. No.: WO2004/035760

PCT Pub. Date: Apr. 29, 2004

(65) Prior Publication Data

US 2006/0269988 A1    Nov. 30, 2006

Related U.S. Application Data

(60) Provisional application No. 60/419,463, filed on Oct. 18, 2002.

(51) Int. Cl.
*C12P 21/06* (2006.01)
(52) U.S. Cl. .......................... 435/69.1; 435/6; 435/325; 435/320.1
(58) Field of Classification Search ........................ None
See application file for complete search history.

(56) References Cited

U.S. PATENT DOCUMENTS 4,525,354 A    6/1985   Birch et al.

FOREIGN PATENT DOCUMENTS

WO    WO 02/24736 A1    3/2002

OTHER PUBLICATIONS

Huang et al. (Gene, vol. 258, Issue 1-2, pp. 193-199, 2000).*
Altschul, S. F. et al. "Gapped BLAST and PSI-BLAST: A New Generation of Protein Database Search Programs", *Nucleic Acids Research*, 1997, pp. 3389-3402, vol. 25, No. 17.
Astua-Monge, G. et al. "Resistance of Tomato and Pepper to T3 Strains of *Xanthomonas campestris* pv. *vesicatoria* Is Specified by a Plant-Inducible Avirulence Gene", *Molecular Plant-Microbe Interactions*, 2000, pp. 911-921, vol. 13, No. 9.

August, P. R. et al. "Biosynthesis of the Ansamycin Antibiotic Rifamycin: Deductions from the Molecular Analysis of the *rif* Biosynthetic Gene Cluster of *Amycolatopsis mediterranei* S699", *Chemistry & Biology*, Feb. 1998, pp. 69-79, vol. 5.
Bardwell, J. C. A. et al. "Ancient Heat Shock Gene is Dispensable", *Journal of Bacteriology*, Jul. 1988, pp. 2977-2983, vol. 170, No. 7.
Birch, R. G. "*Xanthomonas albilineans* and the Antipathogenesis Approach to Disease Control", *Molecular Plant Pathology*, 2001, pp. 1-11, vol. 2, No. 1.
Borkovich, K. A. et al. "hsp82 Is an Essential Protein that is Required in Higher Concentrations for Growth of Cells at Higher Temperatures", *Molecular and Cellular Biology*, Sep. 1989, pp. 3919-3930, vol. 9, No. 9.
Cane, D. E. et al. "The Parallel and Convergent Universes of Polyketide Synthases and Nonribosomal Peptide Synthetases", *Chemistry & Biology*, Dec. 1999, pp. R319-R325, vol. 6.
Challis, G. L. et al. "Predictive, Structure-Based Model of Amino Acid Recognition by Nonribosomal Peptide Synthetase Adenylation Domains", *Chemistry & Biology*, 2000, pp. 211-244, vol. 7.
Conti, E. et al. "Structural Basis for the Activation of Phenylalanine in the Non-Ribosomal Biosynthesis of gramicidin S", *The EMBO Journal*, 1997, pp. 4174-4183, vol. 16, No. 14.
De Feyter, R. et al. "Use of Cloned DNA Methylase Genes to Increase the Frequency of Transfer of Foreign Genes into *Xanthomonas campestris* pv. *malvacearum*", *Journal of Bacteriology*, Oct. 1991, pp. 6421-6427, vol. 173, No. 20.
Von Döhren, H. et al. "The Nonribosomal Code", *Chemistry & Biology*, Oct. 1999, pp. R273-R279, vol. 6.
Du, L. et al. "The Biosynthetic Gene Cluster for the Antitumor Drug Bleomycin from *Streptomyces verticillus* ATCC15003 Supporting Functional Interactions Between Nonribosomal Peptide Synthetases and a Polyketide Synthase", *Chemistry & Biology*, 2000, pp. 623-642, vol. 7.
Duitman, E. H. et al. "The Mycosubtilin Synthetase of *Bacillus subtilis* ATCC6633: A Multifunctional Hybrid Between a Peptide Synthetase, an Amino Transferase, and a Fatty Acid Synthase", *PNAS*, Nov. 9, 1999, pp. 13294-13299, vol. 96, No. 23.
Del Carmen Garrido, M. et al. "The Export of the DNA Replication Inhibitor Microcin B17 Provides Immunity for the Host Cell", *The EMBO Journal*, 1988, pp. 1853-1862, vol. 7, No. 6.
Gehring, A. M. et al. "Iron Acquisition in Plague: Modular Logic in Enzymatic Biogenesis of Yersiniabactin by *Yersinia pestis*", *Chemistry & Biology*, Oct. 1998, pp. 573-586, vol. 5.
Guenzi, E. et al. "Characterization of the Syringomycin Synthetase Gene Cluster", *The Journal of Biological Chemistry*, Dec. 4, 1998, pp. 32857-32863, vol. 273, No. 49.
Jakob, U. et al. "Transient Interaction of Hsp90 with Early Unfolding Intermediates of Citrate Synthase", *The Journal of Biological Chemistry*, Mar. 31, 1995, pp. 7288-7294, vol. 270, No. 13.

(Continued)

*Primary Examiner*—Hope A Robinson
(74) *Attorney, Agent, or Firm*—Saliwanchik, Lloyd & Saliwanchik

(57) ABSTRACT

Three gene clusters that together encode albicidin biosynthesis, the complete gene DNA sequences, and the deduced protein sequences for the enzymes and methods for using the DNA sequences are disclosed and discussed as well as methods for plant protection and creating new antibiotics. The novel Albicidin family of antibiotics is disclosed and their structure deduced.

8 Claims, 13 Drawing Sheets

OTHER PUBLICATIONS

Konz, D. et al. "The Bacitracin Biosynthesis Operon of *Bacillus licheniformis* ATCC 10716: Molecular Characterization of Three Multi-Modular Peptide Synthetases", *Chemistry & Biology*, Dec. 1997, pp. 927-937, vol. 4.

Leong, S. A. et al. "Heme Biosynthesis in *Rhizobium*: Identification of a Cloned Gene Coding for δ-Aminolevulinic Acid Synthetase From *Rhizobium meliloti", The Journal of Biological Chemistry*, Aug. 10, 1982, pp. 8724-8730, vol. 257, No. 15.

Liu, J. et al. "Nucleotide Sequence of a Cluster of *Escherichia coli* Enterobactin Biosynthesis Genes: Identification of *entA* and Purification of Its Product 2,3-Dihydro-2,3-Dihydroxybenzoate Dehydrogenase", *Journal of Bacteriology*, Feb. 1989, pp. 791-798, vol. 171, No. 2.

McDaniel, R. et al. "Multiple Genetic Modifications of the Erythromycin Polyketide Synthase to Produce a Library of Novel "Unnatural" Natural Products", *Proc. Natl. Acad. Sci. USA*, Mar. 1999, pp. 1846-1851, vol. 96.

Mohamed, M. E.-S. et al. "Reinvestigation of a New Type of Aerobic Benzoate Metabolism in the Proteobacterium *Azoarcus evansii", Journal of Bacteriology*, Mar. 2001, pp. 1899-1908, vol. 183, No. 6.

Paitan, Y. et al. "Genetic and Functional Analysis of Genes Required for the Post-Modification of the Polyketide Antibiotic TA of *Myxococcus xanthus", Microbiology*, 1999, pp. 3059-3067, vol. 145.

Quadri, L. E.N. et al. "Identification of a *Mycobacterium tuberculosis* Gene Cluster Encoding the Biosynthetic Enzymes for Assembly of the Virulence-Conferring Siderophore Mycobactin", *Chemistry & Biology*, Nov. 1998, pp. 631-645, vol. 5.

Royer, M. et al. "Albicidin Pathotoxin Produced by *Xanthomonas albilineans* is Encoded by Three Large PKS and NRPS Genes Present in a Gene Cluster Also Containing Several Putative Modifying, Regulatory, and Resistance Genes", *The American Phytopathological Society*, 2004, pp. 414-427, vol. 17, No. 4.

Huang, G. et al. "Analysis of the Genes Flanking *xabB*: A Methyltransferase Gene is Involved in Albicidin Biosynthesis in *Xanthomonas albilineans", Gene*, 2000, pp. 327-333, vol. 255.

Huang, G. et al. "Albicidin Antibiotic and Phytotoxin Biosynthesis in *Xanthomonas albilineans* Requires a Phosphopantetheinyl Transferase Gene", *Gene*, 2000, pp. 193-199, vol. 258.

Huang, G. et al. "A Multifunctional Polyketide-Peptide Synthetase Essential for Albicidin Biosynthesis in *Xanthomonas albilineans", Microbiology*, 2001, pp. 631-642, vol. 142.

Rott, P. C. et al. "At Least Two Seperate Gene Clusters Are Involved in Albicidin Production by *Xanthomonas albilineans", Journal of Bacteriology*, Aug. 1996, pp. 4590-4596, vol. 178, No. 15.

GenBank Accession No. AF403709, Bostock, J. M. et al. "A Gene from *Xanthomonas albilineans* Confers High-Level Albicidin Resistance in *Escherichia coli*", unpublished, Jul. 26, 2001.

* cited by examiner

| | | | | | | |
|---|---|---|---|---|---|---|
| Sgl-TcmO | 173 | FVDLGGARG | 234 | PRADVFIV | 263 | ALTPGGAVLV |
| Sgl-TcmN | 331 | IADLGGGDG | 393 | TGYDAYLF | 423 | IGDDDARLLI |
| Smy-MdmC | 64 | VLEIGTFTG | 135 | GAFDIVFV | 159 | LVRPGGLVAI |
| Mxa-SafC | 63 | TLEVGVFTG | 134 | GTFDLAFI | 158 | LVRPGGLIIL |
| Ser-EryG | 85 | VLDVGFGLG | 149 | ETFDRVTS | 178 | VLKPGGVLAI |
| Spe-DauK | 183 | VLDVGGGKG | 254 | RKADAIIL | 273 | ALEPGGRILI |
| Sal-DmpM | 208 | VVDIGGADG | 269 | GGGDLYVL | 298 | AMPAHARLLV |
| Shy-RapM | 106 | VLEVGCGMG | 155 | VQGDAEEL | 194 | ALRRGGALSH |
| Sav-AveD | 71 | VLDVGCGSG | 124 | GSFDAAWA | 151 | VLRPGGRLAV |
| Sar-Cmet | 158 | VLDVACGHG | 220 | GPYDLSLI | 251 | ATRPGGRIGI |
| AlbII | 174 | VLDVAAGHG | 236 | SGYDVILL | 267 | ALNDDGMVIT |
| | | Motif I | | Motif II | | Motif III |

FIG. 3

| | | | | | | | |
|---|---|---|---|---|---|---|---|
| Sgl-tcmP | 84 | VVLHLACGLDSRAFRMDVPD109 | DVDVPDVIELR | 139 | EDWLDTVP | 150 | PALVVAEGLTPYL |
| Sme-PKS | 84 | TVLHLGCGLDSRIFRIDPGP109 | ELDVPDVISLR | 139 | RGWIERLP | 150 | PTMIVAEGVLPYL |
| Pmu-tcmP | 86 | VVVQLGAGLDARFERLGKPQ111 | DLDLPEVINIR | 141 | TDWMKTVS | 152 | PVLLILEGVLMFF |
| Mtu-Omt | 85 | TVVALAEGLQTSFWRLDVAI113 | TVDLPPIVDLR | 144 | YSWMDSVD | 155 | GVFITAEGLLMYL |
| Mlo-Hp | 84 | IVLHLGCGLDTRVFRVDPPP109 | DADYPQVIELR | 139 | PGWLAEVP | 150 | PAMVVAEGLTPYL |
| Mtu-Hp | 101 | QVAILASGLDSRAYRLPWPT127 | EIDQPKVMEFK | 162 | ADWPTALQ | 178 | PTAWLAEGLLIYL |
| Mtu-Hp2 | 104 | QVVILASGDLSRAWRLPWPD129 | ELDQPKVLEFK | 162 | QDWPKALQ | 178 | PCAWLAEGLVRYL |
| Mtu-Hp3 | 98 | QVVILAAGLDSRAYRLPWPD123 | ELDRPQVLDFK | 156 | DDWPQALR | 172 | PSAWIAEGLLIYL |
| Mtu-Hp4 | 101 | QAVIVAAGLDCRAYRLDWQP126 | EIDVPKVLEFK | 161 | TDWPTPLT | 177 | PSAWSVEGLLPYL |
| Sco-Hp | 93 | QVVLLGAGMDSRAFRMAWPE118 | EVDTPAPLEFK | 153 | EDWPSALA | 169 | PTAWIGEGLLIYL |
| AlbVI | 99 | QVVILAAGMDARAYRLPWPS124 | EIDHMDVLSDK | 157 | EDWPQALK | 173 | ATLWLVEGLLCYL |

Motif I Motif II Motif III Motif IV

XALB1 Strand +
29 bp downstream from the TGA stop codon of *albXVII*

```
            -40  -35  -30  -25  -20  -15  -10   -5  -1+  +5             p      s
              .    .    .    .    .    .    .    .   ..   .
17085=>  ACCATTGTGAACGGCCTTCCCGCTTCGTCCATAGCGATTTTCGATCGCGGC           4.30     0
```

XALB1 Strand +
400 bp downstream from the TAA stop codon of *albIV*

```
            -40  -35  -30  -25  -20  -15  -10   -5  -1+  +5                     p      s
              .    .    .    .    .    .    .    .   ..   .
55617=> CATGGCTGCAGGCCGAGCTCGCTCAGCTACGGGGTGAGACCGAAGCTGCCC <= 55667   4.13    12
```

XALB1 Strand –
62 bp, 170 bp and 560 bp downstream from the TAG stop codon of *albXVI*

```
          -40  -35  -30  -25  -20  -15  -10   -5  -1+  +5                     p      s
            .    .    .    .    .    .    .    .   ..   .
 7030=> GGGGGGCAGTTGCCCGGACCCCGGTTTCTGTAAACGTTTGGCTGTCTGTAG <= 6879    3.95    13

 6922=> AACTCTTAAAAGAGATTGATTTAAATTTCCCTGCGTTTTTGTACGAGAATA <= 6872    4.42     0
 6532=> TACTTAATATAAGATTGCGAAGCTTGCGTTGCGGAATGATTTTTTCAATAT <= 6482    4.27    53
```

XALB3 Strand+

```
            -40  -35  -30  -25  -20  -15  -10   -5  -1+  +5             p      s
              .    .    .    .    .    .    .    .   ..   .
   8065=> GCAAAGAAAAGCGGAAACGAAAAAAGGGCCTACGGGCCCTTTTTTCTTCCA          4.78     0
   8072=> AAAGCGGAAACGAAAAAAGGGCCTACGGGCCCTTTTTTCTTCCATCGTCGA          3.94    86
```

```
14456 GTCGTTGATCAGCACCAGATAAGCCTGTTCCTCGAACGTCATCCTAAAGATACCCCCGGAAGGCTGCTGCGAAGCACGGAAGTTGCTACATCGCAC
      CAGCAACTAGTCGTGGTCTATTCGGACAAGGAGCTTGCAGTAGGATTTCTATGGGGGCCTTCCGACGACGCTTCGTGCCTTCAACGATGTAGCGTG
       D  N  I  L  V  L  Y  A  Q  E  E  F  T  M          RBS
                 albX
          -35 (PalbX: operon 3)   -10 (PalbX: operon 3)
14552 AATGCGATTCAGATGGACCAAGCAAAGCGACTATACATGACGTCACTTCGAAGATGTCAAGAAAAATAGCGCGTGAAGAGCACGTAAGAGTGATGT
      TTACGCTAAGTCTACCTGGTTCGTTTCGCTGATATGTACTGCAGTGAAGCTTCTACAGTTCTTTTTATCGCGCACTTCTCGTGCATTCTCACTACA
                           -10 (PalbXVII: operon 4) -35 (PalbXVII: operon4)

14648 GTTTCGCACCGCTGTACGTCCCATCGCCATCGCGGCAAAGCTTACACGAAAAATTCACCAGGGCATGCGTTCAATACGCGGGTCAAAGCAATATCC
      CAAAGCGTGGCGACATGCAGGGTAGCGGTAGCGCCGTTTCGAATGTGCTTTTTAAGTGGTCCCGTACGCAAGTTATGCGCCCAGTTTCGTTATAGG

14744 TTGCGCTTGCAGAGCTATGTTCGTGCGTAAAGCGCCAAGGCAGTGGGGAGCAACACCTTGGGTTTCGGTTGAGGTGCGGGTAGCAATTTCTGCTTA
      AACGCGAACGTCTCGATACAAGCACGCATTTCGCGGTTCCGTCACCCCTCGTTGTGGAACCCAAAGCCAACTCCACGCCCATCGTTAAAGACGAAT

                                                              RBS
14840 ATATCCACGCGCGGCGGTTTTTGTCTTGCCGGGCGTCAACTGTCTCATCGAGCAGTCTGGGAGGCTATTTTGCGCTGCCTTATCATAAATAATTAC
      TATAGGTGCGCGCCGCCAAAAACAGAACGGCCCGCAGTTGACAGAGTAGCTCGTCAGACCCTCCGATAAAACGCGACGGAATAGTATTTATTAATG
                                                                              M  R  C  L  I  I  N  N  Y
                                                                                  albXVII
```

FIG. 7A

```
17332 GAATGAGGCCCCCACGCTTACGCGCGAACCAGGACGGGCTGCTGATGGATACGGCCGGCCGGGTGGTCGAGGGCTGCACCAGCAATCTGTTCCTCG
      CTTACTCCGGGGGTGCGAATGCGCGCTTGGTCCTGCCCGACGACTACCTATGCCGGCCGGCCCACCAGCTCCCGACGTGGTCGTTAGACAAGGAGC
        M  R  P  P  R  L  R  A  N  Q  D  G  L
                    albXVIII (non expressed ?)

17428 TCGAGAACGGCCATCTGGTGACGCCCGACCTGGGCGTGGCCGGCGTCAGCGGGATCATGCGAGGCAGGGTGATCGAATATGGCCGGCAGCACGGTC
      AGCTCTTGCCGGTAGACCACTGCGGGCTGGACCCGCACCGGCCGCAGTCGCCCTAGTACGCTCCGTCCCACTAGCTTATACCGGCCGTCGTGCCAG

17524 TCGCCTGCGCGGTAAAGCACGTCTATCCGGACCAGCTAGTGCGTGCTCAGGAGGTGTTTCTGACTAACGCCGTGTTCGGCATTCTGCTGGTGCGCA
      AGCGGACGCGCCATTTCGTGCAGATAGGCCTGGTCGATCACGCACGAGTCCTCCACAAAGACTGATTGCGGCACAAGCCGTAAGACGACCACGCGT

                                               -35 (PalbXIX: operon 5)  -10 (PalbXIX: operon 5)
17620 GCATTGACGCTCACAGCTACCGCATCGATCCTGTTACCCTGCGTTTGCTCGATGCCCTGTGTCAGGGCGTATATTTCACCGAACGGTCACTACATC
      CGTAACTGCGAGTGTCGATGGCGTAGCTAGGACAATGGGACGCAAACGAGCTACGGGACACAGTCCCGCATATAAAGTGGCTTGCCAGTGATGTAG

      RBS
17716 AGGTTTCCACCCATGCCGGCCAAGACCCTTGAAAGCAAGGATTACTGTGGAGAAAGCTTCGTCAGCGAAGATCGCTCCGGGCAATCGCTGGAGTCG
      TCCAAAGGTGGGTACGGCCGGTTCTGGGAACTTTCGTTCCTAATGACACCTCTTTCGAAGCAGTCGCTTCTAGCGAGGCCCGTTAGCGACCTCAGC
                  M  P  A  K  L  E  S  K  D  Y  C  G  E  S  F  V  S
                        albXIX
```

FIG. 7B

```
RifA-1   LGRVDVLQPACFAVMVGLAAVWESVGVRPDAVVGHSQGEI
RifA-2   LDQTMYTQGALFAVETALFRLFESWGVRPGLLAGHSIGEL
RifA-3   LDRVDVVQPASFAMMVGLAAVWTSLGVTPDAVLGHSQGEI
RifB-1   LDRVDVVQPASFAVMVGLAAVWESVGVRPDAVVGHSQGEI
RifE-1   LNQTVFTGAGLFAVESALFRLAESWGVRPDVVLGHSIGEI
BlmVIII  ADDTRAAQPALFAVEYALARTLMDWGVRPAAMLGHSLGEV
```

FIG. 10A

```
AlbXIII  LEDRPRHIRAVIDTLTGHAQFGPAIQAHNVAVIGHSVGGY
FenF     TRTMNAQPAILTVSVIAYQVYMQEIGIKPHFLAGHSLGEY
LipA     PDSRGRQLLAALDYLTGRSSVRGRIDSGRLGVMGHSMGGG
```

FIG. 10B

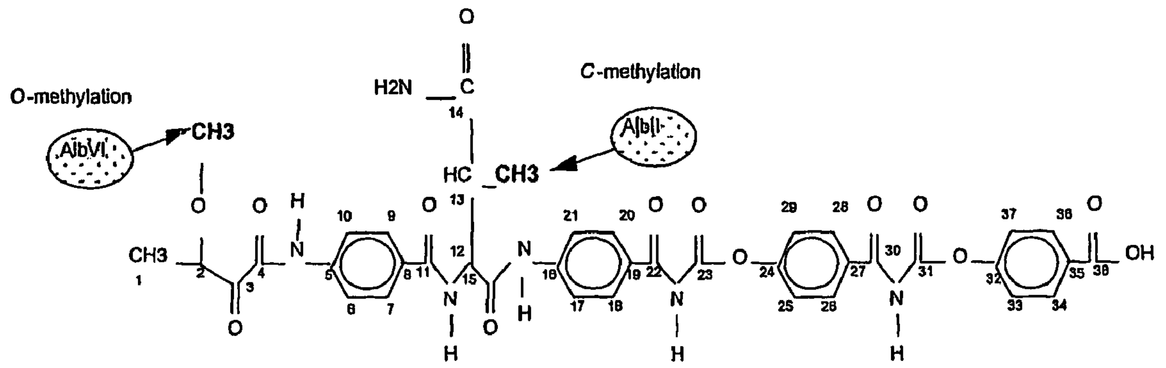
or
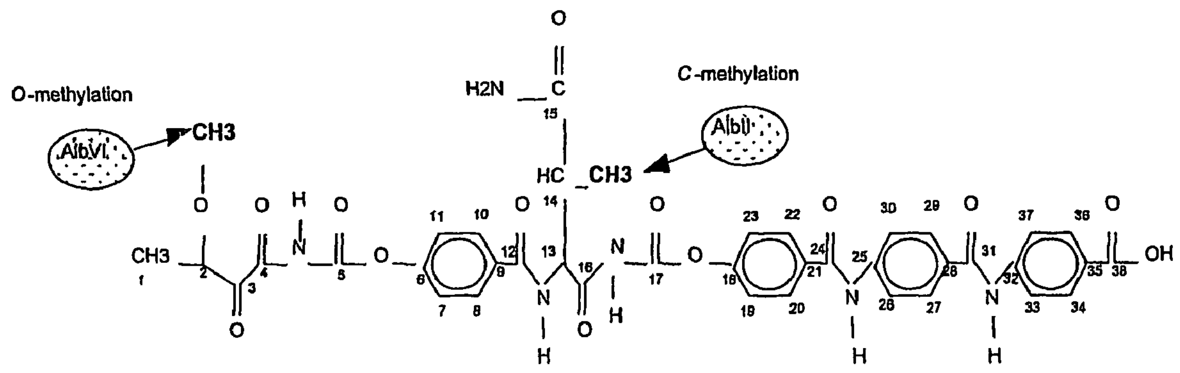
$C_{40}O_{15}N_6H_{35}$
(molecular weight : 839)
FIG. 11B

BIOSYNTHETIC GENES AND HOST CELLS FOR THE SYNTHESIS OF POLYKETIDE ANTIBIOTICS AND METHOD OF USE

CROSS-REFERENCE TO RELATED APPLICATIONS

This application is the U.S. national stage application of International Patent Application No. PCT/US2003/33142 filed Oct. 17, 2003, which claims the benefit of U.S. Provisional patent application with Ser. No. 60/419,463, filed Oct. 18, 2002 the disclosures of which are hereby incorporated by reference in their entirety, including all nucleic acid sequences, amino acid sequences, chemical formulae, tables and figures.

TECHNICAL FIELD

The Sequence Listing for this application is labeled "seqlist-replace.txt" which was created on Jun. 26, 2008 and is 323 KB. The entire contents of the sequence listing is incorporated herein by reference in its entirety.

The invention is in the field of genetic engineering, and in particular the isolation and expression of the biosynthetic genes that produce a family of antibiotics known generically as albicidins.

BACKGROUND OF THE INVENTION

U.S. Pat. No. 4,525,354 to Birch and Patil described a "non-peptide" antibiotic of M.W. "about 842" called "albicidin." Albicidin is described as produced by culturing chlorosis-inducing strains of *Xanthomonas albilineans* isolated from diseased sugarcane, and mutants thereof. The antibiotic was isolated from the culture medium by adsorption on resin and was purified by gel filtration and High Performance Liquid Chromatography (HPLC). The chemical structure of this antibiotic was not determined and remained unknown, although the Birch and Patil patent disclosed spectral data for a fraction having antibiotic activity and the presence of approximately 38 carbon atoms and at least one COOH group.

*Xanthomonas albilineans* is a systemic, xylem-invading pathogen that causes leaf scald disease of sugarcane (interspecific hybrids of *Saccharum* species) (Ricaud and Ryan, 1989; Rott and Davis, 2000). Leaf scald symptoms include chlorosis, necrosis, rapid wilting, and plant death. Chlorosis-inducing strains of the pathogen produce several toxic compounds. The major toxic component, named albicidin, inhibits chloroplast DNA replication, resulting in blocked chloroplast differentiation and chlorotic leaf streaks that are characteristic of the plant disease (Birch and Patil, 1983, 1985b, 1987a and 1987b). Several studies established that albicidin plays a key role in pathogenesis and especially in the development of disease symptoms (Wall and Birch, 1997; Zhang and Birch, 1997; Zhang et al., 1999; Birch, 2001).

The prior art indicates that albicidin inhibits prokaryotic DNA replication and is bactericidal to a range of gram-positive and gram-negative bacteria (Birch and Patil, 1985a). Albicidin is therefore of interest as a potential clinical antibiotic (Birch and Patil, 1985a). However, low yield of toxin production in *X. albilineans* has slowed down studies into the chemical structure of albicidin and its therapeutic application (Zhang et al., 1998). The chemical structure of this albicidin remains unknown, however this albicidin has been partially characterized as a non-peptide antibiotic with a molecular weight of about 842 that contains approximately 38 carbon atoms with three or four aromatic rings, at least one COOH group, two OCH3 groups, a trisubstituted double bond and a CN linkage (Birch and Patil, 1985a; Huang et al., 2001).

Molecular cloning and characterization of the genes governing the biosynthesis of albicidin is of considerable interest because such information provides approaches to engineer overproduction of albicidin, to characterize its chemical structure, to allow therapeutic applications and to clarify the relationship between toxin production and the ability to colonize sugarcane. Two similar mutagenesis and complementation studies have been conducted to identify the genetic basis of albicidin production in *X. albilineans* strains isolated in two different geographical locations, Australia and Florida.

One study of *X. albilineans* strain LS155 from Australia revealed that genes for albicidin biosynthesis and resistance span at least 69 kb (Wall and Birch, 1997). Subsequently, three genes required for albicidin biosynthesis were identified, cloned and sequenced from two Australian strains of *X. albilineans* (LS155 and Xa13): xabA, xabB and xabC (Huang et al., 2001; Huang et al. 2000a, 2000b). The xabB gene encodes a large protein with a predicted size of 525.6 kDa, with a modular architecture indicative of a multi functional polyketide synthase (PKS) linked to a nonribosomal peptide synthetase (NRPS) (Huang et al., 2001). The xabC gene, located immediately downstream from xabB, encodes an S-adenosyl-L-methionine (SAM)-dependent O-methyltransferase (Huang et al., 2000a). The xabA gene, located in another region of the genome, encodes a phosphopantetheinyl transferase required for post-translational activation of PKS and NRPS enzymes (Huang et al., 2000b).

These first results demonstrated that the albicidin biosynthesis apparatus is a PKS and/or NRPS system. Such systems assemble simple acyl-coenzyme A or amino acid monomers to produce polyketides and/or nonribosomal peptides (Marahiel et al., 1997; Cane, 1997; Cane and Walsh, 1999). These metabolites form very large classes of natural products that include numerous important pharmaceuticals, agrochemicals, and veterinary agents such as antibiotics, immunosuppressants, anti-cholesterolemics, as well as antitumor, antifungal and antiparasitic agents. Genetic studies of prokaryotic PKS and NRPS produced detailed information regarding the function and the organization of genes responsible for the biosynthesis of polyketides and nonribosomal peptides. Such knowledge, in turn, made it possible to produce combinations of PKS and NRPS genes from different microorganisms in order to produce novel antibiotics (McDaniel et al., 1999; Rodriguez and McDaniel, 2001; Pfeifer et al., 2001). Investigating the complete albicidin biosynthesis apparatus is therefore of great interest because such results may contribute to the knowledge as to how PKS and NRPS interact and how they might be manipulated to engineer novel molecules.

A second study with *X. albilineans* strain Xa23R1 from Florida revealed that at least two gene clusters, one spanning more than 48 kb, are involved in albicidin production (Rott et al., 1996). This conclusion was based on the following data: (I) fifty Xa23R1 mutants defective in albicidin production were isolated; (ii) a Xa23R1 genomic library of 845 clones, designated pALB1 to pALB845, was constructed; (iii) two overlapping DNA inserts of approximately 47 kb and 41 kb, from clones pALB540 and pALB571 respectively, complemented forty-five mutants and were supposed to contain a major gene cluster involved in albicidin production; (iv) a DNA insert of approximately 36 kb, from clone pALB639, complemented four of the five remaining mutants not complemented by pALB540 and pALB571, and was supposed to contain a second region involved in albicidin production; and (v) the remaining mutant, AM37, which was not complemented by any of the three cosmids pALB540, pALB571 and pALB639, was supposed to be mutated in a third region of the genome involved in albicidin production.

The DNA sequences of all of the genes required to produce the albicidin family of polyketide antibiotics, the expressed protein amino acid sequences of all of the genes, and the deduced structure of Albicidin have not been previously reported, although fragmentary sequences that include three of the biosynthetic genes have been reported. Identification of one albicidin gene, xabC, as a methyltransferase gene involved in albicidin biosynthesis is reported by Huang, G., Zhang, L. & Birch, R. G. (2000a, Gene 255, 327-333) and claimed as biologically active in producing a polyketide antibiotic in PCT WO 02/24736 A1. Identification of a second albicidin gene, xabA, as a phosphopantetheinyl transferase gene is reported by Huang, G., Zhang, L. and Birch, R. G. (2000b) Gene 258, 193-199 and claimed as biologically active in producing a polyketide antibiotic in PCT WO 02/24736 A1. Huang, G., Zhang, L. & Birch, R. G. (2001) Microbiology 147, 631-642, report a DNA sequence of xabB (GenBank accession # AF239749), a multi functional polyketide-peptide synthetase that may be essential for albicidin biosynthesis in *Xanthomonas albilineans*. This xabB gene is reported as full length by Birch in PCT WO 02/24736 A1 (their seq. ID #1) and claimed by Birch in PCT WO 02/24736 A1 as a biologically active polyketide synthase of 4,801 amino acids in length, enabling production of albicidin. However, the DNA sequence reported by Huang et al. (2001) in GenBank AF239749 and by Birch in PCT WO 02/24736 A1 (their seq. ID #1) appears to be incomplete and missing 6,234 bp of DNA sequence encoding 2,078 amino acids. The subject invention provides the complete DNA sequence of xabB (albI, our seq. 20) as 20,637 bp, encoding a biologically active polyketide synthase of 6,879 amino acids of in this application (our seq ID #26). Factors affecting biosynthesis by *Xanthomonas albilineans* of albicidins antibiotics and phytotoxins are discussed in J. Appl. Microbiol. 85, 1023-1028. and Wall, M. K. & Birch, R. G. (1997). Genes for albicidin biosynthesis and resistance span at least 69 kb in the genome of *Xanthomonas albilineans*. Lett. Appl. Microbiol. 24, 256-260. A gene from *X. albilineans* strain Xa13, designed AlbF, which confers high level albicidin resistance in *Escherichia coli* and which encodes a putative albicidin efflux pump, was directly submitted to Genbank by Bostock and Birch (Accession No. AF403709).

SUMMARY OF THE INVENTION

The present invention describes and characterizes the family of antibiotics that is produced by culturing chlorosis-inducing strains of *X. albilineans* and mutants thereof, together with the complete set of twenty biosynthetic genes capable of producing the unique and previously uncharacterized family of antibiotics produced by *X. albilineans* and previously lumped together as "albicidins." The set of twenty biosynthetic genes isolated, purified and cloned from a culture of *X. albilineans* revealed that this set of biosynthetic genes is capable of synthesizing products exhibiting a high level of variation among the products, indicating that albicidins comprise a family of polyketide antibiotics. The albicidins described in the present invention are synthesized by twenty genes, including one polyketide-peptide synthase, one polyketide synthase and two peptide synthases, but the substrates of the polyketide-peptide synthase and of one peptide synthase are not α-amino acids. The biosynthetic enzymes represent a previously undescribed and unique polyketide antibiotic biosynthetic system.

BRIEF DESCRIPTION OF THE DRAWINGS

FIG. 3 shows the conserved sequence motifs in O-methyltransferases and C-methyltransferases involved in antibiotic biosynthesis in bacteria and in AlbII.

FIG. 4 shows the conserved sequence motifs in O-methyltransferases and in different tcmP-like hypothetical proteins and AlbVI.

FIG. 6 shows Rho-independent transcription terminators identified in the intergenic regions of XALB1 and XALB3 clusters (SEQ ID NO: 141, XALB1 Strand+(29 bp downstream from the TGA stop codon of albXVII); SEQ ID NO: 142, XALB1 Strand+(400 bp downstream from the TAA stop codon of albIV); SEQ ID NOs: 143, 144 and 145, XALB1 Strand−(62 bp, 170 bp and 560 bp downstream from the TAG stop codon of albXVI); SEQ ID NOs: 146 and 147, XLAB3 Strand+).

FIG. 7A shows sequences identified as a putative bidirectional promoter between albX and albXVII in XALB1 for transcriptional control of operons 3 and 4 (SEQ ID NOs: 148 and 149).

FIG. 7B shows sequences identified as a putative unidirectional promoter upstream from albXIX for transcriptional control of operon 5 if albXVIII is not expressed (SEQ ID NOs: 152 and 153).

FIG. 10A is an alignment of the conserved motifs in AT domains from RifA-1 (SEQ ID NO: 156), -2(SEQ ID NO: 157), -3 (SEQ ID NO: 158), RifB-1 (SEQ ID NO: 159), RitE-1 (SEQ ID NO: 160) (Rifamycin PKSs, August et al., 1998) and BlmVIII (Bleomycin PKS; Du et al., 2000) (SEQ ID NO: 161).

FIG. 10B is a comparison of AlbXIII (SEQ ID NO: 162), FenF (a malonyl-CoA transacylase located upstream from mycA, Duitman et al., 1999) (SEQ ID NO: 163) and LipA (a lipase; Valdez et al., 1999) (SEQ ID NO: 164).

FIG. 11B shows the proposed compositions and structures of albicidins.

DETAILED DESCRIPTION OF THE INVENTION

Figure 1:
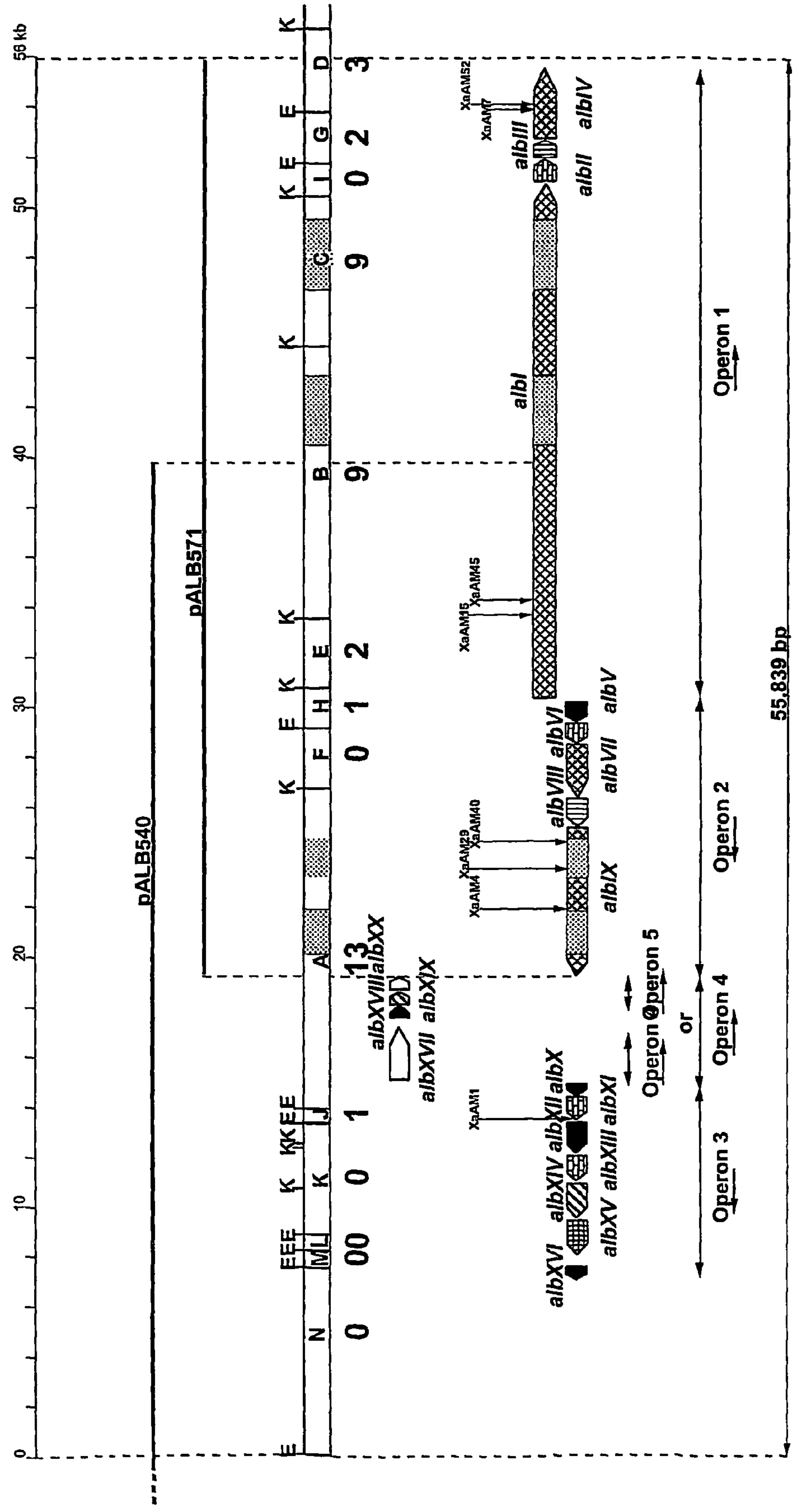
FIG. 1 is a Physical Map and genetic organization of the DNA Region containing the major gene cluster XALB1 involved in the biosynthesis of Albicidins.

The invention results from the DNA sequencing of the complete major gene cluster XALB1, as well as the noncontiguous fragments XALB2 and XALB3. XALB1 is present in the two overlapping DNA inserts of clones pALB540 and pALB571. Reading frame analysis and homology analyses allow one to predict the genetic organization of XALB1 and to assign a function to the genes potentially required for albicidin production. Based on the alignment of the different PKS and/or NRPS enzymes encoded by XALB1 we proposed a model for the albicidin backbone biosynthesis. However the invention disclosed herein does not depend upon the accuracy of the proposed model. The invention includes the successful cloning and DNA sequencing of the second region of the genome (XALB2) involved in albicidin production and mutated in mutant AM37.

The invention includes the characterization of the third region of the genome (XALB3) involved in albicidin production present in clone pALB639. These results allowed the possibility to characterize all enzymes of the albicidin biosynthesis pathway including structural, resistance and regulatory elements and to engineer overproduction of albicidin.

The subject invention provides:

(a) isolated, recombinant, and/or purified polynucleotide sequences comprising a polynucleotide sequence selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, and 25;

(b) isolated, recombinant, and/or purified polynucleotide sequences comprising a polynucleotide encoding a polypeptide selected from the group consisting of SEQ ID NO: 26, 27, 28, 29, 30, 31, 32, 33, 34, 35, 36, 37, 38, 39, 40, 41, 42, 43, 44, 45, 46, and 47;

(c) isolated, recombinant, and/or purified polynucleotide sequences comprising a polynucleotide that is complementary to a polynucleotide selected from the group consisting of 1, 2, 3, 4, 5, 6, 7, 8, 9, 10, 11, 12, 13, 14, 15, 16, 17, 18, 19, 20, 21, 22, 23, 24, and 25;

(d) isolated, recombinant, and/or purified polynucleotide sequences comprising a polynucleotide that is complementary to a polynucleotide encoding a polypeptide selected from the group consisting of SEQ ID NO: 26, 27; 28, 29, 30, 31, 32, 33, 34, 35, 36, 37, 38, 39, 40, 41, 42, 43, 44, 45, 46, and 47; or (e) isolated, recombinant, and/or purified polynucleotide sequences comprising a polynucleotide that is at least 70% homologous to: (1) a polynucleotide selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, and 25; (2) a polynucleotide sequence encoding a polypeptide selected from the group consisting of SEQ ID NO: 26, 27, 28, 29, 30, 31, 32, 33, 34, 35, 36, 37, 38, 39, 40, 41, 42, 43, 44, 45, 46, and 47; (3) a polynucleotide that is complementary to a polynucleotide encoding a polypeptide selected from the group consisting of SEQ ID NO: 26, 27, 28, 29, 30, 31, 32, 33, 34, 35, 36, 37, 38, 39, 40, 41, 42, 43, 44, 45, 46, and 47; (3) a polynucleotide that is complementary to a polynucleotide sequence selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, and 25;

(f) isolated, recombinant, and/or purified polynucleotide sequences comprising a polynucleotide sequence encoding variant (e.g., a variant polypeptide) of a polypeptide selected from the group consisting of SEQ ID NOs: 26, 27, 28, 29, 30, 31, 32, 33, 34, 35, 36, 37, 38, 39, 40, 41, 42, 43, 44, 45, 46, and 47, wherein said variant has at least on of the biological activities associated with the polypeptides of SEQ ID NOs: 26, 27, 28, 29, 30, 31, 32, 33, 34, 35, 36, 37, 38, 39, 40, 41, 42, 43, 44, 45, 46, and 47;

g) isolated, recombinant, and/or purified polynucleotide sequences comprising polynucleotide sequence encoding a fragment of a polypeptide selected from the group consisting of SEQ ID NOs: 26, 27, 28, 29, 30, 31, 32, 33, 34, 35, 36, 37, 38, 39, 40, 41, 42, 43, 44, 45, 46, and 47 or a fragment of a variant polypeptide of SEQ ID NOs: 26, 27, 28, 29, 30, 31, 32, 33, 34, 35, 36, 37, 38, 39, 40, 41, 42, 43, 44, 45, 46, and 47;

h) isolated, recombinant, and/or purified polynucleotide sequences comprising a polynucleotide sequence encoding multimeric construct;

j) a genetic construct comprising a polynucleotide sequence as set forth in (a), (b), (c), (d), (e), (f), (g), or (h);

k) a vector comprising a polynucleotide sequence as set forth in (a), (b), (c), (d), (e), (f), (g), or (h);

l) a host cell comprising a vector a polynucleotide sequence as set forth in (a), (b), (c), (d), (e), (f), (g), or (h);

m) a transformed plant cell comprising a vector comprising a polynucleotide sequence as set forth in (a), (b), (c), (d), (e), (f), (g), or (h);

n) a transformed plant comprising a vector comprising a polynucleotide sequence as set forth in (a), (b), (c), (d), (e), (f), (g), or (h); or;

o) a polynucleotide that hybridizes under low, intermediate or high stringency with a polynucleotide sequence as set forth in (a), (b), (c), (d), (e), (f), (g), or (h).

"Nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). It should also be understood that the present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods.

A homologous polynucleotide or polypeptide sequence, for the purposes of the present invention, encompasses a sequence having a percentage identity with the polynucleotide or polypeptide sequences, set forth herein, of between at least (or at least about) 70.00% to 99.99% (inclusive). The aforementioned range of percent identity is to be taken as including, and providing written description and support for, any fractional percentage, in intervals of 0.01%, between 20.00% and, up to, including 99.99%. These percentages are purely statistical and differences between two nucleic acid sequences can be distributed randomly and over the entire sequence length. For example, homologous sequences can exhibit a percent identity of 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent with the sequences of the instant invention. Typically, the percent identity is calculated with reference to the polynucleotide of a particular SEQ ID NO.; the full-length of a selected polynucleotide, or the native (naturally occurring) polynucleotide. The terms "identical" or percent "identity", in the context of two or more polynucleotide or polypeptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence may also be referred to as an "antisense" polynucleotide sequence or an "antisense" sequence.

Sequence homology and sequence identity can also be determined by hybridization studies under high stringency, intermediate stringency, and/or low stringency. Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under low, intermediate, or high stringency conditions by techniques well known in the art, as described, for example, in Keller, G. H., M. M. Manak [1987] DNA Probes, Stockton Press, New York, N.Y., pp. 169-170.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. [1982] Molecular Cloning: A Laboratory Manual, Cold Spring Harbor Laboratory, New York; Wei et al. [1983] J. Biol. Chem. 258:13006-13512.

The present invention further comprises fragments of the polynucleotide sequences of the instant invention. Representative fragments of the polynucleotide sequences according to the invention will be understood to mean any nucleotide fragment having at least 5 successive nucleotides, preferably at least 12 successive nucleotides, and still more preferably at least 15 or at least 20 successive nucleotides of the sequence from which it is derived. The upper limit for such fragments is the total number of nucleotides found in the full-length sequence encoding a particular polypeptide (e.g., a polypeptide selected from the group consisting of SEQ ID NOs: 26-50). The term "successive" can be interchanged with the term "consecutive". In some embodiments, a polynucleotide fragment may be referred to as "a contiguous span of at least X nucleotides, wherein X is any integer value beginning with 5. The upper limit for polynucleotide fragments of the subject invention is the total number of nucleotides found in the full-length sequence of a particular SEQ ID or the total number of nucleotides encoding a particular polypeptide (e.g., a particular SEQ ID NO).

In some embodiments, the subject invention includes those fragments capable of hybridizing under various conditions of stringency conditions (e.g., high or intermediate or low stringency) with a nucleotide sequence according to the invention; fragments that hybridize with a nucleotide sequence of the subject invention can be, optionally, labeled as set forth below.

Thus, the subject invention also provides detection probes (e.g., fragments of the disclosed polynucleotide sequences) for hybridization with a target sequence or the amplicon generated from the target sequence. Such a detection probe will comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides. Labeled probes or primers are labeled with a radioactive compound or with another type of label as set forth above. Alternatively, non-labeled nucleotide sequences may be used directly as probes or primers; however, the sequences are generally labeled with a radioactive element (32P, 35S, 3H, 125I) or with a molecule such as biotin, acetylaminofluorene, digoxigenin, 5-bromo-deoxyuridine, or fluorescein to provide probes that can be used in numerous applications.

The subject invention also provides for modified nucleotide sequences. Modified nucleic acid sequences will be understood to mean any nucleotide sequence that has been modified, according to techniques well known to persons skilled in the art, and exhibiting modifications in relation to the native, naturally occurring nucleotide sequences.

The subject invention also provides genetic constructs comprising: a) a polynucleotide sequence encoding a polypeptide sequence selected from the group consisting of SEQ ID NOs: 1-25; b) a polynucleotide sequence having at least about 70% to 99.99% identity to a polynucleotide sequence encoding a polypeptide sequence selected from the group consisting of SEQ ID NO: 26-50, wherein said polynucleotide encodes a polypeptide having at least one of the biological activities of the polypeptides (e.g., a catalytic activity as set forth in Table 4); c) a polynucleotide sequence encoding a biologically active fragment of a polypeptide selected from the group consisting of SEQ ID NO: 26-50, wherein said biologically active fragment has at least one of the biological activities of the polypeptides (e.g., a catalytic or transport activity as set forth in Table 4); d) a polynucleotide sequence comprising SEQ ID NO: 1, 2, 3, or combinations thereof; e) a polynucleotide sequence encoding variant (e.g., a variant polypeptide) of a polypeptide selected from the group consisting of SEQ ID NOs: 2648, wherein said variant has at least on of the biological activities associated with the polypeptides (e.g., a catalytic or transport activity as set forth in Table 4); f) a polynucleotide sequence encoding a fragment of a variant polypeptide as set forth in (e); or g) a polynucleotide sequence encoding multimeric construct.

Genetic constructs of the subject invention can also contain additional regulatory elements such as promoters and enhancers and, optionally, selectable markers.

Also within the scope of the subject instant invention are vectors or expression cassettes containing polynucleotides encoding the polypeptides, set forth supra, operably linked to regulatory elements. The vectors and expression cassettes may contain additional transcriptional control sequences as well. The vectors and expression cassettes may further comprise selectable markers. The expression cassette may contain at least one additional gene, operably linked to control elements, to be co-transformed into the organism. Alternatively, the additional gene(s) and control element(s) can be provided on multiple expression cassettes. Such expression cassettes are provided with a plurality of restriction sites for insertion of the sequences of the invention to be under the transcriptional regulation of the regulatory regions. The expression cassette(s) may additionally contain selectable marker genes operably linked to control elements.

In some embodiments, the expression cassette will include in the 5'-3' direction of transcription, a transcriptional and translational initiation region, a DNA sequence of the invention, and a transcriptional and translational termination region functional in plants. The transcriptional initiation region, the promoter, may be native or analogous, or foreign or heterologous, to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcriptional initiation region that is heterologous to the coding sequence.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acid Res. 15:9627-9639.

Where appropriate, the polynucleotides encoding the polypeptides set forth supra can be optimized for expression in the transformed plant That is, the genes can be synthesized using plant-preferred codons corresponding to the plant of interest Methods are available in the art for synthesizing plant-preferred genes. See, for example, U.S. Pat. Nos. 5,380,831 and 5,436,391, and Murray et al. (1989) Nucleic Acids Res. 17:477-498, herein incorporated by reference.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region), Elroy-Stein et al. (1989) PNAS USA 86:6126-6130; potyvirus leaders, for example, TEV leader (Tobacco Etch Virus), Allison et al. (1986); MDMV Leader (Maize Dwarf Mosaic Virus), Virology 154:9-20; human immunoglobulin heavy-chain binding protein (BiP), Macejak et al. (1991) Nature 353:90-94; untranslated leader from the coat protein mRNA of alfalfa mosaic virus (AMV RNA 4), Jobling et al. (1987) Nature 325:622-625; tobacco mosaic virus leader (TMV), Gallie et al. (1989) in Molecular Biology of RNA, ed. Cech (Liss, New York), pp. 237-256; and maize chlorotic mottle virus leader (MCMV), Lommel et al. (1991) Virology 81:382-385. See also, Della-Cioppa et al. (1987) Plant Physiol. 84:965-968. Other methods known to enhance translation can also be utilized.

Also provided are transformed host cells, transformed plant cells and transgenic plants which contain one or more genetic constructs, vectors, or expression cassettes comprising polynucleotides of the subject invention, or biologically active fragments thereof, operably linked to control elements. As used herein, the term "planta" includes algae and higher plants. Thus, algae, monocots, and dicots may be transformed with genetic constructs of the invention, expression cassettes, or vectors according to the invention. In certain embodiments of the subject invention, the transformed cells or transgenic plants comprise at least one polynucleotide sequence selected from the group consisting of SEQ ID NOs: 1-25. In certain preferred embodiments, transformed cells or transgenic plants comprise at least one polynucleotide sequence comprising SEQ ID NOs: 1, 2, or 3. Optionally, the transformed cells or transgenic plants can comprise at least two or all three polynucleotide sequences selected from the group consisting of SEQ ID NOs: 1, 2, and 3.

Methods of transforming cells with genetic constructs, vectors, or expression cassettes comprising the novel polynucleotides of the invention are also provided. These methods comprise transforming a plant or plant cell with a polynucleotide according to the subject invention. Plants and plant cells may be transformed by electroporation, Agrobacterium transformation (including vacuum infiltration), engineered plant virus replicons, electrophoresis, microinjection, micro-projectile bombardment, vacuum infiltration of Agrobacterium, micro-LASER beam-induced perforation of cell wall, or simply by incubation with or without polyethylene glycol (PEG). Plants transformed with a genetic construct of the invention may be produced by standard techniques known in the art for the genetic manipulation of plants. DNA can be transformed into plant cells using any suitable technology, such as a disarmed Ti-plasmid vector carried by *Agrobacterium* exploiting its natural gene transferability. *Agrobacterium* transformation is used by those skilled in the art to transform algae and dicotyledonous species. Substantial progress has been made towards the routine production of stable, fertile transgenic plants in almost all economically relevant monocot plants. In particular, *Agrobacterium* mediated transformation has now emerged as a highly efficient transformation method in monocots. Microprojectile bombardment, electroporation, and direct DNA uptake are preferred where *Agrobacterium* is inefficient or ineffective. Alternatively, a combination of different techniques may be employed to enhance the efficiency of the transformation process, e.g., bombardment with *Agrobacterium*-coated microparticles (EP-A486234) or microprojectile bombardment to induce wounding followed by co-cultivation with *Agrobacterium* (EP-A-486233).

Following transformation, a plant may be regenerated, e.g., from single cells, callus tissue or leaf discs, as is standard in the art. Almost any plant can be entirely regenerated from cells, tissues, and organs of the plant. Available techniques are reviewed in Vasil et al. (1984) in Cell Culture and Somatic Cell Genetics of Plants, Vols. I, II, and II, Laboratory Procedures and Their Applications (Academic press); and Weissbach et al. (1989) Methods for Plant Mol. Biol.

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited, and then seeds harvested to ensure expression of the desired phenotypic characteristic has been achieved.

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

Also according to the invention, there is provided a plant cell having the constructs of the invention. A further aspect of the present invention provides a method of making such a plant cell involving introduction of a vector including the construct into a plant cell. For integration of the construct into the plant genome, such introduction will be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such descendants should show the desired phenotype.

The present invention also provides a plant comprising a plant cell as disclosed. Transformed seeds and plant parts are also encompassed. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to naturally occurring, deliberate, or inadvertent caused mutations. Mutant progeny that have the same function or biological activity as screened for in the originally transformed cell are included. Where distinct designations are intended, it will be clear from the context.

In addition to a plant, the present invention provides any clone of such a plant, seed, or hybrid descendants, and any part of any of these, such as cuttings or seed. The invention provides any plant propagule that is any part which may be used in reproduction or propagation, sexual or asexual, including cuttings, seed, and so on. Also encompassed by the invention is a plant which is a sexually or asexually propagated off-spring, clone, or descendant of such a plant; or any part or propagule of said plant, off-spring, clone, or descendant. Plant extracts and derivatives are also provided.

As is apparent to the routineer in this technology, the disclosed methods allow for the expression of a gene of interest in any plant. The invention thus relates generally to methods for the production of transgenic plants (both monocots and dicots). As used herein, the term "transgenic plants" refers to plants (algae, monocots, or dicots), comprising plant cells in which homologous or heterologous polynucleotides are expressed as the result of manipulation by the hand of man.

As is apparent to one of ordinary skill in the art, the peptides encoded by the disclosed herein may be encoded by multiple polynucleotide sequences because of the redundancy of the genetic code. It is well within the skill of a person trained in the art to create these alternative DNA sequences encoding the same, or essentially the same, amino acid sequences. These variant DNA sequences are within the scope of the subject invention.

The terms "purified" and "isolated", when referring to a polynucleotide, nucleotide, or nucleic acid, indicate a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecules but is not flanked by both of the coding or non-coding sequences that flank that part of the molecule in the genome of the organism in which it naturally occurs (e.g., DNA excised with a restriction enzyme); (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones, e.g., as these occur in a DNA library such as a cDNA or genomic DNA library.

The term "polynucleotide" as used herein refers to a polymeric form of nucleotides of any length, either ribonucleotides or deoxyribonucleotides. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications, such as those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

"Control elements" include both "transcriptional control elements" and "translational control elements". "Transcriptional control elements" include "promoter", "enhancer", and "transcription termination" elements. Promoters and enhancers consist of short arrays of DNA sequences that interact specifically with cellular proteins involved in transcription [Maniatis et al. [1987] Science 236:1237). Promoter and enhancer elements have been isolated from a variety of eukaryotic sources including genes in plants, yeast, insect and mammalian cells and viruses (analogous control elements, i.e., promoters, are also found in prokaryotes). The selection of a particular promoter and enhancer depends on what cell type is to be used to express the peptide of interest. Some eukaryotic promoters and enhancers have a broad host range while others are functional in a limited subset of cell types [for review see Voss et al. [1986] Trends Biochem. Sci. 11:287 and Maniatis et al. [1987] supra. Transcriptional control elements suitable for use in plants are well known in the art. "Translational control elements" include translational initiation regions and translational termination regions functional in plants.

A number of promoters can be used in the practice of the invention. The promoters can be selected based on the desired outcome. Strong promoters may be used to produce high levels of gene transcription. Alternatively, inducible promoters may be used to selectively active gene transcription when the appropriate signal is provided. Constitutive promoters may be utilized to continuously drive gene transcription. Tissue specific promoters may also be used in the practice of the invention in order to provide localized production of gene transcripts in a desired tissue. Developmental promoters may, likewise, be used to drive transcription of a gene during a particular developmental stage of the plant. Thus, a gene of interest can be combined with constitutive, tissue-specific, inducible, developmental, or other promoters for expression in plants depending upon the desired outcome.

Constitutive promoters include, for example, CaMV 35S promoter (Odell et al. (1985) Nature 313:810-812; rice actin (McElroy et al. (1990) Plant Cell 2:163-171; ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include those in U.S. Pat. Nos. 5,608,149; 5,608,144; 5,604,121; 5,569,597; 5,466,785; 5,399,680; 5,268,463; and 5,608,142. Each of the aforementioned patents and references is hereby incorporated by reference in its entirety.

A number of inducible promoters are known in the art. For example, a pathogen-inducible promoter can be utilized. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) Neth. J. Plant Pathol. 89:245-254; Uknes et al. (1992) Plant Cell 4:645-656; and Van Loon (1985) Plant Mol. Virol. 4:111-116; Marineau et al. (1987) Plant Mol. Biol. 9:335-342; Matton et al. (1989) Molecular Plant-Microbe Interactions 2:325-331; Somsisch et al. (1986) Proc. Natl. Acad. Sci. USA 83:2427-2430; Somsisch et al. (1988) Mol. Gen. Genet. 2:93-98; and Yang (1996) Proc. Natl. Acad. Sci. USA 93:14972-14977. See also, Chen et al. (1996) Plant J. 10:955-966; Zhang et al. (1994) Proc. Natl. Acad. Sci. USA 91:2507-2511; Warner et al. (1993) Plant J. 3:191-201; Siebertz et al. (1989) Plant Cell 1:961-968; U.S. Pat. No. 5,750,386; Cordero et al. (1992) Physiol. Mol. Plant Path. 41:189-200; each of which is incorporated by reference in its entirety.

Wound-inducible promoters may be used in the genetic constructs of the invention. Such wound-inducible promoters include potato proteinase inhibitor (pin II) gene (Ryan (1990) Ann. Rev. Phytopath. 28:425-449; Duan et al. (1996) Nature Biotechnology 14:494-498; wun1 and wun2, U.S. Pat. No. 5,428,148; win1 and win2 (Stanford et al. (1989) Mol. Gen. Genet. 215:200-208); systemin (McGurl et al. (1992) Science 225:1570-1573); WIP1 (Rohmeier et al. (1993) Plant Mol. Biol. 22:783-792; Eckelkamp et al. (1993) FEBS Letters 323:73-76); MPI gene (Corderok et al. (1994) Plant J. 6(2):141-150; and the like. These references are also incorporated by reference in their entireties.

Tissue specific promoters can also be used in the practice of the subject invention. For example, leaf-specific promoters can similarly be used if desired, and are taught in references which include Yamamoto et al. (1997) Plant J. 12(2):255-265; Kawamata et al. (1997) Plant Cell Physiol. 38(7):792-803; Hansen et al. (1997) Mol. Gen. Genet. 254(3):337-343; Russel et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5)773-778; Lam (1994) Results Probl. Cell Differ. 20:181-196; Orozco et al. (1993) Plant Mol. Biol. 23(6):1129-1138; Matsuoka et al. (1993) Proc. Natl. Acad. Sci USA:90(20) 9586-9590; and Guevara-Garcia et al. (1993) Plant J. 4(3):495-505. Alternatively, root-specific promoters are known and can be selected from the many available from the literature. See, for example, Hire et al. (1992) Plant Mol. Biol. 20(2):207-218 (soybean root-specific glutamine synthetase gene); Keller and Baumgartner (1991) Plant Cell 3(10):1051-1061 (root-specific control element in the GRP 1.8 gene of French bean); Sanger et al. (1990) Plant Mol. Biol. 14(3):433-443 (root-specific promoter of the mannopine synthase (MAS) gene of *Agrobacterium tumefaciens*) Miao et al. (1991) Plant Cell 3(1):11-22 (full-length cDNA clone encoding cytosolic glutamine synthetase (GS), which is expressed in roots and root nodules of soybean). Bogusz et al. (1990) Plant Cell 2(7):633-641 (root specific promoters from hemoglobin genes from the nitrogen-fixing nonlegume Parasponia andersonii and the related non-nitrogen-fixing nonlegume Trema tomeniosa; Leach and Aoyagi (1991) Plant Science (Limerick) 79(1):69-76 (rolC and rolD root-including genes of *Agrobacterium rhizogenes*); Teeri et al. (1989) EMBO J. 8(2):343-350 (octopine synthase and TR2' gene); (VfENOD-GRP3 gene promoter); Kuster et al. (1995) Plant Mol. Biol. 29(4):759-772 and Capana et al. (1994) Plant Mol. Biol. 25(4):681-691 (rolB promoter). See also U.S. Pat. Nos. 5,837,876; 5,750,386; 5,633,363; 5,459,252; 5,401,836; 5,110,732; and 5,023,179.

Other tissue specific promoters can also be used in the practice of the subject invention (see, for example U.S. Pat. No. 6,544,783). For example, xylem/vascular/tracheid-specific promoters, such as those disclosed in Milioni et al. (2002) Plant Cell, 14:2813-2824; Zhong et al. (1999) Plant Cell, 11:2139-2152; Ito et al. (2002) Plant Cell, 14:3201-3211; Parker et al. (2003) Development 130:2139-2148; Bourquin et al. (2002) Plant Cell 14:3073-3088 (each of which is hereby incorporated by reference in its entirety) can be used in the practice of the subject invention.

“Seed-preferred” promoters include both “seed-specific” promoters (those promoters active during seed development such as promoters of seed storage proteins) as well as “seed-germinating” promoters (those promoters active during seed germination). See Thompson et al. (1989) Bioassays 10:108, herein incorporated by reference. Such seed-preferred promoters include, but are not limited to, Cim1 (cytokinin-induced message); cZ10B1 (Maize 19 kDa zein); celA (cellulose synthase); gama-zein; Glob-1; bean β-phaseolin; napin; β-conglycinin; soybean lectin; cruciferin; maize 15 kDa zein; 22 kDa zein; 27 kDa zein; g-zein; waxy; shrunken 1; shrunken 2; globulin 1; etc.

“Operably linked” refers to a juxtaposition wherein the components so described are in a relationship permitting them to function in their intended manner. A control sequence “operably linked” to a coding sequence is ligated in such a way that expression of the coding sequence is achieved under conditions compatible with the control sequences.

As used herein, the term “expression cassette” refers to a molecule comprising at least one coding sequence operably linked to a control sequence which includes all nucleotide sequences required for the transcription of cloned copies of the coding sequence and the translation of the mRNAs in an appropriate host cell. Such expression cassettes can be used to express eukaryotic genes in a variety of hosts such as bacteria, green algae, cyanobacteria, plant cells, fungal cells, yeast cells, insect cells and animal cells. Under the invention, expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

By "vector" is meant any genetic element, such as a plasmid, phage, transposon, cosmid, chromosome, virus etc., which is capable of replication when associated with the proper control elements and which can transfer gene sequences between cells. Thus, the term includes cloning and expression vehicles, as well as viral vectors.

During the preparation of the constructs, the various fragments of DNA will often be cloned in an appropriate cloning vector, which allows for amplification of the DNA, modification of the DNA or manipulation of the DNA by joining or removing sequences, linkers, or the like. Preferably, the vectors will be capable of replication to at least a relatively high copy number in *E. coli*. A number of vectors are readily available for cloning, including such vectors as pBR322, vectors of the pUC series, the M13 series vectors, and pBluescript vectors (Stratagene; La Jolla, Calif.).

In order to provide a means of selecting transformed plants or plant cells, the vectors for transformation will typically contain a selectable marker gene. Marker genes are expressible DNA sequences which express a polypeptide which resists a natural inhibition by, attenuates, or inactivates a selective substance. Examples of such substances include antibiotics and, in the case of plant cells, herbicides. Selectable markers for use in animal, bacterial, plant, fungal, yeast, and insect cells are well known in the art. Exemplary selectable markers include bacterial transposons Tn5 or Tn 601 (903) conferring resistance to aminoglycosides (selection for Geneticin-resistance (G418R), mycophenolic acid resistance (MPAR) (utilizing *E. coli* guanosine phosphoribosyl transferase (gpt) encoding the enzyme XGPRT; selection is performed on medium containing MPA and xanthin), methotrexate resistance (MTXR), or cadmium-resistance which incorporates the mouse metallotheionein gene (as cDNA cassette) on the vector which detoxifies heavy metal ions by chelating them.

Alternatively, a marker gene may provide some visible indication of cell transformation. For example, it may cause a distinctive appearance or growth pattern relative to plants or plant cells not expressing the selectable marker gene in the presence of some substance, either as applied directly to the plant or plant cells or as present in the plant or plant cell growth media. The use of such a marker for identification of plant cells containing a plastid construct has been described (Svab et al. [1993] supra). Numerous additional promoter regions may also be used to drive expression of the selectable marker gene, including various plant promoters and bacterial promoters which have been shown to function in plants.

A number of other markers have been developed for use with plant cells, such as resistance to chloramphenicol, the aminoglycoside G418, hygromycin, or the like. Other genes which encode a product involved in chloroplast metabolism may also be used as selectable markers. For example, genes which provide resistance to plant herbicides such as glyphosate, bromoxynil or imidazolinone may find particular use. Such genes have been reported (Stalker et al. [1985] J. Biol. Chem. 260:4724-4728 (glyphosate resistant EPSP); Stalker et al. [1985] J. Biol. Chem. 263:6310-6314 (bromoxynil resistant nitrilase gene); and Sathasivan et al. [1990] Nucl. Acids Res. 18:2188 (AHAS imidazolinone resistance gene)).

Another aspect of the invention provides vectors for the cloning and/or the expression of a polynucleotide sequences taught herein in procaryotic or animal cells. The subject invention also provides for the expression of a polypeptide, peptide, derivative, or variant encoded by a polynucleotide sequence disclosed herein comprising the culture of a procaryotic or animal cell (a host cell) transformed with a polynucleotide of the subject invention under conditions that allow for the expression of a polypeptide, biologically active fragment, or multimeric construct encoded by said polynucleotide and, optionally, recovering the expressed polypeptide, peptide, derivative, or analog.

In this aspect of the invention, the polynucleotide sequences can be regulated by a second nucleic acid sequence so that the protein or peptide is expressed in a host cell transformed with the recombinant DNA molecule. For example, expression of a protein or peptide may be controlled by any promoter/enhancer element known in the art. Promoters which may be used to control expression include, but are not limited to, the CMV-IE promoter, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes simplex thymidine kinase promoter (Wagner et al., 1981, Proc. Natl. Acad. Sci. U.S. 78:1441-1445), the regulatory sequences of the metallothionein gene (Brinster et al., 1982, Nature 296:39-42); prokaryotic vectors containing promoters such as the β-lactamase promoter (Villa-Kamaroff, et al., 1978, Proc. Natl. Acad. Sci. U.S. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., 1983, Nature 303: 209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or fungi such as the Gal 4 promoter, the ADC (alcohol dehydrogenase) promoter, PGK (phosphoglycerol kinase) promoter, and/or the alkaline phosphatase promoter.

The vectors according to the invention are, for example, vectors of plasmid or viral origin. In a specific embodiment, a vector is used that comprises a promoter operably linked to a nucleic acid sequence encoding a polypeptide as disclosed herein, one or more origins of replication, and, optionally, one or more selectable markers (e.g., an antibiotic resistance gene). Expression vectors comprise regulatory sequences that control gene expression, including gene expression in a desired host cell. Exemplary vectors for the expression of the polypeptides of the invention include the pET-type plasmid vectors (Promega) or pBAD plasmid vectors (Invitrogen) or those provided in the examples below. Furthermore, the vectors according to the invention are useful for transforming host cells so as to clone or express the polynucleotide sequences of the invention.

The invention also encompasses the host cells transformed by a vector according to the invention. These cells may be obtained by introducing into host cells a nucleotide sequence inserted into a vector as defined above, and then culturing the said cells under conditions allowing the replication and/or the expression of the polynucleotide sequences of the subject invention.

The host cell may be chosen from eukaryotic or prokaryotic systems, such as for example bacterial cells, (Gram negative or Gram positive), yeast cells (for example, *Saccharomyces cereviseae* or *Pichia pastoris*), animal cells (such as Chinese hamster ovary (CHO) cells), plant cells (e.g., algae), and/or insect cells using baculovirus vectors. In some embodiments, the host cells for expression of the polypeptides include, and are not limited to, those taught in U.S. Pat. No. 6,319,691, 6,277,375, 5,643,570, or 5,565,335, each of which is incorporated by reference in its entirety, including all references cited within each respective patent.

Furthermore, a host cell strain may be chosen which modulates the expression of the inserted sequences, or modifies and processes the gene product in the specific fashion desired. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can also to provide glycosylation of a protein.

The subject invention provides one or more isolated polypeptides comprising:

(a) SEQ ID NO: 26, 27, 28, 29, 30, 31, 32, 33, 34, 35, 36, 37, 38, 39, 40, 41, 42, 43, 44, 45, 46, or 47;

(b) a heterologous polypeptide sequence fused, in frame, to a polypeptide comprising SEQ ID NO: 26, 27, 28, 29, 30, 31, 32, 33, 34, 35, 36, 37, 38, 39, 40, 41, 42, 43, 44, 45, 46, or 47;

(c) a fragment of SEQ ID NO: 26, 27, 28, 29, 30, 31, 32, 33, 34, 35, 36, 37, 38, 39, 40, 41, 42, 43, 44, 45, 46, or 47, wherein said fragment exhibits at least one biological function of the polypeptide of SEQ ID NO: 26, 27, 28, 29, 30, 31, 32, 33, 34, 35, 36, 37, 38, 39, 40, 41, 42, 43, 44, 45, 46, or 47; or (d) a variant having at least 70% homology to a polypeptide comprising SEQ ID NO: 26, 27, 28, 29, 30, 31, 32, 33, 34, 35, 36, 37, 38, 39, 40, 41, 42, 43, 44, 45, 46, or 47, wherein said variant exhibits at least one biological function of the polypeptide comprising SEQ ID NO: 26, 27, 28, 29, 30, 31, 32, 33, 34, 35, 36, 37, 38, 39, 40, 41, 42, 43, 44, 45, 46, or 47.

The term "peptide" may be used interchangeably with "oligopeptide" or "polypeptide" in the instant specification to designate a series of residues, typically L-amino acids, connected one to the other, typically by peptide bonds between the α-amino and carboxyl groups of adjacent amino acids. Linker elements can be joined to the polypeptides of the subject invention through peptide bonds or via chemical bonds (e.g., heterobifunctional chemical linker elements).

The subject invention encompasses polypeptide fragments of the full-length polypeptides disclosed herein. Polypeptide fragments, according to the subject invention, usually comprise a contiguous span of at least 5 consecutive (or contiguous) amino acids. The maximum length for a polypeptide fragment in the context of this invention is an integer that is one amino acid less than the full length of a particular SEQ ID NO: from which the fragment was derived. In certain preferred embodiments, fragments of the polypeptides of the subject invention retain at least one biological activity/function of the full-length polypeptide from which they are derived (e.g., such similar or identical enzymatic activity or the ability to provide resistance to an antibiotic or transport an antibiotic out of a cell (see, for example, Table 4).

A "variant" polypeptide (or polypeptide variant) is to be understood to designate polypeptides exhibiting, in relation to the natural polypeptide, certain modifications. These modifications can include a deletion, addition, or substitution of at least one amino acid, a truncation, an extension, a chimeric fusion, a mutation, or polypeptides exhibiting post-translational modifications. Among the homologous polypeptides, those whose amino acid sequences exhibit between at least (or at least about) 70.00% to 99.99% (inclusive) identity to the full length, native, or naturally occurring polypeptide are another aspect of the invention. The aforementioned range of percent identity is to be taken as including, and providing written description and support for, any fractional percentage, in intervals of 0.01%, between 70.00% and, up to, including 99.99%. These percentages are purely statistical and differences between two polypeptide sequences can be distributed randomly and over the entire sequence length. Thus, variant polypeptides can have 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polypeptide sequences of the instant invention. In certain preferred embodiments, variants of the polypeptides of the subject invention retain at least one biological activity/function of the full-length polypeptide from which they are derived (e.g., such as similar or identical enzymatic activity or the ability to provide resistance to an antibiotic or transport an antibiotic out of a cell (see, for example, Table 4).

Variant polypeptides can also comprise one or more heterologous polypeptide sequences (e.g., tags that facilitate purification of the polypeptides of the invention (see, for example, U.S. Pat. No. 6,342,362, hereby incorporated by reference in its entirety; Altendorf et al. [1999-WWW, 2000] "Structure and Function of the Fo Complex of the ATP Synthase from *Escherichia Coli*," J. of Experimental Biology 203:19-28, The Co. of Biologists, Ltd., G. B.; Baneyx [1999] "Recombinant Protein Expression in *Escherichia coli*," Biotechnology 10:411-21, Elsevier Science Ltd.; Eihauer et al. [2001] "The FLAG™ Peptide, a Versatile Fusion Tag for the Purification of Recombinant Proteins," J. Biochem Biophys Methods 49:455-65; Jones et al. J. Chromatography 707:3-22; Jones et al. [1995] "Current Trends in Molecular Recognition and Bioseparation," J. of Chromatography A. 707:3-22, Elsevier Science B. V.; Margolin [2000] "Green Fluorescent Protein as a Reporter for Macromolecular Localization in Bacterial Cells," Methods 20:62-72, Academic Press; Puig et al. [2001] "The Tandem Affinity Purification (TAP) Method: A General Procedure of Protein Complex Purification," Methods 24:218-29, Academic Press; Sassenfeld [1990] "Engineering Proteins for Purification," TibTech 8:88-93; Sheibani [1999] "Prokaryotic Gene Fusion Expression Systems and Their Use in Structural and Functional Studies of Proteins," Prep. Biochem. & Biotechnol. 29(1):77-90, Marcel Dekker, Inc.; Skerra et al. [1999] "Applications of a Peptide Ligand for Streptavidin: the Strep-tag", Biomolecular Engineering 16:79-86, Elsevier Science, B.V.; Smith [1998] "Cookbook for Eukaryotic Protein Expression: Yeast, Insect, and Plant Expression Systems," The Scientist 12(22):20; Smyth et al. [2000] "Eukaryotic Expression and Purification of Recombinant Extracellular Matrix Proteins Carrying the Strep II Tag", Methods in Molecular Biology, 139:49-57; Unger [1997] "Show Me the Money: Prokaryotic Expression Vectors and Purification Systems," The Scientist 11(17):20, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or InVitrogen (San Diego, Calif.). Alternatively, the heterologous sequences may provide for the multimerization of the polypeptides of the subject invention (see, e.g., U.S. Pat. No. 5,478,925, WO 98/49305, or U.S. Pat. No. 5,073,627, Landschulz et al., (1988), Science. 240:1759, WO 94/10308, Hoppe et al., (1994), FEBS Letters. 344:191). Other methods of making multimers include the addition of cysteine or biotin to the C-terminus or N-terminus of the polypeptide using techniques known in the art. Where biotin is attached to a polypeptide, avidin can be utilized to create multimers of the polypeptides to which the biotin element is attached (see, e.g., U.S. Pat. No. 5,478,925 for numerous methods of multimerization). Multimers of the invention may also be generated using chemical or genetic engineering techniques known in the art The invention, thus, provides a novel antibiotic family, Albicidins, produced by three novel biosynthetic gene clusters (XALB1, XALB2, and XALB3) contained within a host cell DNA in which one strand comprises non-contiguously SEQ. ID No. 1, SEQ. ID No. 2 and SEQ ID No. 3, and the cell expresses the DNA to provide peptides including those named AlbI (SEQ ID No. 26) (encoded by SEQ ID No. 20), AlbII (SEQ ID No. 27) (encoded by SEQ ID No. 21), AlbIII (SEQ ID No. 28) (encoded by SEQ ID No. 22), AlbIV (SEQ ID No. 29) (encoded by SEQ ID No. 23), AlbVI (SEQ ID No. 31) (encoded by SEQ ID No. 18), AlbVII (SEQ ID No. 32) (encoded by SEQ ID No. 17), AlbVIII (SEQ ID No. 33) (encoded by SEQ ID No. 16), AlbIX (SEQ ID No. 34) (encoded by SEQ ID No. 15), AlbX (SEQ ID No. 35) (encoded by SEQ ID No. 10), AlbXI (SEQ ID No. 36) (encoded by SEQ ID No. 9), AlbXII (SEQ ID No. 37) (encoded by SEQ ID No. 8), AlbXIII (SEQ ID No. 38) (encoded by SEQ ID No. 7), AlbXIV (SEQ ID No. 39) (encoded by SEQ ID No. 6), AlbXV (SEQ ID No. 40) (encoded by SEQ ID No. 5), AlbXVII (SEQ ID No. 42) (encoded by SEQ ID No. 11), AlbXVIII (SEQ ID No. 43) (encoded by SEQ ID No. 12), AlbXIX (SEQ ID No. 44) (encoded by SEQ ID No. 13), AlbXX (SEQ ID No. 45) (encoded by SEQ ID No. 14), AlbXXI (SEQ ID No. 46) (encoded by SEQ ID No. 24), and AlbXXII (SEQ ID No. 47) (encoded by SEQ ID No. 25), that in turn interact within the host cell to produce one or more antibiotics as more fully illustrated in FIG. 11.

In one embodiment, the invention comprises a plurality of isolated and purified DNA strands which comprise nucleotide sequences selected from the group consisting of SEQ ID No: 1 to SEQ. ID No. 25, each individual sequence, except the transposases AlbV (SEQ ID No. 30) (encoded by SEQ ID No. 19) and AlbXVI (SEQ ID No. 41) (encoded by SEQ ID No. 4) found in the XALB1 cluster, being necessary to the biosynthesis of the novel family of antibiotics, Albicidins.

The invention also includes the peptides or proteins encoded by the genes of the biosynthetic complex expressed by the combination of DNA with a strand having sequences SEQ ID Nos. 1 to 3. Proteins are named with roman numerals and the prefix Alb from AlbI to Alb XXII have the amino acid sequences of SEQ ID Nos. 26 to 47 (not in Roman numeral order but in the order of placement of the genes within sequences SEQ ID Nos. 1 to 3 that express each protein). Expression of the peptides having the amino acid sequences of SEQ ID Nos. 26 to 29, 31 to 40 and 42 to 47, have been found to be all required for the successful biosynthesis of Albicidins.

The invention further provides a method for producing Albicidins comprising providing a modified host cell with a heterologous DNA Albicidin Biosynthetic Gene Cluster or set of genes defined as DNA operably comprising DNA sequences substantially similar to SEQ ID Nos. 1 to 3. Substantially the same means DNA having sufficient homology to provide expressed proteins that function to provide an antibiotic material having the structural components identified herein. Preferably a given sequence will have at least 70 percent homology to one of SEQ ID Nos. 1 to 3, preferably 85% homology and most preferably at least 95% homology. The method includes the steps of modifying the DNA of the host cell to comprise an operable expression system for maintaining the modified host cell under conditions supporting biosynthesis of Albicidins and isolation of Albicidins from the host cell or its environment. The invention further provides a method of production of a group of novel antibiotic materials utilizing at least three of the Sequences selected from the group consisting of DNA SEQ ID No. 1 to SEQ ID No. 25 (excluding transposases encoded by SEQ ID Nos. 4 and 19) inclusive in combination with additional sequences to produce a modified Albicidin-like material.

More specifically, the invention provides DNA Sequences comprising at least about 68,498 base pairs and including an about 55,839 bp region from the genome of *X. albilineans* designated as XALB1 (Albicidin Biosynthetic Gene Cluster 1; SEQ ID. No. 1) an additional non-contiguous region of about 2,986 bp, XALB2 (Albicidin Biosynthetic Gene Cluster 2; SEQ ID. No. 2), and a third region of about 9,673 bp, XALB3 (Albicidin Biosynthetic Gene Cluster 3; SEQ ID. No. 3). Albicidin Biosynthetic Gene Clusters 1-3 may be referred to, collectively, as the Albicidin Biosynthetic Gene Clusters and these sequences were found to be required for biosynthesis of Albicidins. Homology analysis revealed the presence of (i) four large genes with a modular architecture characteristic of polyketide synthases (PKS) and nonribosomal peptide synthetases (NRPS) potentially involved in albicidin precursor biosynthesis; (ii) four smaller genes potentially involved in albicidin substrate biosynthesis (iii) four modifying genes; (iv) one enzyme activating gene, (v) two regulatory genes, (vi) one chaperone gene, (vii) two genes of unknown function; and (viii) two resistance genes. These are named and discussed more fully below. Together these genes allow the successful operation of the biosynthetic pathway when cloned into suitable host cells.

Alignment of individual NRPS and PKS domains revealed an extraordinary biosynthetic apparatus believed to involve a trans-action of separate PKS and NRPS domains which could contribute to the production of multiple, structurally related albicidins by the same gene cluster. Furthermore, analysis of selectivity-conferring residues indicated that four NRPS modules of XALB1 specify an unusual substrate.

In an alternate embodiment the invention provides a method of producing a polyketide carrying para-aminobenzoic acid and/or carbamoyl benzoic acid by inserting at least one DNA fragment that encodes a PKS protein into a cell and causing the cell to express the encoded PKS protein under conditions such that the PKS protein functions to produce a polyketide carrying either a para-aminobenzoic acid or a carbamoyl benzoic acid or both. Another embodiment provides a method of producing polyketide/peptides carrying para-aminobenzoic acid and/or carbamoyl benzoic acid by inserting at least one DNA fragment that encodes a PKS protein into a cell and causing the cell to express the encoded PKS protein under conditions such that the PKS protein functions to produce a polyketide carrying either a para-aminobenzoic acid or a carbamoyl benzoic acid or both. In yet another embodiment, the invention provides a method of activating nonproteinogenic amino acids like paraminobenzoic acid and/or carbamoyl benzoic acid for incorporation into peptides or polyketides by inserting at least one DNA fragment that encodes a PKS protein into a cell and causing the cell to express the encoded PKS protein under conditions such that the PKS protein functions to produce a polyketide carrying either a para-aminobenzoic acid or a carbamoyl benzoic acid or both.

There are three regions of the *X. albilineans* genome specifying albicidin production. XALB2 and XALB3 regions each contain only one gene, both of which are required for post-translational activation and folding of albicidin PKS and NRPS enzymes. The XALB1, XALB2 and XALB3 gene clusters are characterized by an unusual hybrid NRPS-PKS system, indicating that albicidin biosynthesis may provide an excellent model for investigating the biosynthesis of hybrid polyketide-polypeptide metabolites in bacteria. The availability of three genomic regions involved in albicidin production, XALB1 and XALB2 and XALB3, also offers the ability to express individually the enzymes of the albicidin family biosynthetic pathway including structural, resistance, secretory and regulatory elements, and to engineer overproduction of albicidin in mutated or modified host cells of the invention. The invention overcomes prior art limitations in albicidin production due to low yields of toxin production in *X. albilineans* and may also allow characterization of the chemical structure of albicidin as well as application of this potent inhibitor of prokaryote DNA replication.

The invention results from a number of unpredictable results namely the number and complexity of the enzymes involved in biosynthesis. The discovery of the complete sequence required for biosynthesis of Albicidins is previously unreported. The invention provides for a novel process for production of molecule having a polyketide-polypeptide backbone and the formula $C_{40}H_{35}O_{15}N_6$, a molecular weight of 839, and the structural elements shown in FIG. 11.

The invention further includes (a) the Albicidin Family Biosynthetic Gene Cluster including (b) the structural and regulatory elements of the operons that encode c) the enzymes PKS-1, PKS-2, PKS-3, PKS4, NRPS-1, NRPS-2, NRPS-3, NRPS-4, NRPS-5, NRPS-6 and NRPS-7 as well as (d) the proteins AlbI to AlbXXII, (e) the isolated enzymes, proteins, and active forms thereof, as well as mutants, fragments, and fusion proteins comprising any of the forgoing; (f) the uses of the enzymes or proteins encoded by the Albicidins Biosynthesis Gene Cluster or any one of its operons, (g) a host cell expressing one or more enzymes or proteins encoded by the Albicidin Family Biosynthetic Gene Cluster; (h) use of host cells having the Albicidins Biosynthesis Gene Cluster to produce an antibiotic; (i) methods of modifying the DNA sequences to produce members of a series of antibiotic compounds having structures related to Albicidins; (j) DNA sequences that encode the same proteins as any of SEQ. ID. Nos. 1 to 25 but differ in specific codons due to the multiplicity of codons that lead to expression of the same amino acid; (k) antibiotics produced by the process of expression of the Albicidin Family Biosynthetic Genes in a genetically modified host cell sustained in a culture medium and thereafter separation of the antibiotic from the host cell and culture medium; (l) an isolated and purified antibiotic produced by a process that includes at least three proteins coded by DNA sequences selected for the group consisting of SEQ. ID Nos. 1 to 25 in combination with additional enzymes that modify the product to provide a non-naturally occurring Albicidins like product having at least one of the useful properties reported for albicidin; and (m) a process for producing an antibiotic that comprises modifying a host cell to enhance expression of the DNA of the Albicidin Family Biosynthetic Gene Cluster by insertion of expression enhancing DNA into the genome of a *Xanthomonas albilineans* strain in a position operative to enhance expression of the enzymes of the Albicidin Family Biosynthetic Gene Cluster, culturing the modified host cell to produce an antibiotic and isolating the antibiotic. The products and methods described above have utility as proteins or as nucleic acids as the case may be, including such uses sources of pyrimidine or purine bases or amino acids, or as animal food supplements and the like, as well as the more important uses to provide antibiotics, plant disease treatment methods, genetically modified disease resistant plants, phytotoxins and the like.

The subject invention also provides an isolated and purified antibiotic produced by a process that includes at least three proteins coded by the nucleic acids of the subject invention in combination with additional enzymes that modify the product to provide a non-naturally occurring Albicidin-like product having at least one of the useful properties reported for albicidin. In certain embodiments, the antibiotic or antibiotics have at least one of the general structures illustrated in FIG. 11. In other embodiments, antibiotics of the subject invention have at least 4 of the structural elements illustrated in FIG. 11, and an elemental composition of $C_{40}H_{35}N_6O_{15}$.

The invention further provides a method of protecting a plant against damage from albicidin that comprises applying an agent that blocks expression at least one gene in the Albicidin Biosynthetic Gene Clusters to the plant to be protected. Additional inventions include a method of obtaining agents useful in blocking expression of albicidin by screening materials against a modified host cell line that expresses the Albicidin Biosynthesis Gene Clusters and selecting for materials that stop or decrease albicidin production and a method of protecting a plant; against phytotoxic damage from an antibiotic that comprises inserting into the plant and operably expressing at least one resistance gene from the Albicidin Biosynthesis Gene Clusters into the plant to be protected.

EXAMPLE 1

Materials and Methods

Bacterial strains and plasmids. The source of bacterial strains and their relevant characteristics are described in Table 1.

Media, antibiotics, and culture conditions. *X. albilineans* strains were routinely cultured on modified Wilbrink=s (MW) medium at 30□C without benomyl (Rott et al., 1994). For long-term storage, highly turbid distilled water suspensions of *X. albilineans* were supplemented with glycerol to 15% (vol/vol) and frozen at B80□C. For *X. albilineans*, MW medium was supplemented with the following antibiotics as required at the concentrations indicated: kanamnycin, 10 or 25 μg/ml; and rifampicin, 50 μg/ml. *E. coli* strains were grown on Luria-Bertani (LB) agar or in LB broth at 37□C and were maintained and stored according to standard protocols (Sambrook et al., 1989). For *E. coli*, LB medium was supplemented with the following antibiotics as required at the concentrations indicated: kanamycin, 50 μg/ml; ampicillin, 50 μg/ml.

Bacterial conjugation. DNA transfer between *E. coli* donor (DH5_MCR/pAlb389 or pAC389.1, Table 1) and rifampicin-resistant *X. albilineans* recipients (X. strains AM10, AM12, AM13, AM36 and AM37, Table 1) was accomplished by triparental conjugation with plasmid pRK2073 as the helper as described previously (Rott et al., 1996).

Assay of albicidin production. Albicidin production was tested by a microbiological assay as described previously (Rott et al., 1996). Rifampicin and kanamycin exconjugants were spotted with sterile toothpicks (2-mm-diameter spots) onto plates of SPA medium (2% sucrose, 0.5% peptone, 1.5% agar) and incubated at 28° C. for 2-5 days. The plates were then overlaid with a mixture of *E. coli* DH5α ($10^7$ cells in 2 ml of distilled water) plus 2 ml of molten 1.5% (wt/vol) Noble agar (Difco) at ca. 65° C. and examined for inhibition zones after 24 h at 37 C.

Nucleic acid manipulations. Standard molecular techniques were used to manipulate DNA (Sambrook et al., 1989) except for total genomic DNA preparation. Total genomic DNA for southern blot hybridization was prepared as described by Gabriel and De Feyter (1992).

PCR Conditions. PCR amplifications were performed in an automated thermal cycler PTC-100™ (MJ Research, Inc). The 25 μl PCR reaction mix consisted of 100 ng of genomic DNA or 1 ng of plasmid DNA, 2.5 μl of 10×PCR buffer without MgCl2 (Eurobio), 80 μM dNTP mix, 2.5 units of EUROBIOTAQII® (Eurobio), 25 pmoles of each primer, 2.0 mM $MgCl_2$ (Eurobio) and sterilized distilled water to final volume. The PCR program was 95° C. for 2 min, 25 cycles at 94° C. for 1 min, Tm for 1 min and 72° C. for 1 min, with a final 72° C. extension for 5 min. Tm temperature was determined for each couple of primers and varied between 55° C. and 60° C. A 5 μl aliquot of each amplified product was analyzed by electrophoresis through a 1% agarose gel. For sequencing, PCR products were cloned with the pGEM®-T Easy Vector System (Promega).

Oligonucleotide synthesis. Oligonucleotides were purchased from Genome Express (Grenoble or Montreuil, France).

DNA sequencing. Automated DNA sequencing was carried out on double-stranded DNA by the dideoxynucleotide chain termination (Sanger et al., 1977) using a Dye Terminator Cycle Sequencing kit and an ABI Perkin-Elmer sequencer according to the manufacturer's procedure. Both DNA strands were sequenced with universal primers or with internal primers (20mers). This service was provided by Genome Express (Grenoble, France). Computer-aided sequence analyses were carried out using Sequence Navigator™ (Applied Biosystems, Inc) and SeqMan (DNASTAR Inc.) programs.

Sequence analysis. Nucleotide sequences were translated in all six reading frames using EditSeq (DNASTAR Inc.). Potential products of ORFs longer than 100 b were compared to protein databases by the PSI-BLAST program (Swiss-Prot and Genbank) on the NCBI with site (ncbi.nlm.nih.gov/) using Altschul program (Altschul et al., 1997). The TERMINATOR program of the Genetics Computer Group was used to identify putative Rho-independent transcription terminators.

Procedures

EXAMPLE 2

Sequencing of the Double Strand Region of 55,839 Bp from *X. albilineans* Containing XALB1 SEQ ID NO. 1

In FIG. 1 is presented a physical map and genetic organization of XALB1. In the figure, E and K are restriction endonuclease sites for EcoRI and KpnI respectively. Rectangular boxes represent DNA fragments labeled A through N. The numbers below each rectangular box are the number of Tn5-gus insertion sites previously located in each DNA fragment (Rott et al., 1996). The DNA inserts carried by plasmids pALB571 and pALB540 are represented by bold bars above the physical map. The location and direction of putative orfs identified in the XALB1 gene cluster are shown by arrows. Precise positions and proposed functions for individual orfs are summarized in Tables 2 and 3, respectively. Position of insertional sites of eight albicidin-defective mutants determined by sequencing are indicated by vertical arrows. The location and direction of putative ORFS identified in the XALB1 gene cluster are shown by arrow shapes. These twenty putative ORFs are potentially organized in four or five operons, as indicated at the bottom of the figure. Patterns indicate NRPS and PKS genes (diagonal crosshatch), methyl transferase and esterase genes (hollow rectangles), carbamoyl transferase gene (fine crosshatch), benzoate-derived products biosynthesis genes (white), regulatory genes (vertical lined), resistance genes (diagonal lines) and other genes with function of unknown significance to albicidin production (black), and three insertional sites of eight albicidin-defective mutants determined by sequencing are indicated by vertical arrows. Dotted regions in the physical map and in ORFs represent the two internal duplicated DNA regions of XALB1.

The sequence illustrated in FIG. 1 was generated as follows. The sources of DNA are set out in Table 1. DNA fragments F, E, B, C, I, and G, generated by the digestion of cosmid pALB571 (Rott et al., 1996) with EcoRI and/or KpnI, were subcloned into pBCKS (+) and were sequenced from the resulting subclones, pBC/F, pBC/E, pBC/B, pBC/C, pBC/I and pBC/G. DNA fragment D' which corresponds to the part of fragment D present in cosmid pALB571 was sequenced from plasmid pUFR043/D' obtained following self ligation of the complete EcoRI digested cosmid pALB571. DNA fragment H was sequenced from pAM45.1 (Rott et al., 1996), obtained following cloning into vector pBR325 of the 12 kb EcoRI fragment carrying Tn5 and flanking sequences from mutant strain XaAM45. DNA fragment A' contains the part of fragment A present in cosmid pALB571 and was subcloned into vector pBCKS (+) and the resulting plasmid pBC/A' was used for sequencing. The presence of a large internal duplication made alignment of sequence data obtained from pBC/A' difficult. This difficulty was resolved using sequence data obtained from an additional plasmid, pAM4, obtained following cloning into vector pBluescript II KS (+) of the 12 kb EcoRI fragment carrying Tn5 and flanking sequences from mutant strain XaAM4, which contains only one copy of the large internal duplication. Sequence data from pBC/A' were used to determine the first 1542 bp of fragment A' between nucleotides C-19001 and G-20543. Sequence data from pAM4 and pBC/A' were used to determine the last 4823 bp of fragment A' between nucleotides G-21653 and G-26477. The overlapping region between nucleotides G-20469 and C-22159 was amplified by PCR from cosmid pALB571 using primers contig13-1160 (5'gcgtaccgttgtccagtagg3') SEQ ID NO. 48 and pAM4-14 (5'gctggaaaccgagaatctga3') SEQ ID NO. 49, and was sequenced. Resulting sequence data were used to complete sequencing of DNA fragment A'. The junctions A/F, F/H, H/E, E/B, B/C, C/I, I/G, G/D between corresponding DNA fragments were sequenced directly from cosmid pALB571. EcoRI DNA fragment containing fragments A and F was subcloned from pALB540 into pBCKS (+), and the resulting plasmid pBC/AF was used to determine the part of DNA fragment A which was not present in cosmid pALB571 between nucleotides G-13682 and G-19001. EcoRI DNA fragments J, K, L, N were subcloned from pALB540 into pBCKS (+) and were sequenced from resulting plasmid pBC/J, pBC/K, pBC/L, and pBC/N. The junctions L/K, K/J and J/A between corresponding DNA fragments were sequenced directly from cosmid pALB540. DNA region between nucleotides G-7517 and T-8721 was amplified by PCR from cosmid pALB540 using primers E114 (5'gacacgatcagccgctagga3') SEQ ID NO. 50 and EI4-380 (5'accagcagttgggccagcct3') SEQ ID NO. 51 and was sequenced. Resulting sequence data were used to determine the sequence of fragment M and of junctions N/M and M/L.

The nucleotide sequence of 55,839 bp containing the entire major gene cluster involved in Albicidin production was sequenced on both strands.

EXAMPLE 3

Analysis of the Large Internal Duplications in the DNA Sequence of XALB1

The sequence of the 55,839 bp genomic region (SEQ ID NO. 1) contains two large internal duplications as shown by the dotted regions in the physical map of FIG. 1. A direct duplication of 1736 bp was located in DNA fragment A between nucleotides G-19904 and G-21639 and between nucleotides G-23057 and G-24792. Another direct duplication of a 2727 bp was found in DNA fragments B and C between nucleotides C-40410 and G-43136 and between nucleotides C-46644 and G-49370. Comparison of the two copies of each duplication revealed that the two copies of the 1736 bp duplication are identical except for one nucleotide at position 21058, and that the two copies of the 2727 bp duplication are 98.8% identical and differ by 30 nucleotides.

EXAMPLE 4

Comparison of XALB1 with the xabB EcoRI Fragment

Comparison of the DNA sequence of the 55,839 bp genomic region described in this study with the partial DNA sequence of 16,511 bp of the same region in Huang et al., 2001 (described by Huang et al. as an EcoRI fragment including full length xabB from *X. albilineans* strain Xa13 [GenBank accession No. AF239749]), revealed that the DNA sequence from strain Xa13 over 16,511 bp is identical to the sequence from strain Xa23R1, described herein, with the following exceptions: 1) five nucleotides are different at positions 42963, 42972, 42980, 43014 and 43071 of the XALB1 sequence, and 2) nucleotides from positions 43137 to 49370 are missing (internal to albI; refer FIG. 1). Analysis of genomic DNA of seven strains isolated from different countries (Australia, Reunion Island, Kenya, Zimbabwe and USA), digested by KpnI and hybridized with the pBC/C plasmid (Table 1) labeled with $^{32}P$, revealed that two DNA fragments corresponding to the XALB1 fragments B and C were present in all strains (data not shown). This result indicated that all studied strains contain albI and not xabB because in albI the pBC/C plasmid probe hybridizes with the large internal duplication present in both DNA fragments B and C (FIG. 1). Based on this observation we postulated that the DNA sequence of XabB reported as full length by Birch in PCT WO 02/24736 A1 (Their seq. ID#1) appears to be incomplete and missing 6,234 bp of DNA sequence encoding 2,078 amino acids.

EXAMPLE 5

Reading Frame Analysis in XALB1

Analysis of the 55,839 bp double strand region for coding sequences revealed the presence of 20 open reading frames (ORFs) designated albI to albXX (Table 2 below) which are distributed in four groups of genes according to their position and their orientation in the XALB1 cluster (FIG. 1). Genes of each group may form part of the same operon as judged by their overlapping stop and start codons, or by the relatively short intergenic region which varies from 5 to 274 nucleotides. The 20 ORFs appear to be organized in four operons: operon 1 formed by albI-albIV; operon 2 by albV-albIX; operon 3 by albX-albXVI; operon 4 by albXVII-albXX. The majority of alb ORFs are initiated with an ATG codon, except albI and albXVII which are initiated with a TTG codon, and albIV and albVI which are initiated with a GTG start codon. In seven ORFs of XALB1, start codons are preceded by the consensus sequence GAGG which may correspond to the ribosome binding site. Other ORFs are preceded by a less conserved sequence which contain at least three nucleotides A or G and which may serve as a weak ribosome binding site.

EXAMPLE 6

Sequencing of the Tn5 Insertional Site of Eight $Tox^-$ Mutants Previously Located in XALB1

Eight of the 45 *X. albilineans* $Tox^-$ mutants complemented by cosmid pALB540 and/or cosmid pALB571 and previously described (Rott et al., 1996) were further analyzed. All eight mutants contain a single Tn5 insertion and correspond to the following *X. albilineans* strains: XaAM7, XaAM15, XaAM45, and XaAM52 which are complemented by pALB571 but not by pALB540; XaAM4, XaAM29 and XaAM40 which are complemented by both cosmids; and XaAM1 which is complemented by pALB540 but not by pALB571. The Tn5 insertional site of each $Tox^-$ mutant was sequenced from plasmids obtained following cloning in pBR325 or in pBluescript II KS (+) of the EcoRI fragments carrying Tn5 and flanking sequence using the sequencing primer GUSN (5'tgeccacaggccgtcgagt3') SEQ ID No. 52 that annealed 135 bp downstream from the insertional sequence IS50L of Tn5-gusA. The sequence of the Tn5 insertional site was compared with the 55,839 bp sequence containing XALB1 in order to determine the alb gene disrupted in each $Tox^-$ mutant. albI is disrupted by the Tn5 insertion in XaAM15 and XaAM45 at position 33443 and 34229, respectively (FIG. 1). albIV is disrupted by the Tn5 insertion in XaAM7 and XaAM52 at position 53704 and 53915, respectively. albIX is disrupted by the Tn5 insertion in XaAM4, XaAM29 and XaAM40 at position 21653, 23444 and 24376, respectively. alb XI is disrupted by the Tn5 insertion in XaAM1 at position 13301. These results are in accordance with the previous characterization of $Tox^-$ mutants using Southern blot hybridization Rott et al., 1996), except for XaAM1. The Tn5-gusA insertion site of XaAM1 was previously located in DNA fragment A (Rott et al., 1996) but results of this study showed that this site is located in DNA fragment J (FIG. 1).

EXAMPLE 7

Homology Analysis of Proteins Potentially Encoded by XALB1

Preliminary functional assignments of individual ORFs were made by comparison of the deduced gene products with proteins of known functions in the Genbank database. The results are set out in Table 3 below. Among the ORFs identified from the sequenced XALB1 gene cluster, we found (i) four genes, albI SEQ ID No. 20, albIV SEQ ID No. 23, albVII SEQ ID No. 17 and albIX SEQ ID No. 15, encoding PKS and/or NRPS modules; (ii) one carbamoyl transferase gene, albXV SEQ ID No. 5; (iii) two esterase genes, albXI SEQ ID No. 9 and albXIII SEQ ID No. 7; (iv) two methyltransferase genes, albII SEQ ID No. 21 and albVI SEQ ID No. 18; (v) two benzoate-derived products biosynthesis genes, albXVII SEQ ID No. 11 and albXX SEQ ID No. 14; (vi) two putative albicidin biosynthesis regulatory genes, albIII SEQ ID No. 22 and alb VIII SEQ ID No. 16; (vii) two putative albicidin resistance genes, albXIV SEQ D No. 6 and albXIX SEQ ID No. 13; and (viii) two additional ORFs encoding proteins similar to transposition proteins, albV SEQ ID No. 19 and albXVI SEQ ID No. 4. No known function was found in the database for albX SEQ ID No. 10 and albXII SEQ ID No. 8. The potential product of albXVIII SEQ ID No. 12 appeared to be a truncation of an enzyme with strong similarity to 4-amino-4-deoxychorismate lyase and branched-chain amino acid aminotransferase. Since the gene encoding the predicted product is roughly half the length of other such lyase or aminotransferase genes, albXVIII may be the result of a recombination event and may be non functional.

EXAMPLE 8

The alb PKS and/or NRPS Genes

The potential product of albI, designated AlbI SEQ ID No. 20, is a protein of 6879 aa with a predicted size of 755.9 kDa. This protein is very similar to the potential product of the xabB gene from *X. albilineans* strain Xa13 from Australia (Huang et al., 2001), but it differs in length and size (See Table 4 below). XabB is a protein of 4801 amino acids with a predicted size of 525.7 kDa. Comparison of AlbI with XabB revealed that the N-terminal regions from Met-1 to Ile-4325 of both proteins are identical except for five amino-acids which are Tyr-3941, Pro-3952, Ala-4054, Ala-4271 and Gln-4284 in AlbI and His-3941, Ala-3952, Val-4054, Val-4271 and Glu-4284 in XabB. The same comparison revealed that the AlbI C-terminal region from Arg-6404 to the stop codon is 100% identical to the XabB C-terminal region from Arg-4326 to the stop codon.

Figure 2:
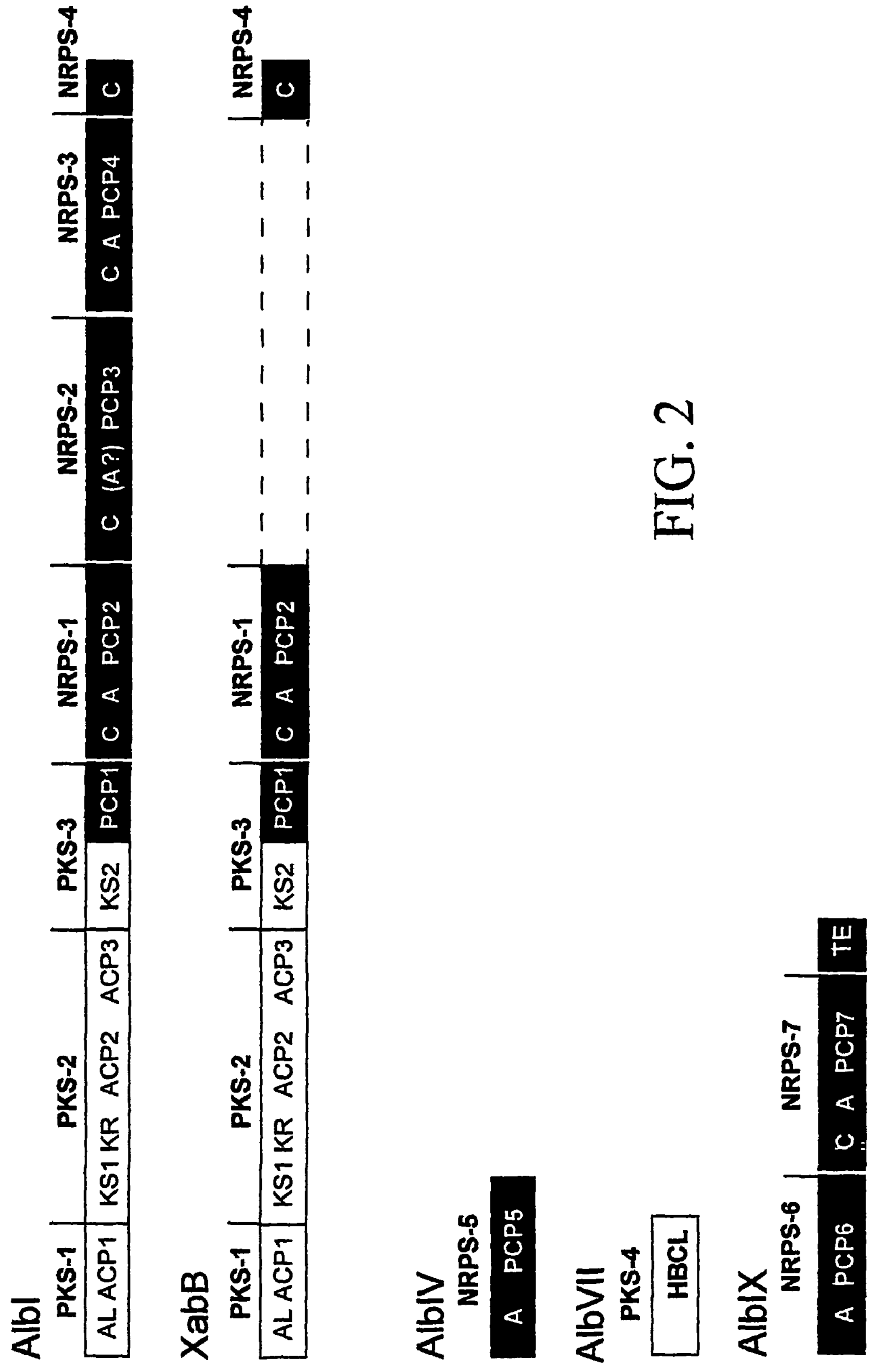
FIG. 2 is an illustration of the organization of the four PKS modules and the seven NRPS modules identified in cluster XALB1 and comparison with the organization of the prior art material XabB.

The N-terminal region (from Met-1 to Asp-3235) of AlbI is 100% identical to the corresponding region in XabB which was previously described as similar to many microbial modular PKS (Huang et al., 2001). This PKS region may be divided into three modules (FIG. 2). Abbreviations used in the Figure are: A, adenylation; ACP, acyl carrier protein; AL, acyl-CoA ligase; C, condensation; KR, β-ketoacyl reductase; KS, β-ketoacyl synthase; NRPS, nonribosomal peptide synthase; PCP, peptidyl carrier protein; PKS, polyketide synthase; TE, thioesterase; HBCL, 4-hydroxybenzoate-CoA ligase. The question mark in the NRPS-2 domain indicates that this A domain is incomplete. The first module designated PKS-1 contains acyl-CoA ligase (AL) and acyl carrier protein (ACP1) domains. The second module designated PKS-2 contains J-ketoacyl synthase (KS1) and β-ketoacyl reductase (KR) domains followed by two consecutive ACP domains (ACP2 and ACP3). The third module designated PKS-3 contains a KS domain (KS2) followed by a PCP domain (PCP1). Apart from their very high similarity with XabB, these three PKS modules exhibited the highest degree of overall similarity with polyketide synthases SafB and PksM from *Myxococcus xanthus* and *Bacillus subtilis*, respectively (Table 4). The motifs characteristic of these domains are 100% identical to those of XabB which were previously aligned with those from other organisms (Huang et al., 2001). The AL domain contains the conserved adenylation core sequence (SGSSG) and the ATPase motif (TGD). The three ACP domains contain a 4'-phosphopantetheinyl-binding cofactor box GxDS(IL), except that A replaced G in ACP1. Both KS domains contain motif GPxxxxxxxCSxSL around the active site Cys, and two His residues downstream from the active site Cys, in motifs characteristic of these enzymes. The KR domain contains the NAD(P)H-binding site GGxGxLG.

The PKS part of AlbI is linked by the PCP1 domain to the four apparent nonribosomal peptide synthase modules designated NRPS-1, NRPS-2, NRPS-3 and NRPS-4 (FIG. 2). NRPS-1, NRPS-2 and NRPS-3 modules display the ordered condensation, adenylation (A) and PCP domains typical of such enzymes (Marahiel et al., 1997), and NRPS-4 consists of an extra C domain which may correspond to an incomplete NRPS module. Known conserved sequences, characteristic of the domains commonly found in peptide synthases (Marahiel et al., 1997), were compared to those from NRPS-1, NRPS-2, NRPS-3 and NRPS-4 (Tables 5, 6 and 7). Sequences characteristic of C, A, or PCP domains are conserved in these four NRPS, except in A domain of NRPS-2 module, suggesting that this latter A domain may be not functional. Comparison of the four NRPS modules among themselves revealed that NRPS-2, NRPS-3 and NRPS-4 modules were 30.7%, 94.4% and 47.5% similar to NRPS-1 module, respectively. Comparison with XabB revealed NRPS-2 and NRPS-3 modules were not present in XabB which contains only NRPS-1 and NRPS-4 modules (FIG. 2). The dotted box in FIG. 2 corresponds to the apparent deletion of the NRPS-2 and NRPS-3 modules in XabB as compared to AlbI. Apart their very high similarity with XabB, Alb I NRPS modules exhibited the highest degree of overall similarity with non-ribosomal peptide synthases NosA and NosC from *Nostoc* sp.

albIV potentially encodes a protein of 941 aa (AlbIV) with a predicted size of 104.8 kDa. AlbIV is similar to several non-ribosomal peptide synthases such as the BA3 peptide synthase involved in bacitracin biosynthesis in *Bacillus licheniformis* (Table 4). AlbIV forms one NRPS module designated NRPS-5 that contains only an A domain and a PCP domain (FIG. 2). Sequences characteristic of the domains A and PCP commonly found in peptide synthases (Marahiel et al., 1997) are conserved in AlbIV (Tables 6 and 7). However the A domain present in AlbIV differs from A domains commonly found in peptide synthases: conserved sequences corresponding to cores A8 and A9 in AlbIV are separated by a very long peptide sequence of 390 amino-acids. This additional peptide sequence exhibits a significative similarity with the protein WbpG of 377 amino acids involved in the biosynthesis of a lipopolysaccharide in *Pseudomonas aeruginosa* (Table 4).

albVII potentially encodes a protein of 765 aa (AlbVII) with a predicted size of 83.0 kDa similar to the 4-hydroxybenzoate-CoA ligase from several bacteria and the closest protein (HbaA) was from *Rhodopseudomonas palustris* (Table 4). High similarity between AlbVII and HbaA suggests that AlbVII is a 4-hydroxybenzoate-CoA ligase and constitutes a fourth PKS module designed PKS-4. The size of HbaA is smaller (539 aa) and the similarity between the two proteins starts only at the residue 277 of AlbVII and at the residue 28 of HbaA. Comparison of AlbVII sequence located upstream from residue 277 produced no significant alignment AlbVII, like 4-hydroxybenzoate-CoA ligases, contains some conserved sequences characteristic of the A domain commonly found in peptide synthases (Table 6).

albIX encodes a protein of 1959 aa (AlbIX) with a predicted size of 218.4 kDa similar to non-ribosomal peptide synthases. Known conserved sequences, characteristic of the domains commonly found in peptide synthases (Marahiel et al., 1997), were compared with those from AlbIX which forms two NRPS modules designated NRPS-6 and NRPS-7 (Tables 5, 6 and 7). NRPS-6 contains only one A and one PCP domain. NRPS-7 contains the three domains characteristic of NRPS modules (A-C-PCP) followed by a TE domain (FIG.

2). Apart their very high similarity with XabB, NRPS-6 and NRPS-7 modules exhibited the highest degree of overall similarity and identity with non-ribosomal peptide synthases DhbF from *B. subtilis* and NosA from *Nostoc* sp. (Table 4).

EXAMPLE 9

The alb Carbamoyl Transferase Gene albXV potentially encodes a protein of 584 aa with a predicted size of 65.2 kDa. This protein, AlbXV, is similar to BlmD, a carbamoyl transferase involved in bleomycin biosynthesis in *Streptomyces vertillus* (Du et al., 2000), and to a probable carbamoyl transferase potentially expressed in *P. aeruginosa* (Table 4). High similarity of AlbXV with these proteins suggests that AlbXV is a carbamoyl transferase.

EXAMPLE 10

The alb Esterase Genes albXV potentially encodes a protein of 315 aa with a predicted size of 35.9 kDa. This protein, AlbXI, exhibits low similarity to SyrC, a putative thioesterase involved in syringomycin biosynthesis by *Pseudomonas syringae* (Zhang et al., 1995), and to a potential hydrolase encoded by *Streptomyces coelicolor* (Table 4). Precise function of SyrC remains unknown but SyrC is similar to a number of thioesterases, including fatty acid thioesterases, haloperoxidases, and acyltransferases that contain a characteristic GxCxG motif. The corresponding SyrC domain GICAG is conserved in AlbXI which contains the sequence GWCQA, except that A replaces the last G, suggesting that AlbXI may be an esterase despite its low overall similarity with SyrC.

albXIII potentially encodes a protein of 317 aa with a predicted size of 34.5 kDa. This protein, AlbXIII, is similar to hypothetical proteins with unknown function from several bacteria including *Caulobacter crescentus* (Table 4). AlbXIII and these hypothetical proteins contain a GxSxG motif characteristic of serine esterases and thioesterases, the corresponding sequence in AlbXIII being GHSVG. In addition, AlbXIII presents a similarity with the 2-acetyl-1-alkylglycerophosphocholine esterase which hydrolyzes the platelet-activating factor in *Canis familiaris* (Table 4), suggesting that AlbXIII is an esterase.

EXAMPLE 11

The alb Methyltransferase Genes albII potentially encodes a protein of 343 aa (AlbII) with a predicted size of 37.7 kDa. albII is 100% identical to the xabC cistron, previously described as encoding an O-methyltransferase downstream xabB (Huang et al., 2000a). This conclusion is based on the similarity of XabC with a family of methyltransferases that utilize S-adenosyl-L-methionine (SAM) as a co-substrate for O-methylation including TcmO protein from *Streptomyces glaucescens* (Huang et al., 2000a). AlbII contains three highly conserved motifs of SAM-dependent methyltransferases, including the motifI involved in SAM binding (FIG. 3). In the Figure, identical or similar amino acids (A=G; D=E; I=L=V) are shown in bold. Numbers indicate the position of the amino acid from the N-terminus of the protein. Abbreviations used in the Figure are: Sgl-TcmO (SEQ ID NOs: 55, 56 and 57) and Sgl-TcmN (SEQ ID NOs: 58, 59 and 60), multifunctional cyclase-hydratase-3-O-Mtase and tetracenomycin polyketide synthesis 8-O-Mtase of *Streptomyces glaucescens*, respectively (accession number: M80674); Smy-MdmC, midecamycin-O-Mtase of *Streptomyces mycarofaciens* (accession number: M93958) (SEQ ID NOs: 61, 62 and 63); Mxa-SafC, Saframycin O-Mtase of *Myxococcus xanthus* (accession number: U24657) (SEQ ID NO:s: 64, 65 and 66); Ser-EryG, erythromycin biosynthesis O-Mtase of *Saccharopolyspora erythraea* (accession number: S18533) (SEQ ID NOs: 67, 68 and 69); Spe-DauK, carminomycin 4-O-Mtase of *Streptomyces peucetius* (accession number: L13453) (SEQ ID NOs: 70, 71 and 72); Sal-DmpM, O-demethylpuromycin-O-Mtase of *Streptomyces alboniger* (accession number: M74560) (SEQ ID NOs: 73, 74 and 75); Shy-RapM, rapamycin O-Mtase of *Streptomyces hygroscopicus* (accession number: X86780) (SEQ ID NOs: 76, 77 and 78) ; Sav-AveD, avermectin B 5-O-Mtase of *Streptomyces avermitilis* (accession number: G5921167) (SEQ ID NOs: 79, 80 and 81), Sar-Cmet, mithramycin C-methyltransferase of *Streptomyces argillaceus* (accession number: AF077869) SEQ ID NOs: 82, 83 and 84); AlbII, putative albicidin biosynthesis C-Methyltransferase of *Xanthomonas albilineans* (SEQ ID No. 27); identical to XabC, accession number: AF239749) (SEQ ID NOs: 85, 86 and 87).

Comparison of AlbII with the Genbank database revealed that AlbII, besides 100% identity to XabC, exhibited the highest degree of overall identity with MtmMII, a C-methyltransferase from *Streptomyces argillaceus* (Table 4) involved in C-methylation of the polyketide chain for mithramycin biosynthesis, suggesting that AlbII is a C-methyltransferase. XabC was not compared by Birch and co-workers with MtmMII (Huang et al., 2000a) because the MtmMII sequence was not available until recently in the Genbank database. The three highly conserved motifs in SAM methyltransfererases are also present in MtmMII (FIG. 3), suggesting that AlbII is a C-methyltransferase SAM-dependent.

albVI potentially encodes a protein of 286 aa (AlbVI) with a predicted size of 32.1 kDa similar to several hypothetical protein from *Mycobacterium tuberculosis* (Genbank accessions No. AAK46042, AAK48238, AAK44517, AAK46218) and from *S. coelicolor* (Genbank accession No. CAC03631). AlbVI is also similar to the tetracenomycine C synthesis protein (TcmP) of *Pasteurella multocida* (Table 4). Four highly conserved motifs in TcmP and other O-methyltransferases are also present in AlbVI (FIG. 4), suggesting that AlbVI is an O-methyltransferase. In the Figure, identical or similar aa (A=G; D=E; I=L=V; K=R) are shown in bold. Numbers indicate the position of aa from the N-terminus of the protein. Abbreviations used in the Figure are: Sgl-tcmP, tetracenomycin C synthesis protein of *Streptomyces glaucescens* (accession number: C47127) (SEQ ID NOs: 88, 89, 90 and 91); Sme-PKS, putative polyketide synthase of *Sinorhizobium meliloti* (accession number: AAK65734) (SEQ ID NOs: 92, 93, 94 and 95); Pmu-tcmP: tetracenomycin C synthesis protein of *Pasteurella multocida* (accession number: AAK03406) (SEQ ID NOs: 96, 97, 98 and 99); Mtu-Omt: putative O-methyltransferase of *Mycobacterium tuberculosis* (accession number: AAK45444) (SEQ ID NOs: 100, 101, 102 and 103); Mlo-Hp: hypothetical protein containing similarity to O-methyltransferase of *Mesorhizobium loti* (accession number: BAB50127) (SEQ ID NOs: 104, 105, 106 and 107); Mtu-Hp: hypothetical protein of *Mycobacterium tuberculosis* (accession number: AAK46042) (SEQ ID NOs: 108, 109, 110 and 111); Mtu-Hp2: hypothetical protein of *Mycobacterium tuberculosis* (accession number: AAK48238) (SEQ ID NOs: 112, 113, 114 and 115); Mtu-Hp3: hypothetical protein of *Mycobacterium tuberculosis* (accession number: AAK44517)(SEQ ID NOs: 116, 117, 118 and 119);

Mtu-Hp4: hypothetical protein of *Mycobacterium tuberculosis* (accession number: AAK46218) (SEQ ID NOs: 120, 121, 122 and 123); Sco-Hp: hypothetical protein of *Streptomyces coelicolor* (accession number: CAC03631) (SEQ ID NOs: 124, 125, 126 and 127); AlbVI, putative albicidin biosynthesis O-Methyltransferase of *Xanthomonas albilineans* (this study) (SEQ ID NOs: 128, 129, 130 and 131).

EXAMPLE 12

The alb Derived-benzoate Products Biosynthesis Genes albXVII potentially encodes a protein of 716 aa with a predicted size of 79.8 kDa. This protein, AlbXVI, is very similar to the para-aminobenzoate (PABA) synthase from *Streptomyces griseus* (Table 4). This enzyme is required for the production of the antibiotic candicidin (Criado et al., 1993).

albXVII potentially encodes a protein of 137 aa with a predicted size of 15.0 kDa. This protein, AlbXIII, is similar to the 4-amino-4-deoxychorismate lyase (ADCL) from *P. aeruginosa* (Table 4). The function of ADCL is to convert 4-amino-4-deoxychorismate into PABA and pyruvate. The length of AlbXVIII is smaller (Table 4) than the length of ADCL and the similarity of AlbXVIII with this protein starts only at residue 161. albXVIII is preceded by a small ORF encoding a sequence of 59 amino acids similar to the first 42 amino acids of ADCL from *P. aeruginosa*. These data suggest that albXVIII is probably a truncated form of albXVIII and probably not functional. albXVIII may, therefore, not be involved in albicidin biosynthesis. The region between albXVII and albXVIII was amplified by PCR from total DNA of *X. albilineans* Xa23R1 strain using primers ORFW (5'gcgagaggacaagctgctgc3') SEQ ID No. 53 and ORFY (5'cgttgaggatgcagcgctcg31') SEQ ID No. 54 and was sequenced. Resulting sequence data showed that the sequence of the PCR fragment was 100% identical to the sequence of pALB540, indicating that the recombination of albXVIII did not occur during cloning of the genomic fragment in pALB540.

albXX potentially encodes a protein of 202 aa with a predicted size of 22.6 kDa. This protein AlbXX is similar to the 4-hydroxybenzoate synthase potentially involved in ubiquinone biosynthesis by *Escherichia coli* (Siebert et al., 1992).

EXAMPLE 13

The alb Regulatory Genes albIII potentially encodes a protein of 167 amino acids with a predicted size of 17.8 kDa that is similar to the transcription factors ComA of different bacteria such as *E. coli* and *B. licheniformis* (Table 4). ComA transcription factors appear to be involved in regulation of antibiotic production in bacteria. In *E. coli*, a gene similar to comA is present in the enterobactin biosynthesis gene cluster (Liu et al., 1989). In *B. subtilis*, ComAB was described as a probable positive activator of lichenysin synthetase transcription (Yakimov et al., 1998) and a gene similar to comA was shown to be essential for bacilysin biosynthesis (Yazgan et al., 2001). These data suggest that AlbIII regulates transcription of genes involved in albicidin biosynthesis.

albVIII potentially encodes a protein of 330 aa with a predicted size of 37.7 kDa. This protein, AlbVIII, is very similar to the SyrP like protein from *S. verticillus* and to SyrP protein from *P. syringae* (Table 4). SyrP participates in a phosphorylation cascade controlling syringomycin synthesis (Zhang et al., 1997) and the syrP like gene was described in the *S. verticillus* bleomycin biosynthetic gene cluster (Du et al., 2000). These data suggest that AlbVIII regulates albicidin biosynthesis in *X. albilineans*.

EXAMPLE 14

The alb Resistance Genes albXIV potentially encodes a protein of 496 aa with a predicted size of 52.7 kDa. This protein, AlbXIV, is 100% identical to AlbF isolated from *X. albilineans* strain Xa13 (GenBank Accession AF403709; direct submission by Bostock and Birch and described as "a putative albicidin efflux pump which confers resistance to albicidin in *E. coli*"). AlbXIV and AlbF are closely related to a family of transmembane transporters involved in antibiotic export and antibiotic resistance in many antibiotic-producing organisms. AlbXIV and AlbF exhibited the highest degree of overall identity with the putative transmembrane efflux protein from *S. coelicolor* (Table 4). These data suggest that AlbXIV and AlbF may be involved in albicidin resistance by transporting the toxin out of the bacterial cells that produce it. Alternatively, AlbXIV and AlbF may simply play a role in antibiotic secretion and/or plant pathogenesis to effect the transport of albicidin outside of producing cells.

albXIX potentially encodes a protein of 200 aa with a predicted size of 22.8 kDa. This protein, AlbXIX, is similar to the McbG protein from *E. coli* (Table 4). In *Enterobacteriae*, the McbG protein, together with two other proteins (McbE and McbF), was shown to cause immunity to the peptide antibiotic microcin B17 which inhibits DNA replication by induction of the SOS repair system (Garrido et al., 1988). McbE and McbF proteins serve as a pump for the export of the active antibiotic from the cytoplasm, whereas a McbG alone also provides some protection: a well-characterized deficient-immunity phenotype is exhibited by microcin B17-producing cells in the absence of the immunity gene mcbG (Garrido et al., 1988). The significant similarity between AlbXIX and McbG, together with the fact that albicidin also blocks DNA replication (Birch and Patil, 1985a) suggests that AlbXIX confers immunity against albicidin in *X. albilineans*.

EXAMPLE 15

Transposition Proteins albV is 100% identical to the thp gene described in a divergent position upstream from xabB (Huang et al., 2000a). The thp gene potentially encodes a protein of 239 aa displaying significant similarity to the IS21-like transposition helper proteins. In *X. albilineans* strain LS155 from Australia, insertional mutagenesis of thp blocked albicidin production, but trans-complementation failed, indicating the involvement in albicidin production of a downstream gene in the thp operon (Huang et al., 2000a).

albXVI potentially encodes a protein of 88 aa with a predicted size of 9.8 kDa similar to the transposases from several bacteria such as *Xanthomonas axonopodis* or *Desulfovibrio vulgaris* (Table 4).

The presence of transposition proteins in the XALB1 cluster is probably a remnant from a past transposition event that may have contributed to the development of the albicidin XALB1 cluster.

EXAMPLE 16

Unknown Functions

AlbX potentially encodes a protein of 83 aa with a predicted size of 9.4 kDa. This protein, AlbX, is similar to an hypothetical protein from *P. aeruginosa* and to the MbtH protein from *Mycobacterium tuberculosis*. MbtH is a protein with unknown function found in the mycobactin gene cluster (Quadri et al., 1998). A MbtH-like protein with unknown function was also described in the bleomycin biosynthetic gene cluster of *S. verticillus* (Du et al., 2000). These data suggest that AlbX is involved in albicidin biosynthesis but its function remains unknown.

albXII potentially encodes a protein of 451 aa with a predicted size of 51.6 kDa. This protein, AlbXII, is very similar to a protein of 55 kDa encoded by the boxB gene in *Azoarcus evansii* (Table 4). This protein is a component of a multicomponent enzyme system involved in the hydroxylation of benzoyl CoA, a step of aerobic benzoate metabolism in Azoarcus evansii, but its function remains unknown (Mohamed et al., 2001).

EXAMPLE 17

Prediction of Amino Acid Specificity of Alb NRPS Modules

In NRPSs, specificity is mainly controlled by A domains which select and load a particular amino-, hydroxy- or carboxy-acid unit (Marahiel et al., 1997). The substrate-binding pocket of the phenylalanine adenylation (A) domain of the gramicidin S synthetase (GrsA) from *Brevibacillus brevis* was recently identified by crystal structure analysis as a stretch of about 100 amino acid residues between highly conserved motifs A4 and A5 (Conti et al., 1997). Based on sequence analysis of known A domains, in relation to the crystal structure of the GrsA (Phe) substrate binding pocket, similar models have been published to predict the amino acid substrate which is recognized by an unknown NRPS A domain (Challis et al., 2000; Stachelhaus et al., 1999). These models postulate specificity-conferring codes for A domains of NRPS consisting of critical amino acid residues putatively involved in substrate specificity. The model proposed by Marahiel and co-workers (Stachelhaus et al., 1999) defined a signature sequence consisting of ten amino acids lining with the ten residues of the phenylalanine-specific binding pocket located at positions 235, 236, 239, 278, 299, 301, 322, 330, 331 and 517 in the GsrA (Phe) sequence (accession number: P14687). The model proposed by Townsend and co-workers (Challis et al., 2000) uses only the first eight of these critical residues.

Preliminary specificity assignments of albicidin synthase AlbI, AlbIV, AlbVII and AlbIX NRPS modules were made by comparison of complete sequences between conserved motifs A4 and A5 with sequences in the Genbank database. The corresponding sequence of the AlbIV NRPS-5 module is most related to domain 5 of bacitracin synthase 3 (BA3) from *B. licheniformis* that was suggested to activate Asn (Konz et al., 1997). Corresponding sequences of AlbI and AlbIX NRPS-1, NRPS-3, NRPS-6 and NRPS-7 modules, apart from their very high similarity with XabB, exhibited the highest degree of overall identity (39%) with the Blm NRPS2 module of the biosynthetic gene cluster for bleomycin from *S. verticillus* that specifies for β-Alanine (Du et al., 2000). The corresponding sequence of AlbVII PKS-4 produced the highest significant alignment with acetate-CoA ligase from *Sulfolobus solfataricus* (Genbank accession number: AAK41550), aryl-CoA ligase from *Comamnonas testosteroni* (Genbank accession number: AAC38458) and 4-hydroxybenzoate-CoA ligase from *R. palustris*. The sequence between motifs A4 and A5 of the AlbI NRPS-2 could not be significantly aligned with any sequence present in the Genbank database. Comparison of this sequence with the corresponding sequence of GrsA (Phe) revealed that parts of the putative core and structural "anchor" sequences of AlbI NRPS-2 are deleted (FIG. 5), suggesting that the AlbI NRPS-2 substrate binding pocket is not functional. In the Figure, amino acids of the six Alb NRPSs and of Alb PKS4 that are identical or similar to GrsA or Blm sequences (A=G; D=E; I=L=V; R=K) are shown in bold. Amino acids underlined in the GsrA sequence correspond to the phenylalanine-specific binding pocket. The positions of these amino acids in the GrsA primary sequence are indicated at the top of the figure. Amino acids underlined in the other sequences correspond to putative constituents of binding pockets, aligned with the seven residues of the phenylalanine-specific binding pocket of GrsA. Shaded amino-acids correspond to the putative core sequences and structural "anchors" based on comparison with the GrsA binding-pocket structure.

Alignment of the primary sequence between conserved motifs A4 and A5 of the AlbI, AlbIV, AlbVII and AlbIX NRPS-1, NRPS-3, NRPS-5, NRPS-6, NRPS-7 and PKS4 modules with the corresponding sequence of GrsA (Phe) (FIG. 5) revealed the putative constituents of binding pockets that constitute the codes as defined by Marahiel and co-workers (Stachelhaus et al., 1999). These codes were compared with those of proteins most related to the sequence between the A4 and A5 motifs (Table 8) and were analyzed with the model proposed by Townsend and co-workers (Challis et al., 2000, jhunix.hcfjhu.edu/~ravel/nrps//). Using these codes, we were able to predict the Asparagine specificity of the AlbIV NRPS-5 module. The AlbIV NRPS-5 signature is 100% identical to BacC-M5 (Asn) and TyrC-M1 (Asn) codes identified in bacitracin synthetase 3 from *B. licheniformis* and in tyrocidine synthetase 3 from *B. brevis* (Table 8). The AlbIV NRPS-5 signature is also identical to the Asn code defined by Marahiel and co-workers (1997), except that I is replaced by L at position 299 (Table 8). The AlbI and AlbIX NRPS-1, 3, 6 and 7 signatures did not match any of those defined by Marahiel and co-workers (1997). Similarly, convincing predictions using the model proposed by Townsend and co-workers were not obtained either (Challis et al., 2000, jhunix.hcfjhu.edu/~ravel/nrps//). The AlbI and AlbIX NRPS-1, 3, 6 and 7 signatures diverged from all NRPS signatures previously described, except from the XabB signature that is identical to the AlbI NRPS-1 and 3 signatures. The signature most closely related to AlbI NRPS-1 and 3 specify Pro and the signature most closely related to AlbIX NRPS-6 and 7 specify Ser, but the degree of similarity in both cases is very weak (Table 8). The PKS-4 signature is similar to the AlbI NRPS-1 and NRPS-3 signatures at positions 235, 299 and 301.

Analysis of alignment of the primary sequence between conserved motifs A4 and A5 of the AlbI and AlbIX NRPS-1, NRPS-3, NRPS-6 and NRPS-7 modules with the corresponding sequences of the bleomycin synthase (Blm) NRPS2 (β-Ala) and gramicidin S synthetase (GrsA) modules (FIG. 5) revealed that (i) sequences of AlbI NRPS-1 and AlbI NRPS-3 differ only at the level of two residues that are not involved in substrate binding, (ii) sequences of AlbIX NRPS-6 and AlbIX NRPS-7 are 100% identical, (iii) sequences of AlbI NRPS-1 and AlbI NRPS-3 are very similar to sequences of AlbIX NRPS-6 and AlbIX NRPS-7 but differ at the level of five putative constituents of binding pocket, (iv) AlbI and AlbIX NRPS residues, which are similar to residues of Blm NRPS2 (β-Ala) or GrsA (Phe), are essentially located at the level of the putative core sequences and structural "anchor", and differ at the level of putative constituents of the binding pocket.

Binding-pocket constituents forming the NRPS signatures have been classified into three subgroups according to their variability among 160 specificity-conferring signature sequences (Stachelhaus et al., 1999): (i) invariant residues Asp235 and Lys517 that mediate key interactions with the α-amino and α-carboxylate group of the substrate, respectively; (ii) moderately variant residues in positions 236, 301 and 330 which correspond to aliphatic amino acids and which may modulate the catalytic activity and fine-tune the specificity of the corresponding domains; (iii) highly variant residues in positions 239, 278, 299, 322 and 331 which may facilitate substrate specificity. AlbI and AlbIX NRPS-1, 3, 6 and 7 signatures are not totally in accordance with this classification. Invariant residue Lys517 is conserved in the four NRPS signatures, indicating the presence of an α-carboxylate group in the corresponding substrates. The Asp235Ala alteration is not consistent with an α-amino acid substrate. Birch and co-workers (Huang et al., 2001) assumed that the initial alanine residue in the XabB signature was consistent with a nonproteinogenic hydroxy acid substrate by analogy with the initial glycine in the signature of the hydroxyisovaleric-acid (HVCL) loading domain of enniatin synthetase. The presence of an initial Alanine in the AlbVII PKS-4 signature (FIG. 8) and in several 4-hydroxybenzoate-CoA ligase codes may confirm this hypothesis. However, the HVCL loading domain of enniatin synthetase (Table 8) and AlbVII PKS4 are not preceded by a C domain and are not followed by a PCP domain, in contrast to the AlbI and AlbIX NRPS-1, 3, 6 and 7 modules. An Asp235Val alteration was recently described in the β-Ala specificity-conferring code (Du et al., 2000, Table 8), suggesting that the substrate of AlbI and AlbIX NRPS-1, 3, 6 and 7 modules may be different from α-amino acids but may contain an amino group. Residue 236 is an aliphatic residue (Val or Ile) in all AlbI and AlbIX NRPS-1, 3, 6 and 7 signatures. Residue 301 is an aliphatic residue (Ala) in the AlbI NRPS-1 and 3 codes, but it is a Ser in the AlbIX NRPS-6 and 7 signatures. Residue 330 is not an aliphatic residue in the four NRPS signatures but an Asp. Similar alterations are present in the β-Ala code: residue 236 is an Asp, residue 301 is a Ser and residue 330 is an aliphatic amino acid. Concerning highly variable residues, AlbI NRPS-1 and 3 signatures differ from AlbIX NRPS-6 and 7 signatures at residue positions 299, 322 and 331, confirming that both types of NRPS modules specify different substrates.

Table 8: Comparison of signature sequences, as defined by Marahiel and co-workers (Stachelhaus et al., 1999), derived from sequences between the A4 and A5 domains of the AlbI, AlbIV, and AlbIX NRPS modules with those of Tyr-M1 (Pro) (Tyrocidine synthetase 2 module 1, accession number: AAC45929), VirS (Pro) (Virginiamycin S synthetase, accession number: CAA72310), HVCL (hydroxyisovaleric acid-CoA ligase, ACL1 enniatin synthetase, accession number: S39842), EntF-M1 (Ser) (Enterobactin synthase, accession number: AAA92015), β-Ala code (β-Ala selectivity-conferring code defined by Du et al., 2000), BacC-M5 (Asn) (Bacitracin synthetase 3, accession number: AAC06348), TyrC-M1 (Asn) (Tyrocidine synthetase 3, accession number: AAC45930) and Asn code (Asn selectivity-conferring code defined by Marahiel and co-workers (Stachelhaus et al., 1999). Amino acids of AlbI NRPS-1 and NRPS-3 signatures identical or similar to TyrB-M1 (Pro), VirS (Pro) and HVCL signatures (A=G; D=E; I=L=V; R=K) are shown in bold. Amino acids of AlbIX NRPS-6 and NRPS-7 signatures identical or similar to Vir (Pro) and Blm (&Ala) signatures (A=G; D=E; I=L=V; R=K) are shown in bold. Variability: 0 indicates invariant residues, +/−moderately variant residues and ++ highly variant residues.

EXAMPLE 18

Identification of Putative Promoters and Putative Terminators in XALB1

Putative rho independent terminators were identified downstream from albIV and albXVI using the Terminator program (Brendel and Trifonov, 1984), run with the Wisconsin Package™ GCG software (FIG. 6). In the Figure, dashes indicate palindromic sequences. Symbols used in the Figure are: P, Primary structure value of putative terminator (minimum threshold value of 3.5 represents 95 percent of known, factor-independent, prokaryotic terminators); S, Secondary structure value of putative terminator. The presence of these terminators confined the proposed genetic organization of operons 1 and 3. A rho-independent terminator was identified in the intergenic region between albXVII and albXVIII, suggesting that the group of genes initially supposed to be organized in operon 4 may be in fact organized in two operons, operon 4 formed by albXVII and operon 5 by albXVIII B albXX. No putative rho independent terminator was found downstream from albIX and from albXX.

The 236 bp region between albI (operon 1) and albV (operon 2) is 100% identical to the sequence between xabB and thp genes that is assumed to contain a bidirectional promoter (Huang et al., 2000a and 2001), suggesting that transcription of operon 1 and 2 is regulated by the same bidirectional promoter region (Huang et al., 2001).

The 412 bp region comprised between albX (operon 3) and albXVII (operon 4) also contains a putative bidirectional promoter (FIG. 7). In the Figure, the sequence of putative promoters are underlined, and putative ATG or TTG start codons are in bold. The closest matches (TTGACA-18x-TATAGT) to the consensus-35 (TTGACA) and -10 (TATAAT) sequences for *E. coli* $\sigma^{70}$ promoters occurs 61 bp upstream from albX (operon 3). The closest matches (TTCAGA-19x-TATACA) to the consensus sequences for *E. coli* $\sigma^{70}$ promoters occur 320 bp upstream from albXVII (operon 4). The region between albXVII and albXVIII lacks any apparent *E. coli* $\sigma^{70}$ promoter. However, the sequence immediately upstream from albXIX, corresponding to the coding sequence of albXVIII, potentially contains an unidirectional promoter (FIG. 7). The closest match (TTGCTC-19x-TATATT) to the consensus sequences for *E. coli* $\sigma^{70}$ promoters occurs 33 bp upstream from albX. The presence of a terminator downstream from albXVII and of a promoter upstream from albXIX suggests that albXVIII is not transcribed and that albXIX and albXX form operon 5.

EXAMPLE 19

Cloning of the XALB2 Gene Cluster

The 6 kb EcoR I fragment carrying Tn5 and flanking sequence from strain AM37 was cloned in pBR325 and the obtained plasmid was designated pAM37 (Table 1). A 1.1 kb Hind III-Hind III DNA fragment from pAM37, named PR37 (Table 1), was labeled with $^{32}P$ and used to probe the 845 clones from the genomic library of *X. albilineans* strain Xa23R1, previously described (Rott et al., 1996). Eight new cosmids hybridized to this probe and restored albicidin production in mutant AM37. One of these cosmid, pALB389, carrying an insert of about 37 kb (Table 1), was used for complementation studies of the five mutants not complemented by pALB540 and pALB571. Cosmid pALB389 complemented mutants AM10 and AM37. Mutant AM10 was initially thought to be complemented by pALB639 (Rott et al., 1996). However, further complementation studies showed that mutant AM10 was not complemented by pALB639 and that only three mutants (AM12, AM13 and AM36) were complemented by pALB639 containing the third genomic region XALB3 involved in albicidin production. A 3 kb EcoRI-EcoRI DNA fragment from pALB389 that hybridized with probe PR37 was sub-cloned in pUFR043 (Table 1). The resulting plasmid pAC389.1 complemented mutants AM10 and AM37, confirming that the second region involved in albicidin production, XALB2, was present in the 3 kb insert of pAC389.1.

EXAMPLE 20

Cloning of the XALB3 Gene Cluster

Cosmid pALB639, carrying an insert of 36 kb (Rott et al., 1996; Table 1) was used as a probe to compare the EcoRI restriction profiles of *X. albilineans* strain Xa23R1 with those of mutants AM12, AM13 and AM36 which were supposed to be mutated in the XALB3 gene cluster. An 11 kb band which was found in strain Xa23R1 but not in the three mutants was supposed to contain the XALB3 gene cluster. A 9.7 kb EcoRI DNA fragment purified from cosmid pALB639 also used as a probe in Southern blot analyse revealed the same 11 kb band. This 9.7 kb EcoRI DNA fragment was sub-cloned in pUFR043 (Table 1) and the resulting plasmid pAlb639A complemented mutants AM12, AM13 and AM36. The third region involved in albicidin production, XALB3, was therefore present in the 9.7 kb insert of pAlb639A.

EXAMPLE 21

Sequencing of the Tn5 Insertional Site of tox' Mutants Located in XALB2 and XALB3 and Sequencing of the Genomic Regions XALB2 and XALB3

Figure 8:
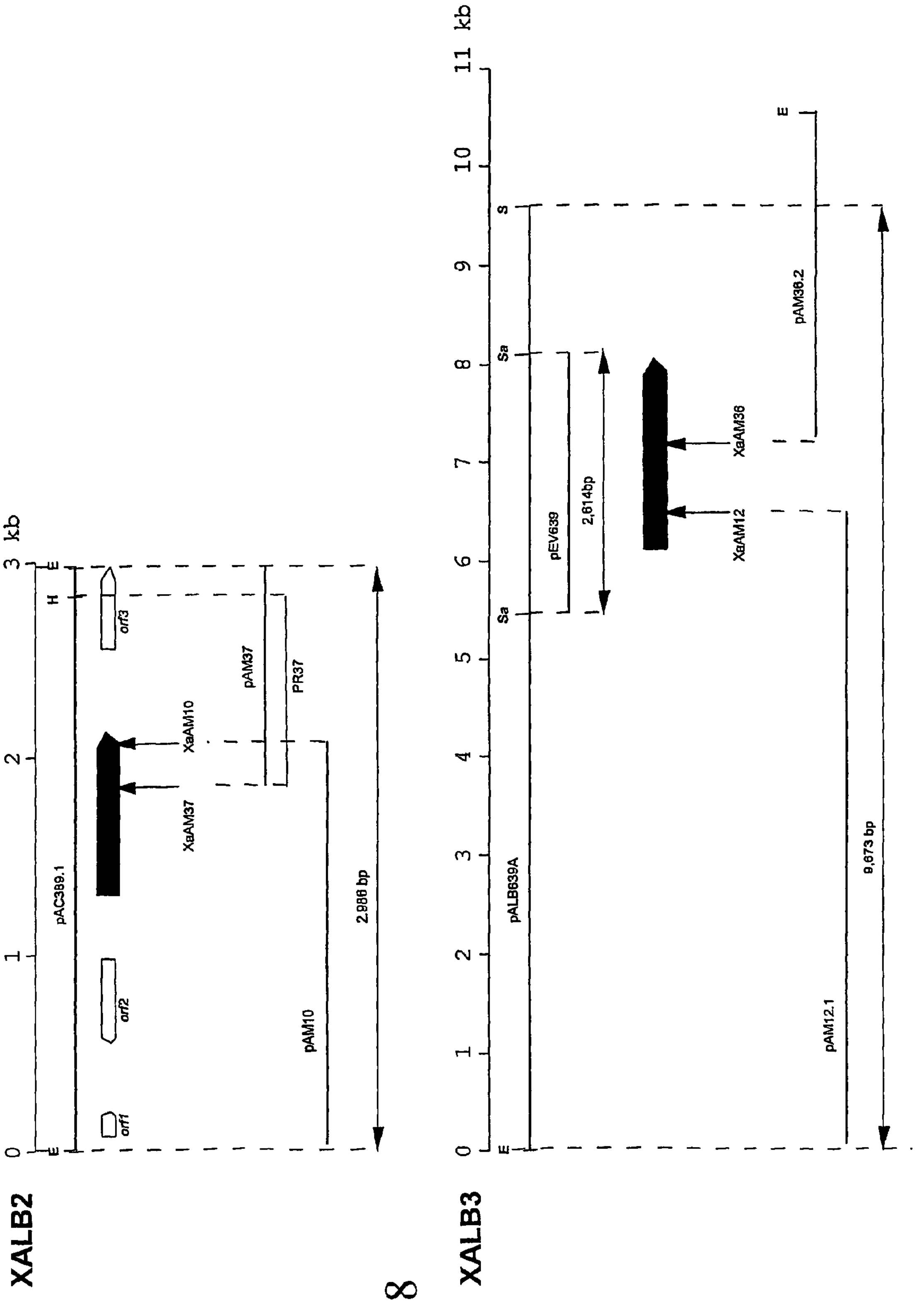
FIG. 8 is a physical map and genetic organization of the DNA region containing the gene clusters XALB2 and XALB3 involved in albicidin production.

In FIG. 8, E, H, Sa and S indicate restriction endonuclease cut sites for EcoRI, HindIII, SalI and Sau3AI, respectively. The DNA inserts carried by plasmids pAC389.1, pALB639A or pEV639 are represented by the bars at the top of the respective figures. Positions of the Tn5 insertional sites of mutants AM10, AM12, AM36 and AM37 were determined by sequencing and are indicated by vertical arrows. The DNA region corresponding to the Tn5 flanking regions in pAM10, pAM12.1, pAM36.2 and pAM37 and in the PR37 DNA fragment are represented by the bars at the bottom of the respective figures. The location and direction of albXXI and albXXII are indicated by thick black arrows. The location of other orfs in XALB2 similar to those described by Huang et al. (2000b) are indicated by thick white arrows.

The 7 kb EcoR I fragment carrying Tn5 and flanking sequence from strain AM10 was cloned in pBluescript II KS (+), and the obtained plasmid was designated pAM10 (Table 1). The sequences between EcoRI sites and the Tn5 insertional site of mutants AM10 and AM37 were sequenced from the resulting plasmids pAM10 and pAM37, respectively. The complete double-strand nucleotide sequence of the 2,986 bp EcoR I B EcoR I insert of pAC389.1 was determined from sequencing results of plasmids pAC389.1, pAM10 and pAM37 (FIG. 8). The Tn5 insertional sites of mutants AM10 and AM37 were sequenced from plasmids pAM10 and pAM37 (Table 1), respectively, using the sequencing primer GUSN (5'tgcccacaggccgtcgagt3') that annealed 135 bp downstream from the insertional sequence IS50L of Tn5-gusA. The Tn5 insertional site of AM10 and AM37 was located at position 2107 and 1882, respectively.

The EcoRI fragments carrying Tn5 and the flanking sequences from mutants AM12 and AM36 were cloned in pBR325 (Rott et al., 1996; Table 1). The sequences between EcoRI site and the Tn5 insertional site of mutants AM12 and AM36 were sequenced from the resulting plasmids pAM12.1 and pAM36.2, respectively. The complete double-strand nucleotide sequence of the 9,673 bp EcoR I B Sau3A I insert of pALB639A was determined from the sequencing results of plasmids pAM12.1, pAM36.2 and pALB639A (FIG. 8). The Tn5 insertional site of mutants AM12 and AM36 was sequenced from plasmids pAM12.1, pAM36.2 using the sequencing primer GUSN (5'tgcccacaggccgtcgagt3') that annealed 135 bp downstream from the insertional sequence IS50L of Tn5-gusA. The Tn5 insertional site of AM12 and AM36 was located at position 6500 and 7232, respectively (FIG. 8).

EXAMPLE 22

Homology Analysis and Genetic Organization of XALB2 (FIG. 8)

The sequence of 2986 bp containing XALB2 is 99.4% identical to the sequence of 2989 bp containing xabA described in *X. albilineans* strain LS155 from Australia (Huang et al., 2000b; accession number AF191324). The Tn5 insertional site of mutant LS156 described in xabA is 15 bp upstream from the insertional site of AM37. The orf disrupted in AM37 and AM10, designed albXXI, is identical to xabA except a C which replaces a T at position 1642. albXXI potentially encodes a protein of 278 aa with a predicted size of 29.3 kDa which is 100% identical to the potential product of xabA, described as a phosphopantetheinyl transferase (Huang et al., 2000b). Region XALB2 contains three additional orfs (orf1, orf2, and orf3) similar to those described by Huang et al., (2000b; orf, rsp6 and aspT). orf2 and orf3 are 100% identical to rsp6 and aspT respectively, and orf1 is similar to but smaller than orf. There are no close matches to the *E. coli* γ70 promoter B10 (TATAAT) and B35 (TTGACA) consensus sequence, and no putative RBS site upstream from the putative start codon ATG of albXXI. The putative factor-independent transcription site described at 42 bp downstream from the TGA stop codon of xabA (Huang et al., 2000b) is also present at the same position downstream from albXXI.

EXAMPLE 23

Homology Analysis and Genetic Organization of XALB3 (FIG. 8)

The orf disrupted in mutants AM12 and AM36 was located between nucleotide 6090 (ATG) and 8009 (TAA) and was designed albXXII. The first ATG at position 6090 is not preceded by a putative ribosome binding sequence, suggesting that the start codon is the ATG at position 6105 which is preceded at position B9 by the putative ribosome binding site sequence GGAG. A putative rho independent terminator was identified at position 8082, 73 b downstream from albXXII (FIG. 6). There are no close matches to *E. coli* $\sigma^{70}$ promoter B10 (TATAAT) and B35 (TTGACA) consensus sequence upstream from the putative start codon. The SalI DNA fragment corresponding to DNA sequence from nucleotide 5510 to nucleotide 8124, which contains the 595 bp upstream from the putative start codon, the orf albXXII and the putative rho independent terminator, was sub-cloned in pUFR043 in the opposite direction to LacZ (Table 1). The resulting plasmid pEV639 (Table 1) complemented mutants AM12, AM13 and AM36, confirming that (i) the third region involved in albicidin production, XALB3, was present in the insert of pEV639; (ii) albXXII is not transcribed as part of a larger operon; and (iii) the 595 bp upstream the putative start codon contain a promoter.

The potential product of albXXII, designated AlbXXII, is a protein of 634 aa with a predicted size of 71.5 kDa. This protein is very similar to the heat shock protein HtpG from *Pseudomonas aeruginosa* (identities=82%) and from *Escherichia coli* (identities=60%) (Table 4). The methionine encoded by the putative start codon at position 6105 was aligned with the first aminoacid of the heat shock protein HtpG from *Pseudomonas aeruginosa*, confirming that albXXII initiates at position 6105.

Complementation of $Tox^-$ Mutants with the albXXII Gene in Fusion with LacZ

A 1,948 bp fragment corresponding to the entire 1,903 bp orf of albXXII and flanking nucleotides was PCR amplified from cosmid pALB639 with the forward primer 5'tttgaattcgcacctaccgatgagcgtgg3' and the reverse primer 5'tttggatccgtgcgtcactgcttacgccg3'. Convenient in frame-EcoRI and BamHI restriction sites for further cloning were simultaneously introduced with forward and reverse PCR primers, respectively. The PCR fragment was cloned into pGEMT vector (Promega) and sequenced. Several clones of the resulting plasmid pGemT/albXXII were sequenced. Because several PCR derived point mutations were observed in all the sequenced clones, a 1,920 bp BglII-SalI fragment from pEV639 (corresponding to the 1,809 5' terminal nucleotides of albXXII orf plus 111 bp downstream the stop codon) was cloned into a pGemT/albXXII clone between the BglII site located at position 94 of the albXXII orf and the SalI site of the vector's multiple cloning site. The resulting plasmid pGemT/albXXIIbis contained an intact albXXII orf that was then subcloned as an EcoRI-SalI fragment into pUFR043 to generate pEValbXXII. This construct of albXXII in fusion with LacZ was transferred by triparental conjugation into Xa23RI insertion mutants. pEValbXXII complemented mutants AM12, AM13 and AM36 (see table 9). These results confirmed that (i) the third region involved in albicidin production, XALB3, was present in the insert of pEValbXXII; and (ii) albXXII is not transcribed as a part of a larger operon.

Complementation of $Tox^-$ Mutants with the htpG Gene from *E. coli*

A 2,343 bp fragment corresponding to the htpG gene of *E. coli* plus 458 bp downstream the stop codon was PCR amplified from purified DH5α genomic DNA with forward primer 5'tttgaattccatgaaaggacaagaaactcgtgg3' and reverse primer 5'gcctgcggaatggtacgcgggaagccgtcc3'. A convenient in frame-EcoRI restriction site was introduced with the forward PCR primer. The PCR fragment was cloned using the pGEMT vector system (Promega). Three resulting clones potentially containing plasmid pGemT/HtpG were sequenced, and one clone containing the correct sequence was selected. The 2,343 bp PCR insert was then subcloned as an EcoRI-SalI fragment into pUFR043 to generate pEVHtpG, the SalI site corresponding to the site of the vector's multiple cloning site. This HtpG gene, in fusion with the LacZ construct, was able to restore albicidin production after transfer by triparental conjugation into AM12, AM13 and AM36 Xa23RI mutants. This result is i/ further evidence of the involvement of a molecular chaperone HtpG in the biosynthesis of albicidin (table 9), ii/ the first report of the requirement of a molecular chaperone HtpG in NRPS and PKS metabolism.

EXAMPLE 24

Heterologous Production of Albicidin in Fast Growing *Xanthomonas axonopodis* pv. *Vesicatoria*

This example illustrates the construction of a heterologous expression system harboring the three XALB regions, its transfer into a fast growing host, *Xanthomonas axonopodis* pv. *vesicatoria* and the subsequent production of a potent toxin with an antibiotic activity similar to that of albicidin. This work is a milestone in the validation of the albicidin biosynthesis model because it gives experimental evidence that the entire biosynthetic machinery required for albicidin biosynthesis has been identified, cloned, sequenced and transferred into an heterologous host, driving the production of albicidin. Cosmid pALB571 which covers the complete sequences of operons 1 and 2 was used to transfer operons 1 and 2 (FIG. 1). Operons 3 and 4 (from pALB540), XALB2 (from pAC389.1) and XALB3 (from pEV639) were subcloned into a single plasmid, pOp3-4/XALB2-3 (see below). Plasmid pOp3-4/XALB2-3 derived from shuttle vector pLAFR3 that carries one selective gene for resistance to tetracyclin and that belongs to incompatibility group IncP (Table 1). Cosmid pALB571 derived from shuttle vector pUFR043 that carries two selective genes for resistance to kanamycine and gentamycine and that belongs to incompatibility group IncW (Table 1).

Figure 12:
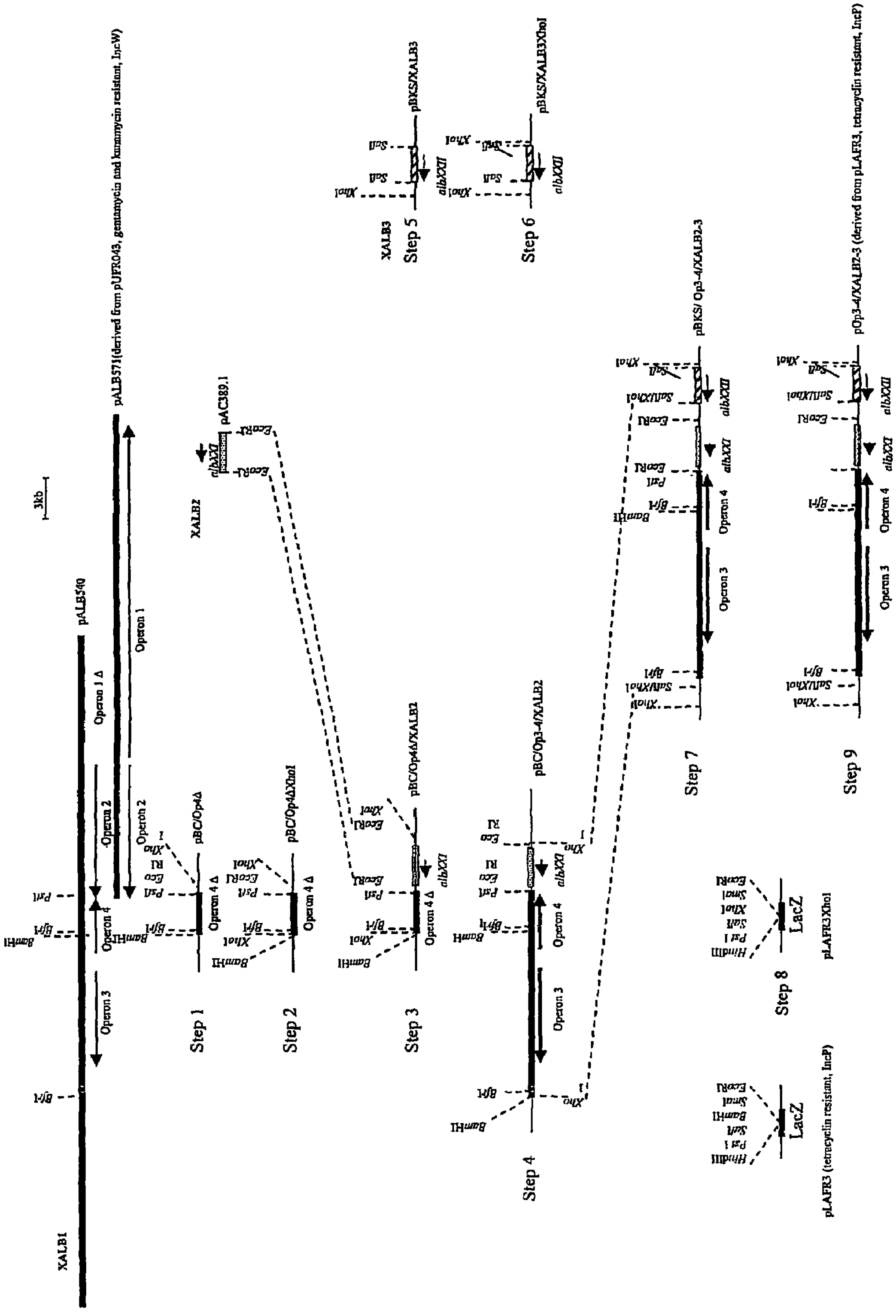
FIG. 12 illustrates subcloning of operons 3 and 4 (from pALB540), XALB2 (from pAC389.1) and XALB3 (from pEV639) into a single plasmid, pOp3-4/XALB2-3. A BamHI-PstI fragment from pALB540, corresponding to a portion of operon 4, was subcloned into pBCKS(+), yielding pBC/Op4D (step 1). A XhoI site was introduced into this vector immediately upstream from the BfrI site by directed mutagenesis, yielding pBC/Op4DXhoI (step 2). The EcoRI fragment from pAC389.1 (XALB2) was then subcloned into pBC/Op4DXhoI, yielding pBC/Op4D/XALB2 (step 3). A BfrI fragment from pALB540 containing complete operon 3 and the beginning of operon 4 was subcloned into pBC/Op4D/XALB2, yielding pBC/Op3-4/XALB2 (step 4). The SalI fragment from pEV639 (XALB3) was subcloned into pBKS, yielding pBKS/XALB3 (step 5). The SalI site located on the KpnI side of the polylinker was then destroyed and substituted by a XhoI restriction site, yielding pBKS/XALB3XhoI (step 6). Finally, the XhoI cassette of pBC/Op3-4/XALB2 was subcloned into the SalI restriction site of pBKS/XALB3XhoI, yielding pBKS/Op3-4/XALB2-3 (step 7). An XhoI site was added to the BamHI site of pLAFR3, yielding pLAFR3XhoI (step 8). The XhoI cassette from pBKS/Op3-4/XALB2-3 was then cloned into pLAFR3XhoI, yielding pOp3-4/XALB2-3 (step 9).

Sub-cloning of Operons 3 and 4 and XALB2 and XALB3 Regions into a Single Plasmid (FIG. 12).

A 2,787 bp BamHI-PstI fragment from pALB540, corresponding to a portion of operon 4, was subcloned into pBCKS (+), yielding pBC/Op4Δ (step 1). A XhoI site was introduced into this vector immediately upstream from the BfrI site by directed mutagenesis. Mutagenesis was performed with primers XhoIAlb anticodant 5'cgccttaagcagctcgagtagactgcaatc3' and XhoIAlbcodant 5'gattgcagtctactcgagctgcttaaggcg3' and yielded plasmid pBC/Op4ΔXhoI (step 2). The 2,986 bp EcoRI fragment from pAC389.1 (containing XALB2) was then subcloned into pBC/Op4ΔXhoI, yielding pBC/Op4Δ/XALB2 (step 3). A 10,762 bp BfrI fragment from pALB540 and containing complete operon 3 and the beginning of operon 4 was subcloned into pBC/Op4Δ/XALB2 yielding pBC/Op3-4/XALB2 (step 4). The 2,615 bp SalI fragment from pEV639 (containing XALB3) was subcloned into pBKS, yielding pBKS/XALB3 (step 5). The SalI site located on the KpnI side of the polylinker was then destroyed and substituted by a XhoI restriction site by directed mutagenesis. This mutagenesis was performed with primers XhoSalXaHTPGR 5'gcttatcgataccctcgaggaaggcgatatcg3' and XhoSalXaHTlPGF 5'cgatatcgccttcctcgagggtategataagc3', yielding pBKS/XALB3XhoI (step 6). Finally, the XhoI cassette of pBC/Op3-4/XALB2 was subcloned into the SalI restriction site of pBKS/XALB3XhoI, yielding pBKS/Op3-4/XALB2-3 (step 7). This construct harbours an XhoI cassette containing complete operons 3 and 4 from XALB1, albXXI from XALB2 and albXXII from XALB3. An XhoI site was added to the BamHI site of the pLAFR3 shuttle vector polylinker using the adaptor AdApTBamHIXhoI 5'gatcgctcgagc3', yielding pLAFR3XhoI (step 8). The XhoI cassette from pBKS/Op34/XALB2-3 was then cloned into pLAFR3XhoI yielding pOp3-4/XALB2-3 (step 9). This last construct was used, along with pALB571 (operons 1 and 2), for heterologous expression of albicidin in *X. axonopodis* pv. *vesicatoria.*

Albicidin Production Assays

The four combinations of plasmids (i.e. pUFR043-pLAFR3, pUFR043-pOp34/XALB2-3, pAlb571-pLAFR3 and pAlb571-pOp3A4XALB2-3) were transferred into *X. axonopodis* pv. *vesicatoria* strain Xcv 91-11BR1 by triparental mating. Exconjugant clones resistant to tetracycline and kanamycin were isolated. Assays for albicidin production were performed with these exconjugants clones using the same method described in Example 1 except that tetracycline (12 mg/ml) and/or kanamycin (50 mg/ml) were added to SPA medium. Tetracycline and kanamycin resistant *E. coli* clones, DH5αKT and DH5αAlb$^r$KT (Table 1), were used as tester strains to evaluate albicidin production to ensure that growth inhibition was not due to the presence of these two antibiotics in SPA medium. Both clones, DH5αKT and DH5αAlb$^r$KT, are tetracycline and kanamycin resistant because they carry plasmids pLAFR3 and pUFR043. The albicidin resistant DH5αAlb$^r$KT clone derived from strain DH5αAlb$^r$ (Table 1) which is a spontaneous albicidin resistant clone isolated in a growth inhibition zone produced by *X. albilineans* strain Xa23R1.

Without antibiotics in the SPA medium, growth of clones DH5αKT and DH5αAlb$^r$KT was not inhibited in all assays performed with the different *X. axonopodis* pv. *vesicatoria* exconjugants. Surprisingly, when kanamycin was present in the SPA medium, growth of both DH5αKT and DH5αAlb$^r$KT was inhibited in all assays performed with the *X. axonopodis* pv. *vesicatoria* exconjugants. These results suggested that, in the presence of kanamycin, all *X. axonopodis* pv. *vesicatoria* exconjugants produced an antibiotic inhibiting growth of *E. coli*. Because exconjugants containing only empty vectors (pUF043 and pLAFR3) induced inhibition of *E. coli*, this antibiotic did not result from the expression of XALB1, XALB2 and/or XALB3. Additionally, there was no cross resistance between this antibiotic and albicidin. When tetracyclin was present in the bioassay medium, but not kanamycin, growth of the albicidin resistant clone (DH5αAlb$^r$KT) was not inhibited by any of the exconjugants. In contrast, growth of the albicidin susceptible *E. coli* strain (DH5αKT) was inhibited by the exconjugants harbouring pALB571 and pOp34/XALB2-3 plasmids, but not by exconjugants harbouring the other three combinations of plasmids (Table 10). This result suggested that expression of the XALB1, XALB2 and XALB3 regions in *X. axonopodis* pv. *vesicatoria* (harbouring pALB571 and pOp34/XALB2-3 plasmids) led to the production of an albicidin-like antibiotic. This product inhibited growth of an albicidin sensitive *E. coli* (DH5αKT) and had no effect on the growth of an albicidin resistant clone (DH5αAlb$^r$KT).

Preliminary results indicated that pLAFR3 derived plasmids were relatively unstable in the absence of tetracycline in the culture medium, suggesting that genes carried by pOp3-4×ALB2-3 were not expressed when *X. axonopodis* pv. *vesicatoria* exconjugants pALB571/pOp34/XALB2-3 were grown without tetracycline. Consequently, these exconjugants did not produce the albicidin-like compound in absence of any antibiotic in the culture medium (Table 10). Preliminary results also indicated that pUFR043 derived plasmids are relatively stable in *X. axonopodis* pv. *vesicatoria* in absence of antibiotic selection, suggesting that genes carried by pALB571 are expressed when *X. axonopodis* pv. *vesicatoria* exconjugants pALB571/pOp34/XALB2-3 were grown on media without kanamycin. Consequently, these exconjugants produced the albicidin-like compound on SPA containing only tetracyclin.

Two *E. coli* DH5αKT clones, that spontaneously grew within the growth inhibition zone of a *X. axonopodis* pv. *vesicatoria* pALB571-pOp3-4/XALB2-3 exconjugant on SPA+tetracycline medium, were isolated and tested for resistance to albicidin. No growth inhibition was observed when these clones were used as tester strains in an albicidin production assay performed with *X. albilineans* Xa23R1. These results showed that cross-resistance occurs between the albicidin-like product of *X. axonopodis* pv. *vesicatoria* and albicidin produced by *X. albilineans*, suggesting that both molecules are similar. Comparison of chemical characteristics of the two molecules will, however, be necessary to confirm that the two molecules are identical.

The invention includes the isolation and sequencing of a region of 55,839 bp from *X. albilineans* strain Xa23R1 containing the major gene cluster XALB1 involved in albicidin production. Analysis of this region allowed us to predict the genetic organization of the gene cluster XALB1 which contains 20 ORFs grouped in four or five operons (FIG. 1). Because albXVII is a truncated gene, XALB1 genes may be organized in five operons. Therefore, we will from now on consider albXVII as part of operon 4 and albXIX and albXX as part of operon 5. Similar operon-type organizations for antibiotic biosynthesis clusters are well known and have been postulated to facilitate cotranslation of genes within the operon to yield equimolar amounts of proteins for optimal interactions to form the biosynthesis complexes (Cane, 1997). Overlapping genes involved in the same process are also quite common in bacteria (Normark et al., 1983).

Previous results of transposon mutagenesis and complementation studies (Rott et al., 1996; Rott, unpublished results) are in accordance with the predicted genetic organization of XALB 1 described in this study, and allowed us to establish that operons 1, 2 and 3 are involved in albicidin biosynthesis: (I) Tox$^-$ mutants with a Tn5-gusA insertion site located in DNA fragments B, C, G and D were complemented by cosmid pALB571 and not by cosmid pALB540, confining that cosmid pALB571 potentially contains the entire operon 1; (ii) Tox$^-$ mutants with a Tn5-gusA insertion site located in DNA fragments A and H were complemented by both cosmids pALB540 and pALB571, confirming that both cosmids potentially contain the entire operon 2; (iii) mutant XaAM1 with a Tn5-gusA insertion site located in DNA fragment J is the only Tn5 Tox$^-$ mutant complemented by cosmid pALB540 and not by cosmid pALB571, confirming that cosmid pALB540 potentially contains the entire operon 3. Our mutagenesis studies did not confirm that operons 4 and 5 are required for biosynthesis of albicidin. The para-aminobenzoate (PABA) is required for the growth of many bacteria probably including *X. albilineans*, suggesting that a mutation in albXVII may be lethal and explaining why we did not obtain any mutant disrupted in this gene.

Putative bidirectional promoters were identified between operons 1 and 2 (Huang et al., 2001) and between 3 and 4 (FIG. 7), confirming the prediction of genetic organization of XALB1. The region upstream from operon 1 is 100% identical to the region upstream from the xabB start codon which was described as a functional promoter during the phase of albicidin accumulation in Australian strain Xa13 of *X. albilineans* (Huang et al., 2001). Involvement of several operons in albicidin biosynthesis suppose that they are transcribed during the same time. Promoter activities of regions upstream from putative operons 2, 3, 4 and 5 need to be determined to precise if these promoters are functional during the same growth phase of *X. albilineans* as the promoter upstream from operon 1.

Potential rho-independent transcription terminators were identified downstream from operons 1, 3 and 4 (FIG. 6) confirming prediction of the genetic organization of these three operons. Because operons 2 and 5 are convergent (FIG. 1) and separated by a very short region of 22 bp between albIX and albXX, stop codons may allow transcription termination in the absence of sequences corresponding to potential rho-independent transcription terminators downstream from these operons. It is quite possible that simultaneous transcription of operons 2 and 5 involving the presence of two RNA polymerases (one on each strand of DNA) may cause RNA polymerases to pause at the end of each operon because of steric interference between both polymerase complexes in the same short region.

The presence of putative RBSs upstream of the ATG start codons of all ORFs, except for albXVIII, suggests that these ORFs are translated in *X. albilineans*. The absence of a canonical RBS upstream from albXVIII further indicates that this ORF is probably not expressed. GTG and TTG codons (usually valine and leucine codons) generally serve as procaryotic start codons when located near the 5' end of an RNA message, but GTG start codons were also described far from the 5' end of messenger RNA in the bacitracin biosynthesis cluster of *B. lucheniformis* (Genbank Accession No. AF184956) or in the bleomycin biosynthetic gene cluster of *S. verticillus* (Genbank Accession No. AF210249). This is in accordance with the fact that the two potential TTG start codons are the first start codons in operons 1 and 4 of XALB1, and that the two potential GTG start codons initiate internal cistrons. The albI and albXVII genes, like xabB (Huang et al., 2001), use TTG as a start codon, which may impose post-transcriptional control of the rate of gene product formation (McCarthy and Gualerzi, 1990).

The predicted genetic organization of operons 1 and 2 presents similarities with the organization of the region involved in albicidin production in strain Xa13 of *X. albilineans* from Australia (Huang et al. 2000a, Huang et al., 2001). This latter region also contains two divergent operons involved in albicidin production, one comprising the xabB gene (similar to albI, but with a large deletion) and the xabC gene (100% identical to albII) and the other containing thp gene (100% identical to albV). In addition, the sequence between the two operons in stain Xa13 is 100% identical to the sequence between operons 1 and 2, indicating that both clusters are controlled by the same bidirectional promoter. However, transposon mutagenesis studies of Xa13 showed no evidence of another cistron downstream of xabC that may be involved in albicidin production (Huang et al., 2000a), suggesting that the Xa13 xab operon differs from the Xa23R1 operon 1, which contains two additional genes downstream from albII that are potentially involved in albicidin production (albIII and albIV; refer FIG. 1).

Homology analysis revealed that four NRPS and/or PKS genes are present in XALB1 (FIG. 2), and these genes may be involved in the biosynthesis of the albicidin polyketide-polypeptide backbone (albI, albIV, albVII and albIV). NRPS and PKS enzymes are generally organized into repeated functional units known as modules, each of which is responsible for a discrete stage of polyketide or polypeptide chain elongation (Cane and Walsh, 1999). Each PKS or NRPS module is made up of a set of three core domains, two of which are catalytic and one of which acts as a carrier, and together are responsible for the central chain-building reactions of polyketide or polypeptide biosynthesis. Both PKS and NRPS core domains utilize analogous acyl-chain elongation strategies in which the growing chain, tethered as an acyl-S-enzyme to the flexible 20 Å long phosphopantetheinyl arm of an acyl carrier protein (ACP) or peptidyl carrier protein (PCP) domain, acts as the electrophilic partner that undergoes attack by a nucleophilic chain-elongation unit, a malonyl- or aminoacyl-S-enzyme derivative, respectively, itself covalently bound to a downstream ACP/PCP domain. In the case of a PKS, the fundamental chain-elongation reaction, a C—C bond-forming step, is mediated by a ketosynthase (KS) domain that catalyzes the transfer of the polyketide acyl chain to an active-site cysteine of the KS domain, followed by condensation with the methylmalonyl- or malonyl-S-ACP by a decarboxylative acylation of the malonyl donor unit. An additional essential component of the core PKS chain-elongation apparatus is an associated acetyltransferase (AT) domain, which catalyzes the priming of the donor ACP side-arm with the appropriate monomer substrate, usually methylmalonyl- or malonyl-CoA. The comparable core domains of an NRPS biosynthetic module function in a chemically distinct but architecturally and mechanistically analogous fashion. In the latter case, the key chain-building reaction, a C—N bond-forming reaction, involves the generation of the characteristic peptide bond by nucleophilic attack of the amino group of an amino acyl-S-PCP donor on the acyl group of an upstream electrophilic acyl- or peptidyl acyl-S-PCP chain, catalyzed by a condensation (C) domain. In functional analogy to the PKS AT domain, the core of the NRPS module utilizes an adenylation (A) domain to activate the donor amino-acid monomer as an acyl-AMP intermediate, which is then loaded onto the downstream PCP side chain. Both the AT and A domains of the respective PKS and NRPS modules act as important gatekeepers for polyketide or polypeptide biosynthesis, exhibiting strict or at least high specificity for their cognate malonyl-CoA, methylmalonyl-CoA or amino acid substrates. In addition to the basic subset of core domains, each PKS or NRPS also has a special set of dedicated domains responsible both for the initiation of acyl-chain assembly by loading of a starter unit onto the first, furthest upstream PKS/NRPS module, as well as a chain-terminating thioesterase (TE) domain, most often found fused to the last module, that is responsible for detachment of the most downstream covalent acyl enzyme intermediate and off-loading of the mature polyketide or polypeptide chain (Cane and Walsh, 1999).

XALB1 potentially encodes four PKS modules and seven NRPS modules. Most of the bacterial NRPS gene clusters described up to now are organized in operon-type structures, encoding multi modular NRPS proteins with individual modules organized along the chromosome in a linear order that parallels the order of amino acids in the resultant peptide, following the “colinearity rule” for the NRPS-template assembly of peptides from amino acids (Cane, 1997; Cane et al., 1998; Cane and Walsh, 1999; von Döhren et al., 1999). PKS and NRPS modules are apparently not organized according to this “colinearity rule” for albicidin biosynthesis because of the following features: (I) NRPS and PKS genes are expressed in two divergent operons; (ii) no AT domain was identified in PKS-2 and PKS-3 domains, suggesting involvement of a separate enzyme; (iii) the A domain of NRPS-2 is not functional, suggesting the involvement of a trans-acting A domain; (iv) a single chain-terminating TE domain was identified in XALB1 which may be responsible of the release of the full length albicidin polyketide-polypeptide backbone from the enzyme complexes. Exception to the "colinearity rule" has also been shown for the syringomycin synthetase of *P. syringae* (Guenzi et al., 1998), for the exochelin synthetase of *Mycobacterium smegmatis* (Yu et al., 1998) and for the bleomycin synthetases of *S. verticillus* (Du et al., 2000).

Figure 9A:
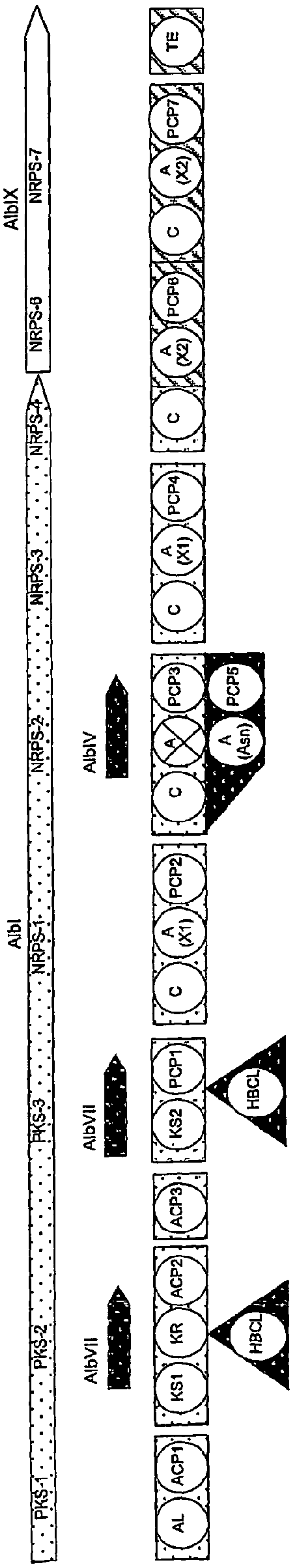
FIG. 9A is linear model 1 leading to the biosynthesis of only one polyketide-polypeptide albicidin backbone.
Figure 9B:
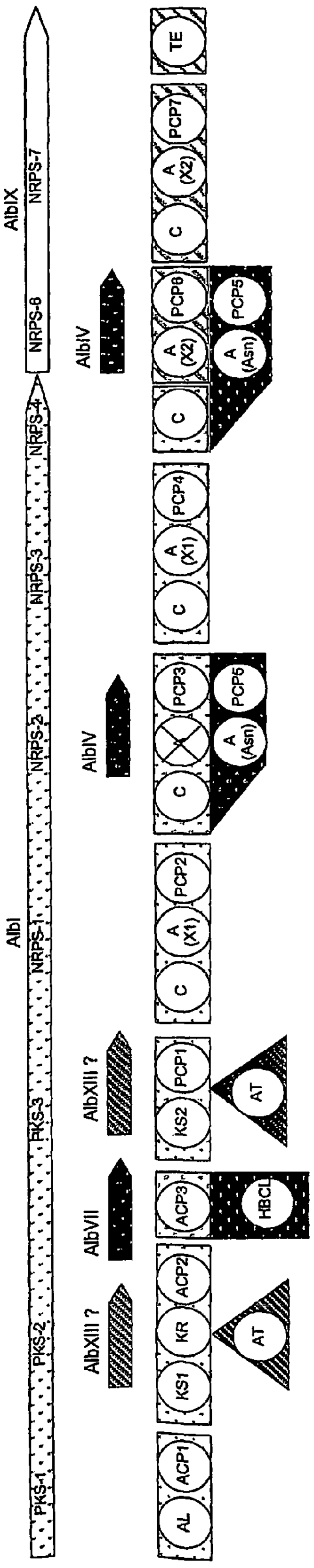
FIG. 9B is linear model 2 leading to the biosynthesis of four different polyketide-polypeptide backbone.

On the basis of the deduced functions of individual NRPS and PKS domains we have aligned the four PKS and the seven NRPS modules to suggest two different putative linear models for the synthesis of the albicidin polyketide-peptide backbone (FIG. 9). In the Figure, NRPS and PKS domains are abbreviated as follows: A, adenylation; ACP, acyl carrier protein; AL, acyl-CoA ligase; AT, acyltransferase; C, condensation; HBCL, hydroxybenzoate-CoA ligase; KR, ketoreductase; KS, ketoacyl synthase; PCP, peptidyl carrier protein. Asn designates asparagine. X1 and X2 indicate substrates incorporated by NRPS-1 and 3 and by NRPS-6 and 7, respectively. The crossed A domain in NRPS-2 indicates that this deleted domain may be not functional. In model 1, (FIG. 9A), (i) the PKS-1 module alone is responsible for the initiation of the acyl-chain assembly, (ii) PKS4 (HBCL) interacts with PKS-2 and PKS-3 as an AT domain to allow acyl transfer and (iii) NRPS-5 interacts with only NRPS-2. In model 2 (FIG. 9B) two different modules, PKS-1 and PKS-4, are responsible for this initiation step. Model 2 leads to the biosynthesis of four different polyketide-polypeptide backbones; in this model (i) PKS-1 (AL) and PKS-4 (HBCL) are in competition for initiation of albicidin precursors; (ii) a separate AT enzyme (potentially AlbXIII) interacts with PKS-2 and PKS-3 to allow acyl transfer; (iii) NRPS-5 interacts with NRPS-2; and (iv) NRPS-5 and NRPS-6 are in competition for interaction with NRPS4.

Both models are based on the fact that PKS-1 contains the AL and ACP1 domains, and PKS-4 shows homology with the hydroxybenzoate-CoA ligases. In other PKS systems, an N-terminal AL domain is involved in the activation and incorporation of an 3,4-dihydroxycyclo hexane carboxylic acid, a 3-amino-5-hydroxybenzoic acid or a long-chain fatty acid as a starter (Aparicio et al., 1996; Motamedi and Shafiee, 1998; Tang et al., 1998; Duitman et al., 1999). PKS-4 may be also involved in the activation and incorporation of hydroxy-benzoate but this latter domain lacks any ACP or PCP domain, suggesting that PKS-4 is responsible for initiation of the acyl-chain assembly (FIG. 9B) onto one of the three ACP domains of AlbI (ACP1, ACP2 or ACP3). The 277 amino-acids preceding the PKS4 module in AlbVII may be necessary for the intercommunication between AlbVII and AlbI. The presence of two different PKS modules potentially involved in the initiation of the acyl-chain assembly suggests a competition of these two modules for the initiation of two different albicidin polyketide-polypeptide backbones, and this could contribute to the production of multiple, structurally related albicidins by the same cluster XALB1. Production of two different components, one initiated by PKS-4 containing an additional aromatic ring due to incorporation of hydroxybenzoate, may explain why partial characterization of albicidin indicated the presence of a variable number (three or four) of aromatic rings (Huang et al., 2001).

In AlbI, PKS-1 is followed by the PKS-2 module which contains a KS domain and a KR domain upstream from two ACP domains (ACP2 and ACP3) and it lacks any discernable AT domain. Tandem ACP domains are unusual within PKS modules but have been shown to occur in the biosynthesis of several fungal and bacterial polyketide synthases (Mayorga and Timberlake, 1992; Yu and Leonard, 1995; Takano et al., 1995; Albertini et al., 1995). However, the significance of the tandem ACP domains in these systems has not been solved yet. In our model 2, one of the tandem ACP (ACP2 or ACP3) may interact with PKS-4 for the initiation of an acyl-chain assembly (FIG. 9B). The absence of an AT domain in the PKS-2 module suggests that a separate AT domain is indispensable for the elongation of the acyl-chain initiated by this module. Separate AT enzymes encoded elsewhere in the genome were described in other systems for two PKS modules lacking AT domains: malonyl-CoA transacyclase gene (fenF) located immediately upstream from the *B. subtilis* PKS-NRPS mycA gene (Duitman et al., 1999) and an AT gene located 20 kb upstream from the M xanthus NRPS-PKS tal gene (Paitan et al., 1999). We have not identified an AT gene in the gene cluster XALB1 and in the two other genomic regions involved in albicidin production, XALB2 and XALB3, suggesting that the trans-acting AT gene may be encoded elsewhere in the genome. However, AlbXIII, which contains the motif GHSxG conserved in AT domains, may be potentially involved in the acyl transfer, but the similarity of AlbXIII with AT domains is not high enough to confirm this potential function of AlbXIII (FIG. 10). FIG. 10A describes alignment of the conserved motifs in AT domains from RifA-1, -2, -3, RifB-1, RifE-1 (Rifamycin PKSs, August et al., 1998) and BlmVIII (Bleomycin PKS; Du et al., 2000), identical amino acids are shown in bold. FIG. 10B describes alignment of AlbXIII (SEQ ID NO. 38), FenF (a malonyl-CoA transacylase located upstream from mycA, Duitman et al., 1999) and LipA (a lipase; Valdez et al., 1999); amino acids identical to conserved AT domains motifs are shown in bold.

AlbXIII contains only four of the eleven amino acids conserved in AT domains of rifamycin PKSs (August et al., 1998) and Bleomycin PKS (Du et al., 2000), and the AlbXIII sequence appears to be more closely related to lipases such as LipA (Valdez et al., 1999) rather than to AT domains (FIG. 10). However, FenF, the trans-acting AT domain involved in mycosubtilin biosynthesis, contains only seven of the eleven amino acids conserved in AT domains (Duitman et al., 1999; FIG. 10). AlbVII, that contains a HBCL domain, may be another candidate for the acyl transfer in PKS-2 (FIG. 9A) because HBCL exhibits some similarity with A domains at the level of cores A1, A2, A3, A4, A5 and A6 (Table 6). However, no HBCL involved in such a function has been described in the PKSs characterized so far.

In AlbI, PKS-2 is followed by the PKS-3 module which contains the KS2 and the PCP1 domains and it lacks any discernable AT or A domain. PKS-3 is located upstream from the NRPS modules and should therefore be involved in the linkage of polyketide and polypeptide moieties. The presence of a PCP domain in the PKS-3 module suggests the involvement of a trans-acting A domain rather than an AT domain. A putative candidate for this trans-acting A domain is the AlbIV NRPS-5 A domain because of the lack of a C domain in the AlbIV NRPS-5 module. However, by analogy with the Blm-VIII PKS module, which is involved in the linkage of polypeptide and polyketide moieties of bleomycin and which contains an AT domain followed by a PCP domain (Du et al, 2000), the presence of a PCP is not incompatible with a possible interaction of the AlbI PKS-3 module with a separate AT domain. This latter trans-acting AT domain may be the same that interacts with the AlbI PKS-2 module, the AlbVII PKS-4 module, AlbXIII or an unindentified separate AT domain.

Figure 5:
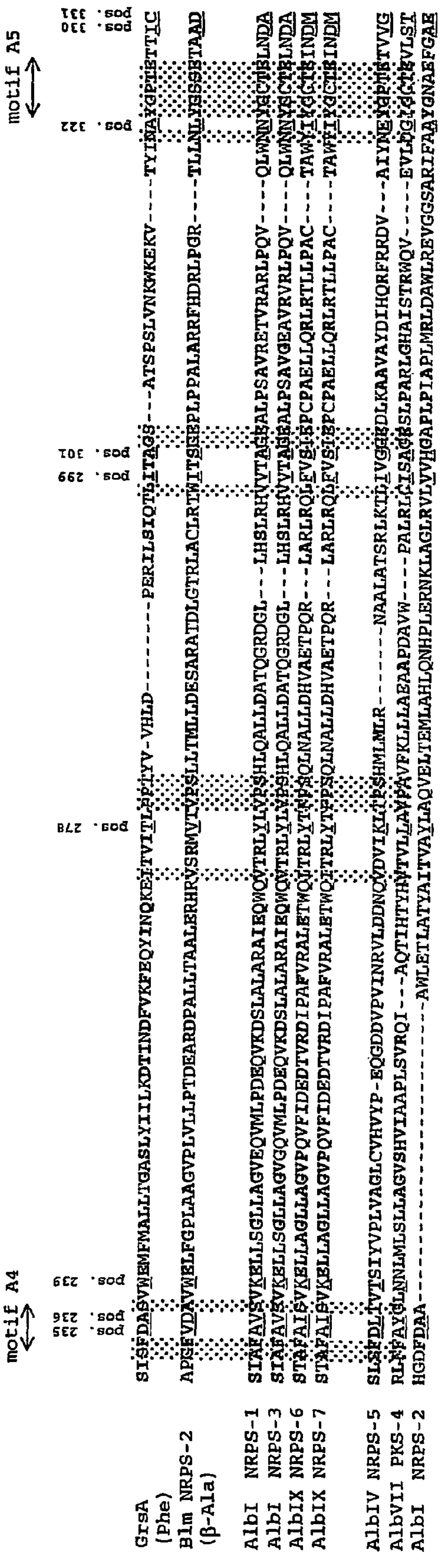
FIG. 5 is an illustration of the alignment of the primary sequences between the conserved motifs A4 and A5 of Alb NPRSs and PKS-4 in *Xanthomonas albilineans* with the corresponding sequences of GrsA (Phe) accession number: P14687 SEQ ID NO: 132 and Blm NRPS-2 (β-Ala) accession number AF210249 (SEQ ID NO: 133); AlbI NRPS-1 (SEQ ID NO: 134); AlbI NRPS-3 (SEQ ID NO: 135); AlbIX NRPS-6 (SEQ ID NO: 136); AlbIX NRPS-7 (SEQ ID NO: 137); AlbIV NRPS-5 (SEQ ID NO: 138); AlbVII PKS-4 (SEQ ID NO: 139); AlbI NRPS-2 (SEQ ID NO: 140).

In AlbI, the PKS-3 module is followed by four NRPS modules. The NRPS-1, 2 and 3 modules display the ordered C, A and PCP domains, suggesting that they are involved in the incorporation of three amino acid residues. The A domain of the NRPS-2 module exhibits poor consensus at A2, A3, A5, A7, A8 A9 and A10 motifs and lacks completely the A6 motif (Table 6). In addition the NRPS-2 substrate binding pocket is partially deleted (FIG. 5). These features strongly suggest that the NRPS-2 A domain is inactive and that the loading of an amino-acid on the NRPS-2 PCP domain (PCP3) is possibly catalyzed by a trans-acting A domain as in HMWP1 (Gehring et al., 1998) and BlmIII (Du et al., 2000). A putative candidate for this trans-acting A domain is the NRPS-5 A domain present in AlbIV because of the lack of a C domain in NRPS-5 (FIG. 2). The additional sequence of 300 amino-acids present in the A domain of NRPS-5 may be necessary for the intercommunication between AlbI and AlbIV. As a consequence of the interaction between NRPS-2 and NRPS-5, a competition between PCP-3 and PCP-5 domains must occur to bind the amino acid activated by the NRPS-5 A domain. A similar competition between two PCP domains was described for syringomycin biosynthesis, during the interaction between SyrB, which contains A and PCP domains, and the last module of SyrE which contains C and PCP domains (Guenzi et al., 1998). The NRPS-4 module contains only a C domain which may transfer the intermediate products synthetized by AlbI to a PCP domain present in an other albicidin synthase. Similar transfers were described for mycosubtilin biosynthesis in which the MycA and MycB C-terminal C domains interact with the MycB and MycC N-terminal A domains, respectively (Duitman et al., 1999). Two different PCP domains may be involved in the transfer of the intermediate products synthetized by AlbI: the PCP-5 and PCP-6 domains which are present in the AlbIV NRPS-5 and AlbIX NRPS-6 modules, respectively. This possible competition between the two NRPS modules that contain two different A domains could also contribute to the production of multiple, structurally related albicidins by the gene cluster XALB1 (FIG. 9B). Because of the absence of a C-domain in the AlbIX NRPS-6 module, the intermediate product bound on the AlbIV PCP-5 domain would be necessarily transferred to the AlbIX PCP-7 domain, like the intermediate product bound on AlbIX PCP-6. AlbIX NRPS-7, which contains the single chain-terminating TE domain, may then be responsible for detachment of the mature albicidin polyketide-polypeptide backbone from the complex of enzymes.

The linear model 1 implies that operon 1 and operon 2 in *X. Albilineans* strain Xa23R1 from Florida potentially produce only one albicidin polyketide-polypetide backbone, with a competion at the level of ACP2/ACP3 and PCP3 and PCP5 which could explain the production by *X. albilineans* of compounds structurally related to albicidin (FIG. 9A). The linear model 2 implies that operon 1 and operon 2 in *X. albilineans* strain Xa23R1 from Florida potentially produce four different albicidin polyketide-polypetide backbones (FIG. 9B) because of (i) the competition of AL and HBCL domains for initation of acyl chain assembly and (ii) the competition of AlbIV NRPS-5 and AlbIX NRPS-6 modules for the incorporation of the next to last amino acid of the albicidin backbone. These four albicidin backbones may lead to the production of four components structurally very different The polyketide moieties of the acyl chains initiated by the AlbI AL domain or by the AbVII HBCL domain may be very different. The polyketide moiety of acyl chains initiated by the AlbVII HBCL domain may be shorter and may contain an additional aromatic ring. The presence of four structuraly different metabolites may explain the difficulty observed by Birch and Patil (1985a) to purify albicidin and to determine its chemical structure.

Homology analysis also revealed that AlbI NRPS-1 and 3 and AlbIX NRPS-6 and 7 specify unusual substrates which seem to contain an amino group and a carboxylate group but to be different from α-amino acids and β-alanine. Identification of several aromatic rings in albicidin (Huang et al., 2001) suggested that NRPS-1, -3, -6 and -7 are involved in incorporation of aromatic substrates. By analogy with the Asp235Val alteration in the β-Ala specificity-conferring code (Du et al. 2000), the Asp235Ala alteration in the NRPS-1, -3, -6 and -7 signatures could be consistent with a large distance between the amino group and the carboxylate group in the substrate specified by these modules. Based on this hypothesis, we suggest that operons 3, 4 and 5 are involved in the biosynthesis of two aromatic substrates: the para-aminobenzoate potentially synthesized by AlbXVII (para-aminobenzoate synthase), and the carbamoyl benzoate potentially synthesized by AlbXX (hydroxybenzoate synthase) and AlbXV (carbamoyl transferase). Incorporation of these nonproteinogenic substrates may explain why albicidin is insensitive to proteases (Birch and Patil, 1985a).

Figure 11A:
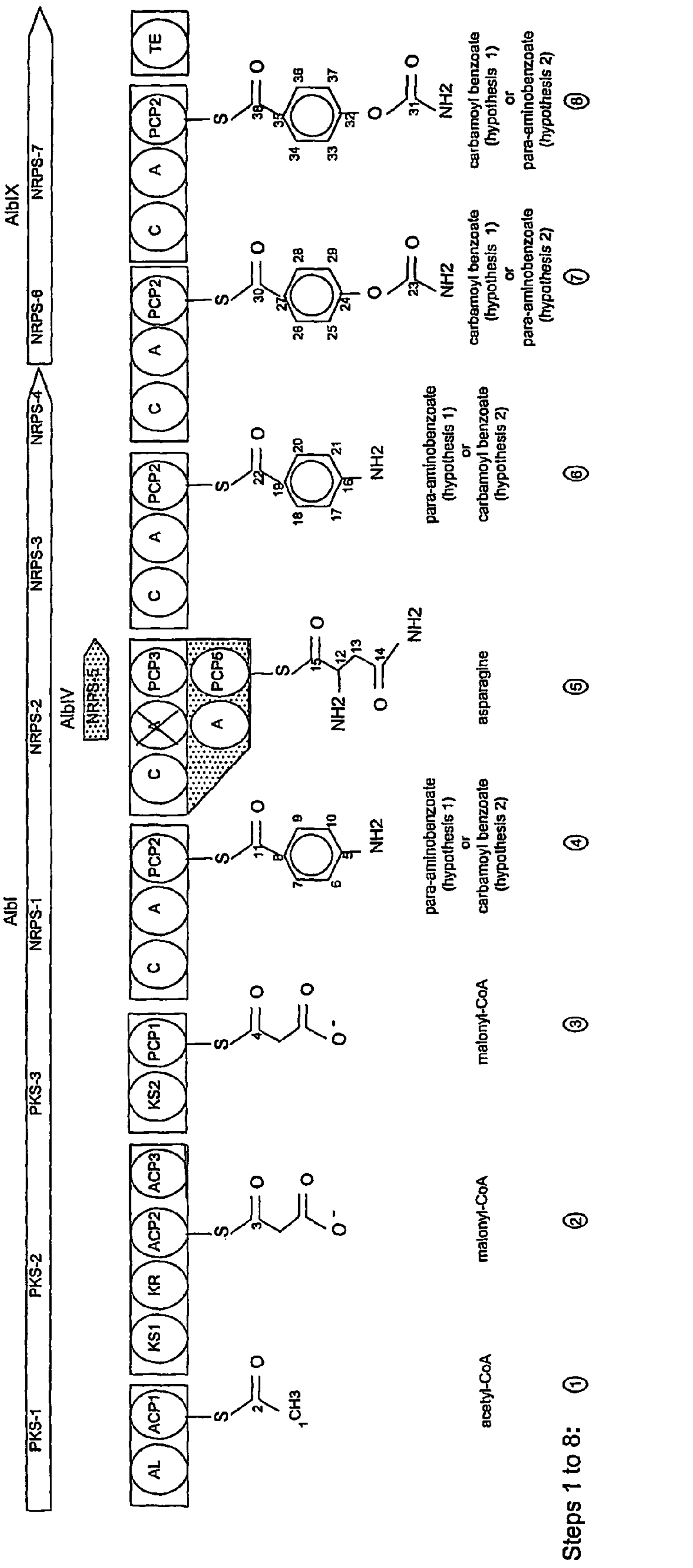
FIG. 11A is a proposed model for biosynthesis of albicidin, including putative substrates of PKS and NRPS modules.

According to biosynthesis model 1 leading to the biosynthesis of only one polyketide-polypeptide albicidin backbone that may correspond to the major component produced by XAlb1, we propose a model allowing prediction of the composition and the structure of albicidin (FIG. 11). In the Figure, NRPS and PKS domains are abbreviated as follows: A, adenylation; ACP, acyl carrier protein; AL, acyl-CoA ligase; C, condensation; KR, β-ketoreductase; KS, β-ketoacyl synthase; PCP, peptidyl carrier protein. C atoms of albicidin-backbone are numbered 1 to 38. Bold methyl groups correspond to methylation of the albicidin backbone by AlbII or AlbVI. In this model, albicidin biosynthesis is initiated by loading of an acetyl-CoA by PKS-1 (step 1), and the chain product is elongated by incorporation of (I) malonyl-CoA by PKS-2 and PKS-3 (steps 2 and 3), (ii) para-aminobenzoate or carbamoyl benzoate by NRPS-1 and NRPS-3 (steps 4 and 6), (iii) asparagine by NRPS-2 coupled to NRPS-5 (step 5) and (iv) para-aminobenzoate or carbamoyl benzoate by NRPS-6 and NRPS-7 (steps 7 and 8). The presence of the KR domain in the PKS-2 module may lead to the formation of an hydroxyl group at the $C_2$ atom of the albicidin backbone. This hydroxyl group might be methylated by AlbVI (O-methyltransferase). The acyl chain may also be modified by AlbII (C-methyltransferase) at $C_{13}$ or $C_{14}$.

The chemical composition ($C_{40}O_{15}N_6H_{35}$), the molecular weight (839), and the structure of the putative XALB1 product are in accordance with the partial characterization of albicidin published by Birch and Patil (1985a) which indicated that albicidin contains approximately 38 carbon atoms and a carboxylate group and that the molecular weight of albicidin was about 842. The presence of two ester linkages in our predicted albicidin structure is also in accordance with the fact that albicidin is detoxified by the AlbD esterase (Zhang and Birch, 1997). However, an unpublished albicidin analysis cited by Huang et al. (2001) indicated the presence of (I) two OCH3 groups and not one as in our predictive albicidin structure, (ii) one CN linkage and not eleven as in our predictive albicidin structure and (iii) a trisubstituted double bond that is not present in the putative XALB1 product.

In conclusion, homology analysis of XALB1 revealed unprecedented features for hybrid polyketide-peptide biosynthesis in bacteria involving a trans-action of four PKS and seven NRPS separate modules which could contribute to the production of multiple, structurally related polyketide-peptide compounds by the same gene cluster. Characterization of the full chemical structure of albicidin may be necessary to validate these models. Four NRPS modules seem to activate a very unusual substrate. Over-expression and purification of A domains from these four NRPS modules will be necessary to examine their substrate specificities. Substrate specificity of each A domain will therefore be determinated by analysis of the ATP-PPi exchange reaction with different substrate putatively incorporated into albicidin. Investigating albicidin backbone biosynthesis will be of great interest because such information adds to the limited knowledge as to how PKS and NRPS interact and how they might be manipulated to engineer novel molecules, and may explain how *X. albilineans* produces several structurally related, toxic compounds.

Cloning and sequencing of XALB2 showed that the same phosphopantetheinyl transferase is required for albicidin production in an *X. albilineans* strain from Florida and in an *X. albilineans* strain from Australia (Huang et al., 2000b), explaining the precedented results showing that strain LS156 mutated in xabA (100% identical to albX) was not complemented by pALB540, pALB571 and pALB639 (Rott et al., 1996). Mutant LS156 was shown to be complemented by a construction containing the coding sequence of xabA in fusion with lacZ, revealing that xabA is required for albicidin production and that no other cistron downstream from xabA was involved in albicidin production (Huang et al., 2000b). However, this complementation study did not allow determination of whether xabA is transcribed as a part of a larger operon. Here we disclose the complementation of mutant AM37 with a 2986 bp insert from *X. albilineans* containing albXXI (100% identical to xabA), confirming that albXXI is involved in albicidin biosynthesis and indicating that the promoter of albXXI is present in the 2986 bp insert and that albXXI is not expressed as part of a operon.

Cloning and sequencing of XALB3 showed that a heat shock protein HtpG was involved in albicidin production in *X. albilineans*. The heat shock protein HtpG is an *Escherichia coli* homologue of eukaryotic HSP90 molecular chaperone. Hsp90 from eukaryotes has been demonstrated to possess chaperone activity (Jakob et al., 1995), acting as a non-ATP dependent "holder," and it also has an important role in signal transduction and the cell cycle. This protein is essential in both *drosophila* and yeast (Borkovich et al., 1989; Cutforth and Rubin, 1994). In contrast, the HtpG gene can be deleted in *E. coli* with no effect on the viability of the strain with the exception of decreased growth rate at high temperatures (Bardwell and Craig, 1988). The in vivo role of the HtpG protein remains unknown. However, preliminary results indicated that HtpG facilitates de novo protein folding in stressed *E. coli* cells, presumably by expanding the ability of the DnaK-DnaJ-GrpE molecular chaperone system to interact with newly synthesized polypeptides (Thomas and Baneyx, 2000). Furthermore, HtpG was copurified in *E. coli* with MccB17 synthetase, an enzyme involved in the biosynthesis of the peptide antibiotic microcin B17 which inhibits DNA replication by induction of the SOS repair system, suggesting the requirement of HtpG for production of the antibiotic (Li et al., 1996). However, when microcin B17 production by the *E. coli* strain deleted for HtpG was compared to the one of the parental strain, there was no effect on microcin B17 production in vivo. This result implied that the copurification of HtpG with the MccB17 synthetase was potentially an artifact, or that another *E. coli* chaperone could substitute for HtpG (Milne et al., 1999). To examine the effect of HtpG on the reconstitution of MccB17 synthetase in vitro, the chaperone was expressed and purified as a fusion to a hexahistidine ($His_6$) tag. Addition of the $His_6$-HtpG did not stimulate MccB17 synthetase reconstitution or heterocyclisation activity in vitro, suggesting that HtpG mediates complex assembly or stabilizes protein subunits prior to the hetero-oligomerisation (Milne et al., 1999). Based on these results, we suggest that the function of AlbXXII is to mediate complex assembly by facilitating de novo protein folding of PKS and NRPS enzymes (AlbI, AlbIV, AlbVII and AlbIX) involved in the albicidin backbone biosynthesis.

Characterization of the complete sequence of XALB1, XALB2 and XALB3 clusters enables one to characterize all enzymes of the albicidin biosynthesis pathway including structural, resistance, secretory and regulatory elements, and to engineer overproduction of albicidin. For example one may insert expression enhancing DNA into the genome of *X. albilineans* in a position operable to enhance expression of the Albicidins Biosynthesis Gene Clusters. One may also modify naturally occurring Albicidins to obtain additional non-naturally occurring antibiotics by adding DNA encoding additional enzymes selected to produce a modified albicidin like molecule. This approach will allow (I) the purification of albicidin and the other compounds structurally related and potentially produced by the same biosynthesis apparatus; (ii) the characterization of chemical structure of albicidin; (iii) the investigation of mode of action of albicidin in the pathogenesis of *X. albilineans* in sugarcane; and (iv) the characterization of the bactericidal activity of albicidin. For example one may also increase the resistance of plants to damage from *X. albilineans* infection by inserting one or more of the resistance genes identified herein into the genome of the plant. One may also provide materials to prevent damage by albicidin produced by *X. albilineans* by applying an agent that blocks expression of the Albicidin Biosynthesis Gene Clusters to the plant to be protected. One may also use portions of the DNA of the Albicidin Biosynthesis Gene Clusters to obtain agents useful in blocking expression of albicidin by screening materials against a modified hast cell line that expresses the Albicidin Biosynthesis Gene Clusters and selecting for materials that stop or decrease albicidin production.

TABLE 1

Bacterial strains and plasmids used in this study

| Strains | Relevant characteristics[a] | Reference or source |
|---|---|---|
| *E. coli* | | |
| DH5α | F-/80dlacZΔM15 Δ(lacZYA-argF)U169 deoR recA1 endA1 hsdR17($r_k^-m_k^+$) supE44 thi-1 gyrA96 relA1 | Gibco-BRL |
| DH5α MCR | DH5αmcrA mcrBC mrr | " |
| Xcv 91-11B | Wild type strain of *Xanthomonas axonopodis* pv. *vesicatoria* from tomato (race 3) | Astua-Monge et al., 2000 |
| Xcv 91-11BR1 | Spontaneous $Rif^r$ derivative of Xcv 91-11B | This study |
| DH5αKT | *Escherichia coli* DH5α strain transformed by both pUFR043 and pLAFR3 plasmids | " |

TABLE 1-continued

Bacterial strains and plasmids used in this study

| Strains | Relevant characteristics[a] | Reference or source |
|---|---|---|
| DH5αAlb$^r$ | Spontaneous Alb$^r$ derivative of DH5α | " |
| DH5αAlb$^r$KT | DH5αAlb$^r$ transformed by both pUFR043 and pLAFR3 plasmids | " |
| Plasmids | | |
| PBR325 | Tc$^r$, Ap$^r$, Cm$^r$ | Gibco-BRL |
| pBCKS (+) | Cm$^r$ | Stratagene |
| pBluescript II KS (+) | Ap$^r$ | " |
| PRK2073 | PRK2013 derivative, Km$^s$ (npt::Tn7), Sp$^r$, Tra$^+$, helper plasmid | Leong et al., 1982 |
| pUFR043 | IncW Mob$^+$ LacZα Gm$^r$, Km$^r$, Cos | De Feyter and Gabriel, 1991 |
| pAlb540 | 47 kb insert from Xa23R1 in pUFR043, Gm$^r$, Km$^r$ | Rott et al., 1996 |
| pAlb571 | 36.8 kb insert from Xa23R1 in pUFR043, Gm$^r$, Km$^r$ | " |
| PAlb639 | 36 kb insert from Xa23R1 in pUFR043, Gm$^r$, Km$^r$ | " |
| pAM15.1 | 24 kb EcoR I fragment carrying Tn5 and flanking sequences of mutant AM15 in pBR325, Km$^r$, Tc$^r$, Ap$^r$, Cm$^r$ | " |
| pAM40.2 | 11 kb EcoR I fragment carrying Tn5 and flanking sequences of mutant AM40 in pBR325, Km$^r$, Tc$^r$, Ap$^r$, Cm$^r$ | " |
| pAM45.1 | 12 kb EcoR I fragment carrying Tn5 and flanking sequences of mutant AM45 in pBR325, Km$^r$, Tc$^r$, Ap$^r$, Cm$^r$ | " |
| pAM12.1 | 13 kb EcoR I fragment carrying Tn5 and flanking sequences of mutant AM12 in pBR325, Km$^r$, Tc$^r$, Ap$^r$, Cm$^r$ | A |
| PAM36.2 | 9 kb EcoR I fragment carrying Tn5 and flanking sequences of mutant AM36 in pBR325, Km$^r$, Tc$^r$, Ap$^r$, Cm$^r$ | A |
| pAlb389 | 37 kb insert from Xa23R1 in pUFR043, Gm$^r$, Km$^r$ | This study |
| pAC389.1 | 2.9 kb insert from Xa23R1 in pUFR043, Gm$^r$, Km$^r$ | " |
| PAlb639A | 9.4 kb insert from Xa23R1 in pUFR043, Gm$^r$, Km$^r$ | " |
| PEV639 | 2.6 kb Sal I insert from Xa23R1 in pUFR043, Gm$^r$, Km$^r$ | " |
| pBC/A' | 7.5 kb Kpn I fragment carrying a part of fragment A from pAlb571 in pBCKS (+), Cm$^r$ | " |
| pBC/AF | 15.2 kb EcoR I fragment carrying fragments A and F from pALB540 in pBCKS (+), Cm$^r$ | " |
| pBC/B | 11.0 kb Kpn I fragment B from pAlb571 in pBCKS (+), Cm$^r$ | " |
| pBC/C | 6.0 kb Kpn I fragment C from pAlb571 in pBCKS (+), Cm$^r$ | " |
| pBC/E | 2.8 kb Kpn I fragment E from pAlb571 in pBCKS (+), Cm$^r$ | " |
| pBC/F | 2.5 kb Kpn I-EdoR I fragment F from pAlb571 in pBCKS (+), Cm$^r$ | " |
| pBC/G | 1.9 kb EcoR I fragment G from pAlb571 in pBCKS (+), Cm$^r$ | " |
| pBC/I | 1.4 kb Kpn I-EcoR I fragment I from pAlb571 in pBCKS (+), Cm$^r$ | " |
| pBC/J | 0.6 kb EcoR I fragment J from pALB540 in pBCKS (+), Cm$^r$ | " |
| pBC/K | 4.7 kb EcoR I fragment K from pALB540 in pBCKS (+), Cm$^r$ | " |
| pBC/L | 0.4 kb EcoR I fragment L from pALB540 in pBCKS (+), Cm$^r$ | " |
| pBC/N | 7.7 kb EcoR I fragment N from pALB540 in pBCKS (+), Cm$^r$ | " |
| pUFR043/D= | 2.2 kb EcoR IBSau3A I fragment carrying a part of fragment D from pAlb571 in pUFR043 | " |
| pAM1 | 5 kb EcoR I fragment carrying Tn5 and flanking sequences of mutant AM1 in pBluescript II KS (+), Km$^r$, Ap$^r$ | " |
| pAM4 | 12 kb EcoR I fragment carrying Tn5 and flanking sequences of mutant AM4 in pBluescript II KS (+), Km$^r$, Ap$^r$ | " |
| pAM7 | 6 kb EcoR I fragment carrying Tn5 and flanking sequences of mutant AM7 in pBluescript II KS (+), Km$^r$, Ap$^r$ | " |
| pAM10 | 7 kb EcoR I fragment carrying Tn5 and flanking sequences of mutant AM10 in pBluescript II KS (+), Km$^r$, Ap$^r$ | " |
| pAM29 | 10 kb EcoR I fragment carrying Tn5 and flanking sequences of mutant AM29 in pBluescript II KS (+), Km$^r$, Ap$^r$ | " |
| pAM37 | 6 kb EcoR I fragment carrying Tn5 and flanking sequences of mutant AM37 in pBR325, Km$^r$, Tc$^r$, Ap$^r$, Cm$^r$ | " |
| pAM52 | 5 kb EcoR I fragment carrying Tn5 and flanking sequences of mutant AM52 in pBluescript II KS (+), Km$^r$, Ap$^r$ | " |
| PLAFR3 | IncP, Mob+, LacZα, Tc$^r$, cos | Staskawicz et al., 1987 |
| PLAFR3XhoI | pLAFR3 with a XhoI site added to the BamHI site using an adaptator | This study |
| pBC/Op4Δ | BamHI-PstI fragment from pALB540 cloned between BamHI and PstI sites of pBCKS(+) | " |
| pBC/Op4ΔXhoI | PBC/Op4Δ with a XhoI site created by directed mutagenesis upstream from the BfrI site | " |
| pBC/Op4Δ/XALB2 | EcoRI DNA fragment from pAC389.1 cloned into the EcoRI site of pBC/Op4ΔXhoI | " |
| pBC/Op3-4/XALB2 | BfrI DNA fragment from pALB540 cloned into the BfrI site of pBC/Op4Δ/XALB2 | " |
| pBKS/XALB3 | SalI DNA fragment from pEV639 cloned into the SalI site of pBluescript II KS (+) | " |

TABLE 1-continued

Bacterial strains and plasmids used in this study

| Strains | Relevant characteristics[a] | Reference or source |
|---|---|---|
| pBKS/XALB3XhoI | pBKS/XALB3 with a KhoI site created by directed mutagenesis to substitute the SalI site located on the KpnI side of the polylinker | " |
| pBKS/Op3-4/XALB2-3 | XhoI DNA fragment from pBC/Op3-4Δ/XALB2 cloned into the SalI site of pBKS/XALB3XhoI | " |
| pOp3-4/XALB2-3 | XhoI DNA fragment from pBKS/Op3-4/XALB2-3 cloned into the XhoI site of pLAFR3XhoI | " |
| pEValbXXII | albXXII in fusion with LacZ in pUFR043, Gm[r], Km[r] | " |
| pEVHtpG | E. coli htpG in fusion with LacZ in pUFR043, Gm[r], Km[r] | " |
| PGemT | ColE1 replicon, Ap[r], LacZα, single 3'-T overhangs at the insertion site | Promega |
| PGemT/albXXII | PCR fragment containing albXXII cloned into pGemT | This study |
| PGemT/albXXII bis | BglII-SalIDNA fragment from pBKS/XALB3 cloned between the BglII and SalI sites of pGemT/albXXII | " |
| PGemT/HtpG | PCR fragment containing the E. coli htpG gene cloned into pGemT | " |
| DNA Fragment | | |
| PR37 | 1.1 kb Hind III-Hind III from pAM37 | " |

[a]Ap[r], Cm[r], Gm[r], Km[r], Rif[r], Sp[r], Tc[r]: resistant to ampicilin, chloramphenicol, gentamycin, kanamycin, rifampicin, spectinomycin, tetracycline, respectively.
Tox-, deficient in albicidin production.
Tn5-gusA, Tn5-uidAl Km[r] Tc[r], forms transcriptional fusions.
Alb[r], Ap[r], Gm[r], Rif[r] and Tc[r]: resistant to albicidin, ampicilin, gentamycin, rifampicin and tetracycline, respectively.

TABLE 2

Analysis of putative translational signals and location of all putative orfs identified in the XALB1 gene cluster

| Intergenic spacing between consecutive ORFs in each putative operon | ORF | Potential RBS[a] (distance from start codon) | Start codon (position) | Stop codon (position) |
|---|---|---|---|---|
| Operon 1 (strand +) | | | | |
| | albI | GAGGG (5 b) | TTG (30166) | TAG (50805) |
| 45 b | albII | GAGGG (5 b) | ATG (50851) | TAA (51882) |
| ATG overlaps TAA | albIII | GAGGG (7 b) | ATG (51882) | TGA (52385) |
| GTG overlaps TGA | albIV | GAGG (7 b) | GTG (52382) | TAA (55207) |
| Operon 2 (strand −) | | | | |
| | albV | GGAGG (8 b) | ATG (29929) | TAA (29210) |
| 87 b | albVI | AAGG (4 b) | GTG (29122) | TGA (28262) |
| 61 b | albVII | GAG (4 b) | ATG (28200) | TAG (25903) |
| 7 b | albVIII | AGGTG (4 b) | ATG (25895) | TAA (24903) |
| 20 b | albIX | GGTG (3 b) | ATG (24882) | TGA (19003) |
| Operon 3 (strand −) | | | | |
| | albX | GGGGG (8 b) | ATG (14497) | TGA (14246) |
| 81 b | albXI | AGGAAA (6 b) | ATG (14164) | TGA (13217) |
| 5 b | albXII | GGCCTGA (5 b) | ATG (13211) | TAA (11856) |
| 36 b | albXIII | GGGG (3 b) | ATG (11819) | TAA (10866) |
| 12 b | albXIV | GGAG (8 b) | ATG (10853) | TAG (9363) |
| 41 b | albXV | GGAA (6 b) | ATG (9321) | TAG (7567) |
| 208 b | albXVI | GGAGG (4 b) | ATG (7358) | TAG (7092) |
| Operon 4 (strand +) | | | | |
| | albXVII | GGGAGG (5 b) | TTG (14909) | TGA (17059) |
| 274 b | albXVIII | GCTCAG (8 b) | ATG (17334) | TGA (17747) |
| Overlap (17 b) | albXIX | AGG (9 b) | ATG (17728) | TGA (18330) |
| 41 b | albXX | GCAA (8 b) | ATG (18372) | TAG 18980) |

[a]Ribosomal Binding Site

TABLE 3

Deduced functions of the ORFs in the major albicidin biosynthetic cluster X-ALB1

| ORF | Number of amino acids | Sequence homolog[a] | Proposed function[b, c] | |
|---|---|---|---|---|
| Operon 1 | | | | |
| AlbI | 6879 | XabB (AAK15074) | Polyketide — peptide synthase | |
| | | | PKS modules | PKS domains |
| | | | PKS-1 | AL ACP1 |
| | | | PKS-2 | KS1 KR ACP2 ACP3 |
| | | | PKS-3 | KS2 PCP1 |
| | | | NRPS modules | NRPS domains |
| | | | NRPS-1 | C A PCP2 |
| | | | NRPS-2 | C A PCP3 |
| | | | NRPS-3 | C A PCP4 |
| | | | NRPS-4 | C |
| Alibi | 343 | XabC (AAK15075) | C-methyltransferase | |
| AlbIII | 167 | ComAB (CAA71583) | Activator of alb genes transcription | |
| AlbIV | 941 | MycA (T44806) | Peptide synthase | |
| | | WbpG (E83253) | NRPS module | NRPS domains |
| | | | NRPS-5 | A PCP5 |
| Operon 2 | | | | |
| AlbV | 239 | Thp (AAK15074) | No function (transposition) | |
| AlbVI | 286 | TcmP (AAA67510) | O-methyltransferase | |
| AlbVII | 765 | HbaA (A58538) | 4-hydroxybenzoate CoA ligase | |
| albVIII | 330 | SyrP (AAB63253) | Regulation | |
| AlbIX | 1959 | DhbF (CAB04779) | Peptide synthase | |
| | | | NRPS modules | NRPS domains |
| | | | NRPS-6 | A PCP6 |
| | | | NRPS-7 | C A PCP7 |
| Operon 3 | | | | |
| AlbX | 83 | MbtH (O05821) | Unknown | |
| AlbXI | 315 | SyrC (U25130) | Thioesterase | |
| AlbXII | 451 | BoxB (AAK006000.1) | Unknown | |
| albXIII | 317 | hp[d] (AAK25001) | Esterase | |
| albXIV | 496 | ActII-2 (p46105) | Albicidin transporter | |
| AlbXV | 584 | hp[d] (08390) | Carbamoyl transferase | |
| AlbXVI | 88 | OrfA (AAC03166) | No function (transposition) | |
| Operon 4 | | | | |
| albXVII | 716 | PabAB (CAC22117) | Para-amino benzoate synthase | |
| Operon 5 | | | | |
| albXVIII | 137 | ADCL (AAG06352) | No function (not functional) | |
| albXIX | 200 | McbG (P05530) | Immunity against albicidin | |
| albXX | 202 | UbiC (S25660) | 4-hydroxybenzoate synthetase | |

[a]Protein accession numbers in Genbank are given in parentheses.
[b]NRPS and PKS domains are abbreviated as follows: A, adenylation;
ACP, acyl carrier protein;
AL, acyl CoA ligase;
C, condensation;
KR, ketoreductase;
KS, ketoacyl synthase;
PCP, peptidyl carrier protein.
[c]Underlined domains are likely inactive due to the lack of highly conserved motifs.
[d]hypothetical protein

TABLE 4

Summary of results obtained from BLAST analyses.

| Putative Alb protein | No. of aa residues | Protein homolog | Origin | Genbank accession # | Score | Expect | Identities | Positives | Gaps |
|---|---|---|---|---|---|---|---|---|---|
| AlbI | 6879 | | | | | | | | |
| PKS-1 | | XabB (4801 aa) | *Xanthomonas albilineans* | AAK15074 | 1352 bits (3498) | 0.0 | 730/730 (100%) | 730/730 (100%) | — |
| | | SafB (1770 aa) | *Myxococcus xanthus* | AAC44128 | 231 bits (589) | 2e-59 | 175/532 (32%) | 269/532 (49%) | 23/532 (4%) |

TABLE 4-continued

Summary of results obtained from BLAST analyses.

| Putative Alb protein | No. of aa residues | Protein homolog | Origin | Genbank accession # | Score | Expect | Identities | Positives | Gaps |
|---|---|---|---|---|---|---|---|---|---|
| PKS-2 | | XabB (4801 aa) | *X. albilineans* | AAK15074 | 3464 bits (8983) | 0.0 | 1882/1882 (100%) | 1882/1882 (100%) | — |
| | | PksM (4273 aa) | *Bacillus subtilis* | CAB13603 | 887 bits (2292) | 0.0 | 626/1896 (33%) | 938/1896 (49%) | 140/1896 = 7% |
| PKS-3 | | XabB (4801 aa) | *X. albilineans* | AAK15074 | 1274 bits (3296) | 0.0 | 653/653 (100%) | 653/653 (100%) | — |
| | | PksM (4273 aa) | *B. subtilis* | CAB13603 | 577 bits (1486) | e-163 | 293/584 (50%) | 391/584 (66%) | 17/584 (2%) |
| NRPS-1 | | XabB (4801 aa) | *X. albilineans* | AAK15074 | 1934 bits (5010) | 0.0 | 1035/1046 (99%) | 1039/1046 (99%) | — |
| | | NosA (4379 aa) | *Nostoc* sp. | AF204805 | 618 bits (1594) | e-176 | 398/1104 (36%) | 586/1104 (53%) | 86/1104 (7%) |
| NRPS-2 | | NosA (4379 aa) | *Nostoc* sp. | AF204805 | 416 bits (1069) | e-115 | 337/1127 (29%) | 496/1127 (43%) | 128/1127 (11%) |
| | | Peptide synthase (5060 aa) | *Anabaena* sp. | CAC01604 | 402 bits (1034) | e-111 | 315/1073 (29%) | 479/1073 (44%) | 114/1073 (10%) |
| NRPS-3 | | XabB (4801 aa) | *X. albilineans* | AAK15074 | 1847 bits (4784) | 0.0 | 997/1044 (95%) | 1007/1044 (96%) | — |
| | | NosA (4379 aa) | *Nostoc* sp. | AF204805 | 610 bits (1573) | e-173 | 392/1069 (36%) | 571/1069 (52%) | 86/1069 (8%) |
| NRPS-4 | | XabB (4801 aa) | *X. albilineans* | AAK15074 | 889 bits (2297) | 0.0 | 468/468 (100%) | 468/468 (100%) | — |
| | | NosC (3317 aa) | *Nostoc* sp. | AAF17280 | 240 bits (613) | 2e-62 | 156/438 (35%) | 229/438 (51%) | 20/438 (4%) |
| AlbII | 343 | XabC (343 aa) | *X. albilineans* | AAK15075 | 633 bits (1633) | 0.0 | 343/343 (100%) | 343/343 (100%) | — |
| | | MtmMII (326 aa) | *Streptomyces argillaceus* | AAD55584 | 144 bits (361) | 1e-34 | 98/323 (30%) | 154/323 (47%) | 4/323 (1%) |
| | | TcmO (339 aa) | *S. glaucescens* | P39896 | 81.7 bits (199) | 1e-14 | 79/314 (25%) | 140/314 (44%) | 12/314 (3%) |
| AlbIII | 167 | comA operon protein 2 (136 aa) | *E. coli* | AAC74756 | 133 bits (335) | 1e-30 | 68/135 (50%) | 89/135 (65%) | — |
| | | ComAB (116 aa) | *Bacillus licheniformis* | CAA71583 | 97.6 bits (242) | 8e-20 | 53/111 (47%) | 68/111 (60%) | 1/111 (0%) |
| AlbIV | 941 | | | | | | | | |
| PKS-4 | | BA3 (6359 aa) | *B. licheniformis* | AAC06348 | 361 bits (926) | 2e-98 | 190/441 (43%) | 267/441 (60%) | 14/441 (3%) |
| | | WbpG (377 aa) | *Pseudomonas aeruginosa* | E83253 | 81.6 bits (200) | 4e-15 | 44/119 (36%) | 70/119 (57%) | 4/119 (3%) |
| AlbV | 239 | Thp (240 aa) | *X. albilineans* | nd | nd | 0.0 | 240/240 (100%) | 240/240 (100%) | — |
| | | IS transposase (260 aa) | *Yersinia pestis* | AAC82714 | 160 bits (404) | 1e-38 | 87/183 (47%) | 122/183 (66%) | 2/183 (1%) |
| AlbVI | 286 | Hypothetical protein TcmP (276 aa) | *Mycobacterium tuberculosis* | AAK46042 | 138 bits (347) | 6e-32 | 92/224 (41%) | 125/224 (55%) | 18/224 (8%) |
| | | | *Pasteurella multocida* | AAK03406 | 36.6 bits (83) | 0.24 | 32/132 (28%) | 65/132 (49%) | 29/197 (6%) |
| AlbVII | 765 | 4-hydroxybenzoate-CoA ligase (539 aa) | *Rhodopseudomonas palustris* | AAA62604 | 203 bits (513) | 5e-51 | 156/492 (31%) | 242/492 (48%) | 31/492 (6%) |
| AlbVIII | 330 | SyrP Like (339 aa) | *S. verticillus* | AF210249 | 245 bits (619) | 6e-64 | 130/309 (42%) | 182/309 (58%) | 2/309 (0%) |
| | | SyrP (353 aa) | *Pseudomonas syringae* | AAB63253 | 182 bits (458) | 5e-45 | 106/306 (34%) | 155/306 (50%) | 4/306 (1%) |
| AlbIX | 1959 | | | | | | | | |
| NRPS-6 | | XabB (4801 aa) | *X. albilineans* | AAK15074 | 481 bits (1239) | e-135 | 286/608 (47%) | 374/608 (61%) | 23/208 (3%) |
| | | DhbF (1278 aa) | *B. subtilis* | CAB15186 | 354 bits (908) | 1e-96 | 222/608 (36%) | 341/608 (55%) | 21/608 (3%) |
| NRPS-7 | | XabB (4801 aa) | *X. albilineans* | AAK15074 | 874 bits (2258) | 0.0 | 515/1110 (46%) | 682/1110 (61%) | 52/1110 (4%) |
| | | NosA (4379 aa) | *Nostoc* sp. | AF204805 | 551 bits (1420) | e-155 | 388/1148 (33%) | 583/1148 (49%) | 84/1148 (7%) |
| AlbX | 83 | Hypothetical protein (72 aa) | *P. aeruginosa* | AAG05800 | 75.6 bits (185) | 1e-13 | 34/61 (55%) | 44/61 (71%) | — |
| | | MbtH (71 aa) | *M. tuberculosis* | CAB08480 | 59 bits (142) | 9e-09 | 25/55 (45%) | 37/55 (66%) | — |
| AlbXI | 315 | SyrC (433 aa) | *P. syringae* | AAA85161 | 34.4 bits (78) | 1.9 | 23/93 (24%) | 40/93 (42%) | — |
| | | Hydrolase (261 aa) | *S. coelicolor* | CAA16200 | 34 bits (77) | 2.9 | 19/60 (31%) | 30/60 (49%) | — |
| AlbXII | 451 | BoxB (473 aa) | *Azoarcus evansii* | AAK00599 | 293 bits (751) | 3e-78 | 174/448 (38%) | 243/448 (53%) | 12/448 (2%) |

TABLE 4-continued

Summary of results obtained from BLAST analyses.

| Putative Alb protein | No. of aa residues | Protein homolog | Origin | Genbank accession # | Score | Expect | Identities | Positives | Gaps |
|---|---|---|---|---|---|---|---|---|---|
| AlbXIII | 317 | Hypothetical protein (335 aa) | *Caulobacter crescentus* | AAK25001 | 99.5 bits (247) | 5e-200 | 88/296 (29%) | 125/296 (41%) | 5/296 (1%) |
| | | Plasma PAF acetylhydrolase (444 aa) | *Canis familiaris* | AAC48484 | 37.5 bits (86) | | 43/156 (28%) | 56/156 | 44/156 |
| AlbXIV | 496 | Putative trans-membrane efflux protein (505 aa) | *S. coelicolor* | CAB90983 | 225 bits (574) | 0 | 154/465 (33%) | 240/465 (51%) | 8/465 (1%) |
| | | AlbF, putative albicidin efflux pump (496 aa) | *X. albilineans* | AF403709 | 736 bits (1900) | | 496/496 (100%) | 496/496 (100%) | — |
| AlbXV | 584 | Probable carbamoyl transferase (585 aa) | *P. aeruginosa* | AAG08390 | 201 bits (513) | 1e-50 | 158/458 (34%) | 222/458 (47%) | 39/458 (8%) |
| | | BlmD (545 aa) | *S. verticillus* | AAG02370 | 192 bits (506) | 1e-47 | 149/441 (33%) | 209/441 (46%) | 33/441 (7%) |
| AlbXVI | 88 | Transposase (363 aa) | *X. axonopodis* | AF263433 | 64.8 bits (157) | 2e-10 | 27/45 (60%) | 40/45 (88%) | — |
| | | Transposase OrfA (88 aa) | *Desulfovibrio vulgaris* | AAC03166 | 61.0 bits (147) | 3e-09 | 29/54 (53%) | 38/54 (69%) | — |
| AlbXVII | 716 | Para-aminobenzoate synthase (723 aa) | *Streptomyces griseus* | CAC22117 | 503 bits (1295) | e-141 | 302/699 (43%) | 409/699 (58%) | 36/699 (5%) |
| AlbXVIII | 137 | 4-amino-4-deoxychorismate lyase (271 aa) | *P. aeruginosa* | AAG06352 | 81.4 bits (200) | 4e-15 | 46/105 (43%) | 65/105 (61%) | — |
| AlbXIX | 200 | McbG (187 aa) | *E. coli* | CAA30724 | 60.5 bits (145) | 9e-09 | 36/141 (25%) | 58/141 (40%) | 5/141 (3%) |
| AlbXX | 202 | 4-hydroxybenzoate synthase (202 aa) | *E. coli* | AAC77009 | 45.6 bits (107) | 5e-04 | 42/161 (26%) | 21/161 (13%) | — |
| AlbXXI | 278 | XabA (278 aa) | *X. albilineans* | AAG28384 | 430 bits (1106) | 0 | 278/278 (100%) | 278/278 (100%) | — |
| AlbXXII | 634 | Heat shock protein HtpG (634) | *P. aeruginosa* | AAG04985 | 1051 bits (2688) | 0 | 523/634 (82%) | 588/634 (92%) | — |
| | | Heat shock protein HtpG (624) | *E. coli* | AAC73575 | 743 bits (1899) | 0 | 376/624 (60%) | 476/624 (76%) | 4/624 (0%) |

TABLE 5

Comparison of conserved sequences in C domains of peptide synthestases and in putative C domains of the Alb modules

| Core | Sequences conserved in peptide synthetases* | Sequence | Alb module |
|---|---|---|---|
| C1 | SxAQxR(L/M)(W/Y)xL | TYAQERLWLV | NRPS-1 |
| | | STAQERMWFL | NRPS-2 |
| | | SYAQERLWLV | NRPS-3 |
| | | SLFQERLWFV | NRPS-4 |
| | | SYQQERLWFV | NRPS-7 |
| C2 | RHExLRTxF | RHEVLRTRF | NRPS-1 and NRPS-3 |
| | | RHAVLRTHF | NRPS-2 |
| | | RHEILRTRF | NRPS-4 |
| | | RHETLRTRI | NRPS-7 |
| C3 | MHHxISDG(W/V)S | IHHIISDGWS | NRPS-1 and NRPS-3 |
| | | IHHIVFDGWS | NRPS-2 |

TABLE 5-continued

Comparison of conserved sequences in C domains of peptide synthestases and in putative C domains of the Alb modules

| Core | Sequences conserved in peptide synthetases* | Sequence | Alb module |
|---|---|---|---|
| | | MHHLIYDAWS | NRPS-4 |
| | | MHHIICDGWS | NRPS-7 |
| C4 | YxD(F/Y)AVW | YADYALW | NRPS-1 and NRPS-3 |
| | | YADYARW | NRPS-2 |
| | | YADYAIW | NRPS-4 |
| | | YADYATW | NRPS-7 |
| C5 | (I/V)GxFVNT(Q/L)(C/A)xR | IGFFINILPLR | NRPS-1, NRPS-3 and NRPS-4 |
| | | IGLFVNTLAVR | NRPS-2 |
| | | IGFFVNILAVR | NRPS-7 |

TABLE 5-continued

Comparison of conserved sequences in C domains of peptide synthestases and in putative C domains of the Alb modules

| Core | Sequences conserved in peptide synthetases* | Sequence | Alb module |
|---|---|---|---|
| C6 | (H/N)QD(Y/V)PFE | HQSVPFE | NRPS-1 and NRPS-3 |
| | | HQDVPFE | NRPS-2 |
| | | NQALPFE | NRPS-4 |
| | | HRALPFE | NRPS-7 |
| C7 | RDxSRNPL | RDSSQIPL | NRPS-1 and NRPS-3 |
| | | RDTARNPL | NRPS-2 |
| | | RDTSRIPL | NRPS-4 |
| | | RDSSQIPL | NRPS-7 |

*Sourced from Marahiel et al., 1997

TABLE 6

Comparison of conserved sequences in A domains of peptide synthestases and in putative A domains of the Alb modules

| Core | Sequences conserved in peptide synthetases* | Sequence | Alb module |
|---|---|---|---|
| A1 | L(T/S)YxEL | WSYAQL | NRPS-1 and NRPS-3 |
| | | LSYAQL | NRPS-2 |
| | | MSYGQL | NRPS-5 |
| | | FSYRQL | PKS-4 |
| | | LSYAQL | NRPS-6 and NRPS-7 |
| A2 | LKAGxAYL(V/L)P(L/I)D | FKAGACYVPID | NRPS-1 and NRPS-3 |
| | | SLCGAASVLID | NRPS-2 |
| | | MKAGAAYVPID | NRPS-5 |
| | | LAGGLVFAPIN | PKS-4 |
| | | LKAGGCYVPLD | NRPS-6 and NRPS-7 |
| A3 | LAYxxYTSG(S/T)TGxPKG | LACVMVTSGSTGRPKG | NRPS-1 and NRPS-3 |
| | | ?TRTIMVESGSLSSRLL? | NRPS-2 |
| | | PVYCIYTSGSTGSPKG | NRPS-5 |
| | | PAVMICTSGSTGTPKA | PKS-4 |
| | | LAYVMYTSGSTGRPKG | NRPS-6 et NRPS-7 |
| A4 | FDxS | FAVS | NRPS-1 and NRPS-3 |
| | | FDAA | NRPS-2 |
| | | FDLT | NRPS-5 |
| | | FAYG | PKS-4 |
| | | FAIS | NRPS-6 and NRPS-7 |
| A5 | NxYGPTE | NNYGCTE | NRPS-1 and NRPS-3 |
| | | ?AAYGNAE? | NRPS-2 |
| | | NEYGPTE | NRPS-5 |
| | | DGIGCTE | PKS-4 |
| | | YIYGCTE | NRPS-6 and NRPS-7 |

TABLE 6-continued

Comparison of conserved sequences in A domains of peptide synthetases and in putative A domains of the Alb modules

| Core | Sequences conserved in peptide synthetases* | Sequence | Alb module |
|---|---|---|---|
| A6 | GELxIxGxG(V/L)ARGYL | GELHVHSVGMARGYW | NRPS-1 and NRPS-3 |
| | | np | NRPS-2 |
| | | GQIHIGGAGVAIGYV | NRPS-5 |
| | | GSLWVRGNTLTRGYV | PKS-4 |
| | | GEVHIESLGITHGYW | NRPS-6 and NRPS-7 |
| A7 | Y(R/K)TGDL | YKTGDM | NRPS-1 and NRPS-3 |
| | | ?YKTDAL? | NRPS-2 |
| | | YASGDL | NRPS-5 |
| | | ?FDTRDL? | PKS-4 |
| | | YRTGDM | NRPS-6 and NRPS-7 |
| A8 | GRxDxQVKIRGxRIELGEIE | GRQDFEVKVRGHRVDTRQVE | NRPS-1 and NRPS-3 |
| | | ?GSLDVQSRIDDPRIDLCVVE? | NRPS-2 |
| | | GRKDSQIKLRGYRIELGEIE | NRPS-5 |
| | | ?GRMGSAIKINGCWLSPETLE? | PKS-4 |
| | | GRRDYEVKVRGYRVDVRQVE | NRPS-6 and NRPS -7 |
| A9 | LPxYM(I/V)P | LPTYMLP | NRPS-1 and NRPS-3 |
| | | ?LPDYLLP? | NRPS-2 |
| | | LPEYMLP | NRPS-5 |
| | | ?LGKHHYP? | PKS-4 |
| | | LPTYMLP | NRPS-6 and NRPS-7 |
| A10 | NGK(V/L)DR | NGKLDR | NRPS-1 and NRPS-3 |
| | | ?HGRVDL? | NRPS-2 |
| | | NGKVNR | NRPS-5 |
| | | ?SGKVIR? | PKS-4 |
| | | NGKLDT | NRPS-6 and NRPS-7 |

*Sourced from Marahiel et al., 1997
?non conserved sequences
np: not present

TABLE 7

Comparison of conserved sequences in PCP and TE domains of peptide synthetases and in putative PCP and TE domains of the Alb modules

| Domain | Sequences conserved in peptide synthetases* | Sequence | Alb module (domain) |
|---|---|---|---|
| PCP | DxFFxxLGG(H/D)S(L/I) | D-FFAVGGHSVL | PKS-3 (PCP1) |
| | | DNFFALGGHSLS | NRPS-1 and NRPS-3 |

TABLE 7-continued

Comparison of conserved sequences in PCP and TE domains of peptide synthetases and in putative PCP and TE domains of the Alb modules

| Domain | Sequences conserved in peptide synthetases* | Sequence | Alb module (domain) |
|---|---|---|---|
| | | | (PCP2 and PCP4) |
| | | DNFFELGGHSVL | NRPS-2 (PCP3) |

TABLE 7-continued

Comparison of conserved sequences in PCP and TE domains of peptide synthestases and in putative PCP and TE domains of the Alb modules

| Domain | Sequences conserved in peptide synthetases* | Sequence | Alb module (domain) |
|---|---|---|---|
| | | DNFFELGGHSLS | NRPS-5 (PCP5) |
| | | DNFFNLGGHSLL | NRPS-6 and NRPS-7 (PCP6 and PCP7) |
| TE | G(H/Y)SxG | GWSSG | NRPS-7 |

*Sourced from Marahiel et al., 1997

TABLE 8

| Domains | Position in GsrA (Phe) and variability 235 0 | 236 +/− | 239 ++ | 278 ++ | 299 ++ | 301 +/− | 322 ++ | 330 +/− | 331 ++ | 517 0 |
|---|---|---|---|---|---|---|---|---|---|---|
| Alb NRPS-1 | A | V | K | Y | V | A | N | D | A | K |
| Alb NRPS-3 | A | V | K | Y | V | A | N | D | A | K |
| TyrB-M1 (Pro) | D | V | Q | S | I | A | N | V | V | K |
| VirS (Pro) | D | V | Q | Y | A | A | H | V | M | K |
| HVCL | G | A | L | H | V | V | G | S | I | K |
| Alb NRPS-6 | A | I | K | Y | F | S | I | D | M | K |
| Alb NRPS-7 | A | I | K | Y | F | S | I | D | M | K |

TABLE 8-continued

| Domains | Position in GsrA (Phe) and variability 235 0 | 236 +/− | 239 ++ | 278 ++ | 299 ++ | 301 +/− | 322 ++ | 330 +/− | 331 ++ | 517 0 |
|---|---|---|---|---|---|---|---|---|---|---|
| VirS (Pro) | D | V | Q | Y | A | A | H | V | M | K |
| EntF-M1 (Ser) | D | V | W | H | F | S | L | V | D | K |
| β-Ala code | V | D | W | V | I | S | L | A | D | K |
| Alb NRPS-5 | D | L | T | K | I | G | E | V | G | K |
| BacC-M5 (Asn) | D | L | T | K | I | G | E | V | G | K |
| TyrC-M1 (Asn) | D | L | T | K | I | G | E | V | G | K |
| Asn code | D | L | T | K | L | G | E | V | G | K |

TABLE 9

Complementation studies of Xa23RI insertion mutants

| Donor | Recipient AM12 | AM13 | AM36 | AM10 | AM15 |
|---|---|---|---|---|---|
| pEV639 | + | + | + | − | − |
| pEValbXXII | + | + | + | − | − |
| pEVHtpG | + | + | + | − | − |
| pALB639 | + | + | + | − | − |
| pUFR043 | − | − | − | − | − |
| none | − | − | − | − | − |

+: restoration of albicidin production by alb[−] mutant,
−: no complementation.
All experiments were performed at least in duplicate with at least 2 exconjugants obtained from two independent triparental conjugations.

TABLE 10

Albicidin production assays with *X. axonopodis* pv. *vesicatoria* exconjugants harbouring different plasmids: analysis of growth inhibition of *E. coli* DH5αKT (susceptible to albicidin) and DH5αAlb[r]KT (resistant to albicidin) in assays performed with different antibiotic combinations (no antibiotic, tetracycline only, kanamycin only and tetracycline + kanamycin).

| Bioassay medium containing | Tester strain | Combination of plasmids: pUFR043 and pLAFR3 | pUFR043 and pOp3-4/XALB2-3 | PALB571 and pLAFR3 | PALB571 and pOp3-4/XALB2-3 |
|---|---|---|---|---|---|
| No antibiotic | DH5αKT | − | − | − | − |
| | DH5αAlb[r]KT | − | − | − | − |
| Tetracycline | DH5αKT | − | − | − | + |
| | DHSαAlb[r]KT | − | − | − | − |
| Kanamycin | DH5αKT | + | + | + | + |
| | DH5αAlb[r]KT | + | + | + | + |
| Tetracycline + kanamycin | DH5αKT | + | + | + | + |
| | DH5αAlb[r]KT | + | + | + | + |

+: presence of a growth inhibition zone
All experiments were performed at least in duplicate with at least 2 exconjugants obtained from two independent triparental conjugations.

REFERENCES

1. Albertini, A. M., Caramori, T., Scoffone, F., Scotti, C. & Galizzi, A. (1995). Sequence around the 159 degree region of the *Bacillus subtilis* genome: the pksX locus spans 33.6 kb. *Microbiology* 141, 299-309.
2. Altschul, S. F., Madden, T. L., Schäffer, A. A., Zhang, J., Zhang, Z., Miller, W. & Lipman, D. J. (1997), "Gapped BLAST and PSI-BLAST: a new generation of protein data base search programs," *Nucleic Acids Res.* 25, 3389-3402.
3. Aparicio, J. F., Molnar, I., Schwecke, T., Konig, A., Haydock, S. F., Khaw, L. E., Staunton, J. & Leadlay, P. F. (1996). Organization of the biosynthetic gene cluster for rapamycin in *Streptomyces hygroscopicus*: analysis of the enzymatic domains in the modular polyketide synthase. *Gene* 169, 9-16.
4. Astua-Monge, G., Minsavage, G. V., Stall, R. E., Davis, M. J., Bonas, U. and Jones, J. B. (2000). Resistance of tomato and pepper to T3 strains of *Xanthomonas campestris* pv. *vesicatoria* is specified by a plant-inducible avirulence gene. Mol. Plant Microbe Interact. 13:911-21.
5. August, P. R., Tang, L., Yoon, Y. J., Ning, S., Muller, R., Yu, T. W., Taylor, M., Hoffmann, D., Kim, C. G., Zhang, X., Hutchinson, C. R. & Floss, H. G. (1998). Biosynthesis of the ansamycin antibiotic rifamycin: deductions from the molecular analysis of the rif biosynthetic gene cluster of *Amycolatopsis mediterranei* S699. *Chem. Biol.* 5, 69-79.
6. Bardwell, J. C. & Craig, E. A. (1988). Ancient heat shock gene is dispensable. *J. Bacteriol.* 170, 2977-83.
7. Birch, R. G. (2001). *Xanthomonas albilineans* and the antipathogenesis approach to disease control. *Mol. Plant Pathol.* 2, 1-11.
8. Birch, R. G. & Patil, S. S. (1983). The relation of blocked chloroplast differentiation to sugarcane leaf sca1 disease. *Phytopathology* 73, 1368-1374.
9. Birch, R. G. & Patil, S. S. (1985a). June 1985. Antibiotic and process for the production thereof U.S. Pat. No. 4,525, 354.
10. Birch, R. G. & Patil, S. S. (1985b) Preliminary characterization of an antibiotic produced by *Xanthomonas albilineans* which inhibits DNA synthesis in *Escherichia coli. J. Gen. Microbiol.* 131, 1069-1075.
11. Birch, R. G. & Patil, S. S. (1987a). Correlation between albicidin production and chlorosis induction by *Xanthomonas albilineans*, the sugarcane leaf scald pathogen. *Physiol. Mol. Plant Pathol.* 30, 199-206.
12. Birch, R. G. & Patil, S. S. (1987b). Evidence that an albicidin-like phytotoxin induces chlorosis in sugarcane leaf scald disease by blocking plastid DNA replication. *Mol. Plant Pathol.* 30, 207-214.
13. Borkovich, K. A., Farrelly, F. W., Finkelstein, D. B., Taulien, J. & Lindquist, S. (1989). Hsp82 is an essential protein that is required in higher concentrations for growth of cells at higher temperatures. *Mol. Cell. Biol.* 9, 3919-30.
14. Brendel, V. & Trifonov, E. N. (1984). A computer algorithm for testing potential prokaryotic terminators. *Nucl. Acids Res.* 12 4411-4427.
15. Cane, D. E. (1997). A special thematic issue on polyketide and nonribosomal polypeptide biosynthesis. *Chem. Rev.* 97, 2463-2706.
16. Cane, D. E., Walsh, C. T. & Khosla, C. (1998). Harnessing the biosynthetic code: combinations, permutations, and mutations. *Science* 282, 63-8.
17. Cane, D. E. & Walsh, C. T. (1999). The parallel and convergent universes of polyketide synthases and nonribosomal peptide synthetases. *Chem. Biol.* 6, R319-R325.
18. Challis, G. L., Ravel, J. & Townsend, C. A. (2000). Predictive, structure-based model of amino acid recognition by nonribosomal peotide synthetase adenylation domains. *Chem. Biol.* 7, 211-224.
19. Conti, E., Stachelhaus, T. Marahiel, M. A. & Brick, P. (1997). Structural basis for the activation of phenylalanine in the non-ribosomal biosynthesis of gramicidin S. *EMBO J.* 16, 4174-4183.
20. Criado, L. M., Martin, J. F. & Gil, J. A. (1993). The pab gene of *Streptomyces griseus*, encoding p-aminobenzoic acid synthase, is located between genes possibly involved in candicidin biosynthesis. *Gene* 126, 135-139.
21. Cutforth, T. & Rubin, G. M. (1994). Mutations in Hsp83 and cdc37 impair signaling by the sevenless receptor tyrosine kinase in *Drosophila. Cell.* 77, 1027-36.
22. De Feyter, R. & Gabriel, D. W. (1991). Use of cloned DNA methylase genes to increase the frequency of transfer of foreign genes into *Xanthomonas campestris* pv. *malvacearum. J. Bacteriol.* 173, 336-342.
23. von Döhren, H., Dieckmann, R. & Pavela-Vrancic, M. (1999). The nonribosomal code. *Chem. Biol.* 6, R273-R279.
24. Du, L., Sanchez, C., Chen, M., Edwards, D. J. & Shen, B. (2000). The biosynthetic gene cluster for the antitumor drug bleomycin from *Streptomyces verticillus* ATCC15003 supporting functional interactions between nonrobosomal peptide synthetases and a polyketide synthase. *Chem. Biol.* 7, 623-642.
25. Duitman, E. H., Hamoen, L. W., Rembold, M., Venema, G., Seitz, H., Saenger, W., Bernhard, F., Reinhardt, R., Schmidt, M., Ullrich, C., Stein, T., Leenders, F. & Vater, J. (1999). The mycosubtilin synthetase of *Bacillus subtilis* ATCC6633: a multifunctional hybrid between a peptide synthetase, an amino transferase, and a fatty acid synthase. *Proc. Natl. Acad. Sci. USA* 96, 13294-13299.
26. Gabriel, D. W & De Feyter, R. (1992). RFLP analyses and gene tagging for bacterial identification and taxonomy. In *Molecular Plant Pathology: A Practical Approach* (Gurr, S. J., McPherson, M. J. & Bowles, D. J. Ed.), vol 1, pp51-66, IRL Press, Oxford.
27. Garrido, M. C., Herrero, M., Kolter, R. & Moreno, F. (1988). The export of the DNA replication inhibitor Microcin B17 provides immunity for the host cell. *EMBO J.* 7, 1853-1862.
28. Gehring, A. M., DeMoll, E., Fetherston, J. D., Mori, I., Mayhew, G. F., Blattner, F. R., Walsh, C. T. & Perry, R. D. (1998). Iron acquisition in plague: modular logic in enzymatic biogenesis of yersiniabactin by *Yersinia pestis. Chem. Biol.* 5, 573-86.
29. Guenzi, E., Galli, G., Grgurina, I., Gross, D. C. & Grandi, G. (1998). Characterization of the syringomycin synthetase gene cluster. A link between prokaryotic and eukaryotic peptide synthetases. *J. Biol. Chem.* 273, 32857-32863.
30. Huang, G., Zhang, L. & Birch, R. G. (2000a). Analysis of the genes flanking xabB: a methyltransferase gene is involved in albicidin biosynthesis in *Xanthomonas albilineans. Gene* 255, 327-333.
31. Huang, G., Zhang, L. & Birch, R. G. (2000b). Albicidin antibiotic and phytotoxin biosynthesis in *Xanthomonas albilineans* requires a phosphopantetheinyl transferase gene. *Gene* 258, 193-199.
32. Huang, G., Zhang, L. & Birch, R. G. (2001). A multifunctional polyketide-peptide synthetase essential for albicidin biosynthesis in *Xanthomonas albilineans. Microbiology* 147, 631-642.

33. Jakob, U., Lilie, H., Meyer, I. & Buchner, J. (1995). Transient interaction of Hsp90 with early unfolding intermediates of citrate synthase. Implications for heat shock in vivo. *J. Biol. Chem.* 270, 7288-94.

34. Konz, D., Klens, A., Schorgendorfer, K. & Marahiel, M. A. (1997). The bacitracin biosynthesis operon of *Bacillus licheniformis* ATCC10716: molecular characterization of three multi-modular peptide synthetase. *Chem. Biol.* 4, 927-937.

35. Leong, S. A., Ditta, G. S. & Helinski, D. R. (1982). Heme biosynthesis in *Rhizobium*: identification of a cloned gene coding for aminolevulinic acid synthetase from *Rhizobium meliloti*. *J Biol. Chem.* 257, 8724-8730.

36. Li, Y. M., Milne, J. C., Madison, L. L., Kolter, R. & Walsh, C. T. (1996). From peptide precursors to oxazole and thiazole-containing peptide antibiotics: microcin B17 synthase. *Science.* 274, 1188-93.

37. Liu, J., Duncan, K. & Walsh, C. T. (1989). Nucleotide sequence of a cluster of *Escherichia coli* enterobactin biosynthesis genes: identification of ent A and purification of its product 2,3-dihydro-2,3-dihydroxybenzoate deshydrogenase. *J. Bacteriol.* 171, 791-798.

38. Marahiel, M. A. Stachelhaus, T. & Mootz, H. D. (1997). Modular peptide synthetases involved in nonribosomal peptide synthesis. *Chem. Rev.* 97, 2651-2673.

39. Mayorga, M. E. & Timberlake, W. E. (1992). The developmentally regulated *Aspergillus nidulans* wA gene encodes a polypeptide homologous to polyketide and fatty acid synthases. *Mol. Gen. Genet.* 235, 205-212.

40. McCarthy, J. E. & Gualerzi, C. (1990). Translational control of prokaryotic gene expression. *Trends Genet.* 6, 78-85.

41. McDaniel, R., Thamchaipenet, A., Gustafsson, C., Fu, H., Betlach, M. & Ashley, G. (1999). Multiple genetic modifications of the erythromycin polyketide synthase to produce a library of novel "unnatural" natural products. *Proc. Natl. Acad. Sci. USA* 96, 1846-1851.

42. Milne, J. C., Roy, R. S., Eliot, A. C., Kelleher, N. L., Wokhlu, A., Nickels, B. & Walsh, C. T. (1999). Cofactor requirements and reconstitution of microcin B17 synthetase: a multienzyme complex that catalyzes the formation of oxazoles and thiazoles in the antibiotic microcin B17. *Biochemistry.* 38, 4768-81.

43. Mohamed, I. S., Rott, P., Davis, M. J. & Chatenet, M. (1996). Differentiation of *Xanthomonas albilineans* strains based on multiplication of the pathogen in sugarcane varieties. In *Proceedings XXII Congress of the International Society of Sugarcane Technologists*. (Cock J. H. and Brekelbaum T. Ed.), vol. 2, pp486-492, Cartagena De Indias, Colombia, 5-14 September 1995.

44. Mohamed, M. E., Zaa, A., Ebenau-Jehle, C. & Fuchs, G. (2001). Reinvestigation of a new type of aerobic benzoate metabolism in the proteobacterium *Azoarcus evansii*. *J. Bacteriol.* 183, 1899-1908.

45. Motamedi, H. & Shafiee, A. (1998). The biosynthetic gene cluster for the macrolactone ring of the immunosuppressant FK506. *Eur. J. Biochem.* 256, 528-534.

46. Normark, S., Bergström, S., Edlund, T., Grundström, T., Jaurin, G., Lindberg, F. P. & Olsson O. (1983). Overlapping genes. *Annu. Rev. Genet.* 17, 499-525.

47. Paitan, Y., Orr, E., Ron, E. Z. & Rosenberg, E. (1999). Genetic and functional analysis of genes required for the post-modification of the polyketide antibiotic TA of *Myxococcus xanthus*. *Microbiology* 145, 3059-67.

48. Pfeifer, B. A., Admiraal, S. J., Gramajo, H., Cane, D. E. & Khosla C. (2001). Biosynthesis of complex polyketides in a metabolically engineered strain of *E. coli*. *Science* 291, 1790-1792.

49. Quadri, L. E., Sello, J., Keating, T. A., Weinreb, P. H. & Walsh, C. T. (1998). Identification of a *Mycobaterium tuberculosis* gene cluster encoding the biosynthetic enzymes for assembly of the virulence-conferring siderophore mycobactin. *Chem. Biol.* 5, 631-645.

50. Ricaud, C. & Ryan, C. C. (1989). Leaf scald. In *Diseases of sugarcane: major diseases*. (Ricaud, C. Egan, B. T., Gillaspie, Jr., A. G. & Hughes, C. G. ed.), pp. 39-58, Elsevier Science Publishers B.V., Amsterdam.

51. Rodriguez, E. & McDaniel, R. (2001). Combinatorial biosynthesis of antimicrobials and other natural products. *Curr. Opin. Microbiol.* 4, 526-34.

52. Rott, P. C., Costet, L., Davis, M. J., Frutos, R. & Gabriel D. W. (1996). At least two separate gene clusters are involved in albicidin production by *Xanthomonas albilineans*. *J. Bacteriol.* 178, 4590-4596.

53. Rott, R. & Davis, M. J. (2000). Leaf scald. In *A guide to sugarcane diseases*. (Rott, P., Bailey, R. A., Comstock, J. C., Croft, B. J. and Saumtally, A. S. ed.), pp. 38, Cirad/Issct, Montpellier.

54. Sambrook, J., Fritsch, E. F. & Maniatis, T. (1989) *Molecular cloning: A laboratory Manual* ($2^{nd}$ edn), Cold Spring Harbor Lab. Press, Plainview, N.Y.

55. Sanger, F., Nicklen, S. & Coulson, A. R. (1977). DNA sequencing with chain-terminating inhibitors. *Proc. Natl. Acad. USA* 74, 5463-5467

56. Siebert, M., Bechthold, A., Melzer, M., May, U., Berger, U. Schroder, G., Schroder, J., Severin, K. & Heide, L. (1992). Ubiquinone biosynthesis. Cloning of the genes coding for chorismate pyruvate-lyase and 4-hydrobenzoate octaprenyl transferase from *Escherichia coli*. *FEBS Lett.* 307, 347-350.

57. Stachelhaus, T., Mootz, H. D. & Marahiel, M. A. (1999). The specificity-conferring code of adenylation domains in nonribosomal peptide synthetases. *Chem. Biol.* 6, 493-505.

58. Staskawicz, B. Dahlbeck, D., Keen, N. and Napoli, C. (1987). Molecular characterization of cloned avirulence genes from race 0 and race 1 of *Pseudomonas syringae* pv. *glycenea*. J. Bacteriol. 169: 5789-5794.

59. Takano, Y., Kubo, Y., Shimizu, K., Mise, K., Okuno, T. & Furusawa, I. (1995). Structural analysis of PKS1, a polyketide synthase gene involved in melanin biosynthesis in *Colletotrichum lagenarium*. *Mol. Gen. Genet.* 249, 162-167.

60. Tang, L., Yoon, Y. J., Choi, C. Y. & Hutchinson, C. R. (1998). Characterization of the enzymatic domains in the modular polyketide synthase involved in rifamycin B biosynthesis by *Amycolatopsis mediterranei*. *Gene* 216, 255-65.

61. Thomas, J. G. & Baneyx, F. (2000). ClpB and HtpG facilitate de novo protein folding in stressed *Escherichia coli* cells. *Mol. Microbiol.* 36, 1360-70.

62. Valdez, F., Gonzalez-Ceron, G., Kieser, H. M., Servin-Gonzalez, L. (1999). The *Streptomyces coelicolor* A3(2) lipAR operon encodes an extracellular lipase and a new type of transcriptional regulator. *Microbiology* 145, 2365-74.

63. Wall, M. K. & Birch, R. G. (1997). Genes for albicidin biosynthesis and resistance span at least 69 kb in the genome of *Xanthomonas albilineans*. *Lett. Appl. Microbiol.* 24,256-260.

64. Yakimov, M. M., Kroger, A., Slepak, T. N., Giuliano, L., Timmis, K. N. & Golyshin, P. N. (1998). A putative lichenysin A synthase operon in *Bacillus licheniformis*: initial characterization. *Biochim. Biophys. Acta.* 1399, 141-153.

65. Yazgan, A., Ozcengiz, G. & Marahiel M. A. (2001). Tn10 insertional mutations of *Bacillus subtilis* that block the biosynthesis of bacilysin. *Biochim. Biophys. Acta.* 1518, 87-94.

66. Yu, J. H. & Leonard, T. J. (1995). Sterigmatocystin biosynthesis in *Aspergillus nidulans* requires a novel type I polyketide synthase. *J. Bacteriol.* 177, 4792-4800.

67. Yu, S., Fiss, E., & Jacobs, W. R. (1998). Analysis of the exochelin locus in *Mycobacterium smegmatis*: biosynthesis genes have homology with genes of the peptide synthetase family. *J. Bacteriol.* 180, 4676-4685.

68. Zhang, L. & Birch, R. G. (1997). The gene for albicidin detoxification from *Pantoea dispersa* encodes an esterase and attenuates pathogenicity of *Xanthomonas albilineans* to sugarcane. *Proc. Natl. Acad. Sci. USA* 94, 9984-9989.

69. Zhang, J. H., Quigley, N. B. & Gross, D. C. (1995). Analysis of the syrB and syrC genes of *Pseudomonas syringae* pv. *syringae* indicates that syringomycin is synthesized by a thiotemplate mechanism. *J. Bacteriol.* 177, 4009-4020.

70. Zhang, J. H., Quigley, N. B. & Gross, D. C. (1997). Analysis of the syrP gene, which regulates syringomycin synthesis by *Pseudomonas syringae* pv. *syringae*. *Appl. Environ. Microbiol.* 63, 2771-2778.

71. Zhang, L., Xu, J. & Birch, R. G. (1998). Factors affecting biosynthesis by *Xanthomonas albilineans* of albicidins antibiotics and phytotoxins. *J. Appl. Microbiol.* 85, 1023-1028.

72. Zhang L., Xu, J. & Birch, R. G. (1999). Engineered detoxification confers resistance against a pathogenic bacterium. *Nat Biotechnol.* 17:1021-1024.

We claim:

1. A transformed isolated host cell that comprises one or more genetic constructs that comprises SEQ ID NO: 1, SEQ ID NO:2 and SEQ ID NO:3, wherein said transformed host cell produces albicidin.

2. The transformed isolated host cell of claim 1 wherein said genetic construct contains a combination of SEQ ID NO:1, SEQ ID NO:2 and SEQ ID NO:3.

3. The transformed isolated host cell claim 1 wherein said host cell has been transformed with a first genetic construct comprising SEQ ID NO:1, a second genetic construct comprising SEQ ID NO:2 and a third genetic construct comprising SEQ ID NO:3.

4. A transformed isolated host cell comprising one or more polynucleotides encoding a biosynthetic pathway for albicidin production, said polynucleotides encoding SEQ ID NO: 26, 27, 28, 29, 30, 31, 32, 33, 34, 35, 36, 37, 39, 39, 40, 41, 42, 43, 44, 45, 46 and 47 and wherein said host cell produces albicidin.

5. A combination of isolated polynucleotides that encodes SEQ ID NO: 26, 27, 28, 29, 30, 31, 32, 33, 34, 35, 36, 37, 39, 39, 40, 41, 42, 43, 44, 45, 46 and 47.

6. The combination of isolated polynucleotides according to claim 5, wherein said combination of polynucleotides comprises SEQ ID NO: 1, SEQ ID NO: 2 and SEQ ID NO: 3.

7. A method of making an antibiotic comprising culturing a transformed host cell according to claim 4 under conditions that allow for the production of said antibiotic.

8. The method according to claim 7, further comprising the isolation of said antibiotic.

* * * * *

UNITED STATES PATENT AND TRADEMARK OFFICE

CERTIFICATE OF CORRECTION

PATENT NO. : 7,510,852 B2
APPLICATION NO. : 10/531351
DATED : March 31, 2009
INVENTOR(S) : Monique Royer et al.

It is certified that error appears in the above-identified patent and that said Letters Patent is hereby corrected as shown below:

Column 4,
Line 23, “P14687 SEQ ID NO: 132” should read --P14687 (SEQ ID NO: 132)--.
Line 56, “RitE-1” should read --RifE-1--.

Column 10,
Line 60, “Vols. I, II, and II” should read --Vols. I, II, and III--.

Column 16,
Line 19, “Proc. Natl. Acad. Sci. U.S.” should read --Proc. Natl. Acad. Sci. U.S.A.--.
Line 23, “Proc. Natl. Acad. Sci. U.S.” should read --Proc. Natl. Acad. Sci. U.S.A.--.

Column 22,
Line 21, “protecting a plant; against” should read --protecting a plant against--.
Line 40, “kanamnycin” should read --kanamycin--.

Column 26,
Line 31, “(5'tgeccacaggccgtcgagt3')” should read --(5'tgcccacaggccgtcgagt3')--.

Column 27,
Line 4, “SEQ D No: 6” should read --SEQ ID No: 6--.
Line 53, “J-ketoacyl synthase” should read --β-ketoacyl synthase--.

Column 29,
Line 22, “albXV” should read --albXI--.
Line 60, “motifI involved” should read --motif I involved--.

Column 31,
Line 15, “AlbXVI” should read --AlbXVII--.
Line 20, “albXVII” should read --albXVIII--.
Line 21, “AlbXIII” should read --AlbXVIII--.
Lines 35-36, “(5'cgttgaggatgcagcgctcg31')” should read --(5'cgttgaggatgcagcgctcg3')--.

Column 34,
Line 7, “from *Comamnonas*” should read --from *Comamonas*--.

UNITED STATES PATENT AND TRADEMARK OFFICE

CERTIFICATE OF CORRECTION

PATENT NO. : 7,510,852 B2
APPLICATION NO. : 10/531351
DATED : March 31, 2009
INVENTOR(S) : Monique Royer et al.

It is certified that error appears in the above-identified patent and that said Letters Patent is hereby corrected as shown below:

Column 36,
Line 9, “BLm (&Ala)” should read --Blm (β-Ala)--.
Line 27, “confined” should read --confirmed--.
Line 58, “from albX” should read --from albXIX--.

Column 40,
Lines 63-64, “and XhoSalXaHT1PGF 5'cgatatcgccttcctcgagggtategataagc3'” should read --and XhoSalXaHTPGF 5'cgatatcgccttcctcgagggtatcgataagc3'--.

Column 41,
Line 14, “pUFR043-pOp34/XALB2-3” should read --pUFR043-pOp3-4/XALB2-3--.
Line 15, “pAlb571-pOp3A4XALB2-3” should read --pAlb571-pOp3-4/XALB2-3--.

Column 42,
Line 29, “Because albXVII” should read --Because albXVIII--.
Line 46, “confining” should read --confirming--.

Column 43,
Line 51, “stain Xa13” should read --strain Xa13--.
Line 64, “and albIV)” should read --and albIX)--.

Column 45,
Line 47, “PKS4 module” should read --PKS-4 module--.

Column 47,
Line 58, “AbVII HBCL” should read --AlbVII HBCL--.

Column 49,
Line 14, “identical to albX)” should read --identical to albXXI)--.

Column 51,
Table 1, row “pBC/f”, “2.5 kb Kpn I-EdoR I” should read --2.5 kb Kpn I-EcoR I--.

Column 53,
Table 1, row “pBKS/XALB3XhoI”, “pBKS/XALB3 with a KhoI site” should read --pBKS/XALB3 with a XhoI site--.

UNITED STATES PATENT AND TRADEMARK OFFICE

CERTIFICATE OF CORRECTION

PATENT NO. : 7,510,852 B2
APPLICATION NO. : 10/531351
DATED : March 31, 2009
INVENTOR(S) : Monique Royer et al.

It is certified that error appears in the above-identified patent and that said Letters Patent is hereby corrected as shown below:

Column 60,
Table 4, row "AlbXIII", Columns "Identities", "Positives", "Gaps",
"43/156 56/156 44/156
(28%)"
should read --43/156 56/156 44/156 (28%)--.

Column 66,
Table 10, row "Tetracycline",
"DH5αKT
DHSαAlb$^r$KT" should read --DH5αKT
DH5αAlb$^r$KT--.

Column 264,
Line 26, "36, 37, 39, 39, 40" should read --36, 37, 38, 39, 40--.
Lines 30-31, "36, 37, 39, 39, 40" should read --36, 37, 38, 39, 40--.

Signed and Sealed this

Twenty-third Day of June, 2009

John Doll

JOHN DOLL
*Acting Director of the United States Patent and Trademark Office*

SEQUENCE LISTING

```
<160> NUMBER OF SEQ ID NOS: 54

<210> SEQ ID NO 1
<211> LENGTH: 55839
<212> TYPE: DNA
<213> ORGANISM: Xanthomonas albilineans

<400> SEQUENCE: 1

gaattctttc gccattgccc gggattgatg actggcatcg ggattgtcgg gaccttctct      60

ggcttgttgc tcggtctgca tcagttcgcg gatgctatcg cgccgaaggc caccgcgttg     120

gctactccgg tgcggcagat tggagcgatg ggacatgcac ccgctagcgc ggccagtgcg     180

ccgatgactg gcggggtgtt cgtctctttt tccgcaacgc cggtgcgatt gcccgcggta     240

acaggcatga aggttctcaa tgagggccat gacggcatgg cgggcgcggc tatcactcat     300

gcggcggtaa aaccggtgat ggctccattg acaggggaca tgttgacagg cgcgttgagc     360

tgcctgctgc acagcgtgtc gggcgctttc ctcgtttcgg ccattgcggt gttgtgcgcg     420

cttttgacca cgttcgtcga aaagttacta gtggcgcaat gctttcatca gcttcaggaa     480

ctgtcgtcga cgattgaccg actgttcgca tttaatcctg gcgacgatcc gatgatgcgt     540

ttgacgttga cgtcggaatc gacagagcgg ctaatcaagc ggatcgcgct tgcattagac     600

gacattgcaa tttcgcgaga tcaagttcag tgagatttta tcgatacgga tttcctgtgc     660

ggcgtgacgt cgagcgtggc caggaagaaa gccccttctg gatttcgctg tcagacatga     720

tgaccggcat gaccgcgctt tttctggtgc tggcctgcag catgctgcta atgcgcatca     780

ccgaatcgaa atcgcccagt ggaacgtcgc ccagcgacga gaaagtcgtt gataccgccg     840

cgccgacgca gcgcaacgag cgttccgtgg gtgcggcagt gaacgcttcg catgatgcga     900

accgacttgc tacctacgaa tcggatattt ccaccgtgtt gaaaaatata tcggcgttat     960

cgcagaaata cggattttcg gtcgatgcta ccactaacac gatcgatctc ggccagtcgg    1020

ggctattccc gcttggaagc gaccgcttga gcgcgacaca ggaaaggttg ctgcgcaatt    1080

atgtcgccga tctcatcgca ctgactcaga acgatccggc catggcacca ttgaagagca    1140

tcaccgtggt cggctataca gatccggctg ggtcgtatct gttcaatctc gatctgagtg    1200

cgcgccgcag cgaacgcctg atgtgcgtgc tacttgccac gctggaaaaa cagagtagca    1260

cgacaggtgc accgacgatg accgaggact cgctgcagac catccggcac ctgttcaggg    1320
```

-continued

```
ttggcggcta ttccgccgac gcacagaagg aaagtgccgc agcaagcagg cgattagcgt   1380
tgaagctgga tttttacaag atcgacgagc cccggcggca agccgctgtg cttgcgatgc   1440
cggtcgggtc gtgcgcgctt ggatcgcgtt agggaaggtc tgaataaccc cctccccagt   1500
aatgcaattt attgatttta taggtgtgaa taagagcgga taacaaaaca tagcgagcga   1560
ctctcaggcg taccgcgcag cacgcaggaa ccggtgtgta cgagtggtac ataaggaatc   1620
cgagcacagc acgcgcccgt ctggcggaca cgcagtagtt ttgttagctg ctctaagcgc   1680
aggatgaggt taatcagagc atcactaaca ggaatgatag tttggaaacg ataacaagta   1740
ttgcgccgtg cgcgctgccg gatgtctggc gtcatgccgc cgaaggcaag accgtcgcct   1800
cgttcgactg cttcgatacg ctgctgtggc gtggcgtgag cgcgccgagc caagtttttt   1860
gtgagttggc cggcaagccg ccgttttcga cgcaaggcta taccgcctac catcgcgtga   1920
tggccgaatc gttggcgcgt cgtgtccggt ttgaacagaa agaggttcca gaagtcacgc   1980
tgcgcgaggt gtatcagcag ttattcccgg agcctgacga tgcaacccgg ataacggcat   2040
gcatggcgtg cgaacaggaa gctgaggcat cgatctgctt cgtcgtgcca gctgtgattg   2100
cctgcatgcg cgaagccagg cgcttgggga tgaccattat cgtcgtcagc gatacctatt   2160
ttaacgctgg ccagctgcgt gcactcattg cgtcagtgtc gcccgaagcc gacgagctgg   2220
tcgaccggat cttctgctct tccgactatc ggaccatgaa gaagtaccag ctatggcacc   2280
gcgtgctcga cgaactgtac gcagcacctg aaacaatcgt gcatttaggc gacaatcgcg   2340
tcgccgacat actaatgccg tcgaagctgg gcatcgcgtg cctgtggcta gatcggtatg   2400
ccggtgcagc catgaccgtg ttgcgccgac gcgaatgcgc gacccgattg atattcagcg   2460
gcgttgaaga gactcggtcc gtgtggacac tttacgacgg cctcgactgt cgaacgcaag   2520
ccgagcgttc gaactggcat gatgaactcg gctggcactt tcttggaccg gtggtctttg   2580
cttttgcgaa aacgctggcc gacgaatttg ccggccaaac acacggaatt gatcagccga   2640
cggttcgctt cgggtttctg atgcgcgatg ctcatctgtt acgcgaagct gcggatatcg   2700
tcgcacctca tgagccgcat ccgtcattgc acatcagtcg aaagaccgcg ttctctgcgt   2760
ccttcgatag tgacgatgcc attctgcatt tcgtcaagtt gggcaggctc gaatatcggt   2820
tgagtgccgc gcaatgtggc gtctgtctac ttctgaacga ggtagagaaa gcgcgtctgg   2880
cggaagcgtt catggcaaaa gaagacacag caggtgcaat gcgggaattt ttttctccgc   2940
agatgttgga cgctatcaag acgcgttcga aagcgttccg tgccaggctc atcaggcaca   3000
tcgtcgcgca gacaggactc aagcgcggcg acacattatg tctcgtcgat acaggttata   3060
atggaacgat tcaatacttg ctgcatgatg tattgcgtaa ggaaatgaac gtcaccgtca   3120
tcggacggta tctaatctac cggcagaacc tcagactgca cggaagggca tcgggcctca   3180
tcgacgaatc gtggctcgac cacggactga ttcatacgct ctcgcagtcg ggtctgtcgt   3240
atctagaggc gctatgcgcc ggtgctggcg gctgcgttgt cgactatgcg cagaatgggc   3300
gctccgtctg caatgcggag atggtctgcc gctcgccatg gatagacgca tgccagcgta   3360
tggcgctgat gttcgtcaat caggtttgcg cctcatccgc gtccgagctg ccgaagctga   3420
cgcgtagccg tttacgcgag tccgcattga cgaacatcag cgccatgctg tttttcccca   3480
gcgagtgcga attgtccgag atcagtcaga tgcagggggga agtgaatctc ggcgccgata   3540
tctgccacag cctgtgcgat ccagaaaaag gcctgagtgg attgcggcgg cgggggctgc   3600
tttatatgac tggcggtggc gagtttcgga gcaattggcc ttttgagctg cgttatgcgg   3660
```

-continued

```
gcgcagatca gctggccctt tacatggcgt gctttcgcaa cggtttgcgg atgaccgagc   3720
ctgcgttttc ttaccgccac attacattgc cgctgacatt cgcatttgaa gcagacgtcg   3780
cgcgtcgatg cgtgcccgca catgcgacat atgatggata ttacactgcc gtttttccac   3840
ttagccaagg taaggtgtac gttgaaatcg gcgctgtcgc acagtggttg caaatcgaat   3900
cggtgaccag ctttccagct gaggcgtacg gctatatatc tgagtccagt gggccacaac   3960
tgcgcttcga gtcaaccgat tatatatttg atgacgtgac gcgccatggt aacggactgc   4020
tggagtgcga tcatgccgcc gtaatgacgt ttgcgccgat tccggaagga acgtcggatt   4080
acatccggct ggtattccgc cctataaccc ttcgcgacga cccacagcta actgcgtggc   4140
ccgccgacca gcaactcgtt gccgtcaacg gtgtggatag ccactgcggc ggcaaagaca   4200
agtcagcgcc gatacccagc tatgcggcgc ttatcgacgc aaaactggct gcgatcggat   4260
cggttctgaa caccgcggtc tataccggat tgtaatgagc aagggaaaat actttttgag   4320
gatttaatat ggatggtgca gtatttcacg gctaccacac cggaggtatc tacaatgcag   4380
gcaagtttga ggagcggcgt tatacgacca taggtattga tggatacaat aggaggctcg   4440
cgggtgagtt ggagtggacc aacaacgttt atccgcgtcc ctatggccct tccgttgacg   4500
attgggtgga tgaacgcgat agggtgccaa aagagcggcg tgtcaaagac gattatcgcc   4560
atccccggtt ttttgccaaa cccaccacga gcgcggcagt ggaggagtgc aggccggctt   4620
cgggcgtcgt gcagcaggcg cggcggctgg acaatgcgag cgcgagccct cttttcgctg   4680
caagcgcggt gcgacgagga atccggtcgt gtgtcccgtc gaatctgcca ccgagtgtcg   4740
ccgtgggcca taggctagca ggaccattgg catctgagta tattcaaaac tcatgcttgc   4800
tcgtcaatcg gcctgcaagt acgtttgtaa cgttagggag tcgtgttacg gcagggcatg   4860
ccctatcgga catcgccagc ggtgcagacg cgaccaaccg cccgcgcaac gtgaaaggca   4920
aacatgaaaa agacgacatg acccaacggg gccaacataa tgcaggcggt cttgtggcga   4980
gaatcaaggc gaatattcgg aattatatcg atgcaaagtt acgccggtat cctgcaagtc   5040
ggacttgagc tgataaatga tgaacgcggt gattcctgta attaaaattc ttaccactga   5100
tgtcactggg ataaattttt cccatcctcc cactttcgca cagaacggga agactttgaa   5160
tagactctta gaactcctgc gcctaccact tcaaacggag ttttcgactg cgcgagatgc   5220
taccgcgtct ggctcgcgcc atgatgctgc accaagctca tgcgcagccg gtcttgcgga   5280
tggccagtaa ttttcatagc cgagaatatt tactaataaa taacataata gcactatctc   5340
atcgccatca tcagaataga tgatcgattt tatttattaa caaggtaatt atatatgttg   5400
caatacgttg gagaaatttg tgccccacat aatttaagtt atggaaaaaa tatagattcc   5460
tcaagaaata gaatagagat tgaaggtaat gtaaaaattc ccaggcctaa attatgcaat   5520
gaaattgcag ccgttttcag cgcagatcag gccataaatg caaatatgaa aattttgcaa   5580
aaatgcgatt ttggacaatc tacgtctgat acttttagaa aaaaatcttt ttttaaccat   5640
gctagtaatc tagtggggaa aacaatacat ccccaagttg cagatcgctt tcgctcggaa   5700
gtttcctttg atggaacggg taaaataatt ggattcaaaa aggaaatttc aaataataaa   5760
tttgattttc taataaaaaa ttgcattcat tctattaatg agactccgca tttaatagaa   5820
aataagatta gaacccctgg ggagtgctta ataaatattg ccatctctct tgacagtgtc   5880
atgccaccaa tcccgcttaa ggatgaaatt caagcgacta taagatatac ttggcttgat   5940
ggtggcttgt cgcgtcaagc ccttgtaaat ttaatcgagc ttatcaagtt gagaaccagg   6000
tttaatgcgc ctgaattata tccaaaaata agaaggaaaa ttgacgatat tgctggaact   6060
```

-continued

```
ttggagaaag aaaccttcca gacgaaacgg aatgacaatt tctatggtcg ccttttgaa   6120
acgcatttat cagaatattt aataaaaaat cctgattatg cgatgatgga ggtccgtgat   6180
gcagtggctg catttatttt gcaagacttc atatctccac ttttaacgtg caaagggaat   6240
gaagaatcgc aatctgcaat ttgtgaaagg ctagcttctc ttatggaaga tgaccctcct   6300
tcttggcggt gcaatattga atcagttaag aaatttcttg cctctaagag tcaagctgac   6360
tttatagaaa tgatgaaata tcatggcgaa ttttctgtgc cattgattct ttcgatagca   6420
gtgaaatata ttactatcgc gccaggattg caagagctta aaaataaagc gagtgaattt   6480
tatattgaaa aaatcattcc gcaacgcaag cttcgcaatc ttatattaag taataatgct   6540
cataataaaa aatccaacct ttatggtttg atgcttccat atcaacgtgg agcaaatgca   6600
ggctattcca tgagtggcgg gatcggcatc aggcctattg atcgttatgc actccctggc   6660
gtggaagatg gtatgcatga ggatgatctg gtagcgtcat ccaatgagat aaccattgcg   6720
actggagttt ctggctcatc aaatattctt aatttttcttt tcaataaaat tcgaaaaaca   6780
tcaacgaatt ttcctatgga tgccgggaga ttggccgtgg cctcttggct tgcttatagt   6840
ggagggcact cttttaatga agcttattct gtattctcgt acaaaaaacgc agggaaattt   6900
aaatcaatct cttttaagag tttagctgaa gactatgatt tgatgaataa aggtgtggag   6960
catgcataca atcaagtact acagacagcc aaacgtttac agaaaccggg gtccgggcaa   7020
ctgccccccc atgtcagagt gtcagcctcc cgtaaaattg atccagccat agctagaggt   7080
ctccgtgcgc actagccacc gaggcgacca acaatgcgca agagcaagtt caccgagagc   7140
cagatcgtcg ccacgctgaa gcaggtggag ggcggtcgcc aggtcaagga tgtatgccgt   7200
gagctgggca tttccgaggc gacgtacttg ctcttccact ggtaataggt cgccgtgctg   7260
atgccgactt ggcgacagat gtctttgact ggaacgcctg cgtcggcctg cttgagcgtg   7320
gcgatgatct gtgtctcgtt gaacttcgat gtgcgcatgg aacctcctga cttgggaacg   7380
atgccagaaa gatctactta tgcggtgtct gcggatcggg ggagcttacg catccagcct   7440
gggtaagtcg cagcagaaga gaagcctaca tcgagaacag tacgttatgc ctagtggttt   7500
ggttcggccc ttgtttgaca cgatcagccg ctaggaaccg ccgccatctg ggttcgccgc   7560
ataagcctac ttttcgatca gtacgtcatc gatgaacatc gcgtccagac cgctggtgaa   7620
gaagatcgac agcgcatcct ccactgaatg ggcgatcggt ttgcccatga cgttgaagct   7680
ggtgttaagc accaggggaa tacccgtcag gcggtagaat tctttgatca gggcgtgata   7740
gcgcgggttc caatgttgct tcaccgtctg cagacgtccg gtgccgtcgt ggtgcacgac   7800
gcccggcacc ttgcgcgtgg cttccgcacg gaacttcagg gtgcgctcca tgtagggcga   7860
ttcctggtac agctcgaaat actccgcgcc gtgctcatgc aaaatcgacg gtgcgaacgg   7920
gcggaactcc tcgcggaact tcacccgcgc attgatgatg tccttgatcg caggcgaacg   7980
cggatctgca aggatcgagc gattgcctag ggcccgtggc ccgaattccg cgcggccttg   8040
cacccaggcg acgatcttac cctcggtcag cagccgggcc gcgcgttgtg ctgcgtcgtc   8100
gaggcaacga gtgaatttgg atagcgcgcc gaagcgctcc acgttatgca aggtctccgc   8160
actcatgctg ctgcccaggt agggcgattg ttcgcgcgca gccggcggtg tctgctcagg   8220
atggtcctcg gcgtgtgccc ataatgcggc gcccaccgcg ttaccgtcat cgccaggggc   8280
ggcgaatacg tgcagatgac ggaacggagt ttcagccagc acgcggccgt tagccgagga   8340
attgagtgca cagccgccgc ccagcaccaa gtggtcggac aagcccaaag cgtgcaggtt   8400
```

-continued

```
gtgcaggaat tcgaagagga cgtcgcagaa cacctgctgg ccggcatagg ccaggttggc   8460
caattcgatc gttggctggc ccttgcatcg gcgcattgca tacagcgtgc gctgcaactg   8520
gctgaattgt gctgcgggcg caaacctcag cgttaggccg tcgacgcgta gcatctggcg   8580
caacaactcg tacagttgcc gatcatgttg cccgtaggcg gccaggccca tcaccttcca   8640
ttcttcgccg gacagggtgc cgaagccgca aacctcgcag atcataccgt agaagaagcc   8700
caggctggcc caactgctgg tctcgctttg gtggatcggc gtaagcttgc cctgttggta   8760
gtggtagcag gccaaagcat tttttcacc catgccgtcc agtactgcgc acaccgcctc    8820
ctcgaacggg ctggtgtagc agccggccac cgcgtgggtt aggtggtgct cgtaatgacg   8880
gtagctgggt ggcttgaagg caggctcggc catgtggctc aagtcatatt cgagcaggtg   8940
tccggggtgc tccaccatcg ccagctgcga acggtagaag aagctctgtg ccacgaattg   9000
cttgttgacg tgccaaggca ggtcgccgaa ggcgctgcgg tattggtcta ccgcttgcgc   9060
ggtcttgccc aggccctccc gcatcagttc aggtgtttgc ccgctccaac tagtagcgac   9120
gaccagttcg gcgccgggat cgccgtattc gtggaccagc ttgatggcgc gctgaaacac   9180
gtccggggca acgccgattg aacgcttgta ctgcaggtag cgctcggtgg cctcggcaaa   9240
gcgcacctga ccatcgtcgc cgacgatagc gatggctgaa tcgtggaagg aattggcgag   9300
tccgatgtaa gtgcgcttca tgtccgattc cagtgaaggg gacgatggat gcttccggat   9360
gcctacggcg atgattgtgg cgcaaattgt gtcagtttga actgcaatcc cagcgtagag   9420
agcgccacga aagcattggc cgcgatgtag tacaccaccg tagccccgaa ggcctgcttg   9480
aaagccagag ctacgcctgc cggcccctgc agatgctggt gcaggccgct aaagaaaatt   9540
tccgagacca gggcgatgcc cagcataccg ccgacctgct ggatgacctg cagcgcgccg   9600
gaacctgcgc cggcatcctt cagaggtacc gtacgcatca ctgtctggaa tagcgaggcg   9660
atggtgatgc cacagcccag tccgccgatc agcaacggca gggtaagcgt ccagggatcc   9720
agcgagcctt cactgcgcgt gatgatgacc cacaaggcca gatagctagc gatcatcaga   9780
caggcgccgc tgaagatttt cgcgcgtagg ctttcgacgt gccgagcgag catagaggca   9840
atcgccacgc cgacagggaa aggagtagtg gcgacgccgg tttccagtgc cgaatacgcc   9900
agtccttgct gcagaaagat cacgaacacc aggaaaaaac cctgcagcgc cgaatagaac   9960
accgacacgg acaaggcgcc caagatgtag tcgcgatggc tcatcaggta gatcggcagc  10020
agggccgggc gcgccaagtg ggcttgccga cgttgccagg cgacgaaggc caccagcagc  10080
ggaataccga gcgcaatggc tgcaaagcac catagcggcc agccgtatgc gcgtccttct  10140
attagtggga acaccaggca caacaaggcg agcgcggcca gggcgatgcc gacccagtcg  10200
ttatggatgc ccgcatgcgc cggcaccttg ggcacccaga tggcggccgc cagcaaggtc  10260
acgaggccga tcggcacgtt gatcaggaag atcgcgcgcc agccgacgcc gaacgcatcg  10320
atgtggatca gcaagccgct gacgaggggg ccggcgaatg aggccaggcc cgcgaccagg  10380
ccgaacaacg agaaggcggc cgcgcgctcc ttcggagcga acatggtttg cgcgatggcc  10440
atcacctgtg gtgccagcat ggctgcggcc aagccctgca aagcgcgcgc gatgatgagc  10500
acgtggatat tgccagcgat ggcgcagaac gcggacatca agataaaacc ggccacgccc  10560
gtgccgaaca tgcgcttgcg gccgagcatg tcacccaacc gccccaacgg cagcaacccc  10620
aacgcaaaca gcagaatgta tatcgctacg atccattcca gctgttgctc gtccgcgccc  10680
aggttcttct ggatactggg cagggcgaca ttgacgatgc ctacgtccag caagttcatg  10740
aaattggcgc tcagcaacac gatcatcgct ggccagcgcc atcggtagtc gaactgcgct  10800
```

-continued

```
ccgggtggtg ccatgccggg cggcataccc agcgcttcct tgggtttttg catgttgtgt  10860
gctccttatc cgcttatggc cgcttcagcc ggtcgcatgg tgacggtgag aaaatgcaag  10920
atgtcgcgct ccaactcgcg ctggaaggcg ctgcggtcga agccaggcgg atcgatggcc  10980
gcctcgccca cgcgagcttt catcgcctcg ggaatacgc tgatgaaggc gtagtggccg  11040
gcattgggca ccacgcgcgc ttccagtcga ccatcattgc ctagcgccgt gcgtgtcgcc  11100
acaatcgttt cgtgcgccca ttgatccttt tcaccgacga tgagcagcac cggtacctcg  11160
actttcgcca gggcatcctc gtgcatgtac aggctgaaat ccggcgcaag cgccaccacg  11220
gcgcgcacgc gcggatcagc tgtgaccggc acggccctga tcggtacccg attttgtcgc  11280
accagcgcgg tccaggcggg ttgttcggcg tgttccgggc gatgcgcaaa atcgaccatg  11340
aaaccggtat gcggttcgcc cccggcgatc gctaaggcgg tgtagccgcc gacggagtgg  11400
ccgatcaccg ctacgttatg ggcctgaatg gcaggaccga actgcgcatg gccggtgagc  11460
gtatcgatca ccgcgcggat gtgccggggg cggtcttcca gattctgata gctgtattcc  11520
agctgatgct ggaacaggtt gtcgcccgga tgctccggca aggcgacgat aaagccgtgc  11580
cgtgctaggt aatgtgccag cgtgcgaaac actaggccgg cgctgcgcgt gccgtgcgag  11640
atcaccgcta gcggaaacgg gccggcttcg atcggcgcgc ccagggccac gtccagcgta  11700
taaggtccca tcgccgtatc ccgtgaaggc gtggcggtgg gatacatcac ccacatcggc  11760
accaccctgc tggcatcacc atcggtttcc agtttttggc aacccacata gctattcatg  11820
cgtaccccaa cgaaagaata aaaaacgcgt gccgcttacg ccggcatcag cttatccaga  11880
cttgcaccgg cgggcgccag ccaaacagcg gtacgacctt cgcccagctc cctgcccatc  11940
aagcctcgca cgccggccag atcctgcggc gttggcagca acgcggccag ccgttggccg  12000
tcggcatcgt gcacggggtt gccatctaag tcgaaggcaa gcccccttgca cgggccgaaa  12060
tcgcggtgga aacgctcgtg cggcagctgt agctcaaaag ccaggccaag gcgcctgagc  12120
tgttgattcc agcggccgat gatagcgccg acttcggcta tgtattgtcg gcgcattacc  12180
gcattgattg ccaactcggc aggtgcggtg gacgagacca gtctgtcttc gcagcgcacg  12240
tcgacggcga cctccgtacc ttcgagcttg tcgaagttgc gtgggctgcg gatgccggcc  12300
tggtacagga cgcgtgaacg ctccgaaacg tcgtggccga acagatcaaa gatcttcggt  12360
agccaatagt taaggtattt ctgaacgact ggcaagggga tcgcaccggc gtcgaagatc  12420
gcgtgcgtat cctcacgcaa ggtaatctcg gcgcttcgat acagcacgcg ctccaggcca  12480
tccacgccga acttaatatg cagaggttcc tcgaacatca tgaagcgggc ggtgcgtgcc  12540
aacggcagga aagctgactg ggtcaccgct tgaatctggt acttgcctac ccggtcggcg  12600
aagaagcacc acatgaaatg cgatagccag tcttcggtgt ggtagttgaa ggcatcgagc  12660
aggcgcgggt tctgcgcatc gccactcatg cgttgcagca ggccctcggc ggcgtcggct  12720
ccgtcgctgc caaagtattc gatcagcaga tgcgacatcg cccaggtgtg ccggccttcc  12780
tctagaaaaa actggaataa gtgctccagg tcgatcgcgc tgggcaccat ttgcgtcagc  12840
tcgtggctct gctcaaccgc ggcgttttct acgtcacctt gcacggtgac atgatccagc  12900
agcaggtcac gatattcttc cggcacgcac gaccatgcca cctgtccctt gcgctcgccg  12960
aacactacgg tgttgcggtc tggcggcatc atgaatacgc cccagcggta gtcgctgggg  13020
cgcatgcggt gatagcgcgt ccactcgctg cccttgacgc caccggtagg catgcgcagg  13080
ttcatctcgc gatcgtggaa ttcgctgggg ccgcggaggc gccaccattg caggaagcga  13140
```

-continued

```
acttggtagg aagtcagttg cctgaccagc gcgctgtgtg gatcaaggtc gatattgtta  13200
ggaatgtaca tgagggtcag gccgcgctgt gcatcgaggt aggggcgact tcgccgaccg  13260
tgagcccgat gaagtcgatg atccgctgag ccacggcacc cggatcattg aacagttgca  13320
ggtgaccgcc atgatctagc aggtccagac gcaaagacgg gtcgtgccta gccaactgca  13380
ccgaggcgga gtagtggctg aagctgtcgt ccttgcagtg cacgatcagg gtagggtgcc  13440
tgcccagggc ggtgggcagc aaggcttgca cggattgctt gttctcttcg taggcacgca  13500
tgtagcgcga gaacaccaat gtgctcgctg gatcggctag gtgcagcatg gtgagctttt  13560
cggccaagtc gtcgccgcgt aaaggttggc cgcggtactt gtccaggatg gcggcgagct  13620
ttttggcctg ttccagaccg tgccgctcga tctgaaggta gatcggcaag gcgcaacgtt  13680
cgaattcgga ttttacgatg ggcggcagca ggcccgccgg cgccacccaa gccatgctgc  13740
gtggtgcgaa gccatgcagc gcaatggcat gcacggccaa ttgtgcagcc tgacaccaac  13800
cgacaaaatg gcaatcggcg tagtcgtgtt ggtgcaggat gcccagcagg gtcgcggctt  13860
ggcgatccag atcgaagtct tccgcggtta ccgatgtctg ggcattcggg cagccgatgg  13920
attcccagca caacacatgg aaatgcctag ccagtcgttg cgccaaccgg ctcagcagca  13980
ggtaggacat gccatagggc ggtagcagca ccagcttggg cgatgcctga gcgcctagcc  14040
aatacagctc aagctgccgt ccatcggtag tgcagtattg cgacagcctt acccctgcga  14100
gcgcgtcgtc cagggcggac agatcttgct tttccagata gtgcggcaag caagcacagc  14160
ccatgagttt cctaccctcg cttgaccaca tgacaagact gcgccgtcac cggtggctgg  14220
aaagcttgcg ccggggcgga acacctcacg agtaactcga ttcgaaccca cttccgtctg  14280
gagagctcgc gtcccctaaa ttcttgtcat cgagttcgcg cagcgataag gggcgcatgt  14340
cggtccaggt ttcgtcgata tacgccatgc actcgtcctt accgccagca tagccttcct  14400
tgcgccagcc aggcgggacc tcaagatcgg acggccacag tgaatactgc agttcgtcgt  14460
tgatcagcac cagataagcc tgttcctcga acgtcatcct aaagataccc ccggaaggct  14520
gctgcgaagc acggaagttg ctacatcgca caatgcgatt cagatggacc aagcaaagcg  14580
actatacatg acgtcacttc gaagatgtca agaaaaatag cgcgtgaaga gcacgtaaga  14640
gtgatgtgtt tcgcaccgct gtacgtccca tcgccatcgc ggcaaagctt acacgaaaaa  14700
ttcaccaggg catgcgttca atacgcgggt caaagcaata tccttgcgct tgcagagcta  14760
tgttcgtgcg taaagcgcca aggcagtggg gagcaacacc ttgggtttcg gttgaggtgc  14820
gggtagcaat ttctgcttaa tatccacgcg cggcggtttt tgtcttgccg ggcgtcaact  14880
gtctcatcga gcagtctggg aggctatttt gcgctgcctt atcataaata attacgattc  14940
gttcacttgg aatctcgccg actacgtagc gcagatcttc ggcgaagatc ccctggtggt  15000
gcacaacgac gagtactcct ggcacgaact gaaggaccgc gggggatttt cctcgatcat  15060
cgtttcgccc ggtcccggct cggtggttaa tgaagcggat tttcacatct cgctgcaggc  15120
gctggagcag aacgaatttc cggtgttagg cgtatgcctg ggctttcagg gacttgcgca  15180
tgtctatggt ggccgcatcc tgcatgcgcc ggtgcccttt catggccgtc gctccaccgt  15240
catcaacacc ggcgacggtt tgttcgaagg catcccgcag cgtttcgagg cagtgcgcta  15300
tcactcgttg atggtctgcc agcaatcgct gccgcctgtg ctgaaagtga cggcgcgtac  15360
cgattgcggt gtggtgatgg gcttgcagca cgtgcaacac ccgaaatggg gagtacagtt  15420
ccaccccgaa tcgatcctca ccgaacacgg caagcgcatt gttgctaact ttgccaagct  15480
ggctgcgcgc cacagtgcac cgttacttgc cgggtcggag caggccggca aggttttaag  15540
```

-continued

```
cgtttgcgcg cccgagatgg tgacaccgcg ggtacgtcgc atgctgagcc ggaagatcaa  15600
gtgccgttgg caggcggaag atgtctttct ggccttgttc gctgacgaaa agcattgctt  15660
ctggctggac agccagctgg tctgcagtcc aatggcgcgc tattcgttca tgggagcggt  15720
gaacgagagc gaggtagtgc ggcattgcgt gcggccaggg agcatggtgc aggaggcagg  15780
cgagcggttt cttgctgaga tggatcgggc gttgcaatcg gtgcttactg aggacgtcgc  15840
cgagcggcca ccgttcgcgt ttcgcggcgg ctacgtgggc tacatgagct acgaaatgaa  15900
atcggtgttc ggcgcgccgg cttcacatgc caatgccatc cccgatgcgt tgtggatgcg  15960
cgtggagcgc ttcgttgcct tcgaccacgc cactgaggag gtatggttgc tggcgctcgc  16020
cgatacggag gatctgtcgg cattggcttg gctagacgcc atcgagcaac gtatccatgc  16080
cattggtcaa gcggctccgg cttgcatttc gctaggcctg cgcagcatgg aaatcgagct  16140
caatcatggt cgtcgcggct accttgaggc aatcgagcgt tgcaaacaac gcatcgtcga  16200
tggcgagtcc tatgaaatct gtcttaccga cctgttctcg ttccaggccg agctggatcc  16260
attgatgctc tatcgctaca tgcggcgagg gaacccagcg ccgttcgggg cctatttgcg  16320
taacggtagc gattgtatcc ttagtacttc accagagcgt tttctggaag tggacggcca  16380
cggcacgatt cagaccaagc caatcaaggg cacctgccgc cgtgccgagg atccccaact  16440
ggaccgtaac ttggccatgc gcctggccgc ctcggaaaag gaccgagcgg aaaacttgat  16500
gatcgtcgac ttgatgcgca acgacctaag ccgcgtggcg gtgcccggca gcgtcaccgt  16560
gcccaagctg atggacatcg aaagctacaa gaccgtgcat cagatggtca gcacggtgga  16620
agcgaggctg cgcgccgatt gcagtctagt cgacctgctt aaggcggtgt tccccggcgg  16680
ctcgatcacc ggcgcaccga agttgcgcag tatggagatt attgatggcc tggagaatgc  16740
gccgcgtggc gtgtattgcg gcagcatcgg ctacctgggc tacaactgcg tcgccgacct  16800
aaacattgcg atccgcagtc tttcttatga cgggcaggaa atacgtttcg gcgccggcgg  16860
cgccatcacc ttcctgtccg acccgcagga tgagttcgac gaagtgttgc tgaaggcgga  16920
ggcgatcctc aagccgatct ggcattatct acatgcgccg aacactcccc tgcactacga  16980
gttgcgagag gacaagctgc tgctagccga gcactgcgtt agcgaaatgc cggccaggca  17040
ggccttcatc gaaccatgag ccgcggcgag agaggtccat gcacaccatt gtgaacggcc  17100
ttcccgcttc gtccatagcg attttcgatc gcggcctaca gtacggcgat ggattgttcg  17160
aaaccctacg gctaggcatc gcgctgccgg acatccgtca gcaggtctgc gaggccatcg  17220
cgactggcgc cgcgccgcgt gccgtggcga aaaactgatc gtgacgcgtg gcagcaccga  17280
gcgcggctat cgttgtcctc tggcggtggc gcccaactgg gtgctcagcc tgaatgaggc  17340
ccccacgctt acgcgcgaac caggacgggc tgctgatgga tacggccggc cgggtggtcg  17400
agggctgcac cagcaatctg ttcctcgtcg agaacggcca tctggtgacg cccgacctgg  17460
gcgtggccgg cgtcagcggg atcatgcgag gcagggtgat cgaatatggc cggcagcacg  17520
gtctcgcctg cgcggtaaag cacgtctatc cggaccagct agtgcgtgct caggaggtgt  17580
ttctgactaa cgccgtgttc ggcattctgc tggtgcgcag cattgacgct cacagctacc  17640
gcatcgatcc tgttaccctg cgtttgctcg atgccctgtg tcagggcgta tatttcaccg  17700
aacggtcact acatcaggtt tccacccatg ccggccaaga cccttgaaag caaggattac  17760
tgtggagaaa gcttcgtcag cgaagatcgc tccgggcaat cgctggagtc gatccgattc  17820
gaggattgta cgttccgaca atgcaacttc accgaggctg agctcaatcg ctgcaagttc  17880
```

-continued

```
cgcgaatgcg agttcgtcga ctgcaacctg agcctcatca gcattccgca aaccagcttc  17940
atggaagtgc gcttcgtcga ctgcaagatg ctcggtgtca actggaccag cgcacaatgg  18000
ccatcggtga agatggaggg ggcgctgtcg ttcgagcgct gcatcctcaa cgacagcttg  18060
ttctacggcc tatacctggc cggggtaaaa atggtggagt gccgtatcca cgatgccaac  18120
ttcaccgaag ccgactgcga ggatgcggac ttcacgcaga gcgacctgaa gggcagcacc  18180
ttccacaaca ccaaactgac cggcgccagc ttcatcgatg cggtgaacta ccacattgac  18240
atcttccaca acgatatcaa gcgggctagg ttcagcctgc cggaagcagc ctcgctgctc  18300
aacagcctgg atatcgagct gtccgattga gcctggccat tcgctaccgt gtgactgatg  18360
caacctggcg gatgcatccg ccgtcgccgt tgaacacgca gcagaaagac tggctgacac  18420
gcggtggttc gttgaccgcg cacctgcgcc tgttggggca ggtacaggtg caagtgcaac  18480
gggagcacaa agccatggcc tggctggatg aatatcgggt gctcggactg tcgcgctgcc  18540
tgcttgtatg ggtgcgtgaa gtggtcctgg tggtggacgc caaaccctat gtctatgcgc  18600
gtagcctgac gccgctgacc gccagttaca acgcctggca ggcagtgcgt agcatcggca  18660
gtcgcccgtt agctgatctg ttgttccgtg atcgcagcgt gctacgttcg gcgttggcga  18720
gtcggcgcat caccgcgcag catccgctgc accggcgcgc atgcaacttc gtggcacagt  18780
cgcatgcgac gcaagccctg ctggcgcgcc gctcggtatt tacgcggcaa ggcgccccgt  18840
tgctgatcac cgaatgcatg ctgccagcgt tgtgggcaac gctggaaccg gtggcagctc  18900
cgcgccaggc gagtctgagt gcggacggcc cttgccggca ttcagcgcag atcgtctcgc  18960
ctgagtcgat gctggaatag ccttggcatc gaagccctcc gatcaggcat cgaggtccgt  19020
caccagcatg cgcgccagct cacgcagcgg gtcgccttgt aacatgctgt agtgattgcc  19080
cgccgcgctc ttgatctgcg aaagtggtac gtaacctgtg atatccggca gtacctcgct  19140
acccccgcgt ggcttggaca tgtcggcata ggacacgtgt accgcagtct gtgcctggta  19200
cagatgagcg ttaggctgca ggcactgcgg ctcgaaaccg gccaacagcc ccaggtgata  19260
gcgcgtaacg cgcaattgct cggccagcgg tggccacatg cggctttcca gagtaaacct  19320
caggtgtgcg agcagtttgt ccagtgatgc ctggtggcgg ctgtagtcga acacgtgctc  19380
gtcgtcaccg tcggcgaaca gcagctgccg ggcttcgtct atttcagcct gctcgaagcc  19440
gcgcttggcc aacgcggcca acgtattgag cgctgccacg aaggtaagct gccggggctc  19500
gcgcgcatgt accggtatca ggctgctatc gagcaggccc acgtaatcga cgcgcaggcc  19560
gcgccgctgc aattgctcag ccacagccag ggctagcacg ccgccggagg accagcccag  19620
caagcggtag ggcgcaccgg tcgggccagc cagcaacgca tcgcagtagt gcgcggccag  19680
gtcggacaaa tgcgcgaagc ggcgcaccgg ttcgcattgc aggccataga ccctggcaga  19740
gtgccctagg gcggcagcca gatcgatgta gcaatgaatc tggccgccga tcgggtggat  19800
ggcatacacc gccgcgcgtt cggtgcgtag gctaagcggt acgataagac ttaccggcat  19860
gctgccggct tggctttggc gcatgccgcg ctcgacgaca gcggcaaaat cttccagcac  19920
aggggattcg aacagcgtgt tgacccgcac ttcgatgtcg aaactctggc ggatacgcga  19980
gaacaactgg gtggcaagca gcgagtgacc gccgaggttg aagaagttgt cgttgaggct  20040
cacgcgtaag gggcggcct gtgcgggggt cagcagttcg ctccacagct tggccagggt  20100
gatttcgacc tcgctgcgcg gagcgaggta gtcgctgtcg ctgctggcgg cttgcggctc  20160
gggcaggctc aaggtatcga gcttgccatt gggcaagcgc ggaagcgccg gcagcgactg  20220
gaagcgcgtt ggcagcatgt aggtaggcaa gcgttcctgc agcagcttgc gcagctcgtc  20280
```

-continued

```
gaggttcagg acaccctggc gtggcaccac gtaggccaac agttccggcg tgggcgagcc  20340
ttgcggccaa ccgatcacgg cggcctcggc gacctgcagg tgggccgcca gggctttctc  20400
cacctggcgc acgtccacgc ggtagccgcg gaccttgacc tcgtagtcgc gccggccgag  20460
cagttccagc gtaccgttgt ccagtaggcg ggccatgtcg ccggtcctgt acagacgcga  20520
gccggggggg ccgtagggat tggcgatgaa gcgcgcggcg gtcaggccgc cctggcgcca  20580
atagccgtgc gtaatgccga ggctttcgat gtgcacttcg cccatgatgc caggcggcaa  20640
cggtcgcagt tgttcgtcga gcacatggac cttggtattg gcgatgggcc gtccgaccgg  20700
gacgaagccg ctgccgctgt gctgctcggc cggatcgcaa taggtcatgt cgttgatttc  20760
ggtacacccg tagatgtacc aggccgtgca ggcaggcagc agcgtcctga gccgttgcag  20820
cagttccgcc gggcagggtt cgatggagac gaagagctgg cgcagtcgcg ccagccgctg  20880
cggtgtctca gcaacgtggt cgagcagcgc gttgagctgg gaaggaaagg tatacaggcg  20940
tgtgatctgc caggtttcca gcgcgcgcac gaaagcgggg atgtcacgca cggtatcctc  21000
gtcgatgaac acctgcggta cgccagcaag taggccggcg agcagttcct tgaccgaaat  21060
ggcaaaggcg atcgaggtct tttgcgccac ccgctccccg gcctcgaaag gcgcacgtgc  21120
ccacagcgca tgcagccagt tgaggatttg ccgatggggc accatcaccc ccttgggacg  21180
accggtggaa ccggaggtat acatcacgta ggccagctgc gccggatgca gggcatgcgg  21240
cagtggcgta tgcggttgac gagcgatggc ggcatcgtcc aggcgcagcc gcggtacttg  21300
gatcagttgc ccgtcgatgt ccttgccgca gagcaacagc cgtggctgcg cgtcgtcgag  21360
gatctgctga atgtaggtgg tggggtaatg cgggtccaac ggcacgtagc agccaccggc  21420
cttgagcacg ccgagtaggg caatgaggaa atcgggcgag cggccgaacc acagggcgac  21480
gcgctcctgc gggcgcaggc cgcgctcgat caggcaatgc gccaggcggt tggcgtgttg  21540
gtccagttgg gcatagctca actgtcggtg ttgatcggca caagccagtt cctcggcgtg  21600
cagtgccact tgcgcatcga acagatccag cacactgcgc gaggtatcca gagtatgagg  21660
ggtgaactcg gtgcgagcga ccggcagcga aaaatccgag aggcggcagc gcggttcttc  21720
cagcatccgc tccagcactc tttggtggtg ggccagcatg cgctgaaccg tagccgccga  21780
aaacagctcc gcggcgtatt cgacagtgac ttccaggtgg cttccgtcgc cgatgaactg  21840
caggtccagc tcgttgggtg tggtgcgttc gccaaattcc atctgagcgc tgaggaagat  21900
ctgggcaaat gcattgacgc cttcggtggc gaaattttgg tgtcggagca tgatcggcac  21960
gagcgggatc tggctgctgt cacgcggttt cttgagagcg cttaagacat gctcgaacgg  22020
cagtgcgcga tgcgcgtagg cgtccagcac ttgctggcgc acgtgctgca gaaaatcctc  22080
ggcaaaggcg tgactgccca agtttaggcg taccgccagg atattgacga aaaagccgat  22140
cagattctcg gtttccagct gatcgcgtcc ggcgctggta gtacctaagc agagttctcg  22200
ccggccggtg tactggtgca agacgatcgc caggctcgcc ataagtgtca tgaacaaggt  22260
gacgcgccgt tcctggctga atgcggcgag acgcgcggcc aaggcgtcgg gataggtcag  22320
gtgtagtatg ccagcacgcc aagctcgatt agccgggcgt ggaaaatcgt agggcaaggc  22380
cagcccttct tcgtaaccat gcaaacgctg tttccaataa tccagatcgg cgctgaaatc  22440
ctgtacgcgc tgccatgtag catagtcggc atattgcagt agcagcggtg gcagtgccgg  22500
tggcgtctgc tgtagcgcgg ctatatagaa agcacgtagg tcgtgaaaga tcaggttaat  22560
cgaccagccg tcgcagatga tgtgatgcat gttcatcagg aacacgtggt aatcgtccga  22620
```

-continued

```
tacgcgcagc accgatacct tgagcagcgg gccgtgggca agatcgaata cgtgcgcggc  22680
gtgctcggcg actaggcgtg gcacttctgc gggtgtcgct gtgatgcaag gcactgggac  22740
ctgcatggcg tcggcgatgt gctggctggg ataatcgccg ccagcgcaag ttgctatgcg  22800
ggtgcgcaag gtttcatgcc tggccaccag cgcctggatc gcctcgcgca gcgctgacat  22860
cgagaaatcg gcactgcgta aatggcaggc gaaggcgaca ttgtaactgg tacgttgctc  22920
gggcatgtgt tcatgcacga accacaggcg ctcctgctga tagctcagcg gaacgggagc  22980
atcgcgcacg gcacgggaag agatggtgtt gccgccagtc ggagcctgtt gttgccgcgc  23040
ttcgttgacc actcgcgcaa aatcttccag cacaggggat tcgaacagcg tgttgacccg  23100
cacttcgatg tcgaaactct ggcggatacg cgagaacaac tgggtggcaa gcagcgagtg  23160
accgccgagg ttgaagaagt tgtcgttgag gctcacgcgt aagggggcgg cctgtgcggg  23220
ggtcagcagt tcgctccaca gcttggccag ggtgatttcg acctcgctgc gcggagcgag  23280
gtagtcgctg tcgctgctgg cggcttgcgg ctcgggcagg ctcaaggtat cgagcttgcc  23340
attgggcaag cgcggaagcg ccggcagcga ctggaagcgc gttggcagca tgtaggtagg  23400
caagcgttcc tgcagcagct tgcgcagctc gtcgaggttc aggacaccct ggcgtggcac  23460
cacgtaggcc aacagttccg gcgtgggcga gccttgcggc caaccgatca cggcggcctc  23520
ggcgacctgc aggtgggccg ccagggcttt ctccacctgg cgcacgtcca cgcggtagcc  23580
gcggaccttg acctcgtagt cgcgccggcc gagcagttcc agcgtaccgt tgtccagtag  23640
gcgggccatg tcgccggtcc tgtacagacg cgagccgggg gggccgtagg gattggcgat  23700
gaagcgcgcg gcggtcaggc cgccctggcg ccaatagccg tgcgtaatgc cgaggctttc  23760
gatgtgcact tcgcccatga tgccaggcgg caacggtcgc agttgttcgt cgagcacatg  23820
gaccttggta ttggcgatgg gccgtccgac cgggacgaag ccgctgccgc tgtgctgctc  23880
ggccggatcg caataggtca tgtcgttgat ttcggtacac ccgtagatgt accaggccgt  23940
gcaggcaggc agcagcgtcc tgagccgttg cagcagttcc gccgggcagg gttcgatgga  24000
gacgaagagc tggcgcagtc gcgccagccg ctgcggtgtc tcagcaacgt ggtcgagcag  24060
cgcgttgagc tgggaaggaa aggtatacag gcgtgtgatc tgccaggttt ccagcgcgcg  24120
cacgaaagcg gggatgtcac gcacggtatc ctcgtcgatg aacacctgcg gtacgccagc  24180
aagtaggccg gcgagcagtt ccttgaccga gatggcaaag gcgatcgagg tcttttgcgc  24240
cacccgctcc ccggcctcga aaggcgcacg tgcccacagc gcatgcagcc agttgaggat  24300
ttgccgatgg ggcaccatca cccccttggg acgaccggtg gaaccggagg tatacatcac  24360
gtaggccagc tgcgccggat gcagggcatg cggcagtggc gtatgcggtt gacgagcgat  24420
ggcggcatcg tccaggcgca gccgcggtac ttggatcagt tgcccgtcga tgtccttgcc  24480
gcagagcaac agccgtggct gcgcgtcgtc gaggatctgc tgaatgtagg tggtggggta  24540
atgcgggtcc aacggcacgt agcagccacc ggccttgagc acgccgagta gggcaatgag  24600
gaaatcgggc gagcggccga accacagggc gacgcgctcc tgcgggcgca ggccgcgctc  24660
gatcaggcaa tgcgccaggc ggttggcgtg ttggtccagt tgggcatagc tcaactgtcg  24720
gtgttgatcg gcacaagcca gttcctcggc gtgcagtgcc acttgcgcat cgaacagatc  24780
cagcacactg cgtgaccaat ccaaggcgag cgcggtatcc ggactggccg cggtcagcgc  24840
gacgtcttcg gcatccagta gcgacatgct tgatagtttc atggggcacc gggtcggcag  24900
ggttaaacgt gcagcttgag catggcttcg ccatcgctgc gcgcagcgat gtcaggggac  24960
gattgttcgg gcgaataagg ttcggccatg cacacgagga tcttgcggct gccctcgtag  25020
```

-continued ggctcgcgtc cgtgcgaaac cagcatattg tcgatcagca gcacgtcgtc ccgatgccag 25080
tcaaaatgga tcttgtgctg ggcgaaaact gtgcgcacat ggtcgagcat ggcggggtcg 25140
atcggcgtgc catcgccgaa ataggcgttg cgcggcagtc cctgctcgcc gaagaacgac 25200
agcatcatct tctgcgcagc tgcctccagc gcagtgtaat gaaacaggtg tgcttggttg 25260
aaccaaactt catcgccggt cgccggatgg cacgcaaagg cccggcagat ctggctggtg 25320
cgcaggccgt cgccggtcca ttcgcattgc atgtcgttgc gggcgcaata agcttctact 25380
tcctgcttgt tgcgggtgtt aaacacgtcc tcccatggca ggtcgacccc tgcacggtag 25440
ttcctgacgt agcgcacctg tttgcgcgca aagatttcgc gcacttgcgg atcgatagcg 25500
gctgtgacct tgagcatgtc agccaacggc gtgcagccgc cctcgctggc cggctgcacg 25560
caatggaaca gcagtttcat cggccagacg cgctggtagg cgttctcgca atgttgcgct 25620
atggacagct gcctgggata ttcggtggcc gtgtagacat gctggccgac gtcggtgcgc 25680
ggtgtggaac gataggtata ggccagtcgc tcatcgaaga aacagcgtga gatctgctcc 25740
aagccaccag ggtgcgcaaa gccacggaac agtaacgccc tgtgttgcca tagcagggta 25800
ggccacgtcg cgcggtgcgt ggcattccaa tcagtcagcg tggcctcggc cgagtcggcc 25860
ttgatggtca ggggaagatc agcgtttgtg tgcatggggc acctaggttc gagcatggcc 25920
gacgaagaac aggtgggatt gcaggtgctt ggcgctagcc agtgtctcca acagcgcagg 25980
ccggattacc ttgccgctgc aggtacgtgg gatcgtgctc acttcgacga atagatgggg 26040
atagtgatgc ttgcctagcg cgttcttgca caaggcgcgt aaggcggccc atagcgcccc 26100
tgtatcgatg ctggcatcga caggcaccac gaaggcggcg gggcggggca agccgaactc 26160
gtcttcgatc aggcagatcg cgcactcctt cacgcaggcg tgcgtctgga tgacgctctc 26220
cagcgtctca ggcgaaagcc aacaaccgtt gatcttgatg gcggagccca ttctgcccaa 26280
gttatggaag cgccccttgg cgtcggcaaa gaacaggtcg cgtgtatcga accagccgtc 26340
gacgaacaat tgggcactga gtatggggtc gccaacatag cccctcgtca gcgtattgcc 26400
cctcacccac aggctgccga cttcgcctat gcggcagatc tctccctgct tgttcaccag 26460
cttcacaaca aagcctggta ccggcgtgcc agtgcaaccc atgagcgcgt ggcctggccg 26520
attggagatg aaggtggaca gtacctcggt gcagccgata ccgtcgagca cttcgacctg 26580
ccaacgcgtg ctgatcgcat gaccaagcct cgccggcaag ctttcgccgg ccgatatgca 26640
caggcgaagc gccggccaca ccgcatccgg cgcggcctcg gcaagcaaca gcttgaacac 26700
ggcgggcacg gcgagcaata cagtgacgtg gtaagtgtgg atggtttgcg cgatctgcct 26760
gacgctaagc ggcgcggcaa tcacatggct gacaccagcg agcagcgaca gcatcaggtt 26820
gttcaggccg taggcgaaaa acaaccgcga cggtgtatac atcacgtcat cgctgcgcag 26880
cccgagcacg gcctgctggt agttgagatg gcagtgcata aaatcggcat gcgagtgcgt 26940
taccgccttg ggcgtaccag tggagccgga cgtgcatatc atcaccgcgg gtgcatcggc 27000
ggagcagggc gcaaccacca gttcgtcgtt ttcgatcacc ggcatcaggc tcgtcagctc 27060
taaggtcggc aggtggcgca acgcggcatg atgggaaggc ggcagttcgg catcgatcag 27120
cacgaggcga ggcttgatgg tcttgagcgt ggtctcaaag tggacgagcg acacaagctc 27180
gtttatcggc gcaaagacca agccaccggc caagcaggcc agcatcaggg caacgcccgc 27240
taggctgtcg atagcaatca gcgccaccgc atcaccgctt tgcaggccaa gcagactcaa 27300
gtgccgggca taggtcgccg cgcgagagcg caactggcga tagctgaagg cctgctggcg 27360

-continued

```
caacggatcg atcatttgcg ccgtcgaagc cagatgcgct gcggaaaaaa tttgcgcgca  27420
cacgttgacc tggaccgacg ggaggaagcc gataggcgca caggcgaaca ccgccgtgct  27480
tgcgtccgac caggacggca tcggcccatc ggtcgagcgt gcgaaccagc tcgcgggcaa  27540
atgactggca atctgacata gtttgccgtg gtcgcaggcc agcagactgg tatccacctc  27600
gatcaggtct tcgacgcagg aaagcgcagg caaagagatc tgcgccgcgc tgccgcatac  27660
ggcactatcg cgcaagtccg gcaggttcct ttggcggtgg tccgcatgcc atagcagcag  27720
gccatcgctg cgtcgcgtgg ccaaggcttc cagtgccatg cccagggcgc cttgcaaccg  27780
gtccagttgc ttgggttcct cgatacggcc caaatccagt gccagggtgt tggcgccggg  27840
gggcgattcg gacagcacga tttggtgccg atgcttgagg taatcgcaaa tcaggccggc  27900
cagcttgcct aaccgtgcat attcccgtag caggctaccg aagctgccac aggggtaagg  27960
tgcggcatag tcaatggtta tgtgctggcc gatcggcgtg tcgctgacat cgatacgcaa  28020
gccaggataa tcgcgccgcc attgatgcag cagcgtggtc cattgacgag cataggcctc  28080
gttgcgccct ggccgcgtct gacctaccga ccaacgcaaa tctagttcgg tgccagagtg  28140
catcggaaga tttgtcagtg ggctatccat aagcgttctc gggtaaggcg atcgacgcat  28200
cgagctcggc tgtgtgcact ggtttggccg gtacgccagc gcgagagact gttcgcaagc  28260
ttcagcgttt cagcgcgtgg accagataac tttgcggcac gccgtgggtg ccgcgcggtg  28320
cgaccggaaa cggccaacgc cccatttgct ggccagcggc ggcgatggtc aacacccctg  28380
gctcccagcc cagtggttgg atcaggcttt ccggttcgtc agtgccaaac tggcgagcca  28440
tcgcgtgcag cactcgggca ttgggcgagt tgagcataga gaggccgata acatcgaaca  28500
acacgctgct gcccttggca ctcaatgcat cgatgcgcgc gaacagcagc atcactgcct  28560
cggcgctcaa gtagcacagc aagccctcga ccagccacaa ggtggcggcg ctgccgacga  28620
atccactctc cttaagtgcc tggggccagt cttcgcgcaa atcgatcggt agcgcaatgc  28680
gctggcaaac gggctgggcg tcatggagtt tttcgtgctt gtcggagagg acatccatgt  28740
ggtcgatctc gtagacccgg gtatcggacg gccaggggag acgataagcg cgtgcatcca  28800
taccggcggc caggatcacc acctggccaa tgccttcact aaccgcctgc atgatcttgt  28860
cgtcgagcca acgcgtccgt acctcgatcg ccggaggcat cggtacgttc tggttgttgc  28920
gtctgagctc ttcaacgaat tcatcgccgg ccagacgccg tgcgaaaggg tcatggaaca  28980
gcgcctgctc ccgctcgctt tccagcgccc gcatgcctgc cacccataaa gcggttcttt  29040
cgatatctct catgcatacg ctccggttcg tggtcggctt gcgccgatgc atcatagata  29100
tgcatgactc gattcgcggc accgtgcctt gatggtggct gcgaagcgaa aacaataacc  29160
aaagggtggt gctcgacggc tttactgtag cgacaccttg tccatcgcct tacggatggt  29220
ctgatccacg caagcgaaag atgagataaa ccacatcagc tgtcaacgcc gatttaaatt  29280
tgacccactt tcctttgaat cgtcgaagta aatctgaccc acccggggtc ttccatcgtc  29340
gggctgctag gctgcgcagg gcaaagcccg tcgcagccca gcagccctgc gccggctcac  29400
gcccgaaggg caggtagccg atctcgtcga ccaccagcag cttcggccct agtaccgcgc  29460
gattgaagta gtccttcagc cggttctgcg ccttgaccgc tgccagttgc atcatcaggt  29520
cggccgcggt gatgaaacgt gccttgtgcc ccgccatcac cgcacgctgg cacagcgcca  29580
gggcgatgtg ggtcttgccg acaccgctgg ggccaagcat caccacgttc tcggcgcgct  29640
cgacgaaggt caggtggccg agctcgacga tctgcgcctt cgaggcgccg ccggcctggg  29700
cccagtcgaa ctgctccagc gtcttgatgg acggcatcct ggcaagtcgc gtcagcaccg  29760
```

-continued

```
tgcgcttgcg ctcttcacgc gcgagctgtt cgcttgccag caccttctcc aggaagtagc  29820
tggcatcctc gcacgcggcg gcctgtgcga gtgcttgcca gtccgagctc aggcgtgcca  29880
gcttcaactg ctcgcacagc gcggcgatgc gcgcacactg caggtccatc acgccacctc  29940
cagcagggtg tcatacacgg ccagcggatg ctgcaggttt tccactggca gggccactgg  30000
ctgtcgtaag ggaagcggtg ccttgagcgc cggtgcggac agtataacga cacgttcctt  30060
ggccaagcgc actgtcggca cggccttgct gatgccgccc atgtagccgc gcgcctggat  30120
ctcgcgtagt agcaccacgc tggccgggat ccatcgaggg cgcgcttgcc caatgcgctc  30180
atgcagataa ctcttgtagc cgtccagttt gcaggcgtat tgttaggcgt caccgctcgc  30240
gcggcgatcc ccaataaggc gggtatgaga cgcgcatggc cgcccttccc gcaggcgtgc  30300
tgtcgctcta ttgcttacct catgcagaga tcgccaatgt cgccgttaca gcaaacgctg  30360
ctaacccgcc tcgccagtgc ggccgcctcc cggacaatga tcgagtttcc gcgtccggag  30420
cacgcatcgc cacaatgttg cgacgatgcc gagcttgcgc gactgatcgt gcagttgtcg  30480
gcgggactgc aaccgctggc gatgccgggt acctacgtga tcattgccgc gccacatggt  30540
ggtttgttcg cggcagccct gcttgcctgt ttgcatgcca acctggtggc ggtgccgttt  30600
ccactggatg ttgctcagcc aaatgagcgg gaacaggcca ggctggagac gatccacgca  30660
caattgatgg agcatggcaa tgtagcggtt ctgcttgacg atgtcgccga tcgcagtgcc  30720
ttcgcgcgca tggcgcatgc tgcgggcacc ttcctggcga ccttcgccga tctaaagcgc  30780
gaatcgacca gcgcctcctt gtgcccggcg tcgccttcgg acgccgcctt gctgttgttt  30840
acctctggtt cctcgggtga gtccaagggc atcctgctta gccaccgcaa cctgcatcat  30900
cagatccagg ctggcatccg gcagtggagc ttggacgagc atagccatgt ggtgacctgg  30960
ctttctcccg cgcacaactt cggcctgcat ttcggcttgc tggcaccctg gttcagtggc  31020
gcgacggtca gtttcatcca tccgcacagt tatatgaaac gacccggctt ctggctggag  31080
acggttgcgg ctagagacgc cacgcacatg gccgcgccga acttcgcgtt cgactactgc  31140
tgcgactggg tgatggtcga gcagcttccg ccgtctgcgt tgtctacgct tacgcatatc  31200
gtgtgtggcg gcgagccggt gcgcgcctcg accatgcagc gcttcttcga gaaattcgcc  31260
ggactcggtg cgcgtacgca gactttcatg ccgcacttcg gcttgtctga aaccggtgcg  31320
ctgagtacct tggacgaggc gccccaacag cgcgtcttgg aactagatgc cgacgccttg  31380
aacaaacgca agcgcgtggc ggcaggggcg agccaggcgc gtgtgacagt gctcaattgc  31440
ggcgccgtcg accaagatgt ggagttgcgt atcgtctgtc ctgaaggcga gacgttgtgc  31500
agaccagatg agatcggcga aatatgggta aagtcgcctg cgatcgcccg tggctacctg  31560
tttgcgaagc ccgccgatca gcgacagttc aactgcagca tccgtcatac cgacgatagc  31620
ggttactttc gtaccggcga cctgggtttc attgccgatg gctgtctgta tgtcaccgga  31680
agggtaaagg aggtgctgat catacgcggt aagaatcatt accccgcaca tatcgaagcc  31740
tcgatcgccg ctaccgcatc gcctggcgcg ctgatgccgg tggtgttcag catcgagcgg  31800
caggacgagg agcgcgtagc tgcggtgatc gccgtcaatc acccgtggac gccggcagca  31860
tgcgccgcgc aggcacacaa gatccggcaa caggtagccg accagcatgg agtcgccctg  31920
gcggagctag cctttgccga acaccggcac gtgttcggca cctatccggg caaactgaag  31980
cggcgcctag tcaaggaagc ctatgtcaac ggccagctgc cgttgttatg gcatgagggt  32040
aagaaccggg acgtaccagc ggccgccgcg gacgatcggc aggcgcaaca cgtggcggac  32100
```

-continued

```
ctgtgtcgga aggtcttttt gccggtgttg ggtgtcgcgc cgccgcatgc ccaatggccg  32160
ctgtgcgaac tggcgctgga ttcgctccaa tgcgtgcgtc ttgccggtgc catcgaagag  32220
tgctacggcg tgcctttcga acccacgttg ctattcaagc ttgagacggt cggggcaatc  32280
gccgaatatg tcctggcgca cggacgtcag gcgcccacgc cgacgcgtgc gccggtggca  32340
agcacaacat gctcagagga accgatcgcc attgtggcga tgcactgtga ggtgcccgga  32400
gcgggcgaga acactgaagc attgtggtcg ttcctgcgga gcgacgtcaa cgcgatccgg  32460
ccgatcgaat caacgcgccc ggacttatgg gcagcgatgc gcgcctatcc cggcctcgcg  32520
ggcgaacagc tgccgcgcta tgcgggtttc ctcgacgacg ttgatgcttt cgatgctgcg  32580
tttttcggta tctcgcgtcg cgaggccgaa tgcatggacc cgcagcagcg caaagtgctg  32640
gagatggtgt ggaagctgat cgagcaagcc ggtcacgatc cgctgtcctg ggcgcggccag  32700
ccggtcggcc tgttcgtggg tgcgcatacg tccgactatg gcgagctgct ggcgagccag  32760
ccgcaactga tggcccaatg tggcgcttac atcgattcgg gttcgcattt gaccatgatt  32820
ccgaaccggg cttcgcgctg gttcaatttc accggcccca gcgaagtaat caacagcgct  32880
tgctccagct cgctggtggc gctgcatcgg gcggttcaat cgctgcgcca aggcgaaagc  32940
agtgtcgccc tggtactcgg cgtgaacctt atcctggctc ccaaggtgct gttagccagt  33000
gcaagcgcgg gcatgctttc gcccgatggc cgctgcaaga cgcttgacgc cgccgccgat  33060
ggcttcgtgc gttcggaagg gatcgcaggg gtgatattga agccactggc gcaggcgctg  33120
gccgatggtg acagggtcta cggtctagtc cgcggcgtgg cggtcaacca tggcggccgt  33180
tccaattcct tgcgtgctcc caacgtcaac gcgcagcggc aactgctgat ccggacttac  33240
caggaagccg gtgtcgagcc ggccagcgtc ggttatgttg aactacacgg cactggtacc  33300
agcctgggtg atccgatcga aatccaggcg ctgaaggaag ctttcattgc gttgggggca  33360
caggccgccc cgtcaaactg cggcatcggt tcggtgaagt ccgcgctggg ccatctagaa  33420
gccgctgcag gcctgaccgg cctgatcaag gtgctgctga tgctcaagca cggcgagcag  33480
gccggcacgc gccatttcag cacgctcaat ccgctgatcg atttgcgagg tacgtcattc  33540
gaagtggtgg cgcagcatcg cgcatggccg tcgcaggtcg gcattcacgg cacactcttg  33600
ccgcgtcgcg cgggtatcag ctcattcggc ttcggcggcg ccaatgcgca tgcgatcgtg  33660
gaagagcatg tcattgccac gccccccctcg acgagctccg ctggcggccc ggtaggtatc  33720
gtgttgtcag ccggtagtga agctgtcttg cggcaacaag tgctggcctt gtcagcctgg  33780
ctaaggcagc aatcgccgac acccgcgcaa atgatcgatg tcgcctacac cttacaggta  33840
ggacgcgcag ccctgtcgca caggttggct tttagcgcga cggacgccga gcaggcattg  33900
gcgaggcttg agggtcgtct ggcgggcgtg atggatgccg aggtccatca cggtgtcgtg  33960
gatgctgccg caacggctcc cgaacatggg cggcagacgc gcgaaggtct tgccggtttg  34020
ctgcgagcct ggactcaggg cgtgcgcgtc gattggtcgg cgctgtacgg catacagcga  34080
ccgcagcgcg ttagcctgcc tgtctacccc ttcgctaggg aacgctattg gctgcccggc  34140
caggctatgc atgccgctgc ggacgctcat ccgatgctgc agctgttgca tgccaatgcc  34200
aaactacatc gctacgcctt gcgtaggtcc ggctgcgcaa gctttcttgt tgatcattgc  34260
gtggatggtc gacaggtact accggcagcc gtgcaactgg aattggtgcg cgccgtggcg  34320
cagcgggtca tggcgcagga tgagggttgt atcgaactgg cgcaggtcgc ctttttgcat  34380
cccctcatga tggaggagac tgagctggag gtcgaaatcg aactgtcgaa gagcgatcaa  34440
gatgagttcg atttccaact tcacgatgct caccgccaac aggtctttag ccaggggcac  34500
```

-continued gtacgtcgcc gggtctatac ggcgacaccg cgcttggatt tagcccagct gcaaaagctt 34560
tgtgccgagc gcgtgttgtc cggcgaagac tgttatgcgc acttcaccgc ctgcggattg 34620
cagctcggcg accggctcaa atccgtgcaa tcgatcggct gcggacgcaa tggcgagggc 34680
gagccgatcg cattgggtgt cctgcgcctg ccaccatcaa gcgttgaaga cagccatgtg 34740
ctgcctccta gcctgcttga tggtgccttg cagtgtagcc ttggcttgca gcgtgatgtc 34800
gagcacatcg ccatgccata cacgctggag cggatgacgg tgcatgcgcc gattcctccc 34860
gaggcctggg tgctgctgcg tcacggccat gcagccagac agtccctgga catcgatctc 34920
ctggattccg aaggtagggt ctgcgtcagc ctcggcaatt acaccggccg tgcaccgaaa 34980
gccgtttccg ccgtcagggc gcttgtcttg gcaccggtct ggcaagcgtt gaccgaaacg 35040
gcgccggcat ggcccgatcc ggccgaacgc atcgttacgg taggagacga tgcatggcgt 35100
agtcacttcg gtttcgacga gccggccttg tccctggagg acagcgtcga agtcatcgcg 35160
acgcgactgg gccagagcgg caagttcgat catctagtct ggatcgtgcc gatagccgag 35220
agtgaaaccg atattgcagc gcaaggttca gcggcgatcg ccggtttccg gttggtcaag 35280
gcgttgcttg cgttgggcta tgcgcatcgc ccgctgggtc tcaccgtgct gactcgccaa 35340
gcccttacgc ggcagccgtc gcacgcggca gtgcacgggc tgatcgggac gctggccaag 35400
gaatactgca actggaaaat ccgtctgctc gacctgccga gcgtaaaatc ttggccgcaa 35460
tgggagcaat tgcggtcgtt gccttggcat gcgcagggcg aagccctgat cggccgtggg 35520
acttgttggt atcggcggca gttgtgtgaa gtgctgccgc tgccgtcgtt ggaaccgccg 35580
ccgtaccgcg taggcggtgt ctacgtcgtg atcggcggcg ctggcggctt gggtgaagta 35640
ttgagcgaac acttgatccg cacgtacgac gcgcagctga tctggatcgg gcggcgcgtg 35700
ctggacgaag gcattgcgcg caagcagacc cggcttgcgt cgctgggccg cgcaccgcat 35760
tacatctccg cggacgcgag tgacccggct gccctgcagg cggcacataa tgagatcgtt 35820
gcgctgcatg gccagcccca tgggctcatc ctaagcaaca tcgtgctgaa ggatgccagt 35880
ctggctcgta tggaggaagc cgatttccgt gacgtgctgg ccgcgaaact cgacgtcagc 35940
gtgtgtgcgg cacaggtgtt cggcacggcc ccccttgatt tcgtgctgtt tttttcttcc 36000
atccagagca ctaccaaggc ggccgggcaa ggtaactacg ccgccggctg ctgctatgtc 36060
gacgctttcg gcgagctatg ggcgcgccgg ggtttgaggg taaagaccat caactggggc 36120
tactggggca gcgtgggcgt cgtagcgggc gaggactatc gccggcgcat ggcgcaaaaa 36180
cacatggctt cgattgaggg tgccgaagcg atgcaggtgt tgtcgcagtt gttgtgtgcg 36240
ccgttgcaac ggcttgccta cgtcaagatc gacgatgcta acgcaatgcg cgctctgggc 36300
gtagtagagg acgagagcgt gcaaatccct gtgcacgcac cggccgagcc tcccagaggg 36360
cagcctggtc ccgtggtcga gttgtcggtg aatctggatg cccggcgcga acgggaaact 36420
ttgctggcgg cctggctgct tgagttgatc gagcaactcg gtggttttcc gccggcaagt 36480
ttcgacatcg ctacgcttgc gcaacgcctg cacatcgtac ccgcctatcg aagctggctg 36540
gaacacagcg tgcggatgct cggcgtgtat ggttacctca gagcgacggg ggaaagccga 36600
ttcgagctgg ccgacaagcc gcccgatgat gccaggggtg cctggaacgc gcatgtgcac 36660
gaggccagcg tcgaagccgg tgaagaggca cagcggcgtc tgctcgatcg ctgcatgcgg 36720
gcgttgccgg cggtccttcg aggcgaacgc aaggccaccg aattgctgtt tccggaaggt 36780
tcgatggcgt gggtcgaggg tatctaccag aacaacccgc ttgccgatta cttcaacgca 36840

-continued

```
caactagtca cgcgactgat tgcctacttg agacgacgac tagagtcgac gcctacggcg  36900
cgcctgaagc tgtgcgagat cggcgccggc agcggtggta ctactgcaag cgtgctacaa  36960
cagttgcagg catatggtga gcatattgag gaatatctct ataccgacct gtcgcctgtc  37020
ttcctgcatc atgcggaaaa acactatcag ccacgagcgc cttatttgag gaccgcctgt  37080
ttcgacgtag cgcgcgcgcc gacggcgcag gccctggaat ctggcggcta cgacgtggtg  37140
attgccgcca acgtactgca tgctacgcgc gatatcgcca agaccttgcg caatgcgaag  37200
gcactcctca aacctggcgg tctgctcttg ctcaacgaag tgatcgagcg cagcctcgtc  37260
ttgcacctga ctttcggtct gctggagagc tggtggttgc cccaggacaa gatcttgcgc  37320
cttgccggct cgccgttgct ggcttgcgcc acctggcgca gcctgctgga ggctgagggt  37380
tttgcggggc tgagcgtgca cagggcgcaa cccgatgccg ggcaggccat catctgtgcc  37440
tacagcgatg ggatagtgcg gcaagccagt acgatcgagg ttgcgcggaa tgaaaaagta  37500
accgttccgt cgcagccggc ggaagccggg gaatcgccgc tggatctggt caaaaaactg  37560
cttggacgca ttctgaaaat ggatccggcc acactcgata ccagccaccc gctggagtac  37620
tacggtgtcg attcgatcgt ggcgatcgaa ctggctatgg cactgcgcga gacattcccg  37680
ggttttgaag tcagcgagct gtttgaaacg caatccatcg ataccttgtt gggctctctt  37740
gagcaggctc ctctccttgc taccctcaca gctccgccgc aacaagacat gctgcagcag  37800
ctgaaacaac tgctggcgcg tacgctgaag ctggacatta cgcagatcga cacgagcaag  37860
acgctggaga gctatggtgt cgactccatc gtcatcatcg aattagccaa cgccttgcgt  37920
gagcgctatc cgagcttgga cgcgtcacag ctgatggaaa ccttatcgat cgaccggctg  37980
gttgcccaat ggcaggcaac ggagcccgcc gtaccggcag agccaacagc ggaaccgccg  38040
gtagccgacg aagacgccgc tgccatcatc ggactggccg gccgctttcc aggcgcggac  38100
acgttggagg agttctggaa caacctgcgc aacggccaaa gcagtatggg agaggtgcca  38160
ggcgagcgct gggatcacca gcactacttc gacagtgaac gccaggcacc gggcaagacg  38220
tatagccgct ggggtgcgtt tctgagggac atagacggct tcgatgcagc cttctttgaa  38280
tggcccgaca gcgtcgcgct ggaatcggat ccgcaagcgc ggatatttct agagcaggcc  38340
tatgccggga tcgaagatgc cggctacacg cctggctcgc tcagcaagag ccaacgcgta  38400
ggtgtattcg taggtgtgat gaatggttac tacagcggcg gagcgcgctt ctggcaaatc  38460
gccaaccgcg tgtcgtacca gttcgatttt cgcgggccaa gcctggcggt ggataccgcc  38520
tgttcggctt cgctcaccgc gatccacctg gcgctggaaa gcctgcgcag cggcagttgc  38580
gaggtcgcac tggccggtgg cgtgaatctg ctggtcgatc cgcagcaata tcttaatttg  38640
gctggcgccg cgatgctctc cgccggcgcc agctgtcggc cgttcggcga ggccgcggac  38700
ggtttcgtgg ccggcgaagc ctgcggcgtg gtgctgctca agccgctcaa gcaagcgagg  38760
gccgatggcg atgtgatcca tgccgtaatc aggggcagca tgatcaatgc cggtgggcac  38820
accagcgcgt tctcctcgcc taaccctgcc gcccaggccg aagtcgtgcg gcaggccttg  38880
cagcgcgcgg gcgtggcgcc cgattcgatc agctacatcg aggcgcatgg caccggcacc  38940
gtactaggcg atgcagtgga gttgggtgct ttgaataaag tgttcgacaa gcgcgcggcg  39000
ccatgcccga tcggctcgct gaaggcgaac atcggccatg ccgaaagcgc cgcgggcatc  39060
gccggcctgg ccaagctggt attgcagttc aggcatggcg agttggtgcc tagtctgaat  39120
gcgtttccct tgaatcccta tattgagttc ggtcgcttcc aggtacaaca gcagccggca  39180
ccgtggccgc gccgtggcgc ccagccgcgg cgcgccgggt tatctgcctt cggtgctggc  39240
```

-continued

```
ggatcgaatg cgcacctagt ggtagaggaa gctccggcta tggctcccgg ggtctcgatc  39300
agcgccagct ctccagcctt gatcgtgctt tcggcgcgaa cgctgcctgc cttgcaacag  39360
cgtgctcgcg atctgctcgt ctggatgcaa gcgcggcagg tggatgacgt catgctggcc  39420
gacgttgctt atacgctgca cttgggccgc gtcgcgatgg agcaacgcct ggcttttacc  39480
gctggctcgg ctgccgagtt gagcgagaaa ttacaggctt acctgggcca tgcgattcgg  39540
gccgacatct atctgagcga ggacacgccc ggcaaaccgg caggcgctcc gatcgtggcc  39600
gaggaagatc tgctcacgct gatggatgcc tggatcgaaa agggccagta cggtcgtttg  39660
ctggagtact ggaccaaggg ccaaccgatc gactggaaca aactctattg gcgcaagctg  39720
tatgcggacg gacggccgcg gcggatcagc ctgcccacct atccgttcga gcaccggcgt  39780
tattggcaaa cgccggtgcc gggcgagcga agcctgcacg ccaccgcgcc agctactcgg  39840
gaaacggttg cggttggtgc catgccggat ccggccggcg ctacggtgca agcccggttg  39900
tgcgccttgt gccaagtgtt gttgggcaaa ccggtcacgg cccagatgga tttctttgcc  39960
gtcggcggcc attcggtgct ggcgatccaa ttggtctcgc gcatccgcaa aagcttcggg  40020
gtggagtatc cggtcagcgc tttgttcgaa tcggcgctgt tgtcggacat ggcgcggcag  40080
atcgaacaat tgcgggtgaa cggagtcgcc aagcgcatgc cggcgttgtt gcctgccggg  40140
cgcgtgggcg cgattcctgc gacttatgca caggagcgcc tatggctcgt ccacgaacat  40200
atgagtgagc aacgcagtag ttacaacatc acctttgcca tgcacttcag aggcgtcgac  40260
ttccgtgctg aagcgatgcg tgccgcattg aacgcgctgg tggtgcggca cgaagtgctg  40320
cgcacacgct ttctttcgga ggacgggcag ctgcaacagg tgatcgctgc ctcgttgacg  40380
ttggaggtgc cggtaagaga gatgtcggtc gaggaggtcg acctgctgct ggccgcgagc  40440
acgcgggaga ctttcgatct gcggcagggg cccttgttca aggcacgcat cctgcgcgtg  40500
gcggccgatc accatgtggt gttgagcagc atccaccaca tcatttccga cggctggtcg  40560
ctgggagtgt tcaaccgtga cctgcaccag ctgtacgagg cgtgtttgcg cggcacgccc  40620
cccacactgc cgacgctggc ggtgcagtat gccgactacg cgctgtggca acggcaatgg  40680
gagctggcgg ctccgctgtc gtactggacg cgggcactgg aaggctacga cgacggcctg  40740
gacttgccct acgaccggcc gcgcggcgcc acgcgggcgt ggcgggcagg gctggtcaaa  40800
caccgctatc cgccgcaact ggcccagcag ttggcggcct acagccaaca gtaccaagcg  40860
acgctgttca tgagcctgct ggcaggcctg gcgttggtgc tgggccgtta cgccgatcgc  40920
aaggacgtgt gcatcggcgc gacggtctcc ggccgcgacc agctggagct ggaagagctg  40980
atcggctttt tcatcaatat tttgccgctg cgggtggacc tgtcgggggga tccgtgcctg  41040
gaggaggtgc tgctgcgcac gcgtcaagtg gtactggatg gcttcgcgca ccagtcggtg  41100
ccgttcgagc acgtgttgca ggcgctgcgg cgtcagcgcg acagtagcca gatcccgctg  41160
gtgccggtga tgctgcgaca ccagaacttc ccgacgcagg agattggcga ttggcccgag  41220
ggagtgcggc tgacgcagat ggagctgggg ctggaccgta gcacgccgag cgagctggat  41280
tggcagttct acggcgacgg cagctcgctg gagctgacgc tggaatacgc gcaggacctc  41340
ttcgacgaag cgacggtgcg gcggatgatc gcacaccacc agcaggcgtt ggaggcgatg  41400
gtgagccggc cacagctgcg ggtgggcaag tgggacatgc tgacggccga agagcgccgg  41460
ctgtttgccg cgctaaatgc gacaggtacg ccacgggagt ggcccagtct ggcgcagcag  41520
ttcgaacggc aggcgcaggc gacgccgcag gccatcgcgt gcgtgagcga tgggcagtcg  41580
```

-continued

```
tggagctatg cgcagttgga ggcgcgcgcc aaccagctgg cacaggcgct gcgggggcag  41640
ggcgcgggcc gggacgtgcg ggtggcggta cagagtgcgc gcacgccgga actgctgatg  41700
gccttgctgg cgatctttaa ggccggtgcg tgctatgtgc cgatcgatcc ggcctacccg  41760
gcggcctacc gcgagcagat cctggccgag gtgcaggtgt cgatcgtgct ggagcaagac  41820
gagctggcgc tggacgagca agggcagttc cacaatccgc gttggcgcga gcaagccccg  41880
acgccgctgg ggctgaggga gcatccgggc gacctggcgt gcgtgatggt gacctccggc  41940
tcgaccggcc ggcccaaggg cgtgatggtg ccgtatgcgc agctgtacaa ctggctgcat  42000
gcaggctggc agcgttctcc gttcgaggcc ggggagcggg tgctgcagaa gacctcgatc  42060
gcctttgcgg tgtcggtaaa ggagttgcta agcgggctgc tggcgggggt ggaacaggtg  42120
atgctgccgg acgagcaggt gaaggacagc ctggcgttgg cgcgggcgat tgagcaatgg  42180
caggtgacgc ggctgtacct agtgccatcg cacctgcagg cgctgctgga cgcgacgcaa  42240
ggacgagacg ggctactgca ctcgctgcgt cacgtggtga cggcggggga agcgttgccg  42300
tctgcggtgc gcgaaacggt gcgggcgcgt ctgccacagg tgcagctatg gaacaactac  42360
ggctgcacgg aactgaacga cgcgacctac caccggtcgg atacggtggc gccaggaacg  42420
tttgtgccga tcggcgcacc gatcgccaac accgaggtat acgtgctgga ccggcagctg  42480
cggcaggtgc cgatcggggt gatgggcgag ctgcacgtac acagcgtggg gatggcgcgc  42540
ggctactgga accggccggg gctgacggcc tcgcgcttca tcgcgcaccc gtatagcgag  42600
gagccgggca cacggctgta caagaccggt gacatggtac gccggctggc ggacgggacg  42660
ctggaatacc tgggccgaca ggacttcgag gtcaaggtgc gcggccaccg ggtggatacg  42720
cggcaggtgg aggcggcctt gcgggcgcag cccgcggtgg ccgaggcggt ggtgagcggt  42780
caccgggtgg acggggacat gcagttggtg gcctatgtgg tggcgcgtga agggcaggca  42840
ccgagcgcgg gcgagttgaa acaacagctg tcggcgcagt tgccgaccta catgctgccg  42900
accgtgtacc agtggctgga gcagttgccg cggctgtcca acggcaagtt ggaccggttg  42960
gccctgccgg caccgcaggc ggtacacgcg caggagtacg tcgcgccacg caaccaggcc  43020
gagcaacggc tggcggcact gtttgccgag gtgctgcggg tggagcaggt aggcatccac  43080
gacaacttct tcgccttggg tgggcactcg ctgtctgcat cgcaactgat ctcgcgtatt  43140
gccagggata tggcgatcga tctgcccctg gccatgctgt tcgagctgcc cacggtagcg  43200
cagcttagcg aatccctcgc cagccatgca cgcgacagcg attacgatgt catccccgca  43260
agcaccgagg aggcgaccat tccgctttcc actgcgcagg agcgcatgtg gttcctgcac  43320
aagttcgtgc aggagacgcc gtacaacacc ccgggtctcg ccttattgca aggcgaactg  43380
gacatttcgg ccttgcaggt agcatttcgc tgtgtgctag aacggcacgc cgtgctgcgt  43440
acccatttcg tggaaaccga gcagcaatgc gtacaggtca ttggcgcagc agagcagttc  43500
gtgctgcagc ttaggtcgat tcgcgacgag gctgatctgc atggcctatt gcacacagcc  43560
gtcagcgaac ccttcgattt agaacgcgag ctgccattgc gcgccctgct gtatcgcctg  43620
gacgaccggc ggcattacct agcagtggtc atccatcaca tcgtcttcga cggctggtcg  43680
acctcaatcc tgtttcgtga gctggccacg cactatgctg catgccgcca tggccaatcc  43740
gcgcctttgc caccgctgga gcttagctat gccgattacg cacgctggga gcgtgcgagg  43800
ctgaaccagg aagacgcgct gcgcaagctc gaatattgga aacgcagcct tgccgatgca  43860
ccgccgctgg tgttgcccac gacctatgcg cggccggttt tccagaactt caatggcgcg  43920
actgtggcgc ttcagatcga gccgccgctg ctgcaacgcc tgcagcgttt cgccgacgca  43980
```

-continued

```
cacagcttta cattgtacat gctacttctg gcagcactgg gcgtcgtatt gtcgcgccat  44040
gcccggcaga agcatttctg cattggcagt ccggtcgcca atcgcgcccg agccgagttg  44100
cacggtttga tcggtttgtt cgtcaacacc ctggcggtac ggctcgattt ggacggcaat  44160
cccagcgtgc gcgagctgct cgaacgcatc cactgcacca cgctggccgc ctacgagcac  44220
caggatgtgc cgttcgaaag aatcgtggaa agcctgaagg taccgcgcga taccgcgcgt  44280
aacccgctgg ggcaggtgat gctcaatttc cagaacatgc caatgtcggc gttcgacctg  44340
gatggtgtcc aggtgcaggt gctccccatg cacaacggca cggccaagtg cgagctgacc  44400
ttcgacctgc tgctggatgg ctcacgccta tccggtttcg tcgaatacgc cactgggctg  44460
tttgcgccgg aatgggtcca ggcgctggta cagcaattca agtgtgtgct ggcggcattg  44520
gtggaacggc cggaggcatc gctgaatgat ttgcccatgg cgcccaacga ggcgcaaccg  44580
gcgtcgccgg cattgatgaa gcatgtcgcg ccgagcttgc ccaacttact tgaggctatg  44640
gcggccaatg atgccgcacg cctcgccttg caagcgccgg aaggtgcgct cagttacgct  44700
cagctaatcg aggcagcaaa cgagttcgcc tggcgtttgc ggtgcgagca cgccggtccg  44760
gacaaagtcg ttgccctgtg cctagcgcct tgctccgcct tggtggttgc tttgctggcc  44820
gcttcattat gcggtgcggc gagcgtgctg atcgatccga cgacgactgc cgaggcgcaa  44880
tacgaccagt tgttcgaaac gcgggccggc atcgtggtga cctgttctag cttgctggag  44940
aagttgccgc tcgacgacca ggctgtagtg ctgatcgacg agcaagctgc agaagcgacg  45000
ccgcgtttga tgcatttcac cgacgatcca gctttgcccg caatgctgta ttgtgtgtgt  45060
gacgaaaagg ggcgaacccg cacgatcatg gtcgaaagcg gcagtttgtc gagtcgcctg  45120
ctcgatagcg tgcagcgttt cagtctcgaa cgcaccgatc gcttcctgct gcgcagcccg  45180
ctttctgccg aactggcgaa taccgaagta ctgcaatggt tggcggcagg cggcagcctc  45240
agcatcgcac ccatgcatgg cgatttcgat gccgctgcct ggctggagac cctcgcgacg  45300
tacgcgatca ccgtggccta cctggctcaa gttgaattga ccgagatgct ggcgcatctg  45360
caaaaccatc ctcttgagcg caacaagctg gccggcttac gcgtgctggt ggtgcatggc  45420
gcgcccttgc cgatcgcgcc actgatgcgc ctagacgcgt ggttgcgaga ggtgggcggt  45480
tccgcacgga tcttcgccgc ctacgggaat gccgagttcg gtgccgaaat attgagccag  45540
gatgtcagcg ctgcattgca agcgggtatt ggcgctcaat acaagcatcg ccgtggtctg  45600
ttcccgttgg gtgccaactc gatgtgtcac gtggtgcaga gcaacggccg catcgcgccc  45660
gacggcatgg ttggtgaatt gtggatcaca cagccagcct gcttgtacaa aaccgatgca  45720
ttggtgcgtc gcctggcaaa tggcaactg  gaatggttgg gctccctcga tgtccagtcg  45780
cgtatcgatg atccccgcat cgatctgtgc gtcgtggagg cacaactgcg cttgtgcgaa  45840
gacgtcggcg aagcggtagt gctgtatgag ccgttgaagc gctgcttggt agcctatctc  45900
tcggcccgta gcacagctgc aatcatgacc gacgagacgc tggccaggat ccgccaggcc  45960
ctgagcgaaa ccttgccgga ttatctactg cctgcaatct gggtgccgct cgcgcactgg  46020
ccacgcttac cccatgggcg ggtcgacctc ggcgccttgc ctgcaccgga tttcgatctt  46080
gcgcggcatg agtcgtacat agcgccacgc acagccgtcg aacaggccgt ggccgaaata  46140
tggcaacgcg tgttgaagcg tacccaggtc ggcgtgcatg acaatttctt cgagctgggc  46200
ggccattcgg tgctggcgat ccagctggtg tccggcttgc gcaaggcttt ggccatcgaa  46260
gtgccggtca ccctggtgtt cgaggcgccg atactggggg cgctggcgcg gcagatcgcc  46320
```

-continued

```
cccttgttgg tcagcgaacg gcgtccgcgc ccgcctggcc tgacgcgcct ggagcataca  46380
gggccgattc cggcttcgta tgcacaggag cggttatggc tggtgcacga gcatatggag  46440
gagcagcgaa ccagctacaa catcagtaac gcagcgcatt tcatcggagc agccttcagc  46500
gtcgaagcga tgcgtgccgc attgaacgcg ctggtggcgc ggcacgaagt gctgcgcaca  46560
cgctttcttt cggaggacgg gcagctgcaa caggtgatcg ctgcctcgtt gacgctggag  46620
gtgccggtac gcgaggtgtc ggccgaggag gtcgacctgc tgctggccgc gagcacgcgg  46680
gagactttcg atctgcggca ggggcccttg ttcaaggcac gcatcctgcg cgtggcggcc  46740
gatcaccatg tggtgttgag cagcatccac cacatcattt ccgacggctg gtcgctggga  46800
gtgttcaacc gtgacctgca ccagctgtac gaggcgtgtt tgcgcggcac gccccccaca  46860
ctgccgacgc tggcggtgca gtatgccgac tacgcgctgt ggcaacggca atgggagctg  46920
gcggctccgc tgtcgtactg gacgcgggca ctggaaggct acgacgacgg cctggacttg  46980
ccctacgacc ggccgcgcgg cgccacgcgg gcgtggcggg cagggctggt caaacaccgc  47040
tatccgccgc aactggccca gcagttggcg gcctacagcc aacagtacca agcgacgctg  47100
ttcatgagcc tgctggcagg cctggcgttg gtgctgggcc gttacgccga tcgcaaggac  47160
gtgtgcatcg gcgcgacggt ctccggccgc gaccagctgg agctggaaga gctgatcggc  47220
tttttcatca atattttgcc gctgcgggtg gacctgtcgg gggatccgtg cctggaggag  47280
gtgctgctgc gcacgcgtca agtggtactg gatggcttcg cgcaccagtc ggtgccgttc  47340
gagcacgtgt tgcaggcgct gcggcgtcag cgcgacagta gccagatccc gctggtgccg  47400
gtgatgctgc gacaccagaa cttcccgacg caggagattg gcgattggcc cgagggagtg  47460
cggctgacgc agatggagct ggggctggac cgtagcacgc cgagcgagct ggattggcag  47520
ttctacggcg acggcagctc gctggagctg acgctggaat acgcgcagga cctcttcgac  47580
gaagcgacgg tgcggcggat gatcgcacac caccagcagg cgttggaggc gatggtgagc  47640
cggccacagc tgcgggtggg caagtgggac atgctgacgg ccgaagagcg ccggctgttt  47700
gccgcgctaa atgcgacagg tacgccacgg gagtggccca gtctggcgca gcagttcgaa  47760
cggcaggcgc aggcgacgcc gcaggccata gcatgcgtga gcgatgggca gtcgtggagc  47820
tatgcgcagt tggaggcgcg cgccaaccag ctggcacagg cgctgcgtgg gcagggcgcg  47880
ggccgggacg tgcgggtggc ggtacagagt gcgcgcacgc cggaactgct gatggccttg  47940
ctggcgatct tcaaggccgg tgcatgctat gtgccgatcg atccggccta cccggcggcc  48000
taccgcgagc aaatcctggc cgaggtgcag gtgtcgatcg tgctggagca aggcgagctg  48060
gcgctggacg agcaagggca gttccgcaat cggcgttggc gcgagcaagc cccgacgccg  48120
ctggggctga ggggacatcc gggcgacctg gcgtgcgtga tggtgacctc cggctcgacc  48180
ggccggccca agggcgtgat ggtgccgtat gcgcagctgc acaactggct gcatgcaggc  48240
tggcagcgtt ctgcgttcga ggccggggag cgggtgctgc agaagacctc gatcgccttt  48300
gcggtgtcgg taaaggagtt gctaagcggg ctgctggcgg gggtggggca ggtgatgctg  48360
ccggacgagc aggtgaagga cagcctggcg ttggcgcggg cgatcgagca atggcaggtg  48420
acgcggctgt acctagtgcc gtcgcacctg caggcgctgc tggacgcgac gcaaggacgc  48480
gacgggctac tgcactcgct gcgtcacgtg gtgacggcgg gggaagcgtt gccgtcggcg  48540
gtgggcgaag cggtgcgggt gcgcctgcca caggtgcagc tatggaacaa ctatggctgc  48600
acggaactga acgacgcgac ctaccatcgg tcggatacgg tggcgccagg aacgtttgtg  48660
ccgatcggcg caccgatcgc caacaccgag gtatacgtgc tggaccggca gctgcggcag  48720
```

-continued

```
gtgccgatcg gggtgatggg cgagctgcac gtacacagcg tggggatggc gcgcggctac  48780
tggaaccggc cggggctgac ggcctcgcgc ttcatcgcgc acccgtatag cgaggagccg  48840
ggcacacggc tgtacaagac cggtgatatg gtacgccggc tggcggacgg gacgctggaa  48900
tacctgggcc gacaggactt cgaggtcaag gtgcgcggcc accgggtgga tacgcggcag  48960
gtggaggcgg ccttgcgggc gcagcccgcg gtggccgagg cggtggtgag cggtcaccgg  49020
gtggacgggg acatgcagtt ggtggcctat gtggtggcgc gtgaagggca ggcaccgagc  49080
gcgggcgagt tgaaacaaca gctgtcggcg cagttgccga cctacatgct gccgaccgtg  49140
taccagtggc tggagcagtt gccgcggctg tccaacggca agttggaccg gttggcgctg  49200
ccggcgccgc aggtggtaca cgcgcaggag tacgtcgcgc cacgcaacga ggccgagcaa  49260
cggctggcgg cactgtttgc cgaggtgctg cgggtggagc aggtgggcat ccacgacaac  49320
ttcttcgcct tgggtgggca ctcgctgtct gcatcgcaac tgatctcgcg catccgccaa  49380
agttttcacg tcgatctgcc gctgagccgg atcttcgagg cacccacgat cgagggcctg  49440
gtcaggcagc tagcgttgcc tagtgaaggc ggcgtggcca gcatcgccag ggtagcgcga  49500
aaccggacga tcccattgtc gctgttccag gaacgcctgt ggttcgtgca ccaacacatg  49560
cctgagcaac gcaccagtta caacggcacg ctcgccttgc gtttgcgtgg tcctttgtcg  49620
gtggaagcga tgcgtgcagc gctgcgtgcg ttagtgctgc gccacgaaat cttgcgtacc  49680
cgcttcgtgt tgccgaccgg tgctagcgag ccggtgcagg tcattgacga gcacagcgat  49740
ttccagctct cagtacagct agtcgaggat actgagatcg cgtcgctgat ggatgaactg  49800
gcaagtcata tctacgactt agccaacggc ccgctgttca ttgcatgcct tttgcaactg  49860
gatgagcaag aacatgtgct gctaatcggc atgcatcacc ttatctacga cgcttggtcg  49920
caattcaccg tgatgaaccg cgatctacgc gtgctgtatc accgccacct cggacttgcc  49980
ggcggagatc tgccggaatt accgatccaa tatgccgact atgcgatctg gcaacgcgcc  50040
cagaacctgg acgcgcaact ggcctattgg caggctatgt tgcacgacta cgacgacggc  50100
ctggagctgc cctacgacta tccgcgtccg cgcaatcgca cctggcacgc agcggtctac  50160
acacacacct atccggctga actggtacag cgctttgccg gcttcgtaca ggcgcatcag  50220
tcgaccttgt tcatcgggct gttggccagc ttcgcggtcg tgttgaacaa atacaccggc  50280
cgggacgact tgtgcatcgg taccaccacg gcagggcgca cgcacctgga gctggagaac  50340
ctgatcggtt tcttcatcaa catcttgcct ttgcgcttgc gcttggacgg cgatccggac  50400
gttgccgaaa tcatgcggcg aacacggttg gtggcgatga gcgcgtttga gaaccaggcg  50460
ctaccgttcg agcacctgct caacgccctg cacaagcaac gtgacaccag ccggattccg  50520
ctagttccgg tggtgatgcg tcatcagaac ttcccggaca cgatcggcga ctggagcgat  50580
ggcatccgta ccgaagtgat ccagcgcgat ctgcgtgcca cccccaatga aatggacctg  50640
caattcttcg gcgacggtac ggggctttcg gtcacagtgg aatacgcggc ggagctgttc  50700
tcagaagcga ccattcgccg cctgatccac catcaccaac tcgtcctgga gcagatgttg  50760
gcggcccatg aaagcgccac gtgccccttg gatgttgccg actagcaaaa gccggccgcc  50820
gtcacccgtt catcgatagc gagggcaatc atggattcag cgttacctac atctgcattt  50880
accttcgatc tcttttacac cacggttaac gcctactatc gcactgccgc agtcaaggcg  50940
gcgatcgaac tggggctatt cgatgtggtg gggcagcagg gccgaactcc cgcagccatc  51000
gccgaggcct gccaggcgtc gccgcgcggc attcgcatcc tttgctatta cctagtatcg  51060
```

-continued

```
atcggttttc tacgccgcaa cggtggcctg ttctacatag atcgcaacat ggccatgtac  51120
ctggatcgta gttcgcccgg ctacctgggt ggcagcatca agttcctgct ctcgccctac  51180
atcatgagcg ccttcaccga tctgaccgcc gtagtcagga ccggcaagat caacctggcg  51240
caggacggcg tggtggcacc ggatcacccg cagtgggtgg aatttgcacg cgcgatggca  51300
ccgatgatgg cgctgccctc ggcgttgatc gccaatatgg tgtcgttgcc cgctgatcgg  51360
ccgattcgtg tgctggacgt ggcagccggc cacggcctgt tcggcatcgc cttcgcgcag  51420
cgcttccgcc aggctgaagt gagcttcctg gactgggaca acgtgctaga cgtagcacgc  51480
gaaaacgccc aggcggccaa agtggccgag cgagcgcgtt tcctgcccgg caacgcattc  51540
gacctcgatt acggcagcgg ctacgacgtg atcttgttga ccaacttcct gcaccatttc  51600
gatgaggtcg atggcgagcg catcttggct aagacgcgcg atgcgctgaa cgacgacggc  51660
atggtgatca ctttcgaatt catcgccgac gaagagcgtt cctcaccgcc gctggccgcc  51720
accttcagca tgatgatgct gggcaccacc ccggcgggcg agtcctacac ctatagcgat  51780
ctggaaagga tgtttcggca tgccggcttc ggccacgtgg aactaaaatc gataccgccg  51840
gccttgctga aagtggtggt ttcccgcaag agggccccat aatgatcgaa tcggcgacat  51900
cccctgtggc gaaaaccgag cgcatctggt gcaccgagct ggacctggat gcactcaacg  51960
ccatgtcggc caacacgatg caggccctgc tcggtatacg catgatcgag atcggctcgg  52020
actatctggt ctcctgcatg tcggtggact ggcgttgcca ccagccctat ggggtattgc  52080
atggcggcgc atcggtcacc ctggccgagg ctaccggcag catggcggcc tccatgtgcg  52140
tgccggccgg ccaacgttgc gttggcctag acatcaatgc caaccacatc gcgagcatct  52200
ccagtggcca agtacagtgc atcgcgcggc cgctgcacat aggggccttg acccaggtat  52260
ggcagatgcg catctatgac gaaggtgacc gcacgatctg cgtgtcgcgc ctgaccatgg  52320
cggtattatc ggtgcacgtc gcgcgcgtat ccccgaatcc agccagcagc ggagtccaga  52380
cgtgaacgaa actgcaactg taaccaaggc taccctcagt tcagcgaagg cgagtataac  52440
gccagcctgc gttcaccaat ggtttgaagc gcaggtgagt tcgacaccgg atgcgcctgc  52500
tgccttctta ggcgagcgtc gaatgagtta tggccagctc aacacccgcg ccaatcggct  52560
tgcacggctg ttgcagtcac agggcgttgg gcctggtgcc cgggtcgcgg tgtggatgaa  52620
tcgcagcccc gaatgcctgg ccgctttgct ggcggtcatg aaggccgggg cagcttatgt  52680
accgatcgac ctgagcctgc cgatccgacg tgtccaatac atcttgcagg acagccaggc  52740
ccggctcgta ctggtcgatg acgaagggca aggccgcctg gacgaacttg agctgggcgc  52800
gatgactgcc gtcgatgtct gcggcactct ggacggcgac gaggcgaatc tggacctgcc  52860
ttgcgatccg gcgcagccgg tttattgcat ctatacctcc ggctccacag gtagccccaa  52920
gggcgtgctg gtacggcaca gcgggttggc taactacgtg gcctgggcta agcggcaata  52980
cgttacggct gacacgacga gtttcgcctt ttactcctcg ctgtcgttcg atctgaccgt  53040
cacctcgatc tacgtgcccc tggtggctgg cctgtgtgtg catgtgtacc cggagcaggg  53100
cgacgacgtg ccggtaatca accgcgtgct ggacgacaac caagtagacg tgatcaagct  53160
gacaccctcg cacatgctga tgctgcgcaa cgcggcactg gcgacgtctc ggctgaagac  53220
gctgatcgtg ggtggcgagg acctgaaagc ggcggtggcg tacgacatcc atcagcggtt  53280
ccgccgcgat gtggcgatct acaacgaata cggtcctacc gaaaccgtag tggggtgcgc  53340
gatccatcgt tacgatccgg cgaccgaacg cgaaggctcg gtgccgattg gtgtgccgat  53400
cgatcacacc agcctccacc tgctcgatga acgtctgcag ccggtcgcac cgggcgaggt  53460
```

-continued

```
cggccagatc cacatcggtg gcgcgggcgt ggccatcggc tatgtgaaca agccggagat  53520
caccgatgcg caattcattg acaatccctt cgaaggcagc ggccggcttt acgccagtgg  53580
cgacctagga cgcatgcgtg ccgacggtaa gcttgaattc cttggccgca aggattcgca  53640
gatcaagctg cgcggctacc gcatcgaact gggcgagata gagaacgttc tgcttggcca  53700
cgcagccttg cgcgaatgca tcgtggatac caccgtggcg ccgcgccgcg actatgacag  53760
caagagcttg cgctattgcg cgcgttgcgg tatcgcttca aatttcccca ataccagctt  53820
cgacgagcac ggtgtctgca accattgcca cgcctacgac aaataccgga acgtggtcga  53880
ggattatttc cggaccgaag atgagctacg tactatcttc gagcaggtca aggcgcacaa  53940
caggctccgc tacgactgcc tggtggcttt cagcggcggc aaggacagca cctatgcgct  54000
atgccgcgta gtggacatgg gcctgcgcgt gttggcgtac accctggaca atggctacat  54060
ctccgacgag gccaaggcaa acgtcgaccg cgtcgtgcgc gagctggggg tggaccatcg  54120
ctatctgggt actccacaca tgaacgccat cttcgtggac agcctgcatc gccacagcaa  54180
cgtctgcaac ggctgcttca agaccatcta tacgctgggt atcaacctgg cgcacgaagt  54240
gggcgtaagc gacattgtaa tgggcctgtc caaaggacag ctgttcgaga cgcgcctgtc  54300
tgagctgttt cgcgccagca ccttcgacaa ccaggtattt gagaagaacc tgatggaggc  54360
gcgcaagatc taccatcgca tcgacgacgc ggcggcccgc ctgctggaca cctcttgcgt  54420
gcgcaacgat cgcttgctcg aaagtacgcg tttcatcgac ttctaccgct actgcagtgt  54480
cagccgcaag gacatgtatc gctatatcgc cgagcgcgta ggctggagcc gtccggctga  54540
caccggccgc tcgactaact gcctgctcaa cgatgtgggc atctacatgc acaagaagca  54600
acgtggctat cacaactatt cgttgcccta cagttgggac gtgcgggtag gccatatccc  54660
aagggaagac gcgatgcgcg agctggagga caccgacgat atagacgagg ccaaggtact  54720
gggcctgctc aagcagatcg gctatgactc aagcctgatc gatacccagg cgggcgatgc  54780
gcagctgatc gcctactacg tggcggcgga ggaactggat ccggtggcat tgcgcaattt  54840
tgctgctgcg atcttgcccg agtacatgct gccttcgtat ttcgtgcggc tggaccgaat  54900
gccgttgacg ccgaatggca aggtgaaccg ccgagcattg ccgaggccgg agttgaagaa  54960
gaacgccagc gaggcgcata ccgagccgag cagtgcgcta gagcaggaac tggtgcaaat  55020
ctggaaagag gtgctgatgg tcgacaaggt cggcgtcagg gacaactttt tcgagctggg  55080
cggccactcg ctgagcgcgc tgatgttgct ctacagcata gccgagcgct accagaagat  55140
ggtcagcatc caggcattct cggttaatcc gaccatcgaa ggtctgtcgg agcatctggt  55200
cgcataaaag ggcaaggacc tcagcgctgt cctctgcatg gtgcggcgtt ggggttcgca  55260
cgccattcaa tatgattgtc atcacttatc gtgagtacgc taatcatagg gcagggcgcc  55320
gacacaggag gcattcacgg cgctgccgac gcacttgtgc cgccggcgaa cgcccgactg  55380
tggagcgcat ccgtgcccac ctaggcactg ggtctccgaa caccgtggtg cgctggctgg  55440
atacctggtg gcaaggcttg ggagatcgaa tcgccaacgt gcctgaagca gtctccgcac  55500
tggtagggca gtggtggacg ctggctttgg atcatgcgcg aagccatgcc ggtgaggcca  55560
tcgctgctga gcgcacagcc ctccaagatg cacgcagcag cttggagggc gaccgccatg  55620
gctgcaggcc gagctcgctc agctacgggg tgagaccgaa gctgcccact aaacggaaca  55680
gctcgcgacg acccgagcta ttgagctgga gcgcctggtc gagcaactcc aacgccagat  55740
taatgagatg gagcggcagc gtgacacggc ggtgcagcgc atcaccgagg ctgaggaggc  55800
```

-continued acgggaggtg ctccggaggc agtacgtgaa aatttgatc 55839

<210> SEQ ID NO 2
<211> LENGTH: 2986
<212> TYPE: DNA
<213> ORGANISM: Xanthomonas albilineans

<400> SEQUENCE: 2
gaattcagcg atgttggctg cggtggccgg caccgccttg ccctgcggca ccaggtagtt 60
gcggccgtaa cccggcttga cgtcgacctt gtcgccgagg ccgcccaggt tggtgacttt 120
ctgcagaaga atcaattgca tggcgttact ccgttattcg ttagcggcgg catgcggcca 180
ccgcaacgcg tgctgtccga ataggacggg attggattgc gcggagtcgg acatgtaccc 240
aaccgacacc cggcggttgc ttcggtcgcc gcacacggga atgcgcgcgc ttccgaacga 300
ctcggatcaa acgtcgtggt tgtccgtgta cgggatcagc gccaggaaac gcgcacgctt 360
gaccgccgtg gccaactgac gctggtactt ggacttggtg ccggtcacgc ggctcggcac 420
gatcttgccg ttctcggtga ggtactggcg cagggtgttg agatccttgt agtcgatctc 480
tttgacgccc tcggcggtga atttgcagaa cttgcgacga cggaagaact tggacatgga 540
cctgctcctt aggcggcttc gacggcgtcg ccgtcggctt cgttggcggc ggcggacaca 600
tcgccatcgt cgtcgtcgcg acgacgacgc tcaccacggt cgggcttgtc gcccttctcg 660
tccttgctct tcatgatcag cgactgctcg gtgtcggcgc catcgcgctt gatcgccagg 720
tgacgcagca cggcgtcgtt gaagcggaag ctctcgacca actcgctcag cacggcctga 780
tccacttcga tgttgagcat gacgtagtgc gccttcacca gattctggat cgggtaggcc 840
aactgtcggc ggccccagtc ttccaggcgg tggatggtgc cgccgccgtt ctcgaccagc 900
gacttgtagc gctcgatcat ggcggggacc tgctcgctct ggtccggatg gaccaggaac 960
acgatttcgt aatgacgact catgtggttg tacctttcgg atgtggccca agggccagtc 1020
agccccccgc aggtggcggt ggagcaaggg ttcccgcccg aataggcgca ggaagccaat 1080
aagtatggca gcgcccttga ccaatgacaa gctcatgcac ccaggacgcc cgctctgctc 1140
cgcgtcgtcc atcgccattg cgcccctccc cgaccccaag catcgaccaa aggaccgaat 1200
gcggcgggta ggcgcgactc tgcgacacta gcgcaatgtt atcgtcgaca ttgacgccca 1260
cagccctcag cgcaacgcaa tgcccaatgc cgtaccgatg cagggcgcgc ggggactccc 1320
gcagccgcaa gcgatgaacc cagggttgcc gagcgtcggc ggcttgagcg caggccagcc 1380
attgcagttg tcgttagcac cggaactgca ggcagccgcg cgcagtgccc accgccatct 1440
gctcgacgac ggcacggcgc tttacctgct ggcgttcgat accgcgcaat tcgacccggg 1500
ggctttcgcg gcaatggcaa tcgcccgccc ggacagcatc gcccgcagcg tgcgcaagcg 1560
tcaggccgag ttcctgttcg gccgtctggc cgcgcgactg gcgctgcaag aggtgctggg 1620
acctgcgcaa gcgcaggcag acattgcaat cggcgcgacg cgcgcgccct gctggcctgc 1680
cggcagcctg ggcagcattt cccattgcga ggactacgcg gccgccatcg ccatggcggc 1740
cggcacccgc cacggcgtgg gcatcgatct ggaacgacca atcacacccg cggcgcgcgc 1800
ggcgttgctg agcatcgcaa tcgatgccga cgaagccgct cgtctggcaa aggcggcaga 1860
cgcgcagtgg ccgcaagacc tgctgctgac cgcactattt tcggccaagg aaagcctgtt 1920
caaagccgcc tacagcgcgg tcggacgcta cttcgacttc agcgcggcac gcctgtgcgg 1980
catcgacctg gcacggcaat gcctgcatct gcgcctgacc gagacactct gcgcgcaatt 2040
cgtggccggg caagtgtgcg aggtcggctt cgcgcgccta ccaccggacc tggtgctcac 2100

-continued

```
ccactacgcc tggtgagcac gcggacagtc gaacccgcca acgccaacgg cactcaagac   2160
gtggcgtgcg ccgcgtcggt cgtgaagctc tccccgcagc cgcactcggc ggtggcattg   2220
ggattgcgga acacgaaggt ctcacccaag ccctgcttgg cgaagtcgat ttcggtgcca   2280
tcgaccaact gcagactggc ggcatcgaca taaatccgca ctccgtcctg ctcgaacacc   2340
gcatcgtccg cgcgtgcctc gtgcgccaga tcggtgacat ggccccaacc ggaacagcct   2400
gtgcgtacca ccccgaaacg tagacccagc gcaccgggag tctggtcgag gaaacgctgc   2460
acgcgtgcaa acgcggcggg ggtgaggcgg atggccatga cgaacgactc caacgacttg   2520
cgatacgaca ttatacgacc gatgcccgca acgcctcgca agcgctacgc tccagccagt   2580
acacttgttc attccatatc gagccactgc ggcgaggatt caagtcatga cggtggtgag   2640
cgttgaacat gcgctggcag ggaagatccc ggtcggcggc gaagtgaccg tccgcggctg   2700
ggtccgtacc cggcgcgact ccaaagcggg gctgtccttc gtcaatgtca gcgacggttc   2760
ctgcttcgcg ccgatccagg tggtggctcc ggccgcgctg cccaactacg aaccggaagt   2820
gaagcgcctg accgccggct gcgcggtgat cgcgcgcggg cacctggtcg cctcgcaagg   2880
ccagggccaa agcttcgaga tccaggccga gagcatcgag gtactgggct gggtcgagga   2940
cccggagacc tacccgatcc aacccaaagc gcattcgctc gaattc                  2986
```

<210> SEQ ID NO 3
<211> LENGTH: 9673
<212> TYPE: DNA
<213> ORGANISM: Xanthomonas albilineans

<400> SEQUENCE: 3

```
gaattcggac ctggcgagta cttggaccgc gctgtgatgg tcaactgcca gggtggaagc     60
ttcgctcccg gcatcgagat gacgttcgtc gtgcgcgatc cggcgctcta ccgcgccgac    120
tggcaaagca gcggctgcgg accattccga atccgaggac gtgcgttgga ctacgccagc    180
gtgcaatacg gccagccatt tctgagcgtt ggctatctcc cctaccaacc cggtccggat    240
ggcatcgacc ccgcgccgct ggagccaggc gacctctcca agtttatgtc gattccttgg    300
caaaccgact acaacgcctg cgcgacgttc actgccgacc cgaatccgga caacagcacc    360
acactttact gggcctggcc agcacagcgc ccattcaccg tgcatgtagc caccgatgtc    420
agggacggca agccaggccc gcaacgctat tccattcgcg gtgcgggcac cacatccgac    480
gatctgagta acgctggccg tttccaaaac catatcgaca tggtgaacaa ctggcaccgc    540
atcggcttcg tcatccaggg cagcgcgatc gacggcgata ttcgctacag cccggacatg    600
tacctggaag tggccagtca actggacgaa ccggagatcg cgccctggcc gatgaatgcc    660
aacagcgcgg acacttgaag catgaatacc cactgcgacg tggcggtcat cggcgcaggg    720
ccggcgggat gcgcggcagc catcgcattg cgccgtgccg gcgtcggcag cgtggtcctg    780
atcgatgccg gcgacggtca gcgcccgcgt tacggcgaga gcctgcctcc ggcgaccggc    840
ctgctgctgc atgcactggg cgtggccgat accttcgctg cgctggacat gcgcagatgc    900
atcggcaacg cctcgtcatg gggagcgcaa acgttgggct acaacgactt cctgttcgat    960
ccacacgggc ccggttggca ggtggatcgc cgcgatttcg atgcgttcct gctgcaacag   1020
gcgagcagcg gcggtaccgg cgtgcgcttg cacacccgcc tggagagtgc ctccgacgcg   1080
gacccggatg gtctgcgact gcgcttgcgc tcgcacggca cggcactaac cacgctgcat   1140
gcccgtttcg ccgtcgatgc cagcggccaa cgcgcacggc tggcacaggc gctgggcgcc   1200
```

-continued

```
gaacgcgtca ccggtgatcg cttggtctgc cttgccgcgc tgttgccggt ggacaccacg   1260
agtcggctcg ggcaacgctc gctgctcgaa gcagtcgact atggctggtg gtatgcggca   1320
ccgttgacgt ccggcgaagc catcgtcgtc ctcgccaccg atgcggcggt cctgcgcgaa   1380
cagcgtctgc aagaacccgc gcgatggtcg gtgcggttgg cacaaaccca ccatatcggc   1440
gccaccgtcg gctggatgcg cagggcacca ccatactgcc tgtccacgcg ccaggcgcgc   1500
tctgcacgat tgagccactg ctgtggagcg cgctggctgg caatcggcga tgcagcgtcc   1560
agctacgatc cgctgtcctc acaaggcgtg cataaggcat tggccgatgc gctcgcagcc   1620
gccccgcgca tttgcgccgt gctcgaacga caccaagaca ctgcggtgat ggaacaggca   1680
cagcagatgc tggcgcgttt cgaaggctac cagcgcatgc gcgagcattt ctatcggcag   1740
gaagcacgct ggctggatgc gccattctgg cgccggcgcc gtgccgcgca aatacctgcc   1800
ccgccccaca cggaccattc ccctataaaa acccaccgca tgaacgtatc gccttgagcg   1860
atcatcaata caaccaaata cccacgacat aggttcatgc tgggacgacg acactgcacc   1920
tgaaccacat gccgatgttc ggctagcagg accgcatcct gaacagcgct gccgcccgcg   1980
cagcacgcaa gcccgcccgg atgcacgacg tgcagcgcgg caccaggatc gccgacgcgc   2040
gcatcgcgtg gtcagtgcgc cggcattgcc agttgcacct cggcactacc gaccttgttg   2100
cgcgggtcgc tggcggcacc tagctcatcg cggcgtttgt cccattccac cgtctgcagg   2160
ttgccccaga catggctgga accgcgcccg tccttggcgc tgtcgccagg caacttgagc   2220
ggatggtcca tcgccttcag cccctgcacg gtggctgcat cgaaggtacc ggtctcggcc   2280
tcgatcacgt ccggcaacca ctggtggtgg tagcgcttca gcgcggcgac ctgttgcgga   2340
tccagaccgt cgtcgtagcc gaggatgcca agcagaacca tggtgatgat acgactaccg   2400
cccggagtac cgagcacgat cgccttgtcc gcgttctcca tgaaggtcgg cgtcatcgag   2460
ctgagcgggc gcttgcccgg tttgggtgca ttggccgcat agcccatcac cccgaatacg   2520
ttgggcgtac ccggacgcaa ggcgaagtcg tccatctcat cgttgagcag cacgccggtg   2580
cccttgggga tcagtcccga gccgtacaac agattgaccg tctgggtggc gccgacacga   2640
ttgccttcac ggtcgatgat cgaaaaatgc gtggtctcat cgtcttccag cggggtcggc   2700
tgacccgaca acaggtcgct gggcgtggcc ttgtccgggt tgatggtcga acgcaggccc   2760
accgcatagt ccttgctcaa taaaatgcgc tgcggcacaa cggtgaaatc cgggtcgccc   2820
aggaagaagg tgcggtcacg gtaggcacgg cgcatcgctt ccacggtcag atggatccgg   2880
tgcaccgggt ccatcgcctt gagatcgtag gcttccagga tctgcagcat gctggccagc   2940
gcaatgccgc cggaggatgg tggcggcgcc gtggtgatcg tccagccctt gtagtcgaag   3000
cggatcggcg tgcgctgctt gaccgtgtag ccggccaact cgtcagcggt ccagcggcca   3060
ccggcctgct tgaccccagc cagcagcttc ctggcggtga cgccgcgata aaagccgtcg   3120
aagcccttgt cggccagcaa ctgcagagtg acggccagtt ccggctgctt gaacaggtcg   3180
ccctcggcga tcggccggcc atgacgcaga taaacctcgc gcgtgcccgg ataacgctcc   3240
atcaccttac gccgggcctg atagccctcg gccatgcgcg catacaccgg gaagccgtcg   3300
cgggcgatgc ggatcgccgg cgccagcgac tgccgcagcg gcaaccgacc atgccgggtc   3360
gccaactcca ccagcgccgc aggcagaccg ggaatgccag cggaccatgg gccgttgacc   3420
gagcggtcgt ggtccagtgc gcccttggcg tcgaggaacg tgtcgggcgt cgccgattcc   3480
ggcgccactt cgcgcgcgtc cagcatcgtg tcctggcccg tcctggcatc gtgcaggaga   3540
aagaaaccgc cgccgccgag accggagctg atcggttcga ccaccgacag cgtcgaggac   3600
```

-continued

```
accgccaccg ccgcatcgaa ggcattgccg ccctcgcgca ggatctgcaa gcccgcctcg   3660
gtggcgaggc ggtggccgct ggcgattgcg tcaccgggcg gatgcgacgt gggcgcagcg   3720
gcgctcgcac cgagcgaggc ctgggcccac gccgatgaca tcagcaccca ggcaagcaac   3780
aggacacagc gaacgctacg cctcatgcgc agcccccgct ccgtgtgggt acaactcggg   3840
gtggtcgcgg cgcaaccgcg ccagcttggc cagcaactgc ggatgggttt ccggaatcgc   3900
cggatccgga tcgatgcact ccacggggca caccaccacg cactacggct catcgaaatg   3960
accgacgcat tcggtgcagc gggccgggtc gatcacgtag atcgtctcgc ccatgaagat   4020
ggcctggttt gggcaggccg gttcgcaaac gtcgcagttg acgcagagcg cgttgatctt   4080
gagggacata gtgcgccatc ggaccctgac cagcgcatct taccggatcg tgatgacacg   4140
accatgcatt gacctgtaca acggcgccac cgcctacgcc tcgccactgc gggcgacgcg   4200
tgcgtgagga cgccggcgcg cgcaacgcgc gccggcgatg cacaacctac ttggcttcga   4260
cgaagatgta atcggcaccg gtcggcttga ccaccgcctc gacacgggca ttgtcggccg   4320
gggcgccgat atagaccacg cgcacgccct tcatgctgtt cggctcgacc ttggcgaagg   4380
ccgctgcgat caggtcggcc atcttggacg atgccgagga gccgaacgcc agcatgttcc   4440
ccggctgaat accacgaccg acggcggtgg tggcgctttc gacctgacgc tcgtacttgg   4500
cctggaactc cgcatccgac tccggcggca agtagtacag gaacgggctg ttggtgacat   4560
tgcccatgtt ctggattgcc acttgctgca ggtatttttt ccaaccggca tcgtcgtcct   4620
tggccggggc agtcagcgcc ggttgcgcat cggcgaccgg tttggccgcc tcttcctttt   4680
tgcaggcgct cacgcccagg gccaacgaga caatcaacaa cgcgcgtgcg gtggtcttca   4740
tggaacggtt tcctctgtgt agtcgatgaa tgacgggcgg ctcagccccg cgtcgcggcc   4800
tggcgggcct gaaccagcgc ctgcaacacc gaaggcggaa cgaagccgga cacgtccccg   4860
ccgaggcgcg caatctcgcg caccagcgag gacgagatga aactgtgttg ctcagccggg   4920
gtgaggaaca gcgtctccac ctcggggatc agatgccggt tcatgctcgc catctggaac   4980
tcgtactcga aatcggacac cgcgcgcagg ccgcgcagca gaaccccacc accgaccgaa   5040
cgcacgaaat gcgccaacag cgtgtcgaag ccgatcacct ccacgttgcg gtgtccagcc   5100
agcgcctcgc gggccagggc cacgcgcaat tccagcgaca gggtgggccc cttggacgga   5160
ctctgcgcca cgccgaccac cacctgctcg aacagcggtg cggcccgatt gaccaaatcg   5220
atatgcccat tggtgatcgg atcgaaggtg ccgggataga cggcgatgcg gctattggcc   5280
acggtcatgc gtaggatacc gcgtgaaagt cgccgggcag tttagcagcg gtgcgtcggt   5340
acagggcagc acggacctcg cggctaccgc cctcgcggta caacgcccag ccgaccggca   5400
gcgctggcgc ctgcccggcg ggcgattcca agtacaacca ggcatcgacc gccaggcgtg   5460
ccggcaaacg ctgcaacgcc ttctcccaca gaccggccgt gaaaggcggg tcgacgaagg   5520
cgatatcggc cagcgcggcg ccatcgtgtt cggccagcca gcgcagcgca tcgccctgca   5580
ccacctccac ctgagtctgg gcctgcaatc tggcgacggt ggcgcgcaac tgtgccgcct   5640
gggccgggtc gcgttcgatc agacaagcgc tgtgcgcgcc gcgcgacacc gcctccaacc   5700
ccagcgcacc gctgcctgcg aacaggtcca acacgcgcgc accgggcagt atcggctgca   5760
accaattgaa cagtgtctcg cggacccggt cggacgtcgg gcgcagcccg gccaggtcgg   5820
gcaccggcaa gcgcgtattg cgccaacgcc cgccgatgat gcgtacctgc cccgcaccgg   5880
gacggttcat cggcagcctc gcgcgggtgt gacggcaaca gaaaccaggc gcagggtcgg   5940
```

-continued

```
catcgacggc aagcgttgcg gaacggaacc cggatgatag accagccccc tctgcggcgt   6000
atgcatcggg cacggcttga agccgacctc tgccgccacc atgtccgctg atagagccgc   6060
gcgcccccgc gcacggccat ccgtcctcca tggagcacct accgatgagc gtggaaaccc   6120
aaaaagaaac cctgggcttt cagaccgagg tcaaacagct gctgcagctg atgatccatt   6180
cgttgtattc caacaaggag atcttcctgc gcgagctgat ctccaatgcc tccgacgcgg   6240
ccgacaaact gcgcttcgag gcactggtca agccggaact tctggacggc gatgcgcaac   6300
tgcgcatccg catcggcttc gacaaggacg ccggcaccgt caccatcgac gacaacggca   6360
tcggcatgag ccgcgaggag atcgtcgcgc acctgggcac catcgccaaa tccggcacct   6420
ccgatttcct caagcatctg tccggcgatc agaagaagga ttcgcacctg atcggccagt   6480
tcggtgtcgg cttctacagt gccttcatcg tcgccgatca agtggacgtg tacagccgtc   6540
gcgccgggct gccggccagc gacggcgtac actggtcctc gcgtggcgaa ggcgagttcg   6600
aggtcgccac catcgacaag cccgagcgcg gcacccgcat cgtgctgcac ttgaaggagg   6660
aagagaaagg cttcgccgac ggttggaagt tgcgcagcat cgtgcgcaag tactccgacc   6720
acatcgcctt gccgatcgag ctaatcaagg aacactacgg cgaggacaag gacaagccgg   6780
aaacccccga gtgggagacc gtcaatcgcg ccagcgcgct gtggacacgg ccgcgcaccg   6840
agatcaagga cgaggaatac caagaactgt acaagcacat tgcccacgac cacgaaaacc   6900
cggtggcgtg gagccataac aaggtcgaag gcaaactgga atacacctcg ctgctgtacc   6960
tgcccggccg cgccccgttc gacctgtacc agcgcgatgc ctcgcgcggg ctcaagctgt   7020
acgtgcagcg cgtcttcatc atggaccagg ccgaccaatt cctgccgctg tacctgcgct   7080
tcatcaaggg catcgtcgat tccagcgacc tgccgctgaa cgtctcgcgc gaaatcctgc   7140
aatctggtcc ggtgatcgac tcgatgaagt cggcgctgac caagcgcgca ctggacatgc   7200
tggaaaagct cgccaaagac gatcccgaac gctacaaggg cgtgtggaag aacttcggcc   7260
aggtgctgaa ggaaggtccg gcccaggact tcggcaaccg cgaaaagatc gccggcctgc   7320
tgcgcttcgc gtccacccac agcggcgacg acgcccagaa cgtgtcgctg gccgactacg   7380
tggcgcggat gaaagacggc caggacaagc tgtactacct gaccggggaa agctacgcgc   7440
aaatcaagga cagcccgcac ctggaggtgt tccgcaagaa gggcatcgag gtgctcctgc   7500
tcaccgaccg catcgacgag tggctgatga gctatctcac cgagttcgac agcaaatcct   7560
tcgtcgatgt ggcgcgcggc gacctggacc tgggcaagct ggacagcgaa gaagaaaagc   7620
aggcgcagga agaagccgcc aaggccaagc aagggctggc cgagcgcatc cagcaggtac   7680
tcaaggacga ggtcgccgag gtgcgggtct cgcaccggct gaccgattcg ccggcgattc   7740
ttgccatcgg ccagggcgac atgggtctgc aaatgcggca gatcctggaa gccagcgggc   7800
agaagctgcc ggagagcaag ccggtgttcg agttcaaccc cgcgcatccg ctgatcgaga   7860
aactggatgc ggaacccgat gtcgatcgtt tcggtgatct ggcgcgggtg ctgttcgatc   7920
aggccgcgct ggccgccggc gacagcctca aggacccggc cgcctacgtg cgtcggctca   7980
acaagctgtt gctggagctg tcggcgtaag cagtgacgca cctgcgcgtc gcaccgcgcg   8040
acgcagtcca cagcgcaccg acattgcaaa gaaaagcgga aacgaaaaaa gggcctacgg   8100
gcccttttttt cttccatcgt cgacatcggc ttgcagcgca cgagcaacgc tgtaatgcgc   8160
cggtgcatca cgctcccgac gcgaccagca gcactcacgc ctgcattaac ttaaaacctc   8220
accagcttag aacttcaccg tcgcccgcgc ccagtaataa cgcccgagta gatcgtaggt   8280
cgccacatcg gtgttggcat tgacgacgtt gttggcgtag tacagtggcg gctgtcggtc   8340
```

-continued

```
ggtcaggttg tccacgccca cttcgaagcg ggtgtgccac ggcttgacct gatagccgac   8400

ctgcacgctg tgatagacat aggtaccgat gtcgcgcacc acattggcct gaccgatatc   8460

ggccgacaac ccctgacgcg cgtcggcact gccaatctcg gtgcggccga cataacgcac   8520

gcgccaagac gcactccagt cgcccagatt ccagctcaac gtgccgaggc cacgccagcg   8580

cggaaaattg ccgtaagcgt aggtgtactt gccggcattg tggatggtga cggtgtcggg   8640

atcggcggta ttcggattga tatcgtagcg gatcacatag gtgccgttga ggctggcatt   8700

gaagctaccc caggcggtct gcggcaagcg atagttcagg ctgaaatcgg caccgctggc   8760

ccacaacttg cccagattca cggtcggctc ggcgatatag ttgatcgtgc cattgtcgtt   8820

gcgatggatc agcggacaga acggactcgc gtcgttggcg tagcactggt tcagcacggt   8880

ctgcgccgac acctgggtga tggtgtcctt caagtcgatc ttccacaggt ccgtgctcag   8940

cgacaggccg tccacccaac ccgggtcgta aaccatgccg aaatcgtagg acttgccggt   9000

ttccggtttg agccggtagc cggccaccac cgcgcctgaa gccttggcgg acacctgatt   9060

gttctcctgc tggtagctgc catcggtggg cacgtgggca caggcagccg cgtgtccgcc   9120

gctgtagccg tcgcacggat cgttgaccgc cggggcatca ccgaccacgc cggagtaaag   9180

ctcgctgatg ttgggcgcac ggaacacctg cgagaccgtg ccgcgcagca acaggttctc   9240

gaccggacgg tactccaacg ccagtttgct gttggtcttg ctgccgaccg tgtcgtaatc   9300

ggaaaagcgg ctgccgacgg tcaggtttag cgaatgcacg ccaggcagcc ccgccagcaa   9360

cgggaacaac gcctcggcat aggcttcctt gacgctgaaa ctgccaccga gcacgctggc   9420

gcagtattcg agcaccccgc agatgccgtt ctcgtcgccc gtccacagcg gatcggcggc   9480

ggtcgaggtg cgttccttgc ggtaagccac accggccgcc agactcactg caccggccgg   9540

cagatcgaac aggttgccgt tgacgttggc ttcgaactgt ttgacggtgt acacgttggt   9600

caccatcgga ttgacttgca gcgcccgcaa cgcggcctgg ttccctgggt tgttgaggtt   9660

gaacacgtcg atc                                                      9673
```

<210> SEQ ID NO 4
<211> LENGTH: 267
<212> TYPE: DNA
<213> ORGANISM: Xanthomonas albilineans

<400> SEQUENCE: 4

```
ctagccaccg aggcgaccaa caatgcgcaa gagcaagttc accgagagcc agatcgtcgc     60

cacgctgaag caggtggagg gcggtcgcca ggtcaaggat gtatgccgtg agctgggcat    120

ttccgaggcg acgtacttgc tcttccactg gtaataggtc gccgtgctga tgccgacttg    180

gcgacagatg tctttgactg gaacgcctgc gtcggcctgc ttgagcgtgg cgatgatctg    240

tgtctcgttg aacttcgatg tgcgcat                                        267
```

<210> SEQ ID NO 5
<211> LENGTH: 1755
<212> TYPE: DNA
<213> ORGANISM: Xanthomonas albilineans

<400> SEQUENCE: 5

```
ctacttttcg atcagtacgt catcgatgaa catcgcgtcc agaccgctgg tgaagaagat     60

cgacagcgca tcctccactg aatgggcgat cggtttgccc atgacgttga agctggtgtt    120

aagcaccagg ggaatacccg tcaggcggta gaattctttg atcagggcgt gatagcgcgg    180
```

-continued

```
gttccaatgt tgcttcaccg tctgcagacg tccggtgccg tcgtggtgca cgacgcccgg    240

caccttgcgc gtggcttccg cacggaactt cagggtgcgc tccatgtagg gcgattcctg    300

gtacagctcg aaatactccg cgccgtgctc atgcaaaatc gacggtgcga acgggcggaa    360

ctcctcgcgg aacttcaccc gcgcattgat gatgtccttg atcgcaggcg aacgcggatc    420

tgcaaggatc gagcgattgc ctagggcccg tggcccgaat tccgcgcggc cttgcaccca    480

ggcgacgatc ttaccctcgg tcagcagccg ggccgcgcgt tgtgctgcgt cgtcgaggca    540

acgagtgaat ttggatagcg cgccgaagcg ctccacgtta tgcaaggtct ccgcactcat    600

gctgctgccc aggtagggcg attgttcgcg cgcagccggc ggtgtctgct caggatggtc    660

ctcggcgtgt gcccataatg cggcgcccac cgcgttaccg tcatcgccag gggcggcgaa    720

tacgtgcaga tgacggaacg gagtttcagc cagcacgcgg ccgttagccg aggaattgag    780

tgcacagccg ccgcccagca ccaagtggtc ggacaagccc aaagcgtgca ggttgtgcag    840

gaattcgaag aggacgtcgc agaacacctg ctggccggca taggccaggt tggccaattc    900

gatcgttggc tggcccttgc atcggcgcat tgcatacagc gtgcgctgca actggctgaa    960

ttgtgctgcg ggcgcaaacc tcagcgttag gccgtcgacg cgtagcatct ggcgcaacaa   1020

ctcgtacagt tgccgatcat gttgcccgta ggcggccagg cccatcacct tccattcttc   1080

gccggacagg gtgccgaagc cgcaaacctc gcagatcata ccgtagaaga agcccaggct   1140

ggcccaactg ctggtctcgc tttggtggat cggcgtaagc ttgccctgtt ggtagtggta   1200

gcaggccaaa gcattttttt cacccatgcc gtccagtact gcgcacaccg cctcctcgaa   1260

cgggctggtg tagcagccgg ccaccgcgtg ggttaggtgg tgctcgtaat gacggtagct   1320

gggtggcttg aaggcaggct cggccatgtg gctcaagtca tattcgagca ggtgtccggg   1380

gtgctccacc atcgccagct gcgaacggta gaagaagctc tgtgccacga attgcttgtt   1440

gacgtgccaa ggcaggtcgc cgaaggcgct gcggtattgg tctaccgctt gcgcggtctt   1500

gcccaggccc tcccgcatca gttcaggtgt ttgcccgctc caactagtag cgacgaccag   1560

ttcggcgccg ggatcgccgt attcgtggac cagcttgatg gcgcgctgaa acacgtccgg   1620

ggcaacgccg attgaacgct tgtactgcag gtagcgctcg gtggcctcgg caaagcgcac   1680

ctgaccatcg tcgccgacga tagcgatggc tgaatcgtgg aaggaattgg cgagtccgat   1740

gtaagtgcgc ttcat                                                    1755


<210> SEQ ID NO 6
<211> LENGTH: 1491
<212> TYPE: DNA
<213> ORGANISM: Xanthomonas albilineans

<400> SEQUENCE: 6

ctacggcgat gattgtggcg caaattgtgt cagtttgaac tgcaatccca gcgtagagag     60

cgccacgaaa gcattggccg cgatgtagta caccaccgta gccccgaagg cctgcttgaa    120

agccagagct acgcctgccg gcccctgcag atgctggtgc aggccgctaa agaaaatttc    180

cgagaccagg gcgatgccca gcataccgcc gacctgctgg atgacctgca gcgcgccgga    240

acctgcgccg gcatccttca gaggtaccgt acgcatcact gtctggaata gcgaggcgat    300

ggtgatgcca cagcccagtc cgccgatcag caacggcagg gtaagcgtcc agggatccag    360

cgagccttca ctgcgcgtga tgatgaccca caaggccaga tagctagcga tcatcagaca    420

ggcgccgctg aagattttcg cgcgtaggct ttcgacgtgc cgagcgagca tagaggcaat    480

cgccacgccg acagggaaag gagtagtggc gacgccggtt tccagtgccg aatacgccag    540
```

-continued

```
tccttgctgc agaaagatca cgaacaccag gaaaaaaccc tgcagcgccg aatagaacac    600
cgacacggac aaggcgccca agatgtagtc gcgatggctc atcaggtaga tcggcagcag    660
ggccgggcgc gccaagtggg cttgccgacg ttgccaggcg acgaaggcca ccagcagcgg    720
aataccgagc gcaatggctg caaagcacca tagcggccag ccgtatgcgc gtccttctat    780
tagtgggaac accaggcaca acaaggcgag cgcggccagg gcgatgccga cccagtcgtt    840
atggatgccc gcatgcgccg gcaccttggg cacccagatg gcggccgcca gcaaggtcac    900
gaggccgatc ggcacgttga tcaggaagat cgcgcgccag ccgacgccga acgcatcgat    960
gtggatcagc aagccgctga cgagggggcc ggcgaatgag gccaggcccg cgaccaggcc   1020
gaacaacgag aaggcggccg cgcgctcctt cggagcgaac atggtttgcg cgatggccat   1080
cacctgtggt gccagcatgg ctgcggccaa gccctgcaaa gcgcgcgcga tgatgagcac   1140
gtggatattg ccagcgatgg cgcagaacgc ggacatcaag ataaaaccgg ccacgcccgt   1200
gccgaacatg cgcttgcggc cgagcatgtc acccaaccgc cccaacggca gcaaccccaa   1260
cgcaaacagc agaatgtata tcgctacgat ccattccagc tgttgctcgt ccgcgcccag   1320
gttcttctgg atactgggca gggcgacatt gacgatgcct acgtccagca agttcatgaa   1380
attggcgctc agcaacacga tcatcgctgg ccagcgccat cggtagtcga actgcgctcc   1440
gggtggtgcc atgccgggcg gcataccag cgcttccttg ggtttttgca t             1491
```

<210> SEQ ID NO 7
<211> LENGTH: 954
<212> TYPE: DNA
<213> ORGANISM: Xanthomonas albilineans

<400> SEQUENCE: 7

```
ttatccgctt atggccgctt cagccggtcg catggtgacg gtgagaaaat gcaagatgtc     60
gcgctccaac tcgcgctgga aggcgctgcg gtcgaagcca ggcggatcga tggccgcctc    120
gcccacgcga gctttcatcg cctcggggaa tacgctgatg aaggcgtagt ggccggcatt    180
gggcaccacg cgcgcttcca gtcgaccatc attgcctagc gccgtgcgtg tcgccacaat    240
cgtttcgtgc gcccattgat ccttttcacc gacgatgagc agcaccggta cctcgacttt    300
cgccagggca tcctcgtgca tgtacaggct gaaatccggc gcaagcgcca ccacggcgcg    360
cacgcgcgga tcagctgtga ccggcacggc cctgatcggt acccgatttt gtcgcaccag    420
cgcggtccag gcgggttgtt cggcgtgttc cgggcgatgc gcaaaatcga ccatgaaacc    480
ggtatgcggt tcgcccccgg cgatcgctaa ggcggtgtag ccgccgacgg agtggccgat    540
caccgctacg ttatgggcct gaatggcagg accgaactgc gcatggccgg tgagcgtatc    600
gatcaccgcg cggatgtgcc gggggcggtc ttccagattc tgatagctgt attccagctg    660
atgctggaac aggttgtcgc ccggatgctc cggcaaggcg acgataaagc cgtgccgtgc    720
taggtaatgt gccagcgtgc gaaacactag gccggcgctg cgcgtgccgt gcgagatcac    780
cgctagcgga aacgggccgg cttcgatcgg cgcgcccagg gccacgtcca gcgtataagg    840
tcccatcgcc gtatcccgtg aaggcgtggc ggtgggatac atcacccaca tcggcaccac    900
cctgctggca tcaccatcgg tttccagttt ttggcaaccc acatagctat tcat          954
```

<210> SEQ ID NO 8
<211> LENGTH: 1356
<212> TYPE: DNA
<213> ORGANISM: Xanthomonas albilineans -continued

<400> SEQUENCE: 8
ttacgccggc atcagcttat ccagacttgc accggcgggc gccagccaaa cagcggtacg 60
accttcgccc agctccctgc ccatcaagcc tcgcacgccg gccagatcct gcggcgttgg 120
cagcaacgcg gccagccgtt ggccgtcggc atcgtgcacg ggttgccat ctaagtcgaa 180
ggcaagcccc ttgcacgggc cgaaatcgcg gtggaaacgc tcgtgcggca gctgtagctc 240
aaaagccagg ccaaggcgcc tgagctgttg attccagcgg ccgatgatag cgccgacttc 300
ggctatgtat tgtcggcgca ttaccgcatt gattgccaac tcggcaggtg cggtggacga 360
gaccagtctg tcttcgcagc gcacgtcgac ggcgacctcc gtaccttcga gcttgtcgaa 420
gttgcgtggg ctgcggatgc cggcctggta caggacgcgt gaacgctccg aaacgtcgtg 480
gccgaacaga tcaaagatct tcggtagcca atagttaagg tatttctgaa cgactggcaa 540
ggggatcgca ccggcgtcga agatcgcgtg cgtatcctca cgcaaggtaa tctcggcgct 600
tcgatacagc acgcgctcca ggccatccac gccgaactta atatgcagag gttcctcgaa 660
catcatgaag cgggcggtgc gtgccaacgg caggaaagct gactgggtca ccgcttgaat 720
ctggtacttg cctacccggt cggcgaagaa gcaccacatg aaatgcgata gccagtcttc 780
ggtgtggtag ttgaaggcat cgagcaggcg cgggttctgc gcatcgccac tcatgcgttg 840
cagcaggccc tcggcggcgt cggctccgtc gctgccaaag tattcgatca gcagatgcga 900
catcgcccag gtgtgccggc cttcctctag aaaaaactgg aataagtgct ccaggtcgat 960
cgcgctgggc accatttgcg tcagctcgtg gctctgctca accgcggcgt tttctacgtc 1020
accttgcacg gtgacatgat ccagcagcag gtcacgatat tcttccggca cgcacgacca 1080
tgccacctgt cccttgcgct cgccgaacac tacggtgttg cggtctggcg gcatcatgaa 1140
tacgccccag cggtagtcgc tggggcgcat gcggtgatag cgcgtccact cgctgccctt 1200
gacgccaccg gtaggcatgc gcaggttcat ctcgcgatcg tggaattcgc tggggccgcg 1260
gaggcgccac cattgcagga agcgaacttg gtaggaagtc agttgcctga ccagcgcgct 1320
gtgtggatca aggtcgatat tgttaggaat gtacat 1356

<210> SEQ ID NO 9
<211> LENGTH: 948
<212> TYPE: DNA
<213> ORGANISM: Xanthomonas albilineans

<400> SEQUENCE: 9
tcaggccgcg ctgtgcatcg aggtaggggc gacttcgccg accgtgagcc cgatgaagtc 60
gatgatccgc tgagccacgg cacccggatc attgaacagt tgcaggtgac cgccatgatc 120
tagcaggtcc agacgcaaag acgggtcgtg cctagccaac tgcaccgagg cggagtagtg 180
gctgaagctg tcgtccttgc agtgcacgat cagggtaggg tgcctgccca gggcggtggg 240
cagcaaggct tgcacggatt gcttgttctc ttcgtaggca cgcatgtagc gcgagaacac 300
caatgtgctc gctggatcgg ctaggtgcag catggtgagc ttttcggcca agtcgtcgcc 360
gcgtaaaggt tggccgcggt acttgtccag gatggcggcg agctttttgg cctgttccag 420
accgtgccgc tcgatctgaa ggtagatcgg caaggcgcaa cgttcgaatt cggattttac 480
gatgggcggc agcaggcccg ccggcgccac ccaagccatg ctgcgtggtg cgaagccatg 540
cagcgcaatg gcatgcacgg ccaattgtgc agcctgacac caaccgacaa aatggcaatc 600
ggcgtagtcg tgttggtgca ggatgcccag cagggtcgcg gcttggcgat ccagatcgaa 660
gtcttccgcg gttaccgatg tctgggcatt cgggcagccg atggattccc agcacaacac 720

-continued

```
atggaaatgc ctagccagtc gttgcgccaa ccggctcagc agcaggtagg acatgccata    780

gggcggtagc agcaccagct tgggcgatgc ctgagcgcct agccaataca gctcaagctg    840

ccgtccatcg gtagtgcagt attgcgacag ccttacccct gcgagcgcgt cgtccagggc    900

ggacagatct tgcttttcca gatagtgcgg caagcaagca cagcccat                948
```

<210> SEQ ID NO 10
<211> LENGTH: 252
<212> TYPE: DNA
<213> ORGANISM: Xanthomonas albilineans

<400> SEQUENCE: 10

```
tcacgagtaa ctcgattcga acccacttcc gtctggagag ctcgcgtccc ctaaattctt     60

gtcatcgagt tcgcgcagcg ataaggggcg catgtcggtc caggtttcgt cgatatacgc    120

catgcactcg tccttaccgc cagcatagcc ttccttgcgc cagccaggcg ggacctcaag    180

atcggacggc cacagtgaat actgcagttc gtcgttgatc agcaccagat aagcctgttc    240

ctcgaacgtc at                                                        252
```

<210> SEQ ID NO 11
<211> LENGTH: 2151
<212> TYPE: DNA
<213> ORGANISM: Xanthomonas albilineans

<400> SEQUENCE: 11

```
ttgcgctgcc ttatcataaa taattacgat tcgttcactt ggaatctcgc cgactacgta     60

gcgcagatct tcggcgaaga tcccctggtg gtgcacaacg acgagtactc ctggcacgaa    120

ctgaaggacc gcgggggatt ttcctcgatc atcgtttcgc ccggtcccgg ctcggtggtt    180

aatgaagcgg attttcacat ctcgctgcag gcgctggagc agaacgaatt tccggtgtta    240

ggcgtatgcc tgggctttca gggacttgcg catgtctatg gtggccgcat cctgcatgcg    300

ccggtgccct ttcatggccg tcgctccacc gtcatcaaca ccggcgacgg tttgttcgaa    360

ggcatcccgc agcgtttcga ggcagtgcgc tatcactcgt tgatggtctg ccagcaatcg    420

ctgccgcctg tgctgaaagt gacggcgcgt accgattgcg gtgtggtgat gggcttgcag    480

cacgtgcaac acccgaaatg gggagtacag ttccaccccg aatcgatcct caccgaacac    540

ggcaagcgca ttgttgctaa ctttgccaag ctggctgcgc gccacagtgc accgttactt    600

gccgggtcgg agcaggccgg caaggtttta agcgtttgcg cgcccgagat ggtgacaccg    660

cgggtacgtc gcatgctgag ccggaagatc aagtgccgtt ggcaggcgga agatgtcttt    720

ctggccttgt tcgctgacga aaagcattgc ttctggctgg acagccagct ggtctgcagt    780

ccaatggcgc gctattcgtt catgggagcg gtgaacgaga gcgaggtagt gcggcattgc    840

gtgcggccag ggagcatggt gcaggaggca ggcgagcggt ttcttgctga gatggatcgg    900

gcgttgcaat cggtgcttac tgaggacgtc gccgagcggc caccgttcgc gtttcgcggc    960

ggctacgtgg gctacatgag ctacgaaatg aaatcggtgt tcggcgcgcc ggcttcacat   1020

gccaatgcca tccccgatgc gttgtggatg cgcgtggagc gcttcgttgc cttcgaccac   1080

gccactgagg aggtatggtt gctggcgctc gccgatacgg aggatctgtc ggcattggct   1140

tggctagacg ccatcgagca acgtatccat gccattggtc aagcggctcc ggcttgcatt   1200

tcgctaggcc tgcgcagcat ggaaatcgag ctcaatcatg gtcgtcgcgg ctaccttgag   1260

gcaatcgagc gttgcaaaca acgcatcgtc gatggcgagt cctatgaaat ctgtcttacc   1320
```

-continued

```
gacctgttct cgttccaggc cgagctggat ccattgatgc tctatcgcta catgcggcga   1380

gggaacccag cgccgttcgg ggcctatttg cgtaacggta gcgattgtat ccttagtact   1440

tcaccagagc gttttctgga agtggacggc cacggcacga ttcagaccaa gccaatcaag   1500

ggcacctgcc gccgtgccga ggatccccaa ctggaccgta acttggccat gcgcctggcc   1560

gcctcggaaa aggaccgagc ggaaaacttg atgatcgtcg acttgatgcg caacgaccta   1620

agccgcgtgg cggtgcccgg cagcgtcacc gtgcccaagc tgatggacat cgaaagctac   1680

aagaccgtgc atcagatggt cagcacggtg gaagcgaggc tgcgcgccga ttgcagtcta   1740

gtcgacctgc ttaaggcggt gttccccggc ggctcgatca ccggcgcacc gaagttgcgc   1800

agtatggaga ttattgatgg cctggagaat gcgccgcgtg gcgtgtattg cggcagcatc   1860

ggctacctgg gctacaactg cgtcgccgac ctaaacattg cgatccgcag tctttcttat   1920

gacgggcagg aaatacgttt cggcgccggc ggcgccatca ccttcctgtc cgacccgcag   1980

gatgagttcg acgaagtgtt gctgaaggcg gaggcgatcc tcaagccgat ctggcattat   2040

ctacatgcgc cgaacactcc cctgcactac gagttgcgag aggacaagct gctgctagcc   2100

gagcactgcg ttagcgaaat gccggccagg caggccttca tcgaaccatg a            2151
```

<210> SEQ ID NO 12
<211> LENGTH: 414
<212> TYPE: DNA
<213> ORGANISM: Xanthomonas albilineans

<400> SEQUENCE: 12

```
atgaggcccc cacgcttacg cgcgaaccag gacgggctgc tgatggatac ggccggccgg     60

gtggtcgagg gctgcaccag caatctgttc ctcgtcgaga acggccatct ggtgacgccc    120

gacctgggcg tggccggcgt cagcgggatc atgcgaggca gggtgatcga atatggccgg    180

cagcacggtc tcgcctgcgc ggtaaagcac gtctatccgg accagctagt gcgtgctcag    240

gaggtgtttc tgactaacgc cgtgttcggc attctgctgg tgcgcagcat tgacgctcac    300

agctaccgca tcgatcctgt taccctgcgt ttgctcgatg ccctgtgtca gggcgtatat    360

ttcaccgaac ggtcactaca tcaggtttcc acccatgccg gccaagaccc ttga          414
```

<210> SEQ ID NO 13
<211> LENGTH: 603
<212> TYPE: DNA
<213> ORGANISM: Xanthomonas albilineans

<400> SEQUENCE: 13

```
atgccggcca agacccttga aagcaaggat tactgtggag aaagcttcgt cagcgaagat     60

cgctccgggc aatcgctgga gtcgatccga ttcgaggatt gtacgttccg acaatgcaac    120

ttcaccgagg ctgagctcaa tcgctgcaag ttccgcgaat gcgagttcgt cgactgcaac    180

ctgagcctca tcagcattcc gcaaaccagc ttcatggaag tgcgcttcgt cgactgcaag    240

atgctcggtg tcaactggac cagcgcacaa tggccatcgg tgaagatgga gggggcgctg    300

tcgttcgagc gctgcatcct caacgacagc ttgttctacg gcctatacct ggccggggta    360

aaaatggtgg agtgccgtat ccacgatgcc aacttcaccg aagccgactg cgaggatgcg    420

gacttcacgc agagcgacct gaagggcagc accttccaca acaccaaact gaccggcgcc    480

agcttcatcg atgcggtgaa ctaccacatt gacatcttcc acaacgatat caagcgggct    540

aggttcagcc tgccggaagc agcctcgctg ctcaacagcc tggatatcga gctgtccgat    600

tga                                                                  603
```

-continued

<210> SEQ ID NO 14
<211> LENGTH: 609
<212> TYPE: DNA
<213> ORGANISM: Xanthomonas albilineans

<400> SEQUENCE: 14
atgcatccgc cgtcgccgtt gaacacgcag cagaaagact ggctgacacg cggtggttcg 60
ttgaccgcgc acctgcgcct gttggggcag gtacaggtgc aagtgcaacg ggagcacaaa 120
gccatggcct ggctggatga atatcgggtg ctcggactgt cgcgctgcct gcttgtatgg 180
gtgcgtgaag tggtcctggt ggtggacgcc aaaccctatg tctatgcgcg tagcctgacg 240
ccgctgaccg ccagttacaa cgcctggcag gcagtgcgta gcatcggcag tcgcccgtta 300
gctgatctgt tgttccgtga tcgcagcgtg ctacgttcgg cgttggcgag tcggcgcatc 360
accgcgcagc atccgctgca ccggcgcgca tgcaacttcg tggcacagtc gcatgcgacg 420
caagccctgc tggcgcgccg ctcggtattt acgcggcaag gcgccccgtt gctgatcacc 480
gaatgcatgc tgccagcgtt gtgggcaacg ctggaaccgg tggcagctcc gcgccaggcg 540
agtctgagtg cggacggccc ttgccggcat tcagcgcaga tcgtctcgcc tgagtcgatg 600
ctggaatag 609

<210> SEQ ID NO 15
<211> LENGTH: 5880
<212> TYPE: DNA
<213> ORGANISM: Xanthomonas albilineans

<400> SEQUENCE: 15
tcaggcatcg aggtccgtca ccagcatgcg cgccagctca cgcagcgggt cgccttgtaa 60
catgctgtag tgattgcccg ccgcgctctt gatctgcgaa agtggtacgt aacctgtgat 120
atccggcagt acctcgctac ccccgcgtgg cttggacatg tcggcatagg acacgtgtac 180
cgcagtctgt gcctggtaca gatgagcgtt aggctgcagg cactgcggct cgaaaccggc 240
caacagcccc aggtgatagc gcgtaacgcg caattgctcg gccagcggtg gccacatgcg 300
gctttccaga gtaaacctca ggtgtgcgag cagtttgtcc agtgatgcct ggtggcggct 360
gtagtcgaac acgtgctcgt cgtcaccgtc ggcgaacagc agctgccggg cttcgtctat 420
ttcagcctgc tcgaagccgc gcttggccaa cgcggccaac gtattgagcg ctgccacgaa 480
ggtaagctgc cggggctcgc gcgcatgtac cggtatcagg ctgctatcga gcaggcccac 540
gtaatcgacg cgcaggccgc gccgctgcaa ttgctcagcc acagccaggg ctagcacgcc 600
gccggaggac cagcccagca agcggtaggg cgcaccggtc gggccagcca gcaacgcatc 660
gcagtagtgc gcggccaggt cggacaaatg cgcgaagcgg cgcaccggtt cgcattgcag 720
gccatagacc ctggcagagt gccctagggc ggcagccaga tcgatgtagc aatgaatctg 780
gccgccgatc gggtggatgg catacaccgc cgcgcgttcg gtgcgtaggc taagcggtac 840
gataagactt accggcatgc tgccggcttg gctttggcgc atgccgcgct cgacgacagc 900
ggcaaaatct tccagcacag gggattcgaa cagcgtgttg acccgcactt cgatgtcgaa 960
actctggcgg atacgcgaga acaactgggt ggcaagcagc gagtgaccgc cgaggttgaa 1020
gaagttgtcg ttgaggctca cgcgtaaggg ggcggcctgt gcgggggtca gcagttcgct 1080
ccacagcttg gccagggtga tttcgacctc gctgcgcgga gcgaggtagt cgctgtcgct 1140
gctggcggct tgcggctcgg gcaggctcaa ggtatcgagc ttgccattgg gcaagcgcgg 1200

-continued

```
aagcgccggc agcgactgga agcgcgttgg cagcatgtag gtaggcaagc gttcctgcag   1260
cagcttgcgc agctcgtcga ggttcaggac accctggcgt ggcaccacgt aggccaacag   1320
ttccggcgtg ggcgagcctt gcggccaacc gatcacggcg gcctcggcga cctgcaggtg   1380
ggccgccagg gctttctcca cctggcgcac gtccacgcgg tagccgcgga ccttgacctc   1440
gtagtcgcgc cggccgagca gttccagcgt accgttgtcc agtaggcggg ccatgtcgcc   1500
ggtcctgtac agacgcgagc cggggggcc gtagggattg gcgatgaagc gcgcggcggt   1560
caggccgccc tggcgccaat agccgtgcgt aatgccgagg ctttcgatgt gcacttcgcc   1620
catgatgcca ggcggcaacg gtcgcagttg ttcgtcgagc acatggacct tggtattggc   1680
gatgggccgt ccgaccggga cgaagccgct gccgctgtgc tgctcggccg gatcgcaata   1740
ggtcatgtcg ttgatttcgg tacacccgta gatgtaccag gccgtgcagg caggcagcag   1800
cgtcctgagc cgttgcagca gttccgccgg gcagggttcg atggagacga agagctggcg   1860
cagtcgcgcc agccgctgcg gtgtctcagc aacgtggtcg agcagcgcgt tgagctggga   1920
aggaaaggta tacaggcgtg tgatctgcca ggtttccagc gcgcgcacga aagcggggat   1980
gtcacgcacg gtatcctcgt cgatgaacac ctgcggtacg ccagcaagta ggccggcgag   2040
cagttccttg accgaaatgg caaaggcgat cgaggtcttt tgcgccaccc gctccccggc   2100
ctcgaaaggc gcacgtgccc acagcgcatg cagccagttg aggatttgcc gatggggcac   2160
catcaccccc ttgggacgac cggtggaacc ggaggtatac atcacgtagg ccagctgcgc   2220
cggatgcagg gcatgcggca gtggcgtatg cggttgacga gcgatggcgg catcgtccag   2280
gcgcagccgc ggtacttgga tcagttgccc gtcgatgtcc ttgccgcaga gcaacagccg   2340
tggctgcgcg tcgtcgagga tctgctgaat gtaggtggtg gggtaatgcg ggtccaacgg   2400
cacgtagcag ccaccggcct tgagcacgcc gagtagggca atgaggaaat cgggcgagcg   2460
gccgaaccac agggcgacgc gctcctgcgg gcgcaggccg cgctcgatca ggcaatgcgc   2520
caggcggttg gcgtgttggt ccagttgggc atagctcaac tgtcggtgtt gatcggcaca   2580
agccagttcc tcggcgtgca gtgccacttg cgcatcgaac agatccagca cactgcgcga   2640
ggtatccaga gtatgagggg tgaactcggt gcgagcgacc ggcagcgaaa aatccgagag   2700
gcggcagcgc ggttcttcca gcatccgctc cagcactctt tggtggtggg ccagcatgcg   2760
ctgaaccgta gccgccgaaa acagctccgc ggcgtattcg acagtgactt ccaggtggct   2820
tccgtcgccg atgaactgca ggtccagctc gttgggtgtg gtgcgttcgc caaattccat   2880
ctgagcgctg aggaagatct gggcaaatgc attgacgcct tcggtggcga aattttggtg   2940
tcggagcatg atcggcacga gcgggatctg gctgctgtca cgcggtttct tgagagcgct   3000
taagacatgc tcgaacggca gtgcgcgatg cgcgtaggcg tccagcactt gctggcgcac   3060
gtgctgcaga aaatcctcgg caaaggcgtg actgcccaag tttaggcgta ccgccaggat   3120
attgacgaaa aagccgatca gattctcggt ttccagctga tcgcgtccgg cgctggtagt   3180
acctaagcag agttctcgcc ggccggtgta ctggtgcaag acgatcgcca ggctcgccat   3240
aagtgtcatg aacaaggtga cgcgccgttc ctggctgaat gcggcgagac gcgcggccaa   3300
ggcgtcggga taggtcaggt gtagtatgcc agcacgccaa gctcgattag ccgggcgtgg   3360
aaaatcgtag ggcaaggcca gcccttcttc gtaaccatgc aaacgctgtt tccaataatc   3420
cagatcggcg ctgaaatcct gtacgcgctg ccatgtagca tagtcggcat attgcagtag   3480
cagcggtggc agtgccggtg gcgtctgctg tagcgcggct atatagaaag cacgtaggtc   3540
gtgaaagatc aggttaatcg accagccgtc gcagatgatg tgatgcatgt tcatcaggaa   3600
```

-continued cacgtggtaa tcgtccgata cgcgcagcac cgataccttg agcagcgggc cgtgggcaag 3660
atcgaatacg tgcgcggcgt gctcggcgac taggcgtggc acttctgcgg gtgtcgctgt 3720
gatgcaaggc actgggacct gcatggcgtc ggcgatgtgc tggctgggat aatcgccgcc 3780
agcgcaagtt gctatgcggg tgcgcaaggt ttcatgcctg gccaccagcg cctggatcgc 3840
ctcgcgcagc gctgacatcg agaaatcggc actgcgtaaa tggcaggcga aggcgacatt 3900
gtaactggta cgttgctcgg gcatgtgttc atgcacgaac cacaggcgct cctgctgata 3960
gctcagcgga acgggagcat cgcgcacggc acgggaagag atggtgttgc cgccagtcgg 4020
agcctgttgt tgccgcgctt cgttgaccac tcgcgcaaaa tcttccagca caggggattc 4080
gaacagcgtg ttgacccgca cttcgatgtc gaaactctgg cggatacgcg agaacaactg 4140
ggtggcaagc agcgagtgac cgccgaggtt gaagaagttg tcgttgaggc tcacgcgtaa 4200
gggggcggcc tgtgcggggg tcagcagttc gctccacagc ttggccaggg tgatttcgac 4260
ctcgctgcgc ggagcgaggt agtcgctgtc gctgctggcg gcttgcggct cgggcaggct 4320
caaggtatcg agcttgccat tgggcaagcg cggaagcgcc ggcagcgact ggaagcgcgt 4380
tggcagcatg taggtaggca agcgttcctg cagcagcttg cgcagctcgt cgaggttcag 4440
gacaccctgg cgtggcacca cgtaggccaa cagttccggc gtgggcgagc cttgcggcca 4500
accgatcacg gcggcctcgg cgacctgcag gtgggccgcc agggctttct ccacctggcg 4560
cacgtccacg cggtagccgc ggaccttgac ctcgtagtcg cgccggccga gcagttccag 4620
cgtaccgttg tccagtaggc gggccatgtc gccggtcctg tacagacgcg agccgggggg 4680
gccgtaggga ttggcgatga agcgcgcggc ggtcaggccg ccctggcgcc aatagccgtg 4740
cgtaatgccg aggctttcga tgtgcacttc gcccatgatg ccaggcggca acggtcgcag 4800
ttgttcgtcg agcacatgga ccttggtatt ggcgatgggc cgtccgaccg ggacgaagcc 4860
gctgccgctg tgctgctcgg ccggatcgca ataggtcatg tcgttgattt cggtacaccc 4920
gtagatgtac caggccgtgc aggcaggcag cagcgtcctg agccgttgca gcagttccgc 4980
cgggcagggt tcgatggaga cgaagagctg gcgcagtcgc gccagccgct gcggtgtctc 5040
agcaacgtgg tcgagcagcg cgttgagctg ggaaggaaag gtatacaggc gtgtgatctg 5100
ccaggtttcc agcgcgcgca cgaaagcggg gatgtcacgc acggtatcct cgtcgatgaa 5160
cacctgcggt acgccagcaa gtaggccggc gagcagttcc ttgaccgaga tggcaaaggc 5220
gatcgaggtc ttttgcgcca cccgctcccc ggcctcgaaa ggcgcacgtg cccacagcgc 5280
atgcagccag ttgaggattt gccgatgggg caccatcacc cccttgggac gaccggtgga 5340
accggaggta tacatcacgt aggccagctg cgccggatgc agggcatgcg gcagtggcgt 5400
atgcggttga cgagcgatgg cggcatcgtc caggcgcagc cgcggtactt ggatcagttg 5460
cccgtcgatg tccttgccgc agagcaacag ccgtggctgc gcgtcgtcga ggatctgctg 5520
aatgtaggtg gtggggtaat gcgggtccaa cggcacgtag cagccaccgg ccttgagcac 5580
gccgagtagg gcaatgagga aatcgggcga gcggccgaac cacagggcga cgcgctcctg 5640
cgggcgcagg ccgcgctcga tcaggcaatg cgccaggcgg ttggcgtgtt ggtccagttg 5700
ggcatagctc aactgtcggt gttgatcggc acaagccagt tcctcggcgt gcagtgccac 5760
ttgcgcatcg aacagatcca gcacactgcg tgaccaatcc aaggcgagcg cggtatccgg 5820
actggccgcg gtcagcgcga cgtcttcggc atccagtagc gacatgcttg atagtttcat 5880

<210> SEQ ID NO 16

-continued

<211> LENGTH: 993
<212> TYPE: DNA
<213> ORGANISM: Xanthomonas albilineans

<400> SEQUENCE: 16
ttaaacgtgc agcttgagca tggcttcgcc atcgctgcgc gcagcgatgt caggggacga 60
ttgttcgggc gaataaggtt cggccatgca cacgaggatc ttgcggctgc cctcgtaggg 120
ctcgcgtccg tgcgaaacca gcatattgtc gatcagcagc acgtcgtccc gatgccagtc 180
aaaatggatc ttgtgctggg cgaaaactgt gcgcacatgg tcgagcatgg cggggtcgat 240
cggcgtgcca tcgccgaaat aggcgttgcg cggcagtccc tgctcgccga agaacgacag 300
catcatcttc tgcgcagctg cctccagcgc agtgtaatga aacaggtgtg cttggttgaa 360
ccaaacttca tcgccggtcg ccggatggca cgcaaaggcc cggcagatct ggctggtgcg 420
caggccgtcg ccggtccatt cgcattgcat gtcgttgcgg gcgcaataag cttctacttc 480
ctgcttgttg cgggtgttaa acacgtcctc ccatggcagg tcgacccctg cacggtagtt 540
cctgacgtag cgcacctgtt tgcgcgcaaa gatttcgcgc acttgcggat cgatagcggc 600
tgtgaccttg agcatgtcag ccaacggcgt gcagccgccc tcgctggccg gctgcacgca 660
atggaacagc agtttcatcg gccagacgcg ctggtaggcg ttctcgcaat gttgcgctat 720
ggacagctgc ctgggatatt cggtggccgt gtagacatgc tggccgacgt cggtgcgcgg 780
tgtggaacga taggtatagg ccagtcgctc atcgaagaaa cagcgtgaga tctgctccaa 840
gccaccaggg tgcgcaaagc cacggaacag taacgccctg tgttgccata gcagggtagg 900
ccacgtcgcg cggtgcgtgg cattccaatc agtcagcgtg gcctcggccg agtcggcctt 960
gatggtcagg ggaagatcag cgtttgtgtg cat 993

<210> SEQ ID NO 17
<211> LENGTH: 2298
<212> TYPE: DNA
<213> ORGANISM: Xanthomonas albilineans

<400> SEQUENCE: 17
ctaggttcga gcatggccga cgaagaacag gtgggattgc aggtgcttgg cgctagccag 60
tgtctccaac agcgcaggcc ggattacctt gccgctgcag gtacgtggga tcgtgctcac 120
ttcgacgaat agatggggat agtgatgctt gcctagcgcg ttcttgcaca aggcgcgtaa 180
ggcggcccat agcgcccctg tatcgatgct ggcatcgaca ggcaccacga aggcggcggg 240
gcggggcaag ccgaactcgt cttcgatcag gcagatcgcg cactccttca cgcaggcgtg 300
cgtctggatg acgctctcca gcgtctcagg cgaaagccaa caaccgttga tcttgatggc 360
ggagcccatt ctgcccaagt tatggaagcg cccccttggcg tcggcaaaga acaggtcgcg 420
tgtatcgaac cagccgtcga cgaacaattg ggcactgagt atggggtcgc caacatagcc 480
cctcgtcagc gtattgcccc tcacccacag gctgccgact tcgcctatgc ggcagatctc 540
tccctgcttg ttcaccagct tcacaacaaa gcctggtacc ggcgtgccag tgcaacccat 600
gagcgcgtgg cctggccgat tggagatgaa ggtggacagt acctcggtgc agccgatacc 660
gtcgagcact tcgacctgcc aacgcgtgct gatcgcatga ccaagcctcg ccggcaagct 720
ttcgccggcc gatatgcaca ggcgaagcgc cggccacacc gcatccggcg cggcctcggc 780
aagcaacagc ttgaacacgg cgggcacggc gagcaataca gtgacgtggt aagtgtggat 840
ggtttgcgcg atctgcctga cgctaagcgg cgcggcaatc acatggctga caccagcgag 900
cagcgacagc atcaggttgt tcaggccgta ggcgaaaaac aaccgcgacg gtgtatacat 960

-continued

```
cacgtcatcg ctgcgcagcc cgagcacggc ctgctggtag ttgagatggc agtgcataaa   1020

atcggcatgc gagtgcgtta ccgccttggg cgtaccagtg gagccggacg tgcatatcat   1080

caccgcgggt gcatcggcgg agcagggcgc aaccaccagt tcgtcgtttt cgatcaccgg   1140

catcaggctc gtcagctcta aggtcggcag gtggcgcaac gcggcatgat gggaaggcgg   1200

cagttcggca tcgatcagca cgaggcgagg cttgatggtc ttgagcgtgg tctcaaagtg   1260

gacgagcgac acaagctcgt ttatcggcgc aaagaccaag ccaccggcca agcaggccag   1320

catcagggca acgcccgcta ggctgtcgat agcaatcagc gccaccgcat caccgctttg   1380

caggccaagc agactcaagt gccgggcata ggtcgccgcg cgagagcgca actggcgata   1440

gctgaaggcc tgctggcgca acggatcgat catttgcgcc gtcgaagcca gatgcgctgc   1500

ggaaaaaatt tgcgcgcaca cgttgacctg gaccgacggg aggaagccga taggcgcaca   1560

ggcgaacacc gccgtgcttg cgtccgacca ggacggcatc ggcccatcgg tcgagcgtgc   1620

gaaccagctc gcgggcaaat gactggcaat ctgacatagt ttgccgtggt cgcaggccag   1680

cagactggta tccacctcga tcaggtcttc gacgcaggaa agcgcaggca aagagatctg   1740

cgccgcgctg ccgcatacgg cactatcgcg caagtccggc aggttccttt ggcggtggtc   1800

cgcatgccat agcagcaggc catcgctgcg tcgcgtggcc aaggcttcca gtgccatgcc   1860

cagggcgcct tgcaaccggt ccagttgctt gggttcctcg atacggccca aatccagtgc   1920

cagggtgttg gcgccggggg gcgattcgga cagcacgatt tggtgccgat gcttgaggta   1980

atcgcaaatc aggccggcca gcttgcctaa ccgtgcatat tcccgtagca ggctaccgaa   2040

gctgccacag gggtaaggtg cggcatagtc aatggttatg tgctggccga tcggcgtgtc   2100

gctgacatcg atacgcaagc caggataatc gcgccgccat tgatgcagca gcgtggtcca   2160

ttgacgagca taggcctcgt tgcgccctgg ccgcgtctga cctaccgacc aacgcaaatc   2220

tagttcggtg ccagagtgca tcggaagatt tgtcagtggg ctatccataa gcgttctcgg   2280

gtaaggcgat cgacgcat                                                 2298


<210> SEQ ID NO 18
<211> LENGTH: 861
<212> TYPE: DNA
<213> ORGANISM: Xanthomonas albilineans

<400> SEQUENCE: 18

tcagcgtttc agcgcgtgga ccagataact ttgcggcacg ccgtgggtgc cgcgcggtgc     60

gaccggaaac ggccaacgcc ccatttgctg gccagcggcg gcgatggtca acacccctgg    120

ctcccagccc agtggttgga tcaggctttc cggttcgtca gtgccaaact ggcgagccat    180

cgcgtgcagc actcgggcat tgggcgagtt gagcatagag aggccgataa catcgaacaa    240

cacgctgctg cccttggcac tcaatgcatc gatgcgcgcg aacagcagca tcactgcctc    300

ggcgctcaag tagcacagca agccctcgac cagccacaag gtggcggcgc tgccgacgaa    360

tccactctcc ttaagtgcct ggggccagtc ttcgcgcaaa tcgatcggta gcgcaatgcg    420

ctggcaaacg ggctgggcgt catggagttt ttcgtgcttg tcggagagga catccatgtg    480

gtcgatctcg tagacccggg tatcggacgg ccaggggaga cgataagcgc gtgcatccat    540

accggcggcc aggatcacca cctggccaat gccttcacta accgcctgca tgatcttgtc    600

gtcgagccaa cgcgtccgta cctcgatcgc cggaggcatc ggtacgttct ggttgttgcg    660

tctgagctct tcaacgaatt catcgccggc cagacgccgt gcgaaagggt catggaacag    720
```

-continued

```
cgcctgctcc cgctcgcttt ccagcgcccg catgcctgcc acccataaag cggttctttc    780

gatatctctc atgcatacgc tccggttcgt ggtcggcttg cgccgatgca tcatagatat    840

gcatgactcg attcgcggca c                                              861


<210> SEQ ID NO 19
<211> LENGTH: 720
<212> TYPE: DNA
<213> ORGANISM: Xanthomonas albilineans

<400> SEQUENCE: 19

ttacggatgg tctgatccac gcaagcgaaa gatgagataa accacatcag ctgtcaacgc     60

cgatttaaat ttgacccact ttcctttgaa tcgtcgaagt aaatctgacc cacccggggt    120

cttccatcgt cgggctgcta ggctgcgcag ggcaaagccc gtcgcagccc agcagccctg    180

cgccggctca cgcccgaagg gcaggtagcc gatctcgtcg accaccagca gcttcggccc    240

tagtaccgcg cgattgaagt agtccttcag ccggttctgc gccttgaccg ctgccagttg    300

catcatcagg tcggccgcgg tgatgaaacg tgccttgtgc cccgccatca ccgcacgctg    360

gcacagcgcc agggcgatgt gggtcttgcc gacaccgctg gggccaagca tcaccacgtt    420

ctcggcgcgc tcgacgaagg tcaggtggcc gagctcgacg atctgcgcct tcgaggcgcc    480

gccggcctgg gcccagtcga actgctccag cgtcttgatg gacggcatcc tggcaagtcg    540

cgtcagcacc gtgcgcttgc gctcttcacg cgcgagctgt tcgcttgcca gcaccttctc    600

caggaagtag ctggcatcct cgcacgcggc ggcctgtgcg agtgcttgcc agtccgagct    660

caggcgtgcc agcttcaact gctcgcacag cgcggcgatg cgcgcacact gcaggtccat    720


<210> SEQ ID NO 20
<211> LENGTH: 20640
<212> TYPE: DNA
<213> ORGANISM: Xanthomonas albilineans

<400> SEQUENCE: 20

ttgcccaatg cgctcatgca gataactctt gtagccgtcc agtttgcagg cgtattgtta     60

ggcgtcaccg ctcgcgcggc gatccccaat aaggcgggta tgagacgcgc atggccgccc    120

ttcccgcagg cgtgctgtcg ctctattgct tacctcatgc agagatcgcc aatgtcgccg    180

ttacagcaaa cgctgctaac ccgcctcgcc agtgcggccg cctcccggac aatgatcgag    240

tttccgcgtc cggagcacgc atcgccacaa tgttgcgacg atgccgagct tgcgcgactg    300

atcgtgcagt tgtcggcggg actgcaaccg ctggcgatgc cgggtaccta cgtgatcatt    360

gccgcgccac atggtggttt gttcgcggca gccctgcttg cctgtttgca tgccaacctg    420

gtggcggtgc cgtttccact ggatgttgct cagccaaatg agcgggaaca ggccaggctg    480

gagacgatcc acgcacaatt gatggagcat ggcaatgtag cggttctgct tgacgatgtc    540

gccgatcgca gtgccttcgc gcgcatggcg catgctgcgg gcaccttcct ggcgaccttc    600

gccgatctaa agcgcgaatc gaccagcgcc tccttgtgcc cggcgtcgcc ttcggacgcc    660

gccttgctgt tgtttacctc tggttcctcg ggtgagtcca agggcatcct gcttagccac    720

cgcaacctgc atcatcagat ccaggctggc atccggcagt ggagcttgga cgagcatagc    780

catgtggtga cctggctttc tcccgcgcac aacttcggcc tgcatttcgg cttgctggca    840

ccctggttca gtggcgcgac ggtcagtttc atccatccgc acagttatat gaaacgaccc    900

ggcttctggc tggagacggt tgcggctaga gacgccacgc acatggccgc gccgaacttc    960

gcgttcgact actgctgcga ctgggtgatg gtcgagcagc ttccgccgtc tgcgttgtct   1020
```

-continued

```
acgcttacgc atatcgtgtg tggcggcgag ccggtgcgcg cctcgaccat gcagcgcttc   1080
ttcgagaaat tcgccggact cggtgcgcgt acgcagactt tcatgccgca cttcggcttg   1140
tctgaaaccg gtgcgctgag taccttggac gaggcgcccc aacagcgcgt cttggaacta   1200
gatgccgacg ccttgaacaa acgcaagcgc gtggcggcag gggcgagcca ggcgcgtgtg   1260
acagtgctca attgcggcgc cgtcgaccaa gatgtggagt tgcgtatcgt ctgtcctgaa   1320
ggcgagacgt tgtgcagacc agatgagatc ggcgaaatat gggtaaagtc gcctgcgatc   1380
gcccgtggct acctgtttgc gaagcccgcc gatcagcgac agttcaactg cagcatccgt   1440
cataccgacg atagcggtta ctttcgtacc ggcgacctgg gtttcattgc cgatggctgt   1500
ctgtatgtca ccggaagggt aaaggaggtg ctgatcatac gcggtaagaa tcattacccc   1560
gcacatatcg aagcctcgat cgccgctacc gcatcgcctg gcgcgctgat gccggtggtg   1620
ttcagcatcg agcggcagga cgaggagcgc gtagctgcgg tgatcgccgt caatcacccg   1680
tggacgccgg cagcatgcgc cgcgcaggca cacaagatcc ggcaacaggt agccgaccag   1740
catggagtcg ccctggcgga gctagccttt gccgaacacc ggcacgtgtt cggcacctat   1800
ccgggcaaac tgaagcggcg cctagtcaag gaagcctatg tcaacggcca gctgccgttg   1860
ttatggcatg agggtaagaa ccgggacgta ccagcggccg ccgcggacga tcggcaggcg   1920
caacacgtgg cggacctgtg tcggaaggtc tttttgccgg tgttgggtgt cgcgccgccg   1980
catgcccaat ggccgctgtg cgaactggcg ctggattcgc tccaatgcgt gcgtcttgcc   2040
ggtgccatcg aagagtgcta cggcgtgcct ttcgaaccca cgttgctatt caagcttgag   2100
acggtcgggg caatcgccga atatgtcctg gcgcacggac gtcaggcgcc cacgccgacg   2160
cgtgcgccgg tggcaagcac aacatgctca gaggaaccga tcgccattgt ggcgatgcac   2220
tgtgaggtgc ccggagcggg cgagaacact gaagcattgt ggtcgttcct gcggagcgac   2280
gtcaacgcga tccggccgat cgaatcaacg cgcccggact tatgggcagc gatgcgcgcc   2340
tatcccggcc tcgcgggcga acagctgccg cgctatgcgg gtttcctcga cgacgttgat   2400
gctttcgatg ctgcgttttt cggtatctcg cgtcgcgagg ccgaatgcat ggacccgcag   2460
cagcgcaaag tgctggagat ggtgtggaag ctgatcgagc aagccggtca cgatccgctg   2520
tcctggggcg gccagccggt cggcctgttc gtgggtgcgc atacgtccga ctatggcgag   2580
ctgctggcga gccagccgca actgatggcc caatgtggcg cttacatcga ttcgggttcg   2640
catttgacca tgattccgaa ccgggcttcg cgctggttca atttcaccgg ccccagcgaa   2700
gtaatcaaca gcgcttgctc cagctcgctg gtggcgctgc atcgggcggt tcaatcgctg   2760
cgccaaggcg aaagcagtgt cgccctggta ctcggcgtga accttatcct ggctcccaag   2820
gtgctgttag ccagtgcaag cgcgggcatg ctttcgcccg atggccgctg caagacgctt   2880
gacgccgccg ccgatggctt cgtgcgttcg gaagggatcg caggggtgat attgaagcca   2940
ctggcgcagg cgctggccga tggtgacagg gtctacggtc tagtccgcgg cgtggcggtc   3000
aaccatggcg gccgttccaa ttccttgcgt gctcccaacg tcaacgcgca gcggcaactg   3060
ctgatccgga cttaccagga agccggtgtc gagccggcca gcgtcggtta tgttgaacta   3120
cacggcactg gtaccagcct gggtgatccg atcgaaatcc aggcgctgaa ggaagctttc   3180
attgcgttgg gggcacaggc cgccccgtca aactgcggca tcggttcggt gaagtccgcg   3240
ctgggccatc tagaagccgc tgcaggcctg accggcctga tcaaggtgct gctgatgctc   3300
aagcacggcg agcaggccgg cacgcgccat ttcagcacgc tcaatccgct gatcgatttg   3360
```

-continued

```
cgaggtacgt cattcgaagt ggtggcgcag catcgcgcat ggccgtcgca ggtcggcatt   3420
cacggcacac tcttgccgcg tcgcgcgggt atcagctcat tcggcttcgg cggcgccaat   3480
gcgcatgcga tcgtggaaga gcatgtcatt gccacgcccc cctcgacgag ctccgctggc   3540
ggcccggtag gtatcgtgtt gtcagccggt agtgaagctg tcttgcggca acaagtgctg   3600
gccttgtcag cctggctaag gcagcaatcg ccgacacccg cgcaaatgat cgatgtcgcc   3660
tacaccttac aggtaggacg cgcagccctg tcgcacaggt tggcttttag cgcgacggac   3720
gccgagcagg cattggcgag gcttgagggt cgtctggcgg gcgtgatgga tgccgaggtc   3780
catcacggtg tcgtggatgc tgccgcaacg gctcccgaac atgggcggca gacgcgcgaa   3840
ggtcttgccg gtttgctgcg agcctggact cagggcgtgc gcgtcgattg gtcggcgctg   3900
tacggcatac agcgaccgca gcgcgttagc ctgcctgtct accccttcgc tagggaacgc   3960
tattggctgc ccggccaggc tatgcatgcc gctgcggacg ctcatccgat gctgcagctg   4020
ttgcatgcca atgccaaact acatcgctac gccttgcgta ggtccggctg cgcaagcttt   4080
cttgttgatc attgcgtgga tggtcgacag gtactaccgg cagccgtgca actggaattg   4140
gtgcgcgccg tggcgcagcg ggtcatggcg caggatgagg gttgtatcga actggcgcag   4200
gtcgcctttt tgcatcccct catgatggag gagactgagc tggaggtcga aatcgaactg   4260
tcgaagagcg atcaagatga gttcgatttc caacttcacg atgctcaccg ccaacaggtc   4320
tttagccagg ggcacgtacg tcgccgggtc tatacggcga caccgcgctt ggatttagcc   4380
cagctgcaaa agctttgtgc cgagcgcgtg ttgtccggcg aagactgtta tgcgcacttc   4440
accgcctgcg gattgcagct cggcgaccgg ctcaaatccg tgcaatcgat cggctgcgga   4500
cgcaatggcg agggcgagcc gatcgcattg ggtgtcctgc gcctgccacc atcaagcgtt   4560
gaagacagcc atgtgctgcc tcctagcctg cttgatggtg ccttgcagtg tagccttggc   4620
ttgcagcgtg atgtcgagca catcgccatg ccatacacgc tggagcggat gacggtgcat   4680
gcgccgattc ctcccgaggc ctgggtgctg ctgcgtcacg gccatgcagc cagacagtcc   4740
ctggacatcg atctcctgga ttccgaaggt agggtctgcg tcagcctcgg caattacacc   4800
ggccgtgcac cgaaagccgt ttccgccgtc agggcgcttg tcttggcacc ggtctggcaa   4860
gcgttgaccg aaacggcgcc ggcatggccc gatccggccg aacgcatcgt tacggtagga   4920
gacgatgcat ggcgtagtca cttcggtttc gacgagccgg ccttgtccct ggaggacagc   4980
gtcgaagtca tcgcgacgcg actgggccag agcggcaagt tcgatcatct agtctggatc   5040
gtgccgatag ccgagagtga aaccgatatt gcagcgcaag gttcagcggc gatcgccggt   5100
ttccggttgg tcaaggcgtt gcttgcgttg ggctatgcgc atcgcccgct gggtctcacc   5160
gtgctgactc gccaagccct tacgcggcag ccgtcgcacg cggcagtgca cgggctgatc   5220
gggacgctgg ccaaggaata ctgcaactgg aaaatccgtc tgctcgacct gccgagcgta   5280
aaatcttggc cgcaatggga gcaattgcgg tcgttgcctt ggcatgcgca gggcgaagcc   5340
ctgatcggcc gtgggacttg ttggtatcgg cggcagttgt gtgaagtgct gccgctgccg   5400
tcgttggaac cgccgccgta ccgcgtaggc ggtgtctacg tcgtgatcgg cggcgctggc   5460
ggcttgggtg aagtattgag cgaacacttg atccgcacgt acgacgcgca gctgatctgg   5520
atcgggcggc gcgtgctgga cgaaggcatt gcgcgcaagc agacccggct tgcgtcgctg   5580
ggccgcgcac cgcattacat ctccgcggac gcgagtgacc cggctgccct gcaggcggca   5640
cataatgaga tcgttgcgct gcatggccag ccccatgggc tcatcctaag caacatcgtg   5700
ctgaaggatg ccagtctggc tcgtatggag gaagccgatt tccgtgacgt gctggccgcg   5760
```

-continued

```
aaactcgacg tcagcgtgtg tgcggcacag gtgttcggca cggcccccct tgatttcgtg   5820
ctgttttttt cttccatcca gagcactacc aaggcggccg ggcaaggtaa ctacgccgcc   5880
ggctgctgct atgtcgacgc tttcggcgag ctatgggcgc gccggggttt gagggtaaag   5940
accatcaact ggggctactg gggcagcgtg ggcgtcgtag cgggcgagga ctatcgccgg   6000
cgcatggcgc aaaaacacat ggcttcgatt gagggtgccg aagcgatgca ggtgttgtcg   6060
cagttgttgt gtgcgccgtt gcaacggctt gcctacgtca agatcgacga tgctaacgca   6120
atgcgcgctc tgggcgtagt agaggacgag agcgtgcaaa tccctgtgca cgcaccggcc   6180
gagcctccca gagggcagcc tggtcccgtg gtcgagttgt cggtgaatct ggatgcccgg   6240
cgcgaacggg aaactttgct ggcggcctgg ctgcttgagt tgatcgagca actcggtggt   6300
tttccgccgg caagtttcga catcgctacg cttgcgcaac gcctgcacat cgtacccgcc   6360
tatcgaagct ggctggaaca cagcgtgcgg atgctcggcg tgtatggtta cctcagagcg   6420
acgggggaaa gccgattcga gctggccgac aagccgcccg atgatgccag gggtgcctgg   6480
aacgcgcatg tgcacgaggc cagcgtcgaa gccggtgaag aggcacagcg gcgtctgctc   6540
gatcgctgca tgcgggcgtt gccggcggtc cttcgaggcg aacgcaaggc caccgaattg   6600
ctgtttccgg aaggttcgat ggcgtgggtc gagggtatct accagaacaa cccgcttgcc   6660
gattacttca acgcacaact agtcacgcga ctgattgcct acttgagacg acgactagag   6720
tcgacgccta cggcgcgcct gaagctgtgc gagatcggcg ccggcagcgg tggtactact   6780
gcaagcgtgc tacaacagtt gcaggcatat ggtgagcata ttgaggaata tctctatacc   6840
gacctgtcgc ctgtcttcct gcatcatgcg gaaaaacact atcagccacg agcgccttat   6900
ttgaggaccg cctgtttcga cgtagcgcgc gcgccgacgg cgcaggccct ggaatctggc   6960
ggctacgacg tggtgattgc cgccaacgta ctgcatgcta cgcgcgatat cgccaagacc   7020
ttgcgcaatg cgaaggcact cctcaaacct ggcggtctgc tcttgctcaa cgaagtgatc   7080
gagcgcagcc tcgtcttgca cctgactttc ggtctgctgg agagctggtg gttgccccag   7140
gacaagatct tgcgccttgc cggctcgccg ttgctggctt gcgccacctg gcgcagcctg   7200
ctggaggctg agggttttgc ggggctgagc gtgcacaggg cgcaacccga tgccgggcag   7260
gccatcatct gtgcctacag cgatgggata gtgcggcaag ccagtacgat cgaggttgcg   7320
cggaatgaaa aagtaaccgt tccgtcgcag ccggcggaag ccggggaatc gccgctggat   7380
ctggtcaaaa aactgcttgg acgcattctg aaaatggatc cggccacact cgataccagc   7440
cacccgctgg agtactacgg tgtcgattcg atcgtggcga tcgaactggc tatggcactg   7500
cgcgagacat tcccgggttt tgaagtcagc gagctgtttg aaacgcaatc catcgatacc   7560
ttgttgggct ctcttgagca ggctcctctc cttgctaccc tcacagctcc gccgcaacaa   7620
gacatgctgc agcagctgaa acaactgctg gcgcgtacgc tgaagctgga cattacgcag   7680
atcgacacga gcaagacgct ggagagctat ggtgtcgact ccatcgtcat catcgaatta   7740
gccaacgcct tgcgtgagcg ctatccgagc ttggacgcgt cacagctgat ggaaacctta   7800
tcgatcgacc ggctggttgc ccaatggcag gcaacggagc ccgccgtacc ggcagagcca   7860
acagcggaac cgccggtagc cgacgaagac gccgctgcca tcatcggact ggccggccgc   7920
tttccaggcg cggacacgtt ggaggagttc tggaacaacc tgcgcaacgg ccaaagcagt   7980
atgggagagg tgccaggcga gcgctgggat caccagcact acttcgacag tgaacgccag   8040
gcaccgggca agacgtatag ccgctggggt gcgtttctga gggacataga cggcttcgat   8100
```

-continued

```
gcagccttct ttgaatggcc cgacagcgtc gcgctggaat cggatccgca agcgcggata   8160
tttctagagc aggcctatgc cgggatcgaa gatgccggct acacgcctgg ctcgctcagc   8220
aagagccaac gcgtaggtgt attcgtaggt gtgatgaatg gttactacag cggcggagcg   8280
cgcttctggc aaatcgccaa ccgcgtgtcg taccagttcg attttcgcgg gccaagcctg   8340
gcggtggata ccgcctgttc ggcttcgctc accgcgatcc acctggcgct ggaaagcctg   8400
cgcagcggca gttgcgaggt cgcactggcc ggtggcgtga atctgctggt cgatccgcag   8460
caatatctta atttggctgg cgccgcgatg ctctccgccg gcgccagctg tcggccgttc   8520
ggcgaggccg cggacggttt cgtggccggc gaagcctgcg gcgtggtgct gctcaagccg   8580
ctcaagcaag cgagggccga tggcgatgtg atccatgccg taatcagggg cagcatgatc   8640
aatgccggtg ggcacaccag cgcgttctcc tcgcctaacc ctgccgccca ggccgaagtc   8700
gtgcggcagg ccttgcagcg cgcgggcgtg gcgcccgatt cgatcagcta catcgaggcg   8760
catggcaccg gcaccgtact aggcgatgca gtggagttgg gtgctttgaa taaagtgttc   8820
gacaagcgcg cggcgccatg cccgatcggc tcgctgaagg cgaacatcgg ccatgccgaa   8880
agcgccgcgg gcatcgccgg cctggccaag ctggtattgc agttcaggca tggcgagttg   8940
gtgcctagtc tgaatgcgtt tcccttgaat ccctatattg agttcggtcg cttccaggta   9000
caacagcagc cggcaccgtg gccgcgccgt ggcgcccagc cgcggcgcgc cgggttatct   9060
gccttcggtg ctggcggatc gaatgcgcac ctagtggtag aggaagctcc ggctatggct   9120
cccggggtct cgatcagcgc cagctctcca gccttgatcg tgctttcggc gcgaacgctg   9180
cctgccttgc aacagcgtgc tcgcgatctg ctcgtctgga tgcaagcgcg gcaggtggat   9240
gacgtcatgc tggccgacgt tgcttatacg ctgcacttgg gccgcgtcgc gatggagcaa   9300
cgcctggctt ttaccgctgg ctcggctgcc gagttgagcg agaaattaca ggcttacctg   9360
ggccatgcga ttcgggccga catctatctg agcgaggaca cgcccggcaa accggcaggc   9420
gctccgatcg tggccgagga agatctgctc acgctgatgg atgcctggat cgaaaagggc   9480
cagtacggtc gtttgctgga gtactggacc aagggccaac cgatcgactg gaacaaactc   9540
tattggcgca agctgtatgc ggacggacgg ccgcggcgga tcagcctgcc cacctatccg   9600
ttcgagcacc ggcgttattg gcaaacgccg gtgccgggcg agcgaagcct gcacgccacc   9660
gcgccagcta ctcgggaaac ggttgcggtt ggtgccatgc cggatccggc cggcgctacg   9720
gtgcaagccc ggttgtgcgc cttgtgccaa gtgttgttgg gcaaaccggt cacggcccag   9780
atggatttct ttgccgtcgg cggccattcg gtgctggcga tccaattggt ctcgcgcatc   9840
cgcaaaagct tcggggtgga gtatccggtc agcgctttgt tcgaatcggc gctgttgtcg   9900
gacatggcgc ggcagatcga acaattgcgg gtgaacggag tcgccaagcg catgccggcg   9960
ttgttgcctg ccgggcgcgt gggcgcgatt cctgcgactt atgcacagga gcgcctatgg  10020
ctcgtccacg aacatatgag tgagcaacgc agtagttaca acatcacctt tgccatgcac  10080
ttcagaggcg tcgacttccg tgctgaagcg atgcgtgccg cattgaacgc gctggtggtg  10140
cggcacgaag tgctgcgcac acgctttctt tcggaggacg ggcagctgca acaggtgatc  10200
gctgcctcgt tgacgttgga ggtgccggta agagagatgt cggtcgagga ggtcgacctg  10260
ctgctggccg cgagcacgcg ggagactttc gatctgcggc aggggccctt gttcaaggca  10320
cgcatcctgc gcgtggcggc cgatcaccat gtggtgttga gcagcatcca ccacatcatt  10380
tccgacggct ggtcgctggg agtgttcaac cgtgacctgc accagctgta cgaggcgtgt  10440
ttgcgcggca cgccccccac actgccgacg ctggcggtgc agtatgccga ctacgcgctg  10500
```

-continued

```
tggcaacggc aatgggagct ggcggctccg ctgtcgtact ggacgcgggc actggaaggc  10560
tacgacgacg gcctggactt gccctacgac cggccgcgcg gcgccacgcg ggcgtggcgg  10620
gcagggctgg tcaaacaccg ctatccgccg caactggccc agcagttggc ggcctacagc  10680
caacagtacc aagcgacgct gttcatgagc ctgctggcag gcctggcgtt ggtgctgggc  10740
cgttacgccg atcgcaagga cgtgtgcatc ggcgcgacgg tctccggccg cgaccagctg  10800
gagctggaag agctgatcgg ctttttcatc aatattttgc cgctgcgggt ggacctgtcg  10860
ggggatccgt gcctggagga ggtgctgctg cgcacgcgtc aagtggtact ggatggcttc  10920
gcgcaccagt cggtgccgtt cgagcacgtg ttgcaggcgc tgcggcgtca gcgcgacagt  10980
agccagatcc cgctggtgcc ggtgatgctg cgacaccaga acttcccgac gcaggagatt  11040
ggcgattggc ccgagggagt gcggctgacg cagatggagc tggggctgga ccgtagcacg  11100
ccgagcgagc tggattggca gttctacggc gacggcagct cgctggagct gacgctggaa  11160
tacgcgcagg acctcttcga cgaagcgacg gtgcggcgga tgatcgcaca ccaccagcag  11220
gcgttggagg cgatggtgag ccggccacag ctgcgggtgg gcaagtggga catgctgacg  11280
gccgaagagc gccggctgtt tgccgcgcta aatgcgacag gtacgccacg ggagtggccc  11340
agtctggcgc agcagttcga acggcaggcg caggcgacgc cgcaggccat cgcgtgcgtg  11400
agcgatgggc agtcgtggag ctatgcgcag ttggaggcgc gcgccaacca gctggcacag  11460
gcgctgcggg ggcagggcgc gggccgggac gtgcgggtgg cggtacagag tgcgcgcacg  11520
ccggaactgc tgatggcctt gctggcgatc tttaaggccg gtgcgtgcta tgtgccgatc  11580
gatccggcct acccggcggc ctaccgcgag cagatcctgg ccgaggtgca ggtgtcgatc  11640
gtgctggagc aagacgagct ggcgctggac gagcaagggc agttccacaa tccgcgttgg  11700
cgcgagcaag ccccgacgcc gctggggctg agggagcatc cgggcgacct ggcgtgcgtg  11760
atggtgacct ccggctcgac cggccggccc aagggcgtga tggtgccgta tgcgcagctg  11820
tacaactggc tgcatgcagg ctggcagcgt tctccgttcg aggccgggga gcgggtgctg  11880
cagaagacct cgatcgcctt tgcggtgtcg gtaaaggagt tgctaagcgg gctgctggcg  11940
ggggtggaac aggtgatgct gccggacgag caggtgaagg acagcctggc gttggcgcgg  12000
gcgattgagc aatggcaggt gacgcggctg tacctagtgc catcgcacct gcaggcgctg  12060
ctggacgcga cgcaaggacg agacgggcta ctgcactcgc tgcgtcacgt ggtgacggcg  12120
ggggaagcgt tgccgtctgc ggtgcgcgaa acggtgcggg cgcgtctgcc acaggtgcag  12180
ctatggaaca actacggctg cacggaactg aacgacgcga cctaccaccg gtcggatacg  12240
gtggcgccag gaacgtttgt gccgatcggc gcaccgatcg ccaacaccga ggtatacgtg  12300
ctggaccggc agctgcggca ggtgccgatc ggggtgatgg gcgagctgca cgtacacagc  12360
gtggggatgg cgcgcggcta ctggaaccgg ccggggctga cggcctcgcg cttcatcgcg  12420
cacccgtata gcgaggagcc gggcacacgg ctgtacaaga ccggtgacat ggtacgccgg  12480
ctggcggacg ggacgctgga atacctgggc cgacaggact tcgaggtcaa ggtgcgcggc  12540
caccgggtgg atacgcggca ggtggaggcg gccttgcggg cgcagcccgc ggtggccgag  12600
gcggtggtga gcggtcaccg ggtggacggg gacatgcagt tggtggccta tgtggtggcg  12660
cgtgaagggc aggcaccgag cgcgggcgag ttgaaacaac agctgtcggc gcagttgccg  12720
acctacatgc tgccgaccgt gtaccagtgg ctggagcagt tgccgcggct gtccaacggc  12780
aagttggacc ggttggccct gccggcaccg caggcggtac acgcgcagga gtacgtcgcg  12840
```

-continued

```
ccacgcaacc aggccgagca acggctggcg gcactgtttg ccgaggtgct gcgggtggag  12900
caggtaggca tccacgacaa cttcttcgcc ttgggtgggc actcgctgtc tgcatcgcaa  12960
ctgatctcgc gtattgccag ggatatggcg atcgatctgc ccctggccat gctgttcgag  13020
ctgcccacgg tagcgcagct tagcgaatcc ctcgccagcc atgcacgcga cagcgattac  13080
gatgtcatcc ccgcaagcac cgaggaggcg accattccgc tttccactgc gcaggagcgc  13140
atgtggttcc tgcacaagtt cgtgcaggag acgccgtaca acaccccggg tctcgcctta  13200
ttgcaaggcg aactggacat ttcggccttg caggtagcat ttcgctgtgt gctagaacgg  13260
cacgccgtgc tgcgtaccca tttcgtggaa accgagcagc aatgcgtaca ggtcattggc  13320
gcagcagagc agttcgtgct gcagcttagg tcgattcgcg acgaggctga tctgcatggc  13380
ctattgcaca cagccgtcag cgaacccttc gatttagaac gcgagctgcc attgcgcgcc  13440
ctgctgtatc gcctggacga ccggcggcat tacctagcag tggtcatcca tcacatcgtc  13500
ttcgacggct ggtcgacctc aatcctgttt cgtgagctgg ccacgcacta tgctgcatgc  13560
cgccatggcc aatccgcgcc tttgccaccg ctggagctta gctatgccga ttacgcacgc  13620
tgggagcgtg cgaggctgaa ccaggaagac gcgctgcgca agctcgaata ttggaaaacg  13680
cagcttgccg atgcaccgcc gctggtgttg cccacgacct atgcgcggcc ggtttttcag  13740
aacttcaatg gcgcgactgt ggcgcttcag atcgagccgc cgctgctgca acgcctgcag  13800
cgtttcgccg acgcacacag ctttacattg tacatgctac ttctggcagc actgggcgtc  13860
gtattgtcgc gccatgcccg gcagaagcat ttctgcattg gcagtccggt cgccaatcgc  13920
gcccgagccg agttgcacgg tttgatcggt ttgttcgtca acaccctggc ggtacggctc  13980
gatttggacg gcaatcccag cgtgcgcgag ctgctcgaac gcatccactg caccacgctg  14040
gccgcctacg agcaccagga tgtgccgttc gaaagaatcg tggaaagcct gaaggtaccg  14100
cgcgataccg cgcgtaaccc gctggggcag gtgatgctca atttccagaa catgccaatg  14160
tcggcgttcg acctggatgg tgtccaggtg caggtgctcc ccatgcacaa cggcacggcc  14220
aagtgcgagc tgaccttcga cctgctgctg gatggctcac gcctatccgg tttcgtcgaa  14280
tacgccactg ggctgtttgc gccggaatgg gtccaggcgc tggtacagca attcaagtgt  14340
gtgctggcgg cattggtgga acggccggag gcatcgctga atgatttgcc catggcgccc  14400
aacgaggcgc aaccggcgtc gccggcattg atgaagcatg tcgcgccgag cttgcccaac  14460
ttacttgagg ctatggcggc caatgatgcc gcacgcctcg ccttgcaagc gccggaaggt  14520
gcgctcagtt acgctcagct aatcgaggca gcaaacgagt tcgcctggcg tttgcggtgc  14580
gagcacgccg gtccggacaa agtcgttgcc ctgtgcctag cgccttgctc cgccttggtg  14640
gttgctttgc tggccgcttc attatgcggt gcggcgagcg tgctgatcga tccgacgacg  14700
actgccgagg cgcaatacga ccagttgttc gaaacgcggg ccggcatcgt ggtgacctgt  14760
tctagcttgc tggagaagtt gccgctcgac gaccaggctg tagtgctgat cgacgagcaa  14820
gctgcagaag cgacgccgcg tttgatgcat ttcaccgacg atccagcttt gcccgcaatg  14880
ctgtattgtg tgtgtgacga aaaggggcga acccgcacga tcatggtcga aagcggcagt  14940
ttgtcgagtc gcctgctcga tagcgtgcag cgtttcagtc tcgaacgcac cgatcgcttc  15000
ctgctgcgca gcccgctttc tgccgaactg gcgaataccg aagtactgca atggttggcg  15060
gcaggcggca gcctcagcat cgcacccatg catggcgatt tcgatgccgc tgcctggctg  15120
gagaccctcg cgacgtacgc gatcaccgtg gcctacctgg ctcaagttga attgaccgag  15180
atgctggcgc atctgcaaaa ccatcctctt gagcgcaaca agctggccgg cttacgcgtg  15240
```

-continued ctggtggtgc atggcgcgcc cttgccgatc gcgccactga tgcgcctaga cgcgtggttg 15300
cgagaggtgg gcggttccgc acggatcttc gccgcctacg ggaatgccga gttcggtgcc 15360
gaaatattga gccaggatgt cagcgctgca ttgcaagcgg gtattggcgc tcaatacaag 15420
catcgccgtg gtctgttccc gttgggtgcc aactcgatgt gtcacgtggt gcagagcaac 15480
ggccgcatcg cgcccgacgg catggttggt gaattgtgga tcacacagcc agcctgcttg 15540
tacaaaaccg atgcattggt gcgtcgcctg gcaaatgggc aactggaatg gttgggctcc 15600
ctcgatgtcc agtcgcgtat cgatgatccc cgcatcgatc tgtgcgtcgt ggaggcacaa 15660
ctgcgcttgt gcgaagacgt cggcgaagcg gtagtgctgt atgagccgtt gaagcgctgc 15720
ttggtagcct atctctcggc ccgtagcaca gctgcaatca tgaccgacga gacgctggcc 15780
aggatccgcc aggccctgag cgaaaccttg ccggattatc tactgcctgc aatctgggtg 15840
ccgctcgcgc actggccacg cttaccccat gggcgggtcg acctcggcgc cttgcctgca 15900
ccggatttcg atcttgcgcg gcatgagtcg tacatagcgc cacgcacagc cgtcgaacag 15960
gccgtggccg aaatatggca acgcgtgttg aagcgtaccc aggtcggcgt gcatgacaat 16020
ttcttcgagc tgggcggcca ttcggtgctg gcgatccagc tggtgtccgg cttgcgcaag 16080
gctttggcca tcgaagtgcc ggtcaccctg gtgttcgagg cgccgatact gggggcgctg 16140
gcgcggcaga tcgccccctt gttggtcagc gaacggcgtc cgcgcccgcc tggcctgacg 16200
cgcctggagc atacagggcc gattccggct tcgtatgcac aggagcggtt atggctggtg 16260
cacgagcata tggaggagca gcgaaccagc tacaacatca gtaacgcagc gcatttcatc 16320
ggagcagcct tcagcgtcga agcgatgcgt gccgcattga acgcgctggt ggcgcggcac 16380
gaagtgctgc gcacacgctt tctttcggag gacgggcagc tgcaacaggt gatcgctgcc 16440
tcgttgacgc tggaggtgcc ggtacgcgag gtgtcggccg aggaggtcga cctgctgctg 16500
gccgcgagca cgcgggagac tttcgatctg cggcaggggc ccttgttcaa ggcacgcatc 16560
ctgcgcgtgg cggccgatca ccatgtggtg ttgagcagca tccaccacat catttccgac 16620
ggctggtcgc tgggagtgtt caaccgtgac ctgcaccagc tgtacgaggc gtgtttgcgc 16680
ggcacgcccc ccacactgcc gacgctggcg gtgcagtatg ccgactacgc gctgtggcaa 16740
cggcaatggg agctggcggc tccgctgtcg tactggacgc gggcactgga aggctacgac 16800
gacggcctgg acttgcccta cgaccggccg cgcggcgcca cgcgggcgtg gcgggcaggg 16860
ctggtcaaac accgctatcc gccgcaactg gcccagcagt tggcggccta cagccaacag 16920
taccaagcga cgctgttcat gagcctgctg gcaggcctgg cgttggtgct gggccgttac 16980
gccgatcgca aggacgtgtg catcggcgcg acggtctccg gccgcgacca gctggagctg 17040
gaagagctga tcggcttttt catcaatatt ttgccgctgc gggtggacct gtcgggggat 17100
ccgtgcctgg aggaggtgct gctgcgcacg cgtcaagtgg tactggatgg cttcgcgcac 17160
cagtcggtgc cgttcgagca cgtgttgcag gcgctgcggc gtcagcgcga cagtagccag 17220
atcccgctgg tgccggtgat gctgcgacac cagaacttcc cgacgcagga gattggcgat 17280
tggcccgagg gagtgcggct gacgcagatg gagctggggc tggaccgtag cacgccgagc 17340
gagctggatt ggcagttcta cggcgacggc agctcgctgg agctgacgct ggaatacgcg 17400
caggacctct tcgacgaagc gacggtgcgg cggatgatcg cacaccacca gcaggcgttg 17460
gaggcgatgg tgagccggcc acagctgcgg gtgggcaagt gggacatgct gacggccgaa 17520
gagcgccggc tgtttgccgc gctaaatgcg acaggtacgc cacgggagtg gcccagtctg 17580

-continued

```
gcgcagcagt tcgaacggca ggcgcaggcg acgccgcagg ccatagcatg cgtgagcgat  17640
gggcagtcgt ggagctatgc gcagttggag gcgcgcgcca accagctggc acaggcgctg  17700
cgtgggcagg gcgcgggccg ggacgtgcgg gtggcggtac agagtgcgcg cacgccggaa  17760
ctgctgatgg ccttgctggc gatcttcaag gccggtgcat gctatgtgcc gatcgatccg  17820
gcctacccgg cggcctaccg cgagcaaatc ctggccgagg tgcaggtgtc gatcgtgctg  17880
gagcaaggcg agctggcgct ggacgagcaa gggcagttcc gcaatcggcg ttggcgcgag  17940
caagccccga cgccgctggg gctgagggga catccgggcg acctggcgtg cgtgatggtg  18000
acctccggct cgaccggccg gcccaagggc gtgatggtgc cgtatgcgca gctgcacaac  18060
tggctgcatg caggctggca gcgttctgcg ttcgaggccg gggagcgggt gctgcagaag  18120
acctcgatcg cctttgcggt gtcggtaaag gagttgctaa gcgggctgct ggcgggggtg  18180
gggcaggtga tgctgccgga cgagcaggtg aaggacagcc tggcgttggc gcgggcgatc  18240
gagcaatggc aggtgacgcg gctgtaccta gtgccgtcgc acctgcaggc gctgctggac  18300
gcgacgcaag gacgcgacgg gctactgcac tcgctgcgtc acgtggtgac ggcgggggaa  18360
gcgttgccgt cggcggtggg cgaagcggtg cgggtgcgcc tgccacaggt gcagctatgg  18420
aacaactatg gctgcacgga actgaacgac gcgacctacc atcggtcgga tacggtggcg  18480
ccaggaacgt ttgtgccgat cggcgcaccg atcgccaaca ccgaggtata cgtgctggac  18540
cggcagctgc ggcaggtgcc gatcggggtg atgggcgagc tgcacgtaca cagcgtgggg  18600
atggcgcgcg gctactggaa ccggccgggg ctgacggcct cgcgcttcat cgcgcacccg  18660
tatagcgagg agccgggcac acggctgtac aagaccggtg atatggtacg ccggctggcg  18720
gacgggacgc tggaatacct gggccgacag gacttcgagg tcaaggtgcg cggccaccgg  18780
gtggatacgc ggcaggtgga ggcggccttg cgggcgcagc ccgcggtggc cgaggcggtg  18840
gtgagcggtc accgggtgga cggggacatg cagttggtgg cctatgtggt ggcgcgtgaa  18900
gggcaggcac cgagcgcggg cgagttgaaa caacagctgt cggcgcagtt gccgacctac  18960
atgctgccga ccgtgtacca gtggctggag cagttgccgc ggctgtccaa cggcaagttg  19020
gaccggttgg cgctgccggc gccgcaggtg gtacacgcgc aggagtacgt cgcgccacgc  19080
aacgaggccg agcaacggct ggcggcactg tttgccgagg tgctgcgggt ggagcaggtg  19140
ggcatccacg acaacttctt cgccttgggt gggcactcgc tgtctgcatc gcaactgatc  19200
tcgcgcatcc gccaaagttt tcacgtcgat ctgccgctga gccggatctt cgaggcaccc  19260
acgatcgagg gcctggtcag gcagctagcg ttgcctagtg aaggcggcgt ggccagcatc  19320
gccagggtag cgcgaaaccg gacgatccca ttgtcgctgt tccaggaacg cctgtggttc  19380
gtgcaccaac acatgcctga gcaacgcacc agttacaacg gcacgctcgc cttgcgtttg  19440
cgtggtcctt tgtcggtgga agcgatgcgt gcagcgctgc gtgcgttagt gctgcgccac  19500
gaaatcttgc gtacccgctt cgtgttgccg accggtgcta gcgagccggt gcaggtcatt  19560
gacgagcaca gcgatttcca gctctcagta cagctagtcg aggatactga gatcgcgtcg  19620
ctgatggatg aactggcaag tcatatctac gacttagcca acggcccgct gttcattgca  19680
tgccttttgc aactggatga gcaagaacat gtgctgctaa tcggcatgca tcaccttatc  19740
tacgacgctt ggtcgcaatt caccgtgatg aaccgcgatc tacgcgtgct gtatcaccgc  19800
cacctcggac ttgccggcgg agatctgccg gaattaccga tccaatatgc cgactatgcg  19860
atctggcaac gcgcccagaa cctggacgcg caactggcct attggcaggc tatgttgcac  19920
gactacgacg acggcctgga gctgccctac gactatccgc gtccgcgcaa tcgcacctgg  19980
```

-continued

```
cacgcagcgg tctacacaca cacctatccg gctgaactgg tacagcgctt tgccggcttc  20040

gtacaggcgc atcagtcgac cttgttcatc gggctgttgg ccagcttcgc ggtcgtgttg  20100

aacaaataca ccggccggga cgacttgtgc atcggtacca ccacggcagg gcgcacgcac  20160

ctggagctgg agaacctgat cggtttcttc atcaacatct tgcctttgcg cttgcgcttg  20220

gacggcgatc cggacgttgc cgaaatcatg cggcgaacac ggttggtggc gatgagcgcg  20280

tttgagaacc aggcgctacc gttcgagcac ctgctcaacg ccctgcacaa gcaacgtgac  20340

accagccgga ttccgctagt tccggtggtg atgcgtcatc agaacttccc ggacacgatc  20400

ggcgactgga gcgatggcat ccgtaccgaa gtgatccagc gcgatctgcg tgccaccccc  20460

aatgaaatgg acctgcaatt cttcggcgac ggtacggggc tttcggtcac agtggaatac  20520

gcggcggagc tgttctcaga agcgaccatt cgccgcctga tccaccatca ccaactcgtc  20580

ctggagcaga tgttggcggc ccatgaaagc gccacgtgcc ccttggatgt tgccgactag  20640
```

<210> SEQ ID NO 21
<211> LENGTH: 1032
<212> TYPE: DNA
<213> ORGANISM: Xanthomonas albilineans

<400> SEQUENCE: 21

```
atggattcag cgttacctac atctgcattt accttcgatc tcttttacac cacggttaac     60

gcctactatc gcactgccgc agtcaaggcg gcgatcgaac tggggctatt cgatgtggtg    120

gggcagcagg gccgaactcc cgcagccatc gccgaggcct gccaggcgtc gccgcgcggc    180

attcgcatcc tttgctatta cctagtatcg atcggttttc tacgccgcaa cggtggcctg    240

ttctacatag atcgcaacat ggccatgtac ctggatcgta gttcgcccgg ctacctgggt    300

ggcagcatca agttcctgct ctcgccctac atcatgagcg ccttcaccga tctgaccgcc    360

gtagtcagga ccggcaagat caacctggcg caggacggcg tggtggcacc ggatcacccg    420

cagtgggtgg aatttgcacg cgcgatggca ccgatgatgg cgctgccctc ggcgttgatc    480

gccaatatgg tgtcgttgcc cgctgatcgg ccgattcgtg tgctggacgt ggcagccggc    540

cacggcctgt tcggcatcgc cttcgcgcag cgcttccgcc aggctgaagt gagcttcctg    600

gactgggaca acgtgctaga cgtagcacgc gaaaacgccc aggcggccaa agtggccgag    660

cgagcgcgtt tcctgcccgg caacgcattc gacctcgatt acggcagcgg ctacgacgtg    720

atcttgttga ccaacttcct gcaccatttc gatgaggtcg atggcgagcg catcttggct    780

aagacgcgcg atgcgctgaa cgacgacggc atggtgatca ctttcgaatt catcgccgac    840

gaagagcgtt cctcaccgcc gctggccgcc accttcagca tgatgatgct gggcaccacc    900

ccggcgggcg agtcctacac ctatagcgat ctggaaagga tgtttcggca tgccggcttc    960

ggccacgtgg aactaaaatc gataccgccg gccttgctga aagtggtggt ttcccgcaag   1020

agggccccat aa                                                       1032
```

<210> SEQ ID NO 22
<211> LENGTH: 504
<212> TYPE: DNA
<213> ORGANISM: Xanthomonas albilineans

<400> SEQUENCE: 22

```
atgatcgaat cggcgacatc ccctgtggcg aaaaccgagc gcatctggtg caccgagctg     60

gacctggatg cactcaacgc catgtcggcc aacacgatgc aggccctgct cggtatacgc    120
```

-continued

```
atgatcgaga tcggctcgga ctatctggtc tcctgcatgt cggtggactg gcgttgccac    180

cagccctatg gggtattgca tggcggcgca tcggtcaccc tggccgaggc taccggcagc    240

atggcggcct ccatgtgcgt gccggccggc caacgttgcg ttggcctaga catcaatgcc    300

aaccacatcg cgagcatctc cagtggccaa gtacagtgca tcgcgcggcc gctgcacata    360

ggggccttga cccaggtatg gcagatgcgc atctatgacg aaggtgaccg cacgatctgc    420

gtgtcgcgcc tgaccatggc ggtattatcg gtgcacgtcg cgcgcgtatc cccgaatcca    480

gccagcagcg gagtccagac gtga                                          504


<210> SEQ ID NO 23
<211> LENGTH: 2826
<212> TYPE: DNA
<213> ORGANISM: Xanthomonas albilineans

<400> SEQUENCE: 23

gtgaacgaaa ctgcaactgt aaccaaggct accctcagtt cagcgaaggc gagtataacg     60

ccagcctgcg ttcaccaatg gtttgaagcg caggtgagtt cgacaccgga tgcgcctgct    120

gccttcttag gcgagcgtcg aatgagttat ggccagctca acacccgcgc caatcggctt    180

gcacggctgt tgcagtcaca gggcgttggg cctggtgccc gggtcgcggt gtggatgaat    240

cgcagccccg aatgcctggc cgctttgctg gcggtcatga aggccggggc agcttatgta    300

ccgatcgacc tgagcctgcc gatccgacgt gtccaataca tcttgcagga cagccaggcc    360

cggctcgtac tggtcgatga cgaagggcaa ggccgcctgg acgaacttga gctgggcgcg    420

atgactgccg tcgatgtctg cggcactctg gacggcgacg aggcgaatct ggacctgcct    480

tgcgatccgg cgcagccggt ttattgcatc tatacctccg gctccacagg tagccccaag    540

ggcgtgctgg tacggcacag cggttggct aactacgtgg cctgggctaa gcggcaatac    600

gttacggctg acacgacgag tttcgccttt tactcctcgc tgtcgttcga tctgaccgtc    660

acctcgatct acgtgcccct ggtggctggc ctgtgtgtgc atgtgtaccc ggagcagggc    720

gacgacgtgc cggtaatcaa ccgcgtgctg gacgacaacc aagtagacgt gatcaagctg    780

acaccctcgc acatgctgat gctgcgcaac gcggcactgg cgacgtctcg gctgaagacg    840

ctgatcgtgg gtggcgagga cctgaaagcg gcggtggcgt acgacatcca tcagcggttc    900

cgccgcgatg tggcgatcta caacgaatac ggtcctaccg aaaccgtagt ggggtgcgcg    960

atccatcgtt acgatccggc gaccgaacgc gaaggctcgg tgccgattgg tgtgccgatc   1020

gatcacacca gcctccacct gctcgatgaa cgtctgcagc cggtcgcacc gggcgaggtc   1080

ggccagatcc acatcggtgg cgcgggcgtg gccatcggct atgtgaacaa gccggagatc   1140

accgatgcgc aattcattga caatcccttc gaaggcagcg gccggcttta cgccagtggc   1200

gacctaggac gcatgcgtgc cgacggtaag cttgaattcc ttggccgcaa ggattcgcag   1260

atcaagctgc gcggctaccg catcgaactg ggcgagatag agaacgttct gcttggccac   1320

gcagccttgc gcgaatgcat cgtggatacc accgtggcgc cgcgccgcga ctatgacagc   1380

aagagcttgc gctattgcgc gcgttgcggt atcgcttcaa atttccccaa taccagcttc   1440

gacgagcacg gtgtctgcaa ccattgccac gcctacgaca aataccggaa cgtggtcgag   1500

gattatttcc ggaccgaaga tgagctacgt actatcttcg agcaggtcaa ggcgcacaac   1560

aggctccgct acgactgcct ggtggctttc agcggcggca aggacagcac ctatgcgcta   1620

tgccgcgtag tggacatggg cctgcgcgtg ttggcgtaca ccctggacaa tggctacatc   1680

tccgacgagg ccaaggcaaa cgtcgaccgc gtcgtgcgcg agctgggggt ggaccatcgc   1740
```

-continued

```
tatctgggta ctccacacat gaacgccatc ttcgtggaca gcctgcatcg ccacagcaac   1800

gtctgcaacg gctgcttcaa gaccatctat acgctgggta tcaacctggc gcacgaagtg   1860

ggcgtaagcg acattgtaat gggcctgtcc aaaggacagc tgttcgagac gcgcctgtct   1920

gagctgtttc gcgccagcac cttcgacaac caggtatttg agaagaacct gatggaggcg   1980

cgcaagatct accatcgcat cgacgacgcg gcggcccgcc tgctggacac ctcttgcgtg   2040

cgcaacgatc gcttgctcga aagtacgcgt ttcatcgact tctaccgcta ctgcagtgtc   2100

agccgcaagg acatgtatcg ctatatcgcc gagcgcgtag gctggagccg tccggctgac   2160

accggccgct cgactaactg cctgctcaac gatgtgggca tctacatgca caagaagcaa   2220

cgtggctatc acaactattc gttgccctac agttgggacg tgcgggtagg ccatatccca   2280

agggaagacg cgatgcgcga gctggaggac accgacgata tagacgaggc caaggtactg   2340

ggcctgctca agcagatcgg ctatgactca agcctgatcg atacccaggc gggcgatgcg   2400

cagctgatcg cctactacgt ggcggcggag gaactggatc cggtggcatt gcgcaatttt   2460

gctgctgcga tcttgcccga gtacatgctg ccttcgtatt tcgtgcggct ggaccgaatg   2520

ccgttgacgc cgaatggcaa ggtgaaccgc cgagcattgc cgaggccgga gttgaagaag   2580

aacgccagcg aggcgcatac cgagccgagc agtgcgctag agcaggaact ggtgcaaatc   2640

tggaaagagg tgctgatggt cgacaaggtc ggcgtcaggg acaacttttt cgagctgggc   2700

ggccactcgc tgagcgcgct gatgttgctc tacagcatag ccgagcgcta ccagaagatg   2760

gtcagcatcc aggcattctc ggttaatccg accatcgaag gtctgtcgga gcatctggtc   2820

gcataa                                                              2826
```

<210> SEQ ID NO 24
<211> LENGTH: 837
<212> TYPE: DNA
<213> ORGANISM: Xanthomonas albilineans

<400> SEQUENCE: 24

```
atgcccaatg ccgtaccgat gcagggcgcg cggggactcc cgcagccgca agcgatgaac     60

ccagggttgc cgagcgtcgg cggcttgagc gcaggccagc cattgcagtt gtcgttagca    120

ccggaactgc aggcagccgc gcgcagtgcc caccgccatc tgctcgacga cggcacggcg    180

ctttacctgc tggcgttcga taccgcgcaa ttcgacccgg gggctttcgc ggcaatggca    240

atcgcccgcc cggacagcat cgcccgcagc gtgcgcaagc gtcaggccga gttcctgttc    300

ggccgtctgg ccgcgcgact ggcgctgcaa gaggtgctgg gacctgcgca agcgcaggca    360

gacattgcaa tcggcgcgac gcgcgcgccc tgctggcctg ccggcagcct gggcagcatt    420

tcccattgcg aggactacgc ggccgccatc gccatggcgg ccggcacccg ccacggcgtg    480

ggcatcgatc tggaacgacc aatcacaccc gcggcgcgcg cggcgttgct gagcatcgca    540

atcgatgccg acgaagccgc tcgtctggca aaggcggcag acgcgcagtg gccgcaagac    600

ctgctgctga ccgcactatt ttcggccaag gaaagcctgt tcaaagccgc ctacagcgcg    660

gtcggacgct acttcgactt cagcgcggca cgcctgtgcg gcatcgacct ggcacggcaa    720

tgcctgcatc tgcgcctgac cgagacactc tgcgcgcaat tcgtggccgg gcaagtgtgc    780

gaggtcggct tcgcgcgcct accaccggac ctggtgctca cccactacgc ctggtga       837
```

<210> SEQ ID NO 25
<211> LENGTH: 1905
<212> TYPE: DNA

-continued

<213> ORGANISM: Xanthomonas albilineans

<400> SEQUENCE: 25
atgagcgtgg aaacccaaaa agaaaccctg ggctttcaga ccgaggtcaa acagctgctg 60
cagctgatga tccattcgtt gtattccaac aaggagatct tcctgcgcga gctgatctcc 120
aatgcctccg acgcggccga caaactgcgc ttcgaggcac tggtcaagcc ggaacttctg 180
gacggcgatg cgcaactgcg catccgcatc ggcttcgaca aggacgccgg caccgtcacc 240
atcgacgaca acggcatcgg catgagccgc gaggagatcg tcgcgcacct gggcaccatc 300
gccaaatccg gcacctccga tttcctcaag catctgtccg gcgatcagaa gaaggattcg 360
cacctgatcg gccagttcgg tgtcggcttc tacagtgcct tcatcgtcgc cgatcaagtg 420
gacgtgtaca gccgtcgcgc cgggctgccg gccagcgacg gcgtacactg gtcctcgcgt 480
ggcgaaggcg agttcgaggt cgccaccatc gacaagcccg agcgcggcac ccgcatcgtg 540
ctgcacttga aggaggaaga gaaaggcttc gccgacggtt ggaagttgcg cagcatcgtg 600
cgcaagtact ccgaccacat cgccttgccg atcgagctaa tcaaggaaca ctacggcgag 660
gacaaggaca agccggaaac ccccgagtgg gagaccgtca atcgcgccag cgcgctgtgg 720
acacggccgc gcaccgagat caaggacgag gaataccaag aactgtacaa gcacattgcc 780
cacgaccacg aaaacccggt ggcgtggagc cataacaagg tcgaaggcaa actggaatac 840
acctcgctgc tgtacctgcc cggccgcgcc ccgttcgacc tgtaccagcg cgatgcctcg 900
cgcgggctca agctgtacgt gcagcgcgtc ttcatcatgg accaggccga ccaattcctg 960
ccgctgtacc tgcgcttcat caagggcatc gtcgattcca gcgacctgcc gctgaacgtc 1020
tcgcgcgaaa tcctgcaatc tggtccggtg atcgactcga tgaagtcggc gctgaccaag 1080
cgcgcactgg acatgctgga aaagctcgcc aaagacgatc ccgaacgcta caagggcgtg 1140
tggaagaact tcggccaggt gctgaaggaa ggtccggccc aggacttcgg caaccgcgaa 1200
aagatcgccg gcctgctgcg cttcgcgtcc acccacagcg gcgacgacgc ccagaacgtg 1260
tcgctggccg actacgtggc gcggatgaaa gacggccagg acaagctgta ctacctgacc 1320
ggggaaagct acgcgcaaat caaggacagc ccgcacctgg aggtgttccg caagaagggc 1380
atcgaggtgc tcctgctcac cgaccgcatc gacgagtggc tgatgagcta tctcaccgag 1440
ttcgacagca aatccttcgt cgatgtggcg cgcggcgacc tggacctggg caagctggac 1500
agcgaagaag aaaagcaggc gcaggaagaa gccgccaagg ccaagcaagg gctggccgag 1560
cgcatccagc aggtactcaa ggacgaggtc gccgaggtgc gggtctcgca ccggctgacc 1620
gattcgccgg cgattcttgc catcggccag ggcgacatgg gtctgcaaat gcggcagatc 1680
ctggaagcca gcgggcagaa gctgccggag agcaagccgg tgttcgagtt caaccccgcg 1740
catccgctga tcgagaaact ggatgcggaa cccgatgtcg atcgtttcgg tgatctggcg 1800
cgggtgctgt tcgatcaggc cgcgctggcc gccggcgaca gcctcaagga cccggccgcc 1860
tacgtgcgtc ggctcaacaa gctgttgctg gagctgtcgg cgtaa 1905

<210> SEQ ID NO 26
<211> LENGTH: 6879
<212> TYPE: PRT
<213> ORGANISM: Xanthomonas albilineans

<400> SEQUENCE: 26

Met Pro Asn Ala Leu Met Gln Ile Thr Leu Val Ala Val Gln Phe Ala
1 5 10 15

-continued

```
Gly Val Leu Leu Gly Val Thr Ala Arg Ala Ala Ile Pro Asn Lys Ala
            20                  25                  30

Gly Met Arg Arg Ala Trp Pro Pro Phe Pro Gln Ala Cys Cys Arg Ser
        35                  40                  45

Ile Ala Tyr Leu Met Gln Arg Ser Pro Met Ser Pro Leu Gln Gln Thr
    50                  55                  60

Leu Leu Thr Arg Leu Ala Ser Ala Ala Ala Ser Arg Thr Met Ile Glu
65                  70                  75                  80

Phe Pro Arg Pro Glu His Ala Ser Pro Gln Cys Cys Asp Asp Ala Glu
                85                  90                  95

Leu Ala Arg Leu Ile Val Gln Leu Ser Ala Gly Leu Gln Pro Leu Ala
            100                 105                 110

Met Pro Gly Thr Tyr Val Ile Ile Ala Ala Pro His Gly Gly Leu Phe
        115                 120                 125

Ala Ala Ala Leu Leu Ala Cys Leu His Ala Asn Leu Val Ala Val Pro
    130                 135                 140

Phe Pro Leu Asp Val Ala Gln Pro Asn Glu Arg Glu Gln Ala Arg Leu
145                 150                 155                 160

Glu Thr Ile His Ala Gln Leu Met Glu His Gly Asn Val Ala Val Leu
                165                 170                 175

Leu Asp Asp Val Ala Asp Arg Ser Ala Phe Ala Arg Met Ala His Ala
            180                 185                 190

Ala Gly Thr Phe Leu Ala Thr Phe Ala Asp Leu Lys Arg Glu Ser Thr
        195                 200                 205

Ser Ala Ser Leu Cys Pro Ala Ser Pro Ser Asp Ala Ala Leu Leu Leu
    210                 215                 220

Phe Thr Ser Gly Ser Ser Gly Glu Ser Lys Gly Ile Leu Leu Ser His
225                 230                 235                 240

Arg Asn Leu His His Gln Ile Gln Ala Gly Ile Arg Gln Trp Ser Leu
                245                 250                 255

Asp Glu His Ser His Val Val Thr Trp Leu Ser Pro Ala His Asn Phe
            260                 265                 270

Gly Leu His Phe Gly Leu Leu Ala Pro Trp Phe Ser Gly Ala Thr Val
        275                 280                 285

Ser Phe Ile His Pro His Ser Tyr Met Lys Arg Pro Gly Phe Trp Leu
    290                 295                 300

Glu Thr Val Ala Ala Arg Asp Ala Thr His Met Ala Ala Pro Asn Phe
305                 310                 315                 320

Ala Phe Asp Tyr Cys Cys Asp Trp Val Met Val Glu Gln Leu Pro Pro
                325                 330                 335

Ser Ala Leu Ser Thr Leu Thr His Ile Val Cys Gly Gly Glu Pro Val
            340                 345                 350

Arg Ala Ser Thr Met Gln Arg Phe Phe Glu Lys Phe Ala Gly Leu Gly
        355                 360                 365

Ala Arg Thr Gln Thr Phe Met Pro His Phe Gly Leu Ser Glu Thr Gly
    370                 375                 380

Ala Leu Ser Thr Leu Asp Glu Ala Pro Gln Gln Arg Val Leu Glu Leu
385                 390                 395                 400

Asp Ala Asp Ala Leu Asn Lys Arg Lys Arg Val Ala Ala Gly Ala Ser
                405                 410                 415

Gln Ala Arg Val Thr Val Leu Asn Cys Gly Ala Val Asp Gln Asp Val
            420                 425                 430

Glu Leu Arg Ile Val Cys Pro Glu Gly Glu Thr Leu Cys Arg Pro Asp
```

-continued

```
        435                 440                 445

Glu Ile Gly Glu Ile Trp Val Lys Ser Pro Ala Ile Ala Arg Gly Tyr
    450                 455                 460

Leu Phe Ala Lys Pro Ala Asp Gln Arg Gln Phe Asn Cys Ser Ile Arg
465                 470                 475                 480

His Thr Asp Asp Ser Gly Tyr Phe Arg Thr Gly Asp Leu Gly Phe Ile
                485                 490                 495

Ala Asp Gly Cys Leu Tyr Val Thr Gly Arg Val Lys Glu Val Leu Ile
            500                 505                 510

Ile Arg Gly Lys Asn His Tyr Pro Ala His Ile Glu Ala Ser Ile Ala
        515                 520                 525

Ala Thr Ala Ser Pro Gly Ala Leu Met Pro Val Val Phe Ser Ile Glu
    530                 535                 540

Arg Gln Asp Glu Glu Arg Val Ala Ala Val Ile Ala Val Asn His Pro
545                 550                 555                 560

Trp Thr Pro Ala Ala Cys Ala Ala Gln Ala His Lys Ile Arg Gln Gln
                565                 570                 575

Val Ala Asp Gln His Gly Val Ala Leu Ala Glu Leu Ala Phe Ala Glu
            580                 585                 590

His Arg His Val Phe Gly Thr Tyr Pro Gly Lys Leu Lys Arg Arg Leu
        595                 600                 605

Val Lys Glu Ala Tyr Val Asn Gly Gln Leu Pro Leu Leu Trp His Glu
    610                 615                 620

Gly Lys Asn Arg Asp Val Pro Ala Ala Ala Ala Asp Asp Arg Gln Ala
625                 630                 635                 640

Gln His Val Ala Asp Leu Cys Arg Lys Val Phe Leu Pro Val Leu Gly
                645                 650                 655

Val Ala Pro Pro His Ala Gln Trp Pro Leu Cys Glu Leu Ala Leu Asp
            660                 665                 670

Ser Leu Gln Cys Val Arg Leu Ala Gly Ala Ile Glu Glu Cys Tyr Gly
        675                 680                 685

Val Pro Phe Glu Pro Thr Leu Leu Phe Lys Leu Glu Thr Val Gly Ala
    690                 695                 700

Ile Ala Glu Tyr Val Leu Ala His Gly Arg Gln Ala Pro Thr Pro Thr
705                 710                 715                 720

Arg Ala Pro Val Ala Ser Thr Thr Cys Ser Glu Glu Pro Ile Ala Ile
                725                 730                 735

Val Ala Met His Cys Glu Val Pro Gly Ala Gly Glu Asn Thr Glu Ala
            740                 745                 750

Leu Trp Ser Phe Leu Arg Ser Asp Val Asn Ala Ile Arg Pro Ile Glu
        755                 760                 765

Ser Thr Arg Pro Asp Leu Trp Ala Ala Met Arg Ala Tyr Pro Gly Leu
    770                 775                 780

Ala Gly Glu Gln Leu Pro Arg Tyr Ala Gly Phe Leu Asp Asp Val Asp
785                 790                 795                 800

Ala Phe Asp Ala Ala Phe Phe Gly Ile Ser Arg Arg Glu Ala Glu Cys
                805                 810                 815

Met Asp Pro Gln Gln Arg Lys Val Leu Glu Met Val Trp Lys Leu Ile
            820                 825                 830

Glu Gln Ala Gly His Asp Pro Leu Ser Trp Gly Gly Gln Pro Val Gly
        835                 840                 845

Leu Phe Val Gly Ala His Thr Ser Asp Tyr Gly Glu Leu Leu Ala Ser
    850                 855                 860
```

-continued

```
Gln Pro Gln Leu Met Ala Gln Cys Gly Ala Tyr Ile Asp Ser Gly Ser
865                 870                 875                 880

His Leu Thr Met Ile Pro Asn Arg Ala Ser Arg Trp Phe Asn Phe Thr
                885                 890                 895

Gly Pro Ser Glu Val Ile Asn Ser Ala Cys Ser Ser Ser Leu Val Ala
            900                 905                 910

Leu His Arg Ala Val Gln Ser Leu Arg Gln Gly Glu Ser Ser Val Ala
        915                 920                 925

Leu Val Leu Gly Val Asn Leu Ile Leu Ala Pro Lys Val Leu Leu Ala
    930                 935                 940

Ser Ala Ser Ala Gly Met Leu Ser Pro Asp Gly Arg Cys Lys Thr Leu
945                 950                 955                 960

Asp Ala Ala Ala Asp Gly Phe Val Arg Ser Glu Gly Ile Ala Gly Val
                965                 970                 975

Ile Leu Lys Pro Leu Ala Gln Ala Leu Ala Asp Gly Asp Arg Val Tyr
            980                 985                 990

Gly Leu Val Arg Gly Val Ala Val  Asn His Gly Gly Arg  Ser Asn Ser
        995                 1000                1005

Leu Arg  Ala Pro Asn Val Asn  Ala Gln Arg Gln Leu  Leu Ile Arg
    1010                 1015                 1020

Thr Tyr  Gln Glu Ala Gly Val  Glu Pro Ala Ser Val  Gly Tyr Val
    1025                 1030                 1035

Glu Leu  His Gly Thr Gly Thr  Ser Leu Gly Asp Pro  Ile Glu Ile
    1040                 1045                 1050

Gln Ala  Leu Lys Glu Ala Phe  Ile Ala Leu Gly Ala  Gln Ala Ala
    1055                 1060                 1065

Pro Ser  Asn Cys Gly Ile Gly  Ser Val Lys Ser Ala  Leu Gly His
    1070                 1075                 1080

Leu Glu  Ala Ala Ala Gly Leu  Thr Gly Leu Ile Lys  Val Leu Leu
    1085                 1090                 1095

Met Leu  Lys His Gly Glu Gln  Ala Gly Thr Arg His  Phe Ser Thr
    1100                 1105                 1110

Leu Asn  Pro Leu Ile Asp Leu  Arg Gly Thr Ser Phe  Glu Val Val
    1115                 1120                 1125

Ala Gln  His Arg Ala Trp Pro  Ser Gln Val Gly Ile  His Gly Thr
    1130                 1135                 1140

Leu Leu  Pro Arg Arg Ala Gly  Ile Ser Ser Phe Gly  Phe Gly Gly
    1145                 1150                 1155

Ala Asn  Ala His Ala Ile Val  Glu Glu His Val Ile  Ala Thr Pro
    1160                 1165                 1170

Pro Ser  Thr Ser Ser Ala Gly  Gly Pro Val Gly Ile  Val Leu Ser
    1175                 1180                 1185

Ala Gly  Ser Glu Ala Val Leu  Arg Gln Gln Val Leu  Ala Leu Ser
    1190                 1195                 1200

Ala Trp  Leu Arg Gln Gln Ser  Pro Thr Pro Ala Gln  Met Ile Asp
    1205                 1210                 1215

Val Ala  Tyr Thr Leu Gln Val  Gly Arg Ala Ala Leu  Ser His Arg
    1220                 1225                 1230

Leu Ala  Phe Ser Ala Thr Asp  Ala Glu Gln Ala Leu  Ala Arg Leu
    1235                 1240                 1245

Glu Gly  Arg Leu Ala Gly Val  Met Asp Ala Glu Val  His His Gly
    1250                 1255                 1260
```

-continued

```
Val Val  Asp Ala Ala Ala Thr  Ala Pro Glu His Gly  Arg Gln Thr
    1265                 1270                 1275

Arg Glu  Gly Leu Ala Gly Leu  Leu Arg Ala Trp Thr  Gln Gly Val
    1280                 1285                 1290

Arg Val  Asp Trp Ser Ala Leu  Tyr Gly Ile Gln Arg  Pro Gln Arg
    1295                 1300                 1305

Val Ser  Leu Pro Val Tyr Pro  Phe Ala Arg Glu Arg  Tyr Trp Leu
    1310                 1315                 1320

Pro Gly  Gln Ala Met His Ala  Ala Ala Asp Ala His  Pro Met Leu
    1325                 1330                 1335

Gln Leu  Leu His Ala Asn Ala  Lys Leu His Arg Tyr  Ala Leu Arg
    1340                 1345                 1350

Arg Ser  Gly Cys Ala Ser Phe  Leu Val Asp His Cys  Val Asp Gly
    1355                 1360                 1365

Arg Gln  Val Leu Pro Ala Ala  Val Gln Leu Glu Leu  Val Arg Ala
    1370                 1375                 1380

Val Ala  Gln Arg Val Met Ala  Gln Asp Glu Gly Cys  Ile Glu Leu
    1385                 1390                 1395

Ala Gln  Val Ala Phe Leu His  Pro Leu Met Met Glu  Glu Thr Glu
    1400                 1405                 1410

Leu Glu  Val Glu Ile Glu Leu  Ser Lys Ser Asp Gln  Asp Glu Phe
    1415                 1420                 1425

Asp Phe  Gln Leu His Asp Ala  His Arg Gln Gln Val  Phe Ser Gln
    1430                 1435                 1440

Gly His  Val Arg Arg Arg Val  Tyr Thr Ala Thr Pro  Arg Leu Asp
    1445                 1450                 1455

Leu Ala  Gln Leu Gln Lys Leu  Cys Ala Glu Arg Val  Leu Ser Gly
    1460                 1465                 1470

Glu Asp  Cys Tyr Ala His Phe  Thr Ala Cys Gly Leu  Gln Leu Gly
    1475                 1480                 1485

Asp Arg  Leu Lys Ser Val Gln  Ser Ile Gly Cys Gly  Arg Asn Gly
    1490                 1495                 1500

Glu Gly  Glu Pro Ile Ala Leu  Gly Val Leu Arg Leu  Pro Pro Ser
    1505                 1510                 1515

Ser Val  Glu Asp Ser His Val  Leu Pro Pro Ser Leu  Leu Asp Gly
    1520                 1525                 1530

Ala Leu  Gln Cys Ser Leu Gly  Leu Gln Arg Asp Val  Glu His Ile
    1535                 1540                 1545

Ala Met  Pro Tyr Thr Leu Glu  Arg Met Thr Val His  Ala Pro Ile
    1550                 1555                 1560

Pro Pro  Glu Ala Trp Val Leu  Leu Arg His Gly His  Ala Ala Arg
    1565                 1570                 1575

Gln Ser  Leu Asp Ile Asp Leu  Leu Asp Ser Glu Gly  Arg Val Cys
    1580                 1585                 1590

Val Ser  Leu Gly Asn Tyr Thr  Gly Arg Ala Pro Lys  Ala Val Ser
    1595                 1600                 1605

Ala Val  Arg Ala Leu Val Leu  Ala Pro Val Trp Gln  Ala Leu Thr
    1610                 1615                 1620

Glu Thr  Ala Pro Ala Trp Pro  Asp Pro Ala Glu Arg  Ile Val Thr
    1625                 1630                 1635

Val Gly  Asp Asp Ala Trp Arg  Ser His Phe Gly Phe  Asp Glu Pro
    1640                 1645                 1650

Ala Leu  Ser Leu Glu Asp Ser  Val Glu Val Ile Ala  Thr Arg Leu
```

-continued

```
    1655                1660                1665

Gly Gln  Ser Gly Lys Phe Asp  His Leu Val Trp Ile  Val Pro Ile
    1670                1675                1680

Ala Glu  Ser Glu Thr Asp Ile  Ala Ala Gln Gly Ser  Ala Ala Ile
    1685                1690                1695

Ala Gly  Phe Arg Leu Val Lys  Ala Leu Leu Ala Leu  Gly Tyr Ala
    1700                1705                1710

His Arg  Pro Leu Gly Leu Thr  Val Leu Thr Arg Gln  Ala Leu Thr
    1715                1720                1725

Arg Gln  Pro Ser His Ala Ala  Val His Gly Leu Ile  Gly Thr Leu
    1730                1735                1740

Ala Lys  Glu Tyr Cys Asn Trp  Lys Ile Arg Leu Leu  Asp Leu Pro
    1745                1750                1755

Ser Val  Lys Ser Trp Pro Gln  Trp Glu Gln Leu Arg  Ser Leu Pro
    1760                1765                1770

Trp His  Ala Gln Gly Glu Ala  Leu Ile Gly Arg Gly  Thr Cys Trp
    1775                1780                1785

Tyr Arg  Arg Gln Leu Cys Glu  Val Leu Pro Leu Pro  Ser Leu Glu
    1790                1795                1800

Pro Pro  Pro Tyr Arg Val Gly  Gly Val Tyr Val Val  Ile Gly Gly
    1805                1810                1815

Ala Gly  Gly Leu Gly Glu Val  Leu Ser Glu His Leu  Ile Arg Thr
    1820                1825                1830

Tyr Asp  Ala Gln Leu Ile Trp  Ile Gly Arg Arg Val  Leu Asp Glu
    1835                1840                1845

Gly Ile  Ala Arg Lys Gln Thr  Arg Leu Ala Ser Leu  Gly Arg Ala
    1850                1855                1860

Pro His  Tyr Ile Ser Ala Asp  Ala Ser Asp Pro Ala  Ala Leu Gln
    1865                1870                1875

Ala Ala  His Asn Glu Ile Val  Ala Leu His Gly Gln  Pro His Gly
    1880                1885                1890

Leu Ile  Leu Ser Asn Ile Val  Leu Lys Asp Ala Ser  Leu Ala Arg
    1895                1900                1905

Met Glu  Glu Ala Asp Phe Arg  Asp Val Leu Ala Ala  Lys Leu Asp
    1910                1915                1920

Val Ser  Val Cys Ala Ala Gln  Val Phe Gly Thr Ala  Pro Leu Asp
    1925                1930                1935

Phe Val  Leu Phe Phe Ser Ser  Ile Gln Ser Thr Thr  Lys Ala Ala
    1940                1945                1950

Gly Gln  Gly Asn Tyr Ala Ala  Gly Cys Cys Tyr Val  Asp Ala Phe
    1955                1960                1965

Gly Glu  Leu Trp Ala Arg Arg  Gly Leu Arg Val Lys  Thr Ile Asn
    1970                1975                1980

Trp Gly  Tyr Trp Gly Ser Val  Gly Val Val Ala Gly  Glu Asp Tyr
    1985                1990                1995

Arg Arg  Arg Met Ala Gln Lys  His Met Ala Ser Ile  Glu Gly Ala
    2000                2005                2010

Glu Ala  Met Gln Val Leu Ser  Gln Leu Leu Cys Ala  Pro Leu Gln
    2015                2020                2025

Arg Leu  Ala Tyr Val Lys Ile  Asp Asp Ala Asn Ala  Met Arg Ala
    2030                2035                2040

Leu Gly  Val Val Glu Asp Glu  Ser Val Gln Ile Pro  Val His Ala
    2045                2050                2055
```

-continued

```
Pro Ala  Glu Pro Pro Arg Gly  Gln Pro Gly Pro Val  Val Glu Leu
    2060                 2065                 2070

Ser Val  Asn Leu Asp Ala Arg  Arg Glu Arg Glu Thr  Leu Leu Ala
    2075                 2080                 2085

Ala Trp  Leu Leu Glu Leu Ile  Glu Gln Leu Gly Gly  Phe Pro Pro
    2090                 2095                 2100

Ala Ser  Phe Asp Ile Ala Thr  Leu Ala Gln Arg Leu  His Ile Val
    2105                 2110                 2115

Pro Ala  Tyr Arg Ser Trp Leu  Glu His Ser Val Arg  Met Leu Gly
    2120                 2125                 2130

Val Tyr  Gly Tyr Leu Arg Ala  Thr Gly Glu Ser Arg  Phe Glu Leu
    2135                 2140                 2145

Ala Asp  Lys Pro Pro Asp Asp  Ala Arg Gly Ala Trp  Asn Ala His
    2150                 2155                 2160

Val His  Glu Ala Ser Val Glu  Ala Gly Glu Glu Ala  Gln Arg Arg
    2165                 2170                 2175

Leu Leu  Asp Arg Cys Met Arg  Ala Leu Pro Ala Val  Leu Arg Gly
    2180                 2185                 2190

Glu Arg  Lys Ala Thr Glu Leu  Leu Phe Pro Glu Gly  Ser Met Ala
    2195                 2200                 2205

Trp Val  Glu Gly Ile Tyr Gln  Asn Asn Pro Leu Ala  Asp Tyr Phe
    2210                 2215                 2220

Asn Ala  Gln Leu Val Thr Arg  Leu Ile Ala Tyr Leu  Arg Arg Arg
    2225                 2230                 2235

Leu Glu  Ser Thr Pro Thr Ala  Arg Leu Lys Leu Cys  Glu Ile Gly
    2240                 2245                 2250

Ala Gly  Ser Gly Gly Thr Thr  Ala Ser Val Leu Gln  Gln Leu Gln
    2255                 2260                 2265

Ala Tyr  Gly Glu His Ile Glu  Glu Tyr Leu Tyr Thr  Asp Leu Ser
    2270                 2275                 2280

Pro Val  Phe Leu His His Ala  Glu Lys His Tyr Gln  Pro Arg Ala
    2285                 2290                 2295

Pro Tyr  Leu Arg Thr Ala Cys  Phe Asp Val Ala Arg  Ala Pro Thr
    2300                 2305                 2310

Ala Gln  Ala Leu Glu Ser Gly  Gly Tyr Asp Val Val  Ile Ala Ala
    2315                 2320                 2325

Asn Val  Leu His Ala Thr Arg  Asp Ile Ala Lys Thr  Leu Arg Asn
    2330                 2335                 2340

Ala Lys  Ala Leu Leu Lys Pro  Gly Gly Leu Leu Leu  Leu Asn Glu
    2345                 2350                 2355

Val Ile  Glu Arg Ser Leu Val  Leu His Leu Thr Phe  Gly Leu Leu
    2360                 2365                 2370

Glu Ser  Trp Trp Leu Pro Gln  Asp Lys Ile Leu Arg  Leu Ala Gly
    2375                 2380                 2385

Ser Pro  Leu Leu Ala Cys Ala  Thr Trp Arg Ser Leu  Leu Glu Ala
    2390                 2395                 2400

Glu Gly  Phe Ala Gly Leu Ser  Val His Arg Ala Gln  Pro Asp Ala
    2405                 2410                 2415

Gly Gln  Ala Ile Ile Cys Ala  Tyr Ser Asp Gly Ile  Val Arg Gln
    2420                 2425                 2430

Ala Ser  Thr Ile Glu Val Ala  Arg Asn Glu Lys Val  Thr Val Pro
    2435                 2440                 2445
```

-continued

```
Ser Gln  Pro Ala Glu Ala Gly  Glu Ser Pro Leu Asp  Leu Val Lys
    2450                 2455                 2460

Lys Leu  Leu Gly Arg Ile Leu  Lys Met Asp Pro Ala  Thr Leu Asp
    2465                 2470                 2475

Thr Ser  His Pro Leu Glu Tyr  Tyr Gly Val Asp Ser  Ile Val Ala
    2480                 2485                 2490

Ile Glu  Leu Ala Met Ala Leu  Arg Glu Thr Phe Pro  Gly Phe Glu
    2495                 2500                 2505

Val Ser  Glu Leu Phe Glu Thr  Gln Ser Ile Asp Thr  Leu Leu Gly
    2510                 2515                 2520

Ser Leu  Glu Gln Ala Pro Leu  Leu Ala Thr Leu Thr  Ala Pro Pro
    2525                 2530                 2535

Gln Gln  Asp Met Leu Gln Gln  Leu Lys Gln Leu Leu  Ala Arg Thr
    2540                 2545                 2550

Leu Lys  Leu Asp Ile Thr Gln  Ile Asp Thr Ser Lys  Thr Leu Glu
    2555                 2560                 2565

Ser Tyr  Gly Val Asp Ser Ile  Val Ile Ile Glu Leu  Ala Asn Ala
    2570                 2575                 2580

Leu Arg  Glu Arg Tyr Pro Ser  Leu Asp Ala Ser Gln  Leu Met Glu
    2585                 2590                 2595

Thr Leu  Ser Ile Asp Arg Leu  Val Ala Gln Trp Gln  Ala Thr Glu
    2600                 2605                 2610

Pro Ala  Val Pro Ala Glu Pro  Thr Ala Glu Pro Pro  Val Ala Asp
    2615                 2620                 2625

Glu Asp  Ala Ala Ala Ile Ile  Gly Leu Ala Gly Arg  Phe Pro Gly
    2630                 2635                 2640

Ala Asp  Thr Leu Glu Glu Phe  Trp Asn Asn Leu Arg  Asn Gly Gln
    2645                 2650                 2655

Ser Ser  Met Gly Glu Val Pro  Gly Glu Arg Trp Asp  His Gln His
    2660                 2665                 2670

Tyr Phe  Asp Ser Glu Arg Gln  Ala Pro Gly Lys Thr  Tyr Ser Arg
    2675                 2680                 2685

Trp Gly  Ala Phe Leu Arg Asp  Ile Asp Gly Phe Asp  Ala Ala Phe
    2690                 2695                 2700

Phe Glu  Trp Pro Asp Ser Val  Ala Leu Glu Ser Asp  Pro Gln Ala
    2705                 2710                 2715

Arg Ile  Phe Leu Glu Gln Ala  Tyr Ala Gly Ile Glu  Asp Ala Gly
    2720                 2725                 2730

Tyr Thr  Pro Gly Ser Leu Ser  Lys Ser Gln Arg Val  Gly Val Phe
    2735                 2740                 2745

Val Gly  Val Met Asn Gly Tyr  Tyr Ser Gly Gly Ala  Arg Phe Trp
    2750                 2755                 2760

Gln Ile  Ala Asn Arg Val Ser  Tyr Gln Phe Asp Phe  Arg Gly Pro
    2765                 2770                 2775

Ser Leu  Ala Val Asp Thr Ala  Cys Ser Ala Ser Leu  Thr Ala Ile
    2780                 2785                 2790

His Leu  Ala Leu Glu Ser Leu  Arg Ser Gly Ser Cys  Glu Val Ala
    2795                 2800                 2805

Leu Ala  Gly Gly Val Asn Leu  Leu Val Asp Pro Gln  Gln Tyr Leu
    2810                 2815                 2820

Asn Leu  Ala Gly Ala Ala Met  Leu Ser Ala Gly Ala  Ser Cys Arg
    2825                 2830                 2835

Pro Phe  Gly Glu Ala Ala Asp  Gly Phe Val Ala Gly  Glu Ala Cys
```

-continued

```
    2840                2845                2850

Gly Val  Val Leu Leu Lys Pro  Leu Lys Gln Ala Arg  Ala Asp Gly
    2855                2860                2865

Asp Val  Ile His Ala Val Ile  Arg Gly Ser Met Ile  Asn Ala Gly
    2870                2875                2880

Gly His  Thr Ser Ala Phe Ser  Ser Pro Asn Pro Ala  Ala Gln Ala
    2885                2890                2895

Glu Val  Val Arg Gln Ala Leu  Gln Arg Ala Gly Val  Ala Pro Asp
    2900                2905                2910

Ser Ile  Ser Tyr Ile Glu Ala  His Gly Thr Gly Thr  Val Leu Gly
    2915                2920                2925

Asp Ala  Val Glu Leu Gly Ala  Leu Asn Lys Val Phe  Asp Lys Arg
    2930                2935                2940

Ala Ala  Pro Cys Pro Ile Gly  Ser Leu Lys Ala Asn  Ile Gly His
    2945                2950                2955

Ala Glu  Ser Ala Ala Gly Ile  Ala Gly Leu Ala Lys  Leu Val Leu
    2960                2965                2970

Gln Phe  Arg His Gly Glu Leu  Val Pro Ser Leu Asn  Ala Phe Pro
    2975                2980                2985

Leu Asn  Pro Tyr Ile Glu Phe  Gly Arg Phe Gln Val  Gln Gln Gln
    2990                2995                3000

Pro Ala  Pro Trp Pro Arg Arg  Gly Ala Gln Pro Arg  Arg Ala Gly
    3005                3010                3015

Leu Ser  Ala Phe Gly Ala Gly  Gly Ser Asn Ala His  Leu Val Val
    3020                3025                3030

Glu Glu  Ala Pro Ala Met Ala  Pro Gly Val Ser Ile  Ser Ala Ser
    3035                3040                3045

Ser Pro  Ala Leu Ile Val Leu  Ser Ala Arg Thr Leu  Pro Ala Leu
    3050                3055                3060

Gln Gln  Arg Ala Arg Asp Leu  Leu Val Trp Met Gln  Ala Arg Gln
    3065                3070                3075

Val Asp  Asp Val Met Leu Ala  Asp Val Ala Tyr Thr  Leu His Leu
    3080                3085                3090

Gly Arg  Val Ala Met Glu Gln  Arg Leu Ala Phe Thr  Ala Gly Ser
    3095                3100                3105

Ala Ala  Glu Leu Ser Glu Lys  Leu Gln Ala Tyr Leu  Gly His Ala
    3110                3115                3120

Ile Arg  Ala Asp Ile Tyr Leu  Ser Glu Asp Thr Pro  Gly Lys Pro
    3125                3130                3135

Ala Gly  Ala Pro Ile Val Ala  Glu Glu Asp Leu Leu  Thr Leu Met
    3140                3145                3150

Asp Ala  Trp Ile Glu Lys Gly  Gln Tyr Gly Arg Leu  Leu Glu Tyr
    3155                3160                3165

Trp Thr  Lys Gly Gln Pro Ile  Asp Trp Asn Lys Leu  Tyr Trp Arg
    3170                3175                3180

Lys Leu  Tyr Ala Asp Gly Arg  Pro Arg Arg Ile Ser  Leu Pro Thr
    3185                3190                3195

Tyr Pro  Phe Glu His Arg Arg  Tyr Trp Gln Thr Pro  Val Pro Gly
    3200                3205                3210

Glu Arg  Ser Leu His Ala Thr  Ala Pro Ala Thr Arg  Glu Thr Val
    3215                3220                3225

Ala Val  Gly Ala Met Pro Asp  Pro Ala Gly Ala Thr  Val Gln Ala
    3230                3235                3240
```

-continued

```
Arg Leu Cys Ala Leu Cys Gln Val Leu Leu Gly Lys Pro Val Thr
    3245                3250                3255

Ala Gln Met Asp Phe Phe Ala Val Gly Gly His Ser Val Leu Ala
    3260                3265                3270

Ile Gln Leu Val Ser Arg Ile Arg Lys Ser Phe Gly Val Glu Tyr
    3275                3280                3285

Pro Val Ser Ala Leu Phe Glu Ser Ala Leu Leu Ser Asp Met Ala
    3290                3295                3300

Arg Gln Ile Glu Gln Leu Arg Val Asn Gly Val Ala Lys Arg Met
    3305                3310                3315

Pro Ala Leu Leu Pro Ala Gly Arg Val Gly Ala Ile Pro Ala Thr
    3320                3325                3330

Tyr Ala Gln Glu Arg Leu Trp Leu Val His Glu His Met Ser Glu
    3335                3340                3345

Gln Arg Ser Ser Tyr Asn Ile Thr Phe Ala Met His Phe Arg Gly
    3350                3355                3360

Val Asp Phe Arg Ala Glu Ala Met Arg Ala Ala Leu Asn Ala Leu
    3365                3370                3375

Val Val Arg His Glu Val Leu Arg Thr Arg Phe Leu Ser Glu Asp
    3380                3385                3390

Gly Gln Leu Gln Gln Val Ile Ala Ala Ser Leu Thr Leu Glu Val
    3395                3400                3405

Pro Val Arg Glu Met Ser Val Glu Glu Val Asp Leu Leu Leu Ala
    3410                3415                3420

Ala Ser Thr Arg Glu Thr Phe Asp Leu Arg Gln Gly Pro Leu Phe
    3425                3430                3435

Lys Ala Arg Ile Leu Arg Val Ala Ala Asp His His Val Val Leu
    3440                3445                3450

Ser Ser Ile His His Ile Ile Ser Asp Gly Trp Ser Leu Gly Val
    3455                3460                3465

Phe Asn Arg Asp Leu His Gln Leu Tyr Glu Ala Cys Leu Arg Gly
    3470                3475                3480

Thr Pro Pro Thr Leu Pro Thr Leu Ala Val Gln Tyr Ala Asp Tyr
    3485                3490                3495

Ala Leu Trp Gln Arg Gln Trp Glu Leu Ala Ala Pro Leu Ser Tyr
    3500                3505                3510

Trp Thr Arg Ala Leu Glu Gly Tyr Asp Asp Gly Leu Asp Leu Pro
    3515                3520                3525

Tyr Asp Arg Pro Arg Gly Ala Thr Arg Ala Trp Arg Ala Gly Leu
    3530                3535                3540

Val Lys His Arg Tyr Pro Pro Gln Leu Ala Gln Gln Leu Ala Ala
    3545                3550                3555

Tyr Ser Gln Gln Tyr Gln Ala Thr Leu Phe Met Ser Leu Leu Ala
    3560                3565                3570

Gly Leu Ala Leu Val Leu Gly Arg Tyr Ala Asp Arg Lys Asp Val
    3575                3580                3585

Cys Ile Gly Ala Thr Val Ser Gly Arg Asp Gln Leu Glu Leu Glu
    3590                3595                3600

Glu Leu Ile Gly Phe Phe Ile Asn Ile Leu Pro Leu Arg Val Asp
    3605                3610                3615

Leu Ser Gly Asp Pro Cys Leu Glu Glu Val Leu Leu Arg Thr Arg
    3620                3625                3630
```

-continued

```
Gln Val Val Leu Asp Gly Phe Ala His Gln Ser Val Pro Phe Glu
    3635                3640                3645

His Val Leu Gln Ala Leu Arg Arg Gln Arg Asp Ser Ser Gln Ile
    3650                3655                3660

Pro Leu Val Pro Val Met Leu Arg His Gln Asn Phe Pro Thr Gln
    3665                3670                3675

Glu Ile Gly Asp Trp Pro Glu Gly Val Arg Leu Thr Gln Met Glu
    3680                3685                3690

Leu Gly Leu Asp Arg Ser Thr Pro Ser Glu Leu Asp Trp Gln Phe
    3695                3700                3705

Tyr Gly Asp Gly Ser Ser Leu Glu Leu Thr Leu Glu Tyr Ala Gln
    3710                3715                3720

Asp Leu Phe Asp Glu Ala Thr Val Arg Arg Met Ile Ala His His
    3725                3730                3735

Gln Gln Ala Leu Glu Ala Met Val Ser Arg Pro Gln Leu Arg Val
    3740                3745                3750

Gly Lys Trp Asp Met Leu Thr Ala Glu Glu Arg Arg Leu Phe Ala
    3755                3760                3765

Ala Leu Asn Ala Thr Gly Thr Pro Arg Glu Trp Pro Ser Leu Ala
    3770                3775                3780

Gln Gln Phe Glu Arg Gln Ala Gln Ala Thr Pro Gln Ala Ile Ala
    3785                3790                3795

Cys Val Ser Asp Gly Gln Ser Trp Ser Tyr Ala Gln Leu Glu Ala
    3800                3805                3810

Arg Ala Asn Gln Leu Ala Gln Ala Leu Arg Gly Gln Gly Ala Gly
    3815                3820                3825

Arg Asp Val Arg Val Ala Val Gln Ser Ala Arg Thr Pro Glu Leu
    3830                3835                3840

Leu Met Ala Leu Leu Ala Ile Phe Lys Ala Gly Ala Cys Tyr Val
    3845                3850                3855

Pro Ile Asp Pro Ala Tyr Pro Ala Ala Tyr Arg Glu Gln Ile Leu
    3860                3865                3870

Ala Glu Val Gln Val Ser Ile Val Leu Glu Gln Asp Glu Leu Ala
    3875                3880                3885

Leu Asp Glu Gln Gly Gln Phe His Asn Pro Arg Trp Arg Glu Gln
    3890                3895                3900

Ala Pro Thr Pro Leu Gly Leu Arg Glu His Pro Gly Asp Leu Ala
    3905                3910                3915

Cys Val Met Val Thr Ser Gly Ser Thr Gly Arg Pro Lys Gly Val
    3920                3925                3930

Met Val Pro Tyr Ala Gln Leu Tyr Asn Trp Leu His Ala Gly Trp
    3935                3940                3945

Gln Arg Ser Pro Phe Glu Ala Gly Glu Arg Val Leu Gln Lys Thr
    3950                3955                3960

Ser Ile Ala Phe Ala Val Ser Val Lys Glu Leu Leu Ser Gly Leu
    3965                3970                3975

Leu Ala Gly Val Glu Gln Val Met Leu Pro Asp Glu Gln Val Lys
    3980                3985                3990

Asp Ser Leu Ala Leu Ala Arg Ala Ile Glu Gln Trp Gln Val Thr
    3995                4000                4005

Arg Leu Tyr Leu Val Pro Ser His Leu Gln Ala Leu Leu Asp Ala
    4010                4015                4020

Thr Gln Gly Arg Asp Gly Leu Leu His Ser Leu Arg His Val Val
```

-continued

```
    4025                4030                4035

Thr Ala  Gly Glu Ala Leu Pro  Ser Ala Val Arg Glu  Thr Val Arg
    4040                4045                4050

Ala Arg  Leu Pro Gln Val Gln  Leu Trp Asn Asn Tyr  Gly Cys Thr
    4055                4060                4065

Glu Leu  Asn Asp Ala Thr Tyr  His Arg Ser Asp Thr  Val Ala Pro
    4070                4075                4080

Gly Thr  Phe Val Pro Ile Gly  Ala Pro Ile Ala Asn  Thr Glu Val
    4085                4090                4095

Tyr Val  Leu Asp Arg Gln Leu  Arg Gln Val Pro Ile  Gly Val Met
    4100                4105                4110

Gly Glu  Leu His Val His Ser  Val Gly Met Ala Arg  Gly Tyr Trp
    4115                4120                4125

Asn Arg  Pro Gly Leu Thr Ala  Ser Arg Phe Ile Ala  His Pro Tyr
    4130                4135                4140

Ser Glu  Glu Pro Gly Thr Arg  Leu Tyr Lys Thr Gly  Asp Met Val
    4145                4150                4155

Arg Arg  Leu Ala Asp Gly Thr  Leu Glu Tyr Leu Gly  Arg Gln Asp
    4160                4165                4170

Phe Glu  Val Lys Val Arg Gly  His Arg Val Asp Thr  Arg Gln Val
    4175                4180                4185

Glu Ala  Ala Leu Arg Ala Gln  Pro Ala Val Ala Glu  Ala Val Val
    4190                4195                4200

Ser Gly  His Arg Val Asp Gly  Asp Met Gln Leu Val  Ala Tyr Val
    4205                4210                4215

Val Ala  Arg Glu Gly Gln Ala  Pro Ser Ala Gly Glu  Leu Lys Gln
    4220                4225                4230

Gln Leu  Ser Ala Gln Leu Pro  Thr Tyr Met Leu Pro  Thr Val Tyr
    4235                4240                4245

Gln Trp  Leu Glu Gln Leu Pro  Arg Leu Ser Asn Gly  Lys Leu Asp
    4250                4255                4260

Arg Leu  Ala Leu Pro Ala Pro  Gln Ala Val His Ala  Gln Glu Tyr
    4265                4270                4275

Val Ala  Pro Arg Asn Gln Ala  Glu Gln Arg Leu Ala  Ala Leu Phe
    4280                4285                4290

Ala Glu  Val Leu Arg Val Glu  Gln Val Gly Ile His  Asp Asn Phe
    4295                4300                4305

Phe Ala  Leu Gly Gly His Ser  Leu Ser Ala Ser Gln  Leu Ile Ser
    4310                4315                4320

Arg Ile  Ala Arg Asp Met Ala  Ile Asp Leu Pro Leu  Ala Met Leu
    4325                4330                4335

Phe Glu  Leu Pro Thr Val Ala  Gln Leu Ser Glu Ser  Leu Ala Ser
    4340                4345                4350

His Ala  Arg Asp Ser Asp Tyr  Asp Val Ile Pro Ala  Ser Thr Glu
    4355                4360                4365

Glu Ala  Thr Ile Pro Leu Ser  Thr Ala Gln Glu Arg  Met Trp Phe
    4370                4375                4380

Leu His  Lys Phe Val Gln Glu  Thr Pro Tyr Asn Thr  Pro Gly Leu
    4385                4390                4395

Ala Leu  Leu Gln Gly Glu Leu  Asp Ile Ser Ala Leu  Gln Val Ala
    4400                4405                4410

Phe Arg  Cys Val Leu Glu Arg  His Ala Val Leu Arg  Thr His Phe
    4415                4420                4425
```

-continued

Val Glu Thr Glu Gln Gln Cys Val Gln Val Ile Gly Ala Ala Glu
4430 4435 4440

Gln Phe Val Leu Gln Leu Arg Ser Ile Arg Asp Glu Ala Asp Leu
4445 4450 4455

His Gly Leu Leu His Thr Ala Val Ser Glu Pro Phe Asp Leu Glu
4460 4465 4470

Arg Glu Leu Pro Leu Arg Ala Leu Leu Tyr Arg Leu Asp Asp Arg
4475 4480 4485

Arg His Tyr Leu Ala Val Val Ile His His Ile Val Phe Asp Gly
4490 4495 4500

Trp Ser Thr Ser Ile Leu Phe Arg Glu Leu Ala Thr His Tyr Ala
4505 4510 4515

Ala Cys Arg His Gly Gln Ser Ala Pro Leu Pro Pro Leu Glu Leu
4520 4525 4530

Ser Tyr Ala Asp Tyr Ala Arg Trp Glu Arg Ala Arg Leu Asn Gln
4535 4540 4545

Glu Asp Ala Leu Arg Lys Leu Glu Tyr Trp Lys Thr Gln Leu Ala
4550 4555 4560

Asp Ala Pro Pro Leu Val Leu Pro Thr Thr Tyr Ala Arg Pro Val
4565 4570 4575

Phe Gln Asn Phe Asn Gly Ala Thr Val Ala Leu Gln Ile Glu Pro
4580 4585 4590

Pro Leu Leu Gln Arg Leu Gln Arg Phe Ala Asp Ala His Ser Phe
4595 4600 4605

Thr Leu Tyr Met Leu Leu Leu Ala Ala Leu Gly Val Val Leu Ser
4610 4615 4620

Arg His Ala Arg Gln Lys His Phe Cys Ile Gly Ser Pro Val Ala
4625 4630 4635

Asn Arg Ala Arg Ala Glu Leu His Gly Leu Ile Gly Leu Phe Val
4640 4645 4650

Asn Thr Leu Ala Val Arg Leu Asp Leu Asp Gly Asn Pro Ser Val
4655 4660 4665

Arg Glu Leu Leu Glu Arg Ile His Cys Thr Thr Leu Ala Ala Tyr
4670 4675 4680

Glu His Gln Asp Val Pro Phe Glu Arg Ile Val Glu Ser Leu Lys
4685 4690 4695

Val Pro Arg Asp Thr Ala Arg Asn Pro Leu Gly Gln Val Met Leu
4700 4705 4710

Asn Phe Gln Asn Met Pro Met Ser Ala Phe Asp Leu Asp Gly Val
4715 4720 4725

Gln Val Gln Val Leu Pro Met His Asn Gly Thr Ala Lys Cys Glu
4730 4735 4740

Leu Thr Phe Asp Leu Leu Leu Asp Gly Ser Arg Leu Ser Gly Phe
4745 4750 4755

Val Glu Tyr Ala Thr Gly Leu Phe Ala Pro Glu Trp Val Gln Ala
4760 4765 4770

Leu Val Gln Gln Phe Lys Cys Val Leu Ala Ala Leu Val Glu Arg
4775 4780 4785

Pro Glu Ala Ser Leu Asn Asp Leu Pro Met Ala Pro Asn Glu Ala
4790 4795 4800

Gln Pro Ala Ser Pro Ala Leu Met Lys His Val Ala Pro Ser Leu
4805 4810 4815

-continued

```
Pro Asn  Leu Leu Glu Ala Met  Ala Ala Asn Asp Ala  Ala Arg Leu
    4820                 4825                 4830

Ala Leu  Gln Ala Pro Glu Gly  Ala Leu Ser Tyr Ala  Gln Leu Ile
    4835                 4840                 4845

Glu Ala  Ala Asn Glu Phe Ala  Trp Arg Leu Arg Cys  Glu His Ala
    4850                 4855                 4860

Gly Pro  Asp Lys Val Val Ala  Leu Cys Leu Ala Pro  Cys Ser Ala
    4865                 4870                 4875

Leu Val  Val Ala Leu Leu Ala  Ala Ser Leu Cys Gly  Ala Ala Ser
    4880                 4885                 4890

Val Leu  Ile Asp Pro Thr Thr  Thr Ala Glu Ala Gln  Tyr Asp Gln
    4895                 4900                 4905

Leu Phe  Glu Thr Arg Ala Gly  Ile Val Val Thr Cys  Ser Ser Leu
    4910                 4915                 4920

Leu Glu  Lys Leu Pro Leu Asp  Asp Gln Ala Val Val  Leu Ile Asp
    4925                 4930                 4935

Glu Gln  Ala Ala Glu Ala Thr  Pro Arg Leu Met His  Phe Thr Asp
    4940                 4945                 4950

Asp Pro  Ala Leu Pro Ala Met  Leu Tyr Cys Val Cys  Asp Glu Lys
    4955                 4960                 4965

Gly Arg  Thr Arg Thr Ile Met  Val Glu Ser Gly Ser  Leu Ser Ser
    4970                 4975                 4980

Arg Leu  Leu Asp Ser Val Gln  Arg Phe Ser Leu Glu  Arg Thr Asp
    4985                 4990                 4995

Arg Phe  Leu Leu Arg Ser Pro  Leu Ser Ala Glu Leu  Ala Asn Thr
    5000                 5005                 5010

Glu Val  Leu Gln Trp Leu Ala  Ala Gly Gly Ser Leu  Ser Ile Ala
    5015                 5020                 5025

Pro Met  His Gly Asp Phe Asp  Ala Ala Ala Trp Leu  Glu Thr Leu
    5030                 5035                 5040

Ala Thr  Tyr Ala Ile Thr Val  Ala Tyr Leu Ala Gln  Val Glu Leu
    5045                 5050                 5055

Thr Glu  Met Leu Ala His Leu  Gln Asn His Pro Leu  Glu Arg Asn
    5060                 5065                 5070

Lys Leu  Ala Gly Leu Arg Val  Leu Val Val His Gly  Ala Pro Leu
    5075                 5080                 5085

Pro Ile  Ala Pro Leu Met Arg  Leu Asp Ala Trp Leu  Arg Glu Val
    5090                 5095                 5100

Gly Gly  Ser Ala Arg Ile Phe  Ala Ala Tyr Gly Asn  Ala Glu Phe
    5105                 5110                 5115

Gly Ala  Glu Ile Leu Ser Gln  Asp Val Ser Ala Ala  Leu Gln Ala
    5120                 5125                 5130

Gly Ile  Gly Ala Gln Tyr Lys  His Arg Arg Gly Leu  Phe Pro Leu
    5135                 5140                 5145

Gly Ala  Asn Ser Met Cys His  Val Val Gln Ser Asn  Gly Arg Ile
    5150                 5155                 5160

Ala Pro  Asp Gly Met Val Gly  Glu Leu Trp Ile Thr  Gln Pro Ala
    5165                 5170                 5175

Cys Leu  Tyr Lys Thr Asp Ala  Leu Val Arg Arg Leu  Ala Asn Gly
    5180                 5185                 5190

Gln Leu  Glu Trp Leu Gly Ser  Leu Asp Val Gln Ser  Arg Ile Asp
    5195                 5200                 5205

Asp Pro  Arg Ile Asp Leu Cys  Val Val Glu Ala Gln  Leu Arg Leu
```

-continued

```
    5210                5215                5220

Cys Glu  Asp Val Gly Glu Ala  Val Val Leu Tyr Glu  Pro Leu Lys
    5225                5230                5235

Arg Cys  Leu Val Ala Tyr Leu  Ser Ala Arg Ser Thr  Ala Ala Ile
    5240                5245                5250

Met Thr  Asp Glu Thr Leu Ala  Arg Ile Arg Gln Ala  Leu Ser Glu
    5255                5260                5265

Thr Leu  Pro Asp Tyr Leu Leu  Pro Ala Ile Trp Val  Pro Leu Ala
    5270                5275                5280

His Trp  Pro Arg Leu Pro His  Gly Arg Val Asp Leu  Gly Ala Leu
    5285                5290                5295

Pro Ala  Pro Asp Phe Asp Leu  Ala Arg His Glu Ser  Tyr Ile Ala
    5300                5305                5310

Pro Arg  Thr Ala Val Glu Gln  Ala Val Ala Glu Ile  Trp Gln Arg
    5315                5320                5325

Val Leu  Lys Arg Thr Gln Val  Gly Val His Asp Asn  Phe Phe Glu
    5330                5335                5340

Leu Gly  Gly His Ser Val Leu  Ala Ile Gln Leu Val  Ser Gly Leu
    5345                5350                5355

Arg Lys  Ala Leu Ala Ile Glu  Val Pro Val Thr Leu  Val Phe Glu
    5360                5365                5370

Ala Pro  Ile Leu Gly Ala Leu  Ala Arg Gln Ile Ala  Pro Leu Leu
    5375                5380                5385

Val Ser  Glu Arg Arg Pro Arg  Pro Pro Gly Leu Thr  Arg Leu Glu
    5390                5395                5400

His Thr  Gly Pro Ile Pro Ala  Ser Tyr Ala Gln Glu  Arg Leu Trp
    5405                5410                5415

Leu Val  His Glu His Met Glu  Glu Gln Arg Thr Ser  Tyr Asn Ile
    5420                5425                5430

Ser Asn  Ala Ala His Phe Ile  Gly Ala Ala Phe Ser  Val Glu Ala
    5435                5440                5445

Met Arg  Ala Ala Leu Asn Ala  Leu Val Ala Arg His  Glu Val Leu
    5450                5455                5460

Arg Thr  Arg Phe Leu Ser Glu  Asp Gly Gln Leu Gln  Gln Val Ile
    5465                5470                5475

Ala Ala  Ser Leu Thr Leu Glu  Val Pro Val Arg Glu  Val Ser Ala
    5480                5485                5490

Glu Glu  Val Asp Leu Leu Leu  Ala Ala Ser Thr Arg  Glu Thr Phe
    5495                5500                5505

Asp Leu  Arg Gln Gly Pro Leu  Phe Lys Ala Arg Ile  Leu Arg Val
    5510                5515                5520

Ala Ala  Asp His His Val Val  Leu Ser Ser Ile His  His Ile Ile
    5525                5530                5535

Ser Asp  Gly Trp Ser Leu Gly  Val Phe Asn Arg Asp  Leu His Gln
    5540                5545                5550

Leu Tyr  Glu Ala Cys Leu Arg  Gly Thr Pro Pro Thr  Leu Pro Thr
    5555                5560                5565

Leu Ala  Val Gln Tyr Ala Asp  Tyr Ala Leu Trp Gln  Arg Gln Trp
    5570                5575                5580

Glu Leu  Ala Ala Pro Leu Ser  Tyr Trp Thr Arg Ala  Leu Glu Gly
    5585                5590                5595

Tyr Asp  Asp Gly Leu Asp Leu  Pro Tyr Asp Arg Pro  Arg Gly Ala
    5600                5605                5610
```

-continued

```
Thr Arg  Ala Trp Arg Ala Gly  Leu Val Lys His Arg  Tyr Pro Pro
    5615                 5620                 5625

Gln Leu  Ala Gln Gln Leu Ala  Ala Tyr Ser Gln Gln  Tyr Gln Ala
    5630                 5635                 5640

Thr Leu  Phe Met Ser Leu Leu  Ala Gly Leu Ala Leu  Val Leu Gly
    5645                 5650                 5655

Arg Tyr  Ala Asp Arg Lys Asp  Val Cys Ile Gly Ala  Thr Val Ser
    5660                 5665                 5670

Gly Arg  Asp Gln Leu Glu Leu  Glu Glu Leu Ile Gly  Phe Phe Ile
    5675                 5680                 5685

Asn Ile  Leu Pro Leu Arg Val  Asp Leu Ser Gly Asp  Pro Cys Leu
    5690                 5695                 5700

Glu Glu  Val Leu Leu Arg Thr  Arg Gln Val Val Leu  Asp Gly Phe
    5705                 5710                 5715

Ala His  Gln Ser Val Pro Phe  Glu His Val Leu Gln  Ala Leu Arg
    5720                 5725                 5730

Arg Gln  Arg Asp Ser Ser Gln  Ile Pro Leu Val Pro  Val Met Leu
    5735                 5740                 5745

Arg His  Gln Asn Phe Pro Thr  Gln Glu Ile Gly Asp  Trp Pro Glu
    5750                 5755                 5760

Gly Val  Arg Leu Thr Gln Met  Glu Leu Gly Leu Asp  Arg Ser Thr
    5765                 5770                 5775

Pro Ser  Glu Leu Asp Trp Gln  Phe Tyr Gly Asp Gly  Ser Ser Leu
    5780                 5785                 5790

Glu Leu  Thr Leu Glu Tyr Ala  Gln Asp Leu Phe Asp  Glu Ala Thr
    5795                 5800                 5805

Val Arg  Arg Met Ile Ala His  His Gln Gln Ala Leu  Glu Ala Met
    5810                 5815                 5820

Val Ser  Arg Pro Gln Leu Arg  Val Gly Lys Trp Asp  Met Leu Thr
    5825                 5830                 5835

Ala Glu  Glu Arg Arg Leu Phe  Ala Ala Leu Asn Ala  Thr Gly Thr
    5840                 5845                 5850

Pro Arg  Glu Trp Pro Ser Leu  Ala Gln Gln Phe Glu  Arg Gln Ala
    5855                 5860                 5865

Gln Ala  Thr Pro Gln Ala Ile  Ala Cys Val Ser Asp  Gly Gln Ser
    5870                 5875                 5880

Trp Ser  Tyr Ala Gln Leu Glu  Ala Arg Ala Asn Gln  Leu Ala Gln
    5885                 5890                 5895

Ala Leu  Arg Gly Gln Gly Ala  Gly Arg Asp Val Arg  Val Ala Val
    5900                 5905                 5910

Gln Ser  Ala Arg Thr Pro Glu  Leu Leu Met Ala Leu  Leu Ala Ile
    5915                 5920                 5925

Phe Lys  Ala Gly Ala Cys Tyr  Val Pro Ile Asp Pro  Ala Tyr Pro
    5930                 5935                 5940

Ala Ala  Tyr Arg Glu Gln Ile  Leu Ala Glu Val Gln  Val Ser Ile
    5945                 5950                 5955

Val Leu  Glu Gln Gly Glu Leu  Ala Leu Asp Glu Gln  Gly Gln Phe
    5960                 5965                 5970

Arg Asn  Arg Arg Trp Arg Glu  Gln Ala Pro Thr Pro  Leu Gly Leu
    5975                 5980                 5985

Arg Gly  His Pro Gly Asp Leu  Ala Cys Val Met Val  Thr Ser Gly
    5990                 5995                 6000
```

-continued

```
Ser Thr  Gly Arg Pro Lys Gly  Val Met Val Pro Tyr  Ala Gln Leu
    6005                 6010                 6015

His Asn  Trp Leu His Ala Gly  Trp Gln Arg Ser Ala  Phe Glu Ala
    6020                 6025                 6030

Gly Glu  Arg Val Leu Gln Lys  Thr Ser Ile Ala Phe  Ala Val Ser
    6035                 6040                 6045

Val Lys  Glu Leu Leu Ser Gly  Leu Leu Ala Gly Val  Gly Gln Val
    6050                 6055                 6060

Met Leu  Pro Asp Glu Gln Val  Lys Asp Ser Leu Ala  Leu Ala Arg
    6065                 6070                 6075

Ala Ile  Glu Gln Trp Gln Val  Thr Arg Leu Tyr Leu  Val Pro Ser
    6080                 6085                 6090

His Leu  Gln Ala Leu Leu Asp  Ala Thr Gln Gly Arg  Asp Gly Leu
    6095                 6100                 6105

Leu His  Ser Leu Arg His Val  Val Thr Ala Gly Glu  Ala Leu Pro
    6110                 6115                 6120

Ser Ala  Val Gly Glu Ala Val  Arg Val Arg Leu Pro  Gln Val Gln
    6125                 6130                 6135

Leu Trp  Asn Asn Tyr Gly Cys  Thr Glu Leu Asn Asp  Ala Thr Tyr
    6140                 6145                 6150

His Arg  Ser Asp Thr Val Ala  Pro Gly Thr Phe Val  Pro Ile Gly
    6155                 6160                 6165

Ala Pro  Ile Ala Asn Thr Glu  Val Tyr Val Leu Asp  Arg Gln Leu
    6170                 6175                 6180

Arg Gln  Val Pro Ile Gly Val  Met Gly Glu Leu His  Val His Ser
    6185                 6190                 6195

Val Gly  Met Ala Arg Gly Tyr  Trp Asn Arg Pro Gly  Leu Thr Ala
    6200                 6205                 6210

Ser Arg  Phe Ile Ala His Pro  Tyr Ser Glu Glu Pro  Gly Thr Arg
    6215                 6220                 6225

Leu Tyr  Lys Thr Gly Asp Met  Val Arg Arg Leu Ala  Asp Gly Thr
    6230                 6235                 6240

Leu Glu  Tyr Leu Gly Arg Gln  Asp Phe Glu Val Lys  Val Arg Gly
    6245                 6250                 6255

His Arg  Val Asp Thr Arg Gln  Val Glu Ala Ala Leu  Arg Ala Gln
    6260                 6265                 6270

Pro Ala  Val Ala Glu Ala Val  Val Ser Gly His Arg  Val Asp Gly
    6275                 6280                 6285

Asp Met  Gln Leu Val Ala Tyr  Val Val Ala Arg Glu  Gly Gln Ala
    6290                 6295                 6300

Pro Ser  Ala Gly Glu Leu Lys  Gln Gln Leu Ser Ala  Gln Leu Pro
    6305                 6310                 6315

Thr Tyr  Met Leu Pro Thr Val  Tyr Gln Trp Leu Glu  Gln Leu Pro
    6320                 6325                 6330

Arg Leu  Ser Asn Gly Lys Leu  Asp Arg Leu Ala Leu  Pro Ala Pro
    6335                 6340                 6345

Gln Val  Val His Ala Gln Glu  Tyr Val Ala Pro Arg  Asn Glu Ala
    6350                 6355                 6360

Glu Gln  Arg Leu Ala Ala Leu  Phe Ala Glu Val Leu  Arg Val Glu
    6365                 6370                 6375

Gln Val  Gly Ile His Asp Asn  Phe Phe Ala Leu Gly  Gly His Ser
    6380                 6385                 6390

Leu Ser  Ala Ser Gln Leu Ile  Ser Arg Ile Arg Gln  Ser Phe His
```

-continued

```
    6395                6400                6405

Val Asp  Leu Pro Leu Ser Arg  Ile Phe Glu Ala Pro  Thr Ile Glu
    6410                6415                6420

Gly Leu  Val Arg Gln Leu Ala  Leu Pro Ser Glu Gly  Gly Val Ala
    6425                6430                6435

Ser Ile  Ala Arg Val Ala Arg  Asn Arg Thr Ile Pro  Leu Ser Leu
    6440                6445                6450

Phe Gln  Glu Arg Leu Trp Phe  Val His Gln His Met  Pro Glu Gln
    6455                6460                6465

Arg Thr  Ser Tyr Asn Gly Thr  Leu Ala Leu Arg Leu  Arg Gly Pro
    6470                6475                6480

Leu Ser  Val Glu Ala Met Arg  Ala Ala Leu Arg Ala  Leu Val Leu
    6485                6490                6495

Arg His  Glu Ile Leu Arg Thr  Arg Phe Val Leu Pro  Thr Gly Ala
    6500                6505                6510

Ser Glu  Pro Val Gln Val Ile  Asp Glu His Ser Asp  Phe Gln Leu
    6515                6520                6525

Ser Val  Gln Leu Val Glu Asp  Thr Glu Ile Ala Ser  Leu Met Asp
    6530                6535                6540

Glu Leu  Ala Ser His Ile Tyr  Asp Leu Ala Asn Gly  Pro Leu Phe
    6545                6550                6555

Ile Ala  Cys Leu Leu Gln Leu  Asp Glu Gln Glu His  Val Leu Leu
    6560                6565                6570

Ile Gly  Met His His Leu Ile  Tyr Asp Ala Trp Ser  Gln Phe Thr
    6575                6580                6585

Val Met  Asn Arg Asp Leu Arg  Val Leu Tyr His Arg  His Leu Gly
    6590                6595                6600

Leu Ala  Gly Gly Asp Leu Pro  Glu Leu Pro Ile Gln  Tyr Ala Asp
    6605                6610                6615

Tyr Ala  Ile Trp Gln Arg Ala  Gln Asn Leu Asp Ala  Gln Leu Ala
    6620                6625                6630

Tyr Trp  Gln Ala Met Leu His  Asp Tyr Asp Asp Gly  Leu Glu Leu
    6635                6640                6645

Pro Tyr  Asp Tyr Pro Arg Pro  Arg Asn Arg Thr Trp  His Ala Ala
    6650                6655                6660

Val Tyr  Thr His Thr Tyr Pro  Ala Glu Leu Val Gln  Arg Phe Ala
    6665                6670                6675

Gly Phe  Val Gln Ala His Gln  Ser Thr Leu Phe Ile  Gly Leu Leu
    6680                6685                6690

Ala Ser  Phe Ala Val Val Leu  Asn Lys Tyr Thr Gly  Arg Asp Asp
    6695                6700                6705

Leu Cys  Ile Gly Thr Thr Thr  Ala Gly Arg Thr His  Leu Glu Leu
    6710                6715                6720

Glu Asn  Leu Ile Gly Phe Phe  Ile Asn Ile Leu Pro  Leu Arg Leu
    6725                6730                6735

Arg Leu  Asp Gly Asp Pro Asp  Val Ala Glu Ile Met  Arg Arg Thr
    6740                6745                6750

Arg Leu  Val Ala Met Ser Ala  Phe Glu Asn Gln Ala  Leu Pro Phe
    6755                6760                6765

Glu His  Leu Leu Asn Ala Leu  His Lys Gln Arg Asp  Thr Ser Arg
    6770                6775                6780

Ile Pro  Leu Val Pro Val Val  Met Arg His Gln Asn  Phe Pro Asp
    6785                6790                6795
```

-continued

```
Thr Ile  Gly Asp Trp Ser Asp  Gly Ile Arg Thr Glu  Val Ile Gln
    6800                 6805                 6810

Arg Asp  Leu Arg Ala Thr Pro  Asn Glu Met Asp Leu  Gln Phe Phe
    6815                 6820                 6825

Gly Asp  Gly Thr Gly Leu Ser  Val Thr Val Glu Tyr  Ala Ala Glu
    6830                 6835                 6840

Leu Phe  Ser Glu Ala Thr Ile  Arg Arg Leu Ile His  His His Gln
    6845                 6850                 6855

Leu Val  Leu Glu Gln Met Leu  Ala Ala His Glu Ser  Ala Thr Cys
    6860                 6865                 6870

Pro Leu  Asp Val Ala Asp
    6875


<210> SEQ ID NO 27
<211> LENGTH: 343
<212> TYPE: PRT
<213> ORGANISM: Xanthomonas albilineans

<400> SEQUENCE: 27

Met Asp Ser Ala Leu Pro Thr Ser Ala Phe Thr Phe Asp Leu Phe Tyr
1               5                   10                  15

Thr Thr Val Asn Ala Tyr Tyr Arg Thr Ala Ala Val Lys Ala Ala Ile
            20                  25                  30

Glu Leu Gly Leu Phe Asp Val Val Gly Gln Gln Gly Arg Thr Pro Ala
        35                  40                  45

Ala Ile Ala Glu Ala Cys Gln Ala Ser Pro Arg Gly Ile Arg Ile Leu
    50                  55                  60

Cys Tyr Tyr Leu Val Ser Ile Gly Phe Leu Arg Arg Asn Gly Gly Leu
65                  70                  75                  80

Phe Tyr Ile Asp Arg Asn Met Ala Met Tyr Leu Asp Arg Ser Ser Pro
                85                  90                  95

Gly Tyr Leu Gly Gly Ser Ile Lys Phe Leu Leu Ser Pro Tyr Ile Met
            100                 105                 110

Ser Ala Phe Thr Asp Leu Thr Ala Val Val Arg Thr Gly Lys Ile Asn
        115                 120                 125

Leu Ala Gln Asp Gly Val Val Ala Pro Asp His Pro Gln Trp Val Glu
    130                 135                 140

Phe Ala Arg Ala Met Ala Pro Met Met Ala Leu Pro Ser Ala Leu Ile
145                 150                 155                 160

Ala Asn Met Val Ser Leu Pro Ala Asp Arg Pro Ile Arg Val Leu Asp
                165                 170                 175

Val Ala Ala Gly His Gly Leu Phe Gly Ile Ala Phe Ala Gln Arg Phe
            180                 185                 190

Arg Gln Ala Glu Val Ser Phe Leu Asp Trp Asp Asn Val Leu Asp Val
        195                 200                 205

Ala Arg Glu Asn Ala Gln Ala Ala Lys Val Ala Glu Arg Ala Arg Phe
    210                 215                 220

Leu Pro Gly Asn Ala Phe Asp Leu Asp Tyr Gly Ser Gly Tyr Asp Val
225                 230                 235                 240

Ile Leu Leu Thr Asn Phe Leu His His Phe Asp Glu Val Asp Gly Glu
                245                 250                 255

Arg Ile Leu Ala Lys Thr Arg Asp Ala Leu Asn Asp Asp Gly Met Val
            260                 265                 270

Ile Thr Phe Glu Phe Ile Ala Asp Glu Glu Arg Ser Ser Pro Pro Leu
```

-continued

```
        275                 280                 285

Ala Ala Thr Phe Ser Met Met Met Leu Gly Thr Thr Pro Ala Gly Glu
    290                 295                 300

Ser Tyr Thr Tyr Ser Asp Leu Glu Arg Met Phe Arg His Ala Gly Phe
305                 310                 315                 320

Gly His Val Glu Leu Lys Ser Ile Pro Pro Ala Leu Leu Lys Val Val
                325                 330                 335

Val Ser Arg Lys Arg Ala Pro
            340
```

<210> SEQ ID NO 28
<211> LENGTH: 167
<212> TYPE: PRT
<213> ORGANISM: Xanthomonas albilineans

<400> SEQUENCE: 28

```
Met Ile Glu Ser Ala Thr Ser Pro Val Ala Lys Thr Glu Arg Ile Trp
1               5                   10                  15

Cys Thr Glu Leu Asp Leu Asp Ala Leu Asn Ala Met Ser Ala Asn Thr
            20                  25                  30

Met Gln Ala Leu Leu Gly Ile Arg Met Ile Glu Ile Gly Ser Asp Tyr
        35                  40                  45

Leu Val Ser Cys Met Ser Val Asp Trp Arg Cys His Gln Pro Tyr Gly
    50                  55                  60

Val Leu His Gly Gly Ala Ser Val Thr Leu Ala Glu Ala Thr Gly Ser
65                  70                  75                  80

Met Ala Ala Ser Met Cys Val Pro Ala Gly Gln Arg Cys Val Gly Leu
                85                  90                  95

Asp Ile Asn Ala Asn His Ile Ala Ser Ile Ser Ser Gly Gln Val Gln
            100                 105                 110

Cys Ile Ala Arg Pro Leu His Ile Gly Ala Leu Thr Gln Val Trp Gln
        115                 120                 125

Met Arg Ile Tyr Asp Glu Gly Asp Arg Thr Ile Cys Val Ser Arg Leu
    130                 135                 140

Thr Met Ala Val Leu Ser Val His Val Ala Arg Val Ser Pro Asn Pro
145                 150                 155                 160

Ala Ser Ser Gly Val Gln Thr
                165
```

<210> SEQ ID NO 29
<211> LENGTH: 941
<212> TYPE: PRT
<213> ORGANISM: Xanthomonas albilineans

<400> SEQUENCE: 29

```
Met Asn Glu Thr Ala Thr Val Thr Lys Ala Thr Leu Ser Ser Ala Lys
1               5                   10                  15

Ala Ser Ile Thr Pro Ala Cys Val His Gln Trp Phe Glu Ala Gln Val
            20                  25                  30

Ser Ser Thr Pro Asp Ala Pro Ala Ala Phe Leu Gly Glu Arg Arg Met
        35                  40                  45

Ser Tyr Gly Gln Leu Asn Thr Arg Ala Asn Arg Leu Ala Arg Leu Leu
    50                  55                  60

Gln Ser Gln Gly Val Gly Pro Gly Ala Arg Val Ala Val Trp Met Asn
65                  70                  75                  80

Arg Ser Pro Glu Cys Leu Ala Ala Leu Leu Ala Val Met Lys Ala Gly
```

-continued

```
                85                  90                  95

Ala Ala Tyr Val Pro Ile Asp Leu Ser Leu Pro Ile Arg Arg Val Gln
            100                 105                 110

Tyr Ile Leu Gln Asp Ser Gln Ala Arg Leu Val Leu Val Asp Asp Glu
        115                 120                 125

Gly Gln Gly Arg Leu Asp Glu Leu Glu Leu Gly Ala Met Thr Ala Val
    130                 135                 140

Asp Val Cys Gly Thr Leu Asp Gly Asp Glu Ala Asn Leu Asp Leu Pro
145                 150                 155                 160

Cys Asp Pro Ala Gln Pro Val Tyr Cys Ile Tyr Thr Ser Gly Ser Thr
                165                 170                 175

Gly Ser Pro Lys Gly Val Leu Val Arg His Ser Gly Leu Ala Asn Tyr
            180                 185                 190

Val Ala Trp Ala Lys Arg Gln Tyr Val Thr Ala Asp Thr Thr Ser Phe
        195                 200                 205

Ala Phe Tyr Ser Ser Leu Ser Phe Asp Leu Thr Val Thr Ser Ile Tyr
    210                 215                 220

Val Pro Leu Val Ala Gly Leu Cys Val His Val Tyr Pro Glu Gln Gly
225                 230                 235                 240

Asp Asp Val Pro Val Ile Asn Arg Val Leu Asp Asp Asn Gln Val Asp
                245                 250                 255

Val Ile Lys Leu Thr Pro Ser His Met Leu Met Leu Arg Asn Ala Ala
            260                 265                 270

Leu Ala Thr Ser Arg Leu Lys Thr Leu Ile Val Gly Gly Glu Asp Leu
        275                 280                 285

Lys Ala Ala Val Ala Tyr Asp Ile His Gln Arg Phe Arg Arg Asp Val
    290                 295                 300

Ala Ile Tyr Asn Glu Tyr Gly Pro Thr Glu Thr Val Val Gly Cys Ala
305                 310                 315                 320

Ile His Arg Tyr Asp Pro Ala Thr Glu Arg Glu Gly Ser Val Pro Ile
                325                 330                 335

Gly Val Pro Ile Asp His Thr Ser Leu His Leu Leu Asp Glu Arg Leu
            340                 345                 350

Gln Pro Val Ala Pro Gly Glu Val Gly Gln Ile His Ile Gly Gly Ala
        355                 360                 365

Gly Val Ala Ile Gly Tyr Val Asn Lys Pro Glu Ile Thr Asp Ala Gln
    370                 375                 380

Phe Ile Asp Asn Pro Phe Glu Gly Ser Gly Arg Leu Tyr Ala Ser Gly
385                 390                 395                 400

Asp Leu Gly Arg Met Arg Ala Asp Gly Lys Leu Glu Phe Leu Gly Arg
                405                 410                 415

Lys Asp Ser Gln Ile Lys Leu Arg Gly Tyr Arg Ile Glu Leu Gly Glu
            420                 425                 430

Ile Glu Asn Val Leu Leu Gly His Ala Ala Leu Arg Glu Cys Ile Val
        435                 440                 445

Asp Thr Thr Val Ala Pro Arg Arg Asp Tyr Asp Ser Lys Ser Leu Arg
    450                 455                 460

Tyr Cys Ala Arg Cys Gly Ile Ala Ser Asn Phe Pro Asn Thr Ser Phe
465                 470                 475                 480

Asp Glu His Gly Val Cys Asn His Cys His Ala Tyr Asp Lys Tyr Arg
                485                 490                 495

Asn Val Val Glu Asp Tyr Phe Arg Thr Glu Asp Glu Leu Arg Thr Ile
            500                 505                 510
```

```
Phe Glu Gln Val Lys Ala His Asn Arg Leu Arg Tyr Asp Cys Leu Val
        515                 520                 525

Ala Phe Ser Gly Gly Lys Asp Ser Thr Tyr Ala Leu Cys Arg Val Val
    530                 535                 540

Asp Met Gly Leu Arg Val Leu Ala Tyr Thr Leu Asp Asn Gly Tyr Ile
545                 550                 555                 560

Ser Asp Glu Ala Lys Ala Asn Val Asp Arg Val Val Arg Glu Leu Gly
                565                 570                 575

Val Asp His Arg Tyr Leu Gly Thr Pro His Met Asn Ala Ile Phe Val
            580                 585                 590

Asp Ser Leu His Arg His Ser Asn Val Cys Asn Gly Cys Phe Lys Thr
        595                 600                 605

Ile Tyr Thr Leu Gly Ile Asn Leu Ala His Glu Val Gly Val Ser Asp
    610                 615                 620

Ile Val Met Gly Leu Ser Lys Gly Gln Leu Phe Glu Thr Arg Leu Ser
625                 630                 635                 640

Glu Leu Phe Arg Ala Ser Thr Phe Asp Asn Gln Val Phe Glu Lys Asn
                645                 650                 655

Leu Met Glu Ala Arg Lys Ile Tyr His Arg Ile Asp Asp Ala Ala Ala
            660                 665                 670

Arg Leu Leu Asp Thr Ser Cys Val Arg Asn Asp Arg Leu Leu Glu Ser
        675                 680                 685

Thr Arg Phe Ile Asp Phe Tyr Arg Tyr Cys Ser Val Ser Arg Lys Asp
    690                 695                 700

Met Tyr Arg Tyr Ile Ala Glu Arg Val Gly Trp Ser Arg Pro Ala Asp
705                 710                 715                 720

Thr Gly Arg Ser Thr Asn Cys Leu Leu Asn Asp Val Gly Ile Tyr Met
                725                 730                 735

His Lys Lys Gln Arg Gly Tyr His Asn Tyr Ser Leu Pro Tyr Ser Trp
            740                 745                 750

Asp Val Arg Val Gly His Ile Pro Arg Glu Asp Ala Met Arg Glu Leu
        755                 760                 765

Glu Asp Thr Asp Asp Ile Asp Glu Ala Lys Val Leu Gly Leu Leu Lys
    770                 775                 780

Gln Ile Gly Tyr Asp Ser Ser Leu Ile Asp Thr Gln Ala Gly Asp Ala
785                 790                 795                 800

Gln Leu Ile Ala Tyr Tyr Val Ala Ala Glu Glu Leu Asp Pro Val Ala
                805                 810                 815

Leu Arg Asn Phe Ala Ala Ala Ile Leu Pro Glu Tyr Met Leu Pro Ser
            820                 825                 830

Tyr Phe Val Arg Leu Asp Arg Met Pro Leu Thr Pro Asn Gly Lys Val
        835                 840                 845

Asn Arg Arg Ala Leu Pro Arg Pro Glu Leu Lys Lys Asn Ala Ser Glu
    850                 855                 860

Ala His Thr Glu Pro Ser Ser Ala Leu Glu Gln Glu Leu Val Gln Ile
865                 870                 875                 880

Trp Lys Glu Val Leu Met Val Asp Lys Val Gly Val Arg Asp Asn Phe
                885                 890                 895

Phe Glu Leu Gly Gly His Ser Leu Ser Ala Leu Met Leu Leu Tyr Ser
            900                 905                 910

Ile Ala Glu Arg Tyr Gln Lys Met Val Ser Ile Gln Ala Phe Ser Val
        915                 920                 925
```

-continued

```
Asn Pro Thr Ile Glu Gly Leu Ser Glu His Leu Val Ala
    930                 935                 940


<210> SEQ ID NO 30
<211> LENGTH: 239
<212> TYPE: PRT
<213> ORGANISM: Xanthomonas albilineans

<400> SEQUENCE: 30

Met Asp Leu Gln Cys Ala Arg Ile Ala Ala Leu Cys Glu Gln Leu Lys
1               5                   10                  15

Leu Ala Arg Leu Ser Ser Asp Trp Gln Ala Leu Ala Gln Ala Ala Ala
            20                  25                  30

Cys Glu Asp Ala Ser Tyr Phe Leu Glu Lys Val Leu Ala Ser Glu Gln
        35                  40                  45

Leu Ala Arg Glu Glu Arg Lys Arg Thr Val Leu Thr Arg Leu Ala Arg
    50                  55                  60

Met Pro Ser Ile Lys Thr Leu Glu Gln Phe Asp Trp Ala Gln Ala Gly
65                  70                  75                  80

Gly Ala Ser Lys Ala Gln Ile Val Glu Leu Gly His Leu Thr Phe Val
                85                  90                  95

Glu Arg Ala Glu Asn Val Val Met Leu Gly Pro Ser Gly Val Gly Lys
            100                 105                 110

Thr His Ile Ala Leu Ala Leu Cys Gln Arg Ala Val Met Ala Gly His
        115                 120                 125

Lys Ala Arg Phe Ile Thr Ala Ala Asp Leu Met Met Gln Leu Ala Ala
    130                 135                 140

Val Lys Ala Gln Asn Arg Leu Lys Asp Tyr Phe Asn Arg Ala Val Leu
145                 150                 155                 160

Gly Pro Lys Leu Leu Val Val Asp Glu Ile Gly Tyr Leu Pro Phe Gly
                165                 170                 175

Arg Glu Pro Ala Gln Gly Cys Trp Ala Ala Thr Gly Phe Ala Leu Arg
            180                 185                 190

Ser Leu Ala Ala Arg Arg Trp Lys Thr Pro Gly Gly Ser Asp Leu Leu
        195                 200                 205

Arg Arg Phe Lys Gly Lys Trp Val Lys Phe Lys Ser Ala Leu Thr Ala
    210                 215                 220

Asp Val Val Tyr Leu Ile Phe Arg Leu Arg Gly Ser Asp His Pro
225                 230                 235


<210> SEQ ID NO 31
<211> LENGTH: 286
<212> TYPE: PRT
<213> ORGANISM: Xanthomonas albilineans

<400> SEQUENCE: 31

Met Pro Arg Ile Glu Tyr Cys Ile Ser Met Met His Arg Arg Lys Pro
1               5                   10                  15

Thr Thr Asn Arg Ser Val Cys Met Arg Asp Ile Glu Arg Thr Ala Leu
            20                  25                  30

Trp Val Ala Gly Met Arg Ala Leu Glu Ser Glu Arg Glu Gln Ala Leu
        35                  40                  45

Phe His Asp Pro Phe Ala Arg Arg Leu Ala Gly Asp Glu Phe Val Glu
    50                  55                  60

Glu Leu Arg Arg Asn Asn Gln Asn Val Pro Met Pro Pro Ala Ile Glu
65                  70                  75                  80
```

-continued

Val Arg Thr Arg Trp Leu Asp Asp Lys Ile Met Gln Ala Val Ser Glu
85 90 95

Gly Ile Gly Gln Val Val Ile Leu Ala Ala Gly Met Asp Ala Arg Ala
100 105 110

Tyr Arg Leu Pro Trp Pro Ser Asp Thr Arg Val Tyr Glu Ile Asp His
115 120 125

Met Asp Val Leu Ser Asp Lys His Glu Lys Leu His Asp Ala Gln Pro
130 135 140

Val Cys Gln Arg Ile Ala Leu Pro Ile Asp Leu Arg Glu Asp Trp Pro
145 150 155 160

Gln Ala Leu Lys Glu Ser Gly Phe Val Gly Ser Ala Ala Thr Leu Trp
165 170 175

Leu Val Glu Gly Leu Leu Cys Tyr Leu Ser Ala Glu Ala Val Met Leu
180 185 190

Leu Phe Ala Arg Ile Asp Ala Leu Ser Ala Lys Gly Ser Ser Val Leu
195 200 205

Phe Asp Val Ile Gly Leu Ser Met Leu Asn Ser Pro Asn Ala Arg Val
210 215 220

Leu His Ala Met Ala Arg Gln Phe Gly Thr Asp Glu Pro Glu Ser Leu
225 230 235 240

Ile Gln Pro Leu Gly Trp Glu Pro Gly Val Leu Thr Ile Ala Ala Ala
245 250 255

Gly Gln Gln Met Gly Arg Trp Pro Phe Pro Val Ala Pro Arg Gly Thr
260 265 270

His Gly Val Pro Gln Ser Tyr Leu Val His Ala Leu Lys Arg
275 280 285

<210> SEQ ID NO 32
<211> LENGTH: 765
<212> TYPE: PRT
<213> ORGANISM: Xanthomonas albilineans

<400> SEQUENCE: 32

Met Arg Arg Ser Pro Tyr Pro Arg Thr Leu Met Asp Ser Pro Leu Thr
1 5 10 15

Asn Leu Pro Met His Ser Gly Thr Glu Leu Asp Leu Arg Trp Ser Val
20 25 30

Gly Gln Thr Arg Pro Gly Arg Asn Glu Ala Tyr Ala Arg Gln Trp Thr
35 40 45

Thr Leu Leu His Gln Trp Arg Arg Asp Tyr Pro Gly Leu Arg Ile Asp
50 55 60

Val Ser Asp Thr Pro Ile Gly Gln His Ile Thr Ile Asp Tyr Ala Ala
65 70 75 80

Pro Tyr Pro Cys Gly Ser Phe Gly Ser Leu Leu Arg Glu Tyr Ala Arg
85 90 95

Leu Gly Lys Leu Ala Gly Leu Ile Cys Asp Tyr Leu Lys His Arg His
100 105 110

Gln Ile Val Leu Ser Glu Ser Pro Pro Gly Ala Asn Thr Leu Ala Leu
115 120 125

Asp Leu Gly Arg Ile Glu Glu Pro Lys Gln Leu Asp Arg Leu Gln Gly
130 135 140

Ala Leu Gly Met Ala Leu Glu Ala Leu Ala Thr Arg Arg Ser Asp Gly
145 150 155 160

Leu Leu Leu Trp His Ala Asp His Arg Gln Arg Asn Leu Pro Asp Leu
165 170 175

-continued

```
Arg Asp Ser Ala Val Cys Gly Ser Ala Ala Gln Ile Ser Leu Pro Ala
            180                 185                 190

Leu Ser Cys Val Glu Asp Leu Ile Glu Val Asp Thr Ser Leu Leu Ala
        195                 200                 205

Cys Asp His Gly Lys Leu Cys Gln Ile Ala Ser His Leu Pro Ala Ser
    210                 215                 220

Trp Phe Ala Arg Ser Thr Asp Gly Pro Met Pro Ser Trp Ser Asp Ala
225                 230                 235                 240

Ser Thr Ala Val Phe Ala Cys Ala Pro Ile Gly Phe Leu Pro Ser Val
                245                 250                 255

Gln Val Asn Val Cys Ala Gln Ile Phe Ser Ala Ala His Leu Ala Ser
            260                 265                 270

Thr Ala Gln Met Ile Asp Pro Leu Arg Gln Gln Ala Phe Ser Tyr Arg
        275                 280                 285

Gln Leu Arg Ser Arg Ala Ala Thr Tyr Ala Arg His Leu Ser Leu Leu
    290                 295                 300

Gly Leu Gln Ser Gly Asp Ala Val Ala Leu Ile Ala Ile Asp Ser Leu
305                 310                 315                 320

Ala Gly Val Ala Leu Met Leu Ala Cys Leu Ala Gly Gly Leu Val Phe
                325                 330                 335

Ala Pro Ile Asn Glu Leu Val Ser Leu Val His Phe Glu Thr Thr Leu
            340                 345                 350

Lys Thr Ile Lys Pro Arg Leu Val Leu Ile Asp Ala Glu Leu Pro Pro
        355                 360                 365

Ser His His Ala Ala Leu Arg His Leu Pro Thr Leu Glu Leu Thr Ser
    370                 375                 380

Leu Met Pro Val Ile Glu Asn Asp Glu Leu Val Val Ala Pro Cys Ser
385                 390                 395                 400

Ala Asp Ala Pro Ala Val Met Ile Cys Thr Ser Gly Ser Thr Gly Thr
                405                 410                 415

Pro Lys Ala Val Thr His Ser His Ala Asp Phe Met His Cys His Leu
            420                 425                 430

Asn Tyr Gln Gln Ala Val Leu Gly Leu Arg Ser Asp Asp Val Met Tyr
        435                 440                 445

Thr Pro Ser Arg Leu Phe Phe Ala Tyr Gly Leu Asn Asn Leu Met Leu
    450                 455                 460

Ser Leu Leu Ala Gly Val Ser His Val Ile Ala Ala Pro Leu Ser Val
465                 470                 475                 480

Arg Gln Ile Ala Gln Thr Ile His Thr Tyr His Val Thr Val Leu Leu
                485                 490                 495

Ala Val Pro Ala Val Phe Lys Leu Leu Leu Ala Glu Ala Ala Pro Asp
            500                 505                 510

Ala Val Trp Pro Ala Leu Arg Leu Cys Ile Ser Ala Gly Glu Ser Leu
        515                 520                 525

Pro Ala Arg Leu Gly His Ala Ile Ser Thr Arg Trp Gln Val Glu Val
    530                 535                 540

Leu Asp Gly Ile Gly Cys Thr Glu Val Leu Ser Thr Phe Ile Ser Asn
545                 550                 555                 560

Arg Pro Gly His Ala Leu Met Gly Cys Thr Gly Thr Pro Val Pro Gly
                565                 570                 575

Phe Val Val Lys Leu Val Asn Lys Gln Gly Glu Ile Cys Arg Ile Gly
            580                 585                 590
```

-continued

```
Glu Val Gly Ser Leu Trp Val Arg Gly Asn Thr Leu Thr Arg Gly Tyr
        595                 600                 605

Val Gly Asp Pro Ile Leu Ser Ala Gln Leu Phe Val Asp Gly Trp Phe
    610                 615                 620

Asp Thr Arg Asp Leu Phe Phe Ala Asp Ala Lys Gly Arg Phe His Asn
625                 630                 635                 640

Leu Gly Arg Met Gly Ser Ala Ile Lys Ile Asn Gly Cys Trp Leu Ser
                645                 650                 655

Pro Glu Thr Leu Glu Ser Val Ile Gln Thr His Ala Cys Val Lys Glu
            660                 665                 670

Cys Ala Ile Cys Leu Ile Glu Asp Glu Phe Gly Leu Pro Arg Pro Ala
        675                 680                 685

Ala Phe Val Val Pro Val Asp Ala Ser Ile Asp Thr Gly Ala Leu Trp
    690                 695                 700

Ala Ala Leu Arg Ala Leu Cys Lys Asn Ala Leu Gly Lys His His Tyr
705                 710                 715                 720

Pro His Leu Phe Val Glu Val Ser Thr Ile Pro Arg Thr Cys Ser Gly
                725                 730                 735

Lys Val Ile Arg Pro Ala Leu Leu Glu Thr Leu Ala Ser Ala Lys His
            740                 745                 750

Leu Gln Ser His Leu Phe Phe Val Gly His Ala Arg Thr
        755                 760                 765


<210> SEQ ID NO 33
<211> LENGTH: 330
<212> TYPE: PRT
<213> ORGANISM: Xanthomonas albilineans

<400> SEQUENCE: 33

Met His Thr Asn Ala Asp Leu Pro Leu Thr Ile Lys Ala Asp Ser Ala
1               5                   10                  15

Glu Ala Thr Leu Thr Asp Trp Asn Ala Thr His Arg Ala Thr Trp Pro
            20                  25                  30

Thr Leu Leu Trp Gln His Arg Ala Leu Leu Phe Arg Gly Phe Ala His
        35                  40                  45

Pro Gly Gly Leu Glu Gln Ile Ser Arg Cys Phe Phe Asp Glu Arg Leu
    50                  55                  60

Ala Tyr Thr Tyr Arg Ser Thr Pro Arg Thr Asp Val Gly Gln His Val
65                  70                  75                  80

Tyr Thr Ala Thr Glu Tyr Pro Arg Gln Leu Ser Ile Ala Gln His Cys
                85                  90                  95

Glu Asn Ala Tyr Gln Arg Val Trp Pro Met Lys Leu Leu Phe His Cys
            100                 105                 110

Val Gln Pro Ala Ser Glu Gly Gly Cys Thr Pro Leu Ala Asp Met Leu
        115                 120                 125

Lys Val Thr Ala Ala Ile Asp Pro Gln Val Arg Glu Ile Phe Ala Arg
    130                 135                 140

Lys Gln Val Arg Tyr Val Arg Asn Tyr Arg Ala Gly Val Asp Leu Pro
145                 150                 155                 160

Trp Glu Asp Val Phe Asn Thr Arg Asn Lys Gln Glu Val Glu Ala Tyr
                165                 170                 175

Cys Ala Arg Asn Asp Met Gln Cys Glu Trp Thr Gly Asp Gly Leu Arg
            180                 185                 190

Thr Ser Gln Ile Cys Arg Ala Phe Ala Cys His Pro Ala Thr Gly Asp
        195                 200                 205
```

-continued

Glu Val Trp Phe Asn Gln Ala His Leu Phe His Tyr Thr Ala Leu Glu
    210                 215                 220

Ala Ala Ala Gln Lys Met Met Leu Ser Phe Phe Gly Glu Gln Gly Leu
225                 230                 235                 240

Pro Arg Asn Ala Tyr Phe Gly Asp Gly Thr Pro Ile Asp Pro Ala Met
                245                 250                 255

Leu Asp His Val Arg Thr Val Phe Ala Gln His Lys Ile His Phe Asp
            260                 265                 270

Trp His Arg Asp Asp Val Leu Leu Ile Asp Asn Met Leu Val Ser His
        275                 280                 285

Gly Arg Glu Pro Tyr Glu Gly Ser Arg Lys Ile Leu Val Cys Met Ala
    290                 295                 300

Glu Pro Tyr Ser Pro Glu Gln Ser Ser Pro Asp Ile Ala Ala Arg Ser
305                 310                 315                 320

Asp Gly Glu Ala Met Leu Lys Leu His Val
                325                 330

<210> SEQ ID NO 34
<211> LENGTH: 1959
<212> TYPE: PRT
<213> ORGANISM: Xanthomonas albilineans

<400> SEQUENCE: 34

Met Lys Leu Ser Ser Met Ser Leu Leu Asp Ala Glu Asp Val Ala Leu
1               5                   10                  15

Thr Ala Ala Ser Pro Asp Thr Ala Leu Ala Leu Asp Trp Ser Arg Ser
            20                  25                  30

Val Leu Asp Leu Phe Asp Ala Gln Val Ala Leu His Ala Glu Glu Leu
        35                  40                  45

Ala Cys Ala Asp Gln His Arg Gln Leu Ser Tyr Ala Gln Leu Asp Gln
    50                  55                  60

His Ala Asn Arg Leu Ala His Cys Leu Ile Glu Arg Gly Leu Arg Pro
65                  70                  75                  80

Gln Glu Arg Val Ala Leu Trp Phe Gly Arg Ser Pro Asp Phe Leu Ile
                85                  90                  95

Ala Leu Leu Gly Val Leu Lys Ala Gly Gly Cys Tyr Val Pro Leu Asp
            100                 105                 110

Pro His Tyr Pro Thr Thr Tyr Ile Gln Gln Ile Leu Asp Asp Ala Gln
        115                 120                 125

Pro Arg Leu Leu Leu Cys Gly Lys Asp Ile Asp Gly Gln Leu Ile Gln
    130                 135                 140

Val Pro Arg Leu Arg Leu Asp Asp Ala Ala Ile Ala Arg Gln Pro His
145                 150                 155                 160

Thr Pro Leu Pro His Ala Leu His Pro Ala Gln Leu Ala Tyr Val Met
                165                 170                 175

Tyr Thr Ser Gly Ser Thr Gly Arg Pro Lys Gly Val Met Val Pro His
            180                 185                 190

Arg Gln Ile Leu Asn Trp Leu His Ala Leu Trp Ala Arg Ala Pro Phe
        195                 200                 205

Glu Ala Gly Glu Arg Val Ala Gln Lys Thr Ser Ile Ala Phe Ala Ile
    210                 215                 220

Ser Val Lys Glu Leu Leu Ala Gly Leu Leu Ala Gly Val Pro Gln Val
225                 230                 235                 240

Phe Ile Asp Glu Asp Thr Val Arg Asp Ile Pro Ala Phe Val Arg Ala

-continued

```
                245                 250                 255
Leu Glu Thr Trp Gln Ile Thr Arg Leu Tyr Thr Phe Pro Ser Gln Leu
            260                 265                 270
Asn Ala Leu Leu Asp His Val Ala Glu Thr Pro Gln Arg Leu Ala Arg
        275                 280                 285
Leu Arg Gln Leu Phe Val Ser Ile Glu Pro Cys Pro Ala Glu Leu Leu
    290                 295                 300
Gln Arg Leu Arg Thr Leu Leu Pro Ala Cys Thr Ala Trp Tyr Ile Tyr
305                 310                 315                 320
Gly Cys Thr Glu Ile Asn Asp Met Thr Tyr Cys Asp Pro Ala Glu Gln
                325                 330                 335
His Ser Gly Ser Gly Phe Val Pro Val Gly Arg Pro Ile Ala Asn Thr
            340                 345                 350
Lys Val His Val Leu Asp Glu Gln Leu Arg Pro Leu Pro Pro Gly Ile
        355                 360                 365
Met Gly Glu Val His Ile Glu Ser Leu Gly Ile Thr His Gly Tyr Trp
    370                 375                 380
Arg Gln Gly Gly Leu Thr Ala Ala Arg Phe Ile Ala Asn Pro Tyr Gly
385                 390                 395                 400
Pro Pro Gly Ser Arg Leu Tyr Arg Thr Gly Asp Met Ala Arg Leu Leu
                405                 410                 415
Asp Asn Gly Thr Leu Glu Leu Leu Gly Arg Arg Asp Tyr Glu Val Lys
            420                 425                 430
Val Arg Gly Tyr Arg Val Asp Val Arg Gln Val Glu Lys Ala Leu Ala
        435                 440                 445
Ala His Leu Gln Val Ala Glu Ala Ala Val Ile Gly Trp Pro Gln Gly
    450                 455                 460
Ser Pro Thr Pro Glu Leu Leu Ala Tyr Val Val Pro Arg Gln Gly Val
465                 470                 475                 480
Leu Asn Leu Asp Glu Leu Arg Lys Leu Leu Gln Glu Arg Leu Pro Thr
                485                 490                 495
Tyr Met Leu Pro Thr Arg Phe Gln Ser Leu Pro Ala Leu Pro Arg Leu
            500                 505                 510
Pro Asn Gly Lys Leu Asp Thr Leu Ser Leu Pro Glu Pro Gln Ala Ala
        515                 520                 525
Ser Ser Asp Ser Asp Tyr Leu Ala Pro Arg Ser Glu Val Glu Ile Thr
    530                 535                 540
Leu Ala Lys Leu Trp Ser Glu Leu Leu Thr Pro Ala Gln Ala Ala Pro
545                 550                 555                 560
Leu Arg Val Ser Leu Asn Asp Asn Phe Phe Asn Leu Gly Gly His Ser
                565                 570                 575
Leu Leu Ala Thr Gln Leu Phe Ser Arg Ile Arg Gln Ser Phe Asp Ile
            580                 585                 590
Glu Val Arg Val Asn Thr Leu Phe Glu Ser Pro Val Leu Glu Asp Phe
        595                 600                 605
Ala Arg Val Val Asn Glu Ala Arg Gln Gln Gln Ala Pro Thr Gly Gly
    610                 615                 620
Asn Thr Ile Ser Ser Arg Ala Val Arg Asp Ala Pro Val Pro Leu Ser
625                 630                 635                 640
Tyr Gln Gln Glu Arg Leu Trp Phe Val His Glu His Met Pro Glu Gln
                645                 650                 655
Arg Thr Ser Tyr Asn Val Ala Phe Ala Cys His Leu Arg Ser Ala Asp
            660                 665                 670
```

-continued

```
Phe Ser Met Ser Ala Leu Arg Glu Ala Ile Gln Ala Leu Val Ala Arg
        675                 680                 685

His Glu Thr Leu Arg Thr Arg Ile Ala Thr Cys Ala Gly Gly Asp Tyr
    690                 695                 700

Pro Ser Gln His Ile Ala Asp Ala Met Gln Val Pro Val Pro Cys Ile
705                 710                 715                 720

Thr Ala Thr Pro Ala Glu Val Pro Arg Leu Val Ala Glu His Ala Ala
                725                 730                 735

His Val Phe Asp Leu Ala His Gly Pro Leu Leu Lys Val Ser Val Leu
            740                 745                 750

Arg Val Ser Asp Asp Tyr His Val Phe Leu Met Asn Met His His Ile
        755                 760                 765

Ile Cys Asp Gly Trp Ser Ile Asn Leu Ile Phe His Asp Leu Arg Ala
    770                 775                 780

Phe Tyr Ile Ala Ala Leu Gln Gln Thr Pro Pro Ala Leu Pro Pro Leu
785                 790                 795                 800

Leu Leu Gln Tyr Ala Asp Tyr Ala Thr Trp Gln Arg Val Gln Asp Phe
                805                 810                 815

Ser Ala Asp Leu Asp Tyr Trp Lys Gln Arg Leu His Gly Tyr Glu Glu
            820                 825                 830

Gly Leu Ala Leu Pro Tyr Asp Phe Pro Arg Pro Ala Asn Arg Ala Trp
        835                 840                 845

Arg Ala Gly Ile Leu His Leu Thr Tyr Pro Asp Ala Leu Ala Ala Arg
    850                 855                 860

Leu Ala Ala Phe Ser Gln Glu Arg Arg Val Thr Leu Phe Met Thr Leu
865                 870                 875                 880

Met Ala Ser Leu Ala Ile Val Leu His Gln Tyr Thr Gly Arg Arg Glu
                885                 890                 895

Leu Cys Leu Gly Thr Thr Ser Ala Gly Arg Asp Gln Leu Glu Thr Glu
            900                 905                 910

Asn Leu Ile Gly Phe Phe Val Asn Ile Leu Ala Val Arg Leu Asn Leu
        915                 920                 925

Gly Ser His Ala Phe Ala Glu Asp Phe Leu Gln His Val Arg Gln Gln
    930                 935                 940

Val Leu Asp Ala Tyr Ala His Arg Ala Leu Pro Phe Glu His Val Leu
945                 950                 955                 960

Ser Ala Leu Lys Lys Pro Arg Asp Ser Ser Gln Ile Pro Leu Val Pro
                965                 970                 975

Ile Met Leu Arg His Gln Asn Phe Ala Thr Glu Gly Val Asn Ala Phe
            980                 985                 990

Ala Gln Ile Phe Leu Ser Ala Gln  Met Glu Phe Gly Glu  Arg Thr Thr
        995                 1000                1005

Pro Asn  Glu Leu Asp Leu Gln  Phe Ile Gly Asp Gly  Ser His Leu
    1010                1015                1020

Glu Val  Thr Val Glu Tyr Ala  Ala Glu Leu Phe Ser  Ala Ala Thr
    1025                1030                1035

Val Gln  Arg Met Leu Ala His  His Gln Arg Val Leu  Glu Arg Met
    1040                1045                1050

Leu Glu  Glu Pro Arg Cys Arg  Leu Ser Asp Phe Ser  Leu Pro Val
    1055                1060                1065

Ala Arg  Thr Glu Phe Thr Pro  His Thr Leu Asp Thr  Ser Arg Ser
    1070                1075                1080
```

-continued

```
Val Leu  Asp Leu Phe Asp Ala  Gln Val Ala Leu His  Ala Glu Glu
    1085                 1090                 1095

Leu Ala  Cys Ala Asp Gln His  Arg Gln Leu Ser Tyr  Ala Gln Leu
    1100                 1105                 1110

Asp Gln  His Ala Asn Arg Leu  Ala His Cys Leu Ile  Glu Arg Gly
    1115                 1120                 1125

Leu Arg  Pro Gln Glu Arg Val  Ala Leu Trp Phe Gly  Arg Ser Pro
    1130                 1135                 1140

Asp Phe  Leu Ile Ala Leu Leu  Gly Val Leu Lys Ala  Gly Gly Cys
    1145                 1150                 1155

Tyr Val  Pro Leu Asp Pro His  Tyr Pro Thr Thr Tyr  Ile Gln Gln
    1160                 1165                 1170

Ile Leu  Asp Asp Ala Gln Pro  Arg Leu Leu Leu Cys  Gly Lys Asp
    1175                 1180                 1185

Ile Asp  Gly Gln Leu Ile Gln  Val Pro Arg Leu Arg  Leu Asp Asp
    1190                 1195                 1200

Ala Ala  Ile Ala Arg Gln Pro  His Thr Pro Leu Pro  His Ala Leu
    1205                 1210                 1215

His Pro  Ala Gln Leu Ala Tyr  Val Met Tyr Thr Ser  Gly Ser Thr
    1220                 1225                 1230

Gly Arg  Pro Lys Gly Val Met  Val Pro His Arg Gln  Ile Leu Asn
    1235                 1240                 1245

Trp Leu  His Ala Leu Trp Ala  Arg Ala Pro Phe Glu  Ala Gly Lys
    1250                 1255                 1260

Arg Val  Ala Gln Lys Thr Ser  Ile Ala Phe Ala Ile  Ser Val Lys
    1265                 1270                 1275

Glu Leu  Leu Ala Gly Leu Leu  Ala Gly Val Pro Gln  Val Phe Ile
    1280                 1285                 1290

Asp Glu  Asp Thr Val Arg Asp  Ile Pro Ala Phe Val  Arg Ala Leu
    1295                 1300                 1305

Glu Thr  Trp Gln Ile Thr Arg  Leu Tyr Thr Phe Pro  Ser Gln Leu
    1310                 1315                 1320

Asn Ala  Leu Leu Asp His Val  Ala Glu Thr Pro Gln  Arg Leu Ala
    1325                 1330                 1335

Arg Leu  Arg Gln Leu Phe Val  Ser Ile Glu Pro Cys  Pro Ala Glu
    1340                 1345                 1350

Leu Leu  Gln Arg Leu Arg Thr  Leu Leu Pro Ala Cys  Thr Ala Trp
    1355                 1360                 1365

Tyr Ile  Tyr Gly Cys Thr Glu  Ile Asn Asp Met Thr  Tyr Cys Asp
    1370                 1375                 1380

Pro Ala  Glu Gln His Ser Gly  Ser Gly Phe Val Pro  Val Gly Arg
    1385                 1390                 1395

Pro Ile  Ala Asn Thr Lys Val  His Val Leu Asp Glu  Gln Leu Arg
    1400                 1405                 1410

Pro Leu  Pro Pro Gly Ile Met  Gly Glu Val His Ile  Glu Ser Leu
    1415                 1420                 1425

Gly Ile  Thr His Gly Tyr Trp  Arg Gln Gly Gly Leu  Thr Ala Ala
    1430                 1435                 1440

Arg Phe  Ile Ala Asn Pro Tyr  Gly Pro Pro Gly Ser  Arg Leu Tyr
    1445                 1450                 1455

Arg Thr  Gly Asp Met Ala Arg  Leu Leu Asp Asn Gly  Thr Leu Glu
    1460                 1465                 1470

Leu Leu  Gly Arg Arg Asp Tyr  Glu Val Lys Val Arg  Gly Tyr Arg
```

-continued

```
    1475                1480                1485

Val Asp  Val Arg Gln Val Glu  Lys Ala Leu Ala Ala  His Leu Gln
    1490                1495                1500

Val Ala  Glu Ala Ala Val Ile  Gly Trp Pro Gln Gly  Ser Pro Thr
    1505                1510                1515

Pro Glu  Leu Leu Ala Tyr Val  Val Pro Arg Gln Gly  Val Leu Asn
    1520                1525                1530

Leu Asp  Glu Leu Arg Lys Leu  Leu Gln Glu Arg Leu  Pro Thr Tyr
    1535                1540                1545

Met Leu  Pro Thr Arg Phe Gln  Ser Leu Pro Ala Leu  Pro Arg Leu
    1550                1555                1560

Pro Asn  Gly Lys Leu Asp Thr  Leu Ser Leu Pro Glu  Pro Gln Ala
    1565                1570                1575

Ala Ser  Ser Asp Ser Asp Tyr  Leu Ala Pro Arg Ser  Glu Val Glu
    1580                1585                1590

Ile Thr  Leu Ala Lys Leu Trp  Ser Glu Leu Leu Thr  Pro Ala Gln
    1595                1600                1605

Ala Ala  Pro Leu Arg Val Ser  Leu Asn Asp Asn Phe  Phe Asn Leu
    1610                1615                1620

Gly Gly  His Ser Leu Leu Ala  Thr Gln Leu Phe Ser  Arg Ile Arg
    1625                1630                1635

Gln Ser  Phe Asp Ile Glu Val  Arg Val Asn Thr Leu  Phe Glu Ser
    1640                1645                1650

Pro Val  Leu Glu Asp Phe Ala  Ala Val Val Glu Arg  Gly Met Arg
    1655                1660                1665

Gln Ser  Gln Ala Gly Ser Met  Pro Val Ser Leu Ile  Val Pro Leu
    1670                1675                1680

Ser Leu  Arg Thr Glu Arg Ala  Ala Val Tyr Ala Ile  His Pro Ile
    1685                1690                1695

Gly Gly  Gln Ile His Cys Tyr  Ile Asp Leu Ala Ala  Ala Leu Gly
    1700                1705                1710

His Ser  Ala Arg Val Tyr Gly  Leu Gln Cys Glu Pro  Val Arg Arg
    1715                1720                1725

Phe Ala  His Leu Ser Asp Leu  Ala Ala His Tyr Cys  Asp Ala Leu
    1730                1735                1740

Leu Ala  Gly Pro Thr Gly Ala  Pro Tyr Arg Leu Leu  Gly Trp Ser
    1745                1750                1755

Ser Gly  Gly Val Leu Ala Leu  Ala Val Ala Glu Gln  Leu Gln Arg
    1760                1765                1770

Arg Gly  Leu Arg Val Asp Tyr  Val Gly Leu Leu Asp  Ser Ser Leu
    1775                1780                1785

Ile Pro  Val His Ala Arg Glu  Pro Arg Gln Leu Thr  Phe Val Ala
    1790                1795                1800

Ala Leu  Asn Thr Leu Ala Ala  Leu Ala Lys Arg Gly  Phe Glu Gln
    1805                1810                1815

Ala Glu  Ile Asp Glu Ala Arg  Gln Leu Leu Phe Ala  Asp Gly Asp
    1820                1825                1830

Asp Glu  His Val Phe Asp Tyr  Ser Arg His Gln Ala  Ser Leu Asp
    1835                1840                1845

Lys Leu  Leu Ala His Leu Arg  Phe Thr Leu Glu Ser  Arg Met Trp
    1850                1855                1860

Pro Pro  Leu Ala Glu Gln Leu  Arg Val Thr Arg Tyr  His Leu Gly
    1865                1870                1875
```

-continued

```
Leu Leu  Ala Gly Phe Glu Pro  Gln Cys Leu Gln Pro  Asn Ala His
    1880                 1885                 1890

Leu Tyr  Gln Ala Gln Thr Ala  Val His Val Ser Tyr  Ala Asp Met
    1895                 1900                 1905

Ser Lys  Pro Arg Gly Gly Ser  Glu Val Leu Pro Asp  Ile Thr Gly
    1910                 1915                 1920

Tyr Val  Pro Leu Ser Gln Ile  Lys Ser Ala Ala Gly  Asn His Tyr
    1925                 1930                 1935

Ser Met  Leu Gln Gly Asp Pro  Leu Arg Glu Leu Ala  Arg Met Leu
    1940                 1945                 1950

Val Thr  Asp Leu Asp Ala
    1955


<210> SEQ ID NO 35
<211> LENGTH: 83
<212> TYPE: PRT
<213> ORGANISM: Xanthomonas albilineans

<400> SEQUENCE: 35

Met Thr Phe Glu Glu Gln Ala Tyr Leu Val Leu Ile Asn Asp Glu Leu
1               5                   10                  15

Gln Tyr Ser Leu Trp Pro Ser Asp Leu Glu Val Pro Pro Gly Trp Arg
            20                  25                  30

Lys Glu Gly Tyr Ala Gly Gly Lys Asp Glu Cys Met Ala Tyr Ile Asp
        35                  40                  45

Glu Thr Trp Thr Asp Met Arg Pro Leu Ser Leu Arg Glu Leu Asp Asp
    50                  55                  60

Lys Asn Leu Gly Asp Ala Ser Ser Pro Asp Gly Ser Gly Phe Glu Ser
65                  70                  75                  80

Ser Tyr Ser


<210> SEQ ID NO 36
<211> LENGTH: 315
<212> TYPE: PRT
<213> ORGANISM: Xanthomonas albilineans

<400> SEQUENCE: 36

Met Gly Cys Ala Cys Leu Pro His Tyr Leu Glu Lys Gln Asp Leu Ser
1               5                   10                  15

Ala Leu Asp Asp Ala Leu Ala Gly Val Arg Leu Ser Gln Tyr Cys Thr
            20                  25                  30

Thr Asp Gly Arg Gln Leu Glu Leu Tyr Trp Leu Gly Ala Gln Ala Ser
        35                  40                  45

Pro Lys Leu Val Leu Leu Pro Pro Tyr Gly Met Ser Tyr Leu Leu Leu
    50                  55                  60

Ser Arg Leu Ala Gln Arg Leu Ala Arg His Phe His Val Leu Cys Trp
65                  70                  75                  80

Glu Ser Ile Gly Cys Pro Asn Ala Gln Thr Ser Val Thr Ala Glu Asp
                85                  90                  95

Phe Asp Leu Asp Arg Gln Ala Ala Thr Leu Leu Gly Ile Leu His Gln
            100                 105                 110

His Asp Tyr Ala Asp Cys His Phe Val Gly Trp Cys Gln Ala Ala Gln
        115                 120                 125

Leu Ala Val His Ala Ile Ala Leu His Gly Phe Ala Pro Arg Ser Met
    130                 135                 140
```

-continued

```
Ala Trp Val Ala Pro Ala Gly Leu Leu Pro Pro Ile Val Lys Ser Glu
145                 150                 155                 160

Phe Glu Arg Cys Ala Leu Pro Ile Tyr Leu Gln Ile Glu Arg His Gly
                165                 170                 175

Leu Glu Gln Ala Lys Lys Leu Ala Ala Ile Leu Asp Lys Tyr Arg Gly
            180                 185                 190

Gln Pro Leu Arg Gly Asp Asp Leu Ala Glu Lys Leu Thr Met Leu His
        195                 200                 205

Leu Ala Asp Pro Ala Ser Thr Leu Val Phe Ser Arg Tyr Met Arg Ala
    210                 215                 220

Tyr Glu Glu Asn Lys Gln Ser Val Gln Ala Leu Leu Pro Thr Ala Leu
225                 230                 235                 240

Gly Arg His Pro Thr Leu Ile Val His Cys Lys Asp Asp Ser Phe Ser
                245                 250                 255

His Tyr Ser Ala Ser Val Gln Leu Ala Arg His Asp Pro Ser Leu Arg
            260                 265                 270

Leu Asp Leu Leu Asp His Gly Gly His Leu Gln Leu Phe Asn Asp Pro
        275                 280                 285

Gly Ala Val Ala Gln Arg Ile Ile Asp Phe Ile Gly Leu Thr Val Gly
    290                 295                 300

Glu Val Ala Pro Thr Ser Met His Ser Ala Ala
305                 310                 315
```

<210> SEQ ID NO 37
<211> LENGTH: 451
<212> TYPE: PRT
<213> ORGANISM: Xanthomonas albilineans

<400> SEQUENCE: 37

```
Met Tyr Ile Pro Asn Asn Ile Asp Leu Asp Pro His Ser Ala Leu Val
1               5                   10                  15

Arg Gln Leu Thr Ser Tyr Gln Val Arg Phe Leu Gln Trp Trp Arg Leu
            20                  25                  30

Arg Gly Pro Ser Glu Phe His Asp Arg Glu Met Asn Leu Arg Met Pro
        35                  40                  45

Thr Gly Gly Val Lys Gly Ser Glu Trp Thr Arg Tyr His Arg Met Arg
    50                  55                  60

Pro Ser Asp Tyr Arg Trp Gly Val Phe Met Met Pro Pro Asp Arg Asn
65                  70                  75                  80

Thr Val Val Phe Gly Glu Arg Lys Gly Gln Val Ala Trp Ser Cys Val
                85                  90                  95

Pro Glu Glu Tyr Arg Asp Leu Leu Leu Asp His Val Thr Val Gln Gly
            100                 105                 110

Asp Val Glu Asn Ala Ala Val Glu Gln Ser His Glu Leu Thr Gln Met
        115                 120                 125

Val Pro Ser Ala Ile Asp Leu Glu His Leu Phe Gln Phe Phe Leu Glu
    130                 135                 140

Glu Gly Arg His Thr Trp Ala Met Ser His Leu Leu Ile Glu Tyr Phe
145                 150                 155                 160

Gly Ser Asp Gly Ala Asp Ala Ala Glu Gly Leu Leu Gln Arg Met Ser
                165                 170                 175

Gly Asp Ala Gln Asn Pro Arg Leu Leu Asp Ala Phe Asn Tyr His Thr
            180                 185                 190

Glu Asp Trp Leu Ser His Phe Met Trp Cys Phe Phe Ala Asp Arg Val
        195                 200                 205
```

-continued

Gly Lys Tyr Gln Ile Gln Ala Val Thr Gln Ser Ala Phe Leu Pro Leu
    210                 215                 220

Ala Arg Thr Ala Arg Phe Met Met Phe Glu Glu Pro Leu His Ile Lys
225                 230                 235                 240

Phe Gly Val Asp Gly Leu Glu Arg Val Leu Tyr Arg Ser Ala Glu Ile
                245                 250                 255

Thr Leu Arg Glu Asp Thr His Ala Ile Phe Asp Ala Gly Ala Ile Pro
            260                 265                 270

Leu Pro Val Val Gln Lys Tyr Leu Asn Tyr Trp Leu Pro Lys Ile Phe
        275                 280                 285

Asp Leu Phe Gly His Asp Val Ser Glu Arg Ser Arg Val Leu Tyr Gln
    290                 295                 300

Ala Gly Ile Arg Ser Pro Arg Asn Phe Asp Lys Leu Glu Gly Thr Glu
305                 310                 315                 320

Val Ala Val Asp Val Arg Cys Glu Asp Arg Leu Val Ser Ser Thr Ala
                325                 330                 335

Pro Ala Glu Leu Ala Ile Asn Ala Val Met Arg Arg Gln Tyr Ile Ala
            340                 345                 350

Glu Val Gly Ala Ile Ile Gly Arg Trp Asn Gln Gln Leu Arg Arg Leu
        355                 360                 365

Gly Leu Ala Phe Glu Leu Gln Leu Pro His Glu Arg Phe His Arg Asp
    370                 375                 380

Phe Gly Pro Cys Lys Gly Leu Ala Phe Asp Leu Asp Gly Asn Pro Val
385                 390                 395                 400

His Asp Ala Asp Gly Gln Arg Leu Ala Ala Leu Leu Pro Thr Pro Gln
                405                 410                 415

Asp Leu Ala Gly Val Arg Gly Leu Met Gly Arg Glu Leu Gly Glu Gly
            420                 425                 430

Arg Thr Ala Val Trp Leu Ala Pro Ala Gly Ala Ser Leu Asp Lys Leu
        435                 440                 445

Met Pro Ala
    450

<210> SEQ ID NO 38
<211> LENGTH: 317
<212> TYPE: PRT
<213> ORGANISM: Xanthomonas albilineans

<400> SEQUENCE: 38

Met Asn Ser Tyr Val Gly Cys Gln Lys Leu Glu Thr Asp Gly Asp Ala
1               5                   10                  15

Ser Arg Val Val Pro Met Trp Val Met Tyr Pro Thr Ala Thr Pro Ser
            20                  25                  30

Arg Asp Thr Ala Met Gly Pro Tyr Thr Leu Asp Val Ala Leu Gly Ala
        35                  40                  45

Pro Ile Glu Ala Gly Pro Phe Pro Leu Ala Val Ile Ser His Gly Thr
    50                  55                  60

Arg Ser Ala Gly Leu Val Phe Arg Thr Leu Ala His Tyr Leu Ala Arg
65                  70                  75                  80

His Gly Phe Ile Val Ala Leu Pro Glu His Pro Gly Asp Asn Leu Phe
                85                  90                  95

Gln His Gln Leu Glu Tyr Ser Tyr Gln Asn Leu Glu Asp Arg Pro Arg
            100                 105                 110

His Ile Arg Ala Val Ile Asp Thr Leu Thr Gly His Ala Gln Phe Gly

-continued

```
        115                 120                 125

Pro Ala Ile Gln Ala His Asn Val Ala Val Ile Gly His Ser Val Gly
    130                 135                 140

Gly Tyr Thr Ala Leu Ala Ile Ala Gly Gly Glu Pro His Thr Gly Phe
145                 150                 155                 160

Met Val Asp Phe Ala His Arg Pro Glu His Ala Glu Gln Pro Ala Trp
                165                 170                 175

Thr Ala Leu Val Arg Gln Asn Arg Val Pro Ile Arg Ala Val Pro Val
            180                 185                 190

Thr Ala Asp Pro Arg Val Arg Ala Val Val Ala Leu Ala Pro Asp Phe
        195                 200                 205

Ser Leu Tyr Met His Glu Asp Ala Leu Ala Lys Val Glu Val Pro Val
    210                 215                 220

Leu Leu Ile Val Gly Glu Lys Asp Gln Trp Ala His Glu Thr Ile Val
225                 230                 235                 240

Ala Thr Arg Thr Ala Leu Gly Asn Asp Gly Arg Leu Glu Ala Arg Val
                245                 250                 255

Val Pro Asn Ala Gly His Tyr Ala Phe Ile Ser Val Phe Pro Glu Ala
            260                 265                 270

Met Lys Ala Arg Val Gly Glu Ala Ala Ile Asp Pro Pro Gly Phe Asp
        275                 280                 285

Arg Ser Ala Phe Gln Arg Glu Leu Glu Arg Asp Ile Leu His Phe Leu
    290                 295                 300

Thr Val Thr Met Arg Pro Ala Glu Ala Ala Ile Ser Gly
305                 310                 315


<210> SEQ ID NO 39
<211> LENGTH: 496
<212> TYPE: PRT
<213> ORGANISM: Xanthomonas albilineans

<400> SEQUENCE: 39

Met Gln Lys Pro Lys Glu Ala Leu Gly Met Pro Pro Gly Met Ala Pro
1               5                   10                  15

Pro Gly Ala Gln Phe Asp Tyr Arg Trp Arg Trp Pro Ala Met Ile Val
            20                  25                  30

Leu Leu Ser Ala Asn Phe Met Asn Leu Leu Asp Val Gly Ile Val Asn
        35                  40                  45

Val Ala Leu Pro Ser Ile Gln Lys Asn Leu Gly Ala Asp Glu Gln Gln
    50                  55                  60

Leu Glu Trp Ile Val Ala Ile Tyr Ile Leu Leu Phe Ala Leu Gly Leu
65                  70                  75                  80

Leu Pro Leu Gly Arg Leu Gly Asp Met Leu Gly Arg Lys Arg Met Phe
                85                  90                  95

Gly Thr Gly Val Ala Gly Phe Ile Leu Met Ser Ala Phe Cys Ala Ile
            100                 105                 110

Ala Gly Asn Ile His Val Leu Ile Ile Ala Arg Ala Leu Gln Gly Leu
        115                 120                 125

Ala Ala Ala Met Leu Ala Pro Gln Val Met Ala Ile Ala Gln Thr Met
    130                 135                 140

Phe Ala Pro Lys Glu Arg Ala Ala Ala Phe Ser Leu Phe Gly Leu Val
145                 150                 155                 160

Ala Gly Leu Ala Ser Phe Ala Gly Pro Leu Val Ser Gly Leu Leu Ile
                165                 170                 175
```

-continued

His Ile Asp Ala Phe Gly Val Gly Trp Arg Ala Ile Phe Leu Ile Asn
180 185 190

Val Pro Ile Gly Leu Val Thr Leu Leu Ala Ala Ala Ile Trp Val Pro
195 200 205

Lys Val Pro Ala His Ala Gly Ile His Asn Asp Trp Val Gly Ile Ala
210 215 220

Leu Ala Ala Leu Ala Leu Leu Cys Leu Val Phe Pro Leu Ile Glu Gly
225 230 235 240

Arg Ala Tyr Gly Trp Pro Leu Trp Cys Phe Ala Ala Ile Ala Leu Gly
245 250 255

Ile Pro Leu Leu Val Ala Phe Val Ala Trp Gln Arg Arg Gln Ala His
260 265 270

Leu Ala Arg Pro Ala Leu Leu Pro Ile Tyr Leu Met Ser His Arg Asp
275 280 285

Tyr Ile Leu Gly Ala Leu Ser Val Ser Val Phe Tyr Ser Ala Leu Gln
290 295 300

Gly Phe Phe Leu Val Phe Val Ile Phe Leu Gln Gln Gly Leu Ala Tyr
305 310 315 320

Ser Ala Leu Glu Thr Gly Val Ala Thr Thr Pro Phe Pro Val Gly Val
325 330 335

Ala Ile Ala Ser Met Leu Ala Arg His Val Glu Ser Leu Arg Ala Lys
340 345 350

Ile Phe Ser Gly Ala Cys Leu Met Ile Ala Ser Tyr Leu Ala Leu Trp
355 360 365

Val Ile Ile Thr Arg Ser Glu Gly Ser Leu Asp Pro Trp Thr Leu Thr
370 375 380

Leu Pro Leu Leu Ile Gly Gly Leu Gly Cys Gly Ile Thr Ile Ala Ser
385 390 395 400

Leu Phe Gln Thr Val Met Arg Thr Val Pro Leu Lys Asp Ala Gly Ala
405 410 415

Gly Ser Gly Ala Leu Gln Val Ile Gln Gln Val Gly Gly Met Leu Gly
420 425 430

Ile Ala Leu Val Ser Glu Ile Phe Phe Ser Gly Leu His Gln His Leu
435 440 445

Gln Gly Pro Ala Gly Val Ala Leu Ala Phe Lys Gln Ala Phe Gly Ala
450 455 460

Thr Val Val Tyr Tyr Ile Ala Ala Asn Ala Phe Val Ala Leu Ser Thr
465 470 475 480

Leu Gly Leu Gln Phe Lys Leu Thr Gln Phe Ala Pro Gln Ser Ser Pro
485 490 495

<210> SEQ ID NO 40
<211> LENGTH: 584
<212> TYPE: PRT
<213> ORGANISM: Xanthomonas albilineans

<400> SEQUENCE: 40

Met Lys Arg Thr Tyr Ile Gly Leu Ala Asn Ser Phe His Asp Ser Ala
1 5 10 15

Ile Ala Ile Val Gly Asp Asp Gly Gln Val Arg Phe Ala Glu Ala Thr
20 25 30

Glu Arg Tyr Leu Gln Tyr Lys Arg Ser Ile Gly Val Ala Pro Asp Val
35 40 45

Phe Gln Arg Ala Ile Lys Leu Val His Glu Tyr Gly Asp Pro Gly Ala
50 55 60

-continued

```
Glu Leu Val Val Ala Thr Ser Trp Ser Gly Gln Thr Pro Glu Leu Met
65                  70                  75                  80

Arg Glu Gly Leu Gly Lys Thr Ala Gln Ala Val Asp Gln Tyr Arg Ser
                85                  90                  95

Ala Phe Gly Asp Leu Pro Trp His Val Asn Lys Gln Phe Val Ala Gln
            100                 105                 110

Ser Phe Phe Tyr Arg Ser Gln Leu Ala Met Val Glu His Pro Gly His
        115                 120                 125

Leu Leu Glu Tyr Asp Leu Ser His Met Ala Glu Pro Ala Phe Lys Pro
    130                 135                 140

Pro Ser Tyr Arg His Tyr Glu His His Leu Thr His Ala Val Ala Gly
145                 150                 155                 160

Cys Tyr Thr Ser Pro Phe Glu Glu Ala Val Cys Ala Val Leu Asp Gly
                165                 170                 175

Met Gly Glu Lys Asn Ala Leu Ala Cys Tyr His Tyr Gln Gln Gly Lys
            180                 185                 190

Leu Thr Pro Ile His Gln Ser Glu Thr Ser Ser Trp Ala Ser Leu Gly
        195                 200                 205

Phe Phe Tyr Gly Met Ile Cys Glu Val Cys Gly Phe Gly Thr Leu Ser
    210                 215                 220

Gly Glu Glu Trp Lys Val Met Gly Leu Ala Ala Tyr Gly Gln His Asp
225                 230                 235                 240

Arg Gln Leu Tyr Glu Leu Leu Arg Gln Met Leu Arg Val Asp Gly Leu
                245                 250                 255

Thr Leu Arg Phe Ala Pro Ala Ala Gln Phe Ser Gln Leu Gln Arg Thr
            260                 265                 270

Leu Tyr Ala Met Arg Arg Cys Lys Gly Gln Pro Thr Ile Glu Leu Ala
        275                 280                 285

Asn Leu Ala Tyr Ala Gly Gln Gln Val Phe Cys Asp Val Leu Phe Glu
    290                 295                 300

Phe Leu His Asn Leu His Ala Leu Gly Leu Ser Asp His Leu Val Leu
305                 310                 315                 320

Gly Gly Gly Cys Ala Leu Asn Ser Ser Ala Asn Gly Arg Val Leu Ala
                325                 330                 335

Glu Thr Pro Phe Arg His Leu His Val Phe Ala Ala Pro Gly Asp Asp
            340                 345                 350

Gly Asn Ala Val Gly Ala Ala Leu Trp Ala His Ala Glu Asp His Pro
        355                 360                 365

Glu Gln Thr Pro Pro Ala Ala Arg Glu Gln Ser Pro Tyr Leu Gly Ser
    370                 375                 380

Ser Met Ser Ala Glu Thr Leu His Asn Val Glu Arg Phe Gly Ala Leu
385                 390                 395                 400

Ser Lys Phe Thr Arg Cys Leu Asp Asp Ala Ala Gln Arg Ala Ala Arg
                405                 410                 415

Leu Leu Thr Glu Gly Lys Ile Val Ala Trp Val Gln Gly Arg Ala Glu
            420                 425                 430

Phe Gly Pro Arg Ala Leu Gly Asn Arg Ser Ile Leu Ala Asp Pro Arg
        435                 440                 445

Ser Pro Ala Ile Lys Asp Ile Ile Asn Ala Arg Val Lys Phe Arg Glu
    450                 455                 460

Glu Phe Arg Pro Phe Ala Pro Ser Ile Leu His Glu His Gly Ala Glu
465                 470                 475                 480
```

-continued

```
Tyr Phe Glu Leu Tyr Gln Glu Ser Pro Tyr Met Glu Arg Thr Leu Lys
                485                 490                 495

Phe Arg Ala Glu Ala Thr Arg Lys Val Pro Gly Val Val His His Asp
            500                 505                 510

Gly Thr Gly Arg Leu Gln Thr Val Lys Gln His Trp Asn Pro Arg Tyr
        515                 520                 525

His Ala Leu Ile Lys Glu Phe Tyr Arg Leu Thr Gly Ile Pro Leu Val
    530                 535                 540

Leu Asn Thr Ser Phe Asn Val Met Gly Lys Pro Ile Ala His Ser Val
545                 550                 555                 560

Glu Asp Ala Leu Ser Ile Phe Phe Thr Ser Gly Leu Asp Ala Met Phe
                565                 570                 575

Ile Asp Asp Val Leu Ile Glu Lys
            580


<210> SEQ ID NO 41
<211> LENGTH: 88
<212> TYPE: PRT
<213> ORGANISM: Xanthomonas albilineans

<400> SEQUENCE: 41

Met Arg Thr Ser Lys Phe Asn Glu Thr Gln Ile Ile Ala Thr Leu Lys
1               5                   10                  15

Gln Ala Asp Ala Gly Val Pro Val Lys Asp Ile Cys Arg Gln Val Gly
            20                  25                  30

Ile Ser Thr Ala Thr Tyr Tyr Gln Trp Lys Ser Lys Tyr Val Ala Ser
        35                  40                  45

Glu Met Pro Ser Ser Arg His Thr Ser Leu Thr Trp Arg Pro Pro Ser
    50                  55                  60

Thr Cys Phe Ser Val Ala Thr Ile Trp Leu Ser Val Asn Leu Leu Leu
65                  70                  75                  80

Arg Ile Val Gly Arg Leu Gly Gly
                85


<210> SEQ ID NO 42
<211> LENGTH: 716
<212> TYPE: PRT
<213> ORGANISM: Xanthomonas albilineans

<400> SEQUENCE: 42

Met Arg Cys Leu Ile Ile Asn Asn Tyr Asp Ser Phe Thr Trp Asn Leu
1               5                   10                  15

Ala Asp Tyr Val Ala Gln Ile Phe Gly Glu Asp Pro Leu Val Val His
            20                  25                  30

Asn Asp Glu Tyr Ser Trp His Glu Leu Lys Asp Arg Gly Gly Phe Ser
        35                  40                  45

Ser Ile Ile Val Ser Pro Gly Pro Gly Ser Val Val Asn Glu Ala Asp
    50                  55                  60

Phe His Ile Ser Leu Gln Ala Leu Glu Gln Asn Glu Phe Pro Val Leu
65                  70                  75                  80

Gly Val Cys Leu Gly Phe Gln Gly Leu Ala His Val Tyr Gly Gly Arg
                85                  90                  95

Ile Leu His Ala Pro Val Pro Phe His Gly Arg Arg Ser Thr Val Ile
            100                 105                 110

Asn Thr Gly Asp Gly Leu Phe Glu Gly Ile Pro Gln Arg Phe Glu Ala
        115                 120                 125
```

-continued

```
Val Arg Tyr His Ser Leu Met Val Cys Gln Gln Ser Leu Pro Pro Val
    130                 135                 140

Leu Lys Val Thr Ala Arg Thr Asp Cys Gly Val Val Met Gly Leu Gln
145                 150                 155                 160

His Val Gln His Pro Lys Trp Gly Val Gln Phe His Pro Glu Ser Ile
                165                 170                 175

Leu Thr Glu His Gly Lys Arg Ile Val Ala Asn Phe Ala Lys Leu Ala
            180                 185                 190

Ala Arg His Ser Ala Pro Leu Leu Ala Gly Ser Glu Gln Ala Gly Lys
        195                 200                 205

Val Leu Ser Val Cys Ala Pro Glu Met Val Thr Pro Arg Val Arg Arg
    210                 215                 220

Met Leu Ser Arg Lys Ile Lys Cys Arg Trp Gln Ala Glu Asp Val Phe
225                 230                 235                 240

Leu Ala Leu Phe Ala Asp Glu Lys His Cys Phe Trp Leu Asp Ser Gln
                245                 250                 255

Leu Val Cys Ser Pro Met Ala Arg Tyr Ser Phe Met Gly Ala Val Asn
            260                 265                 270

Glu Ser Glu Val Val Arg His Cys Val Arg Pro Gly Ser Met Val Gln
        275                 280                 285

Glu Ala Gly Glu Arg Phe Leu Ala Glu Met Asp Arg Ala Leu Gln Ser
    290                 295                 300

Val Leu Thr Glu Asp Val Ala Glu Arg Pro Pro Phe Ala Phe Arg Gly
305                 310                 315                 320

Gly Tyr Val Gly Tyr Met Ser Tyr Glu Met Lys Ser Val Phe Gly Ala
                325                 330                 335

Pro Ala Ser His Ala Asn Ala Ile Pro Asp Ala Leu Trp Met Arg Val
            340                 345                 350

Glu Arg Phe Val Ala Phe Asp His Ala Thr Glu Glu Val Trp Leu Leu
        355                 360                 365

Ala Leu Ala Asp Thr Glu Asp Leu Ser Ala Leu Ala Trp Leu Asp Ala
    370                 375                 380

Ile Glu Gln Arg Ile His Ala Ile Gly Gln Ala Ala Pro Ala Cys Ile
385                 390                 395                 400

Ser Leu Gly Leu Arg Ser Met Glu Ile Glu Leu Asn His Gly Arg Arg
                405                 410                 415

Gly Tyr Leu Glu Ala Ile Glu Arg Cys Lys Gln Arg Ile Val Asp Gly
            420                 425                 430

Glu Ser Tyr Glu Ile Cys Leu Thr Asp Leu Phe Ser Phe Gln Ala Glu
        435                 440                 445

Leu Asp Pro Leu Met Leu Tyr Arg Tyr Met Arg Arg Gly Asn Pro Ala
    450                 455                 460

Pro Phe Gly Ala Tyr Leu Arg Asn Gly Ser Asp Cys Ile Leu Ser Thr
465                 470                 475                 480

Ser Pro Glu Arg Phe Leu Glu Val Asp Gly His Gly Thr Ile Gln Thr
                485                 490                 495

Lys Pro Ile Lys Gly Thr Cys Arg Arg Ala Glu Asp Pro Gln Leu Asp
            500                 505                 510

Arg Asn Leu Ala Met Arg Leu Ala Ala Ser Glu Lys Asp Arg Ala Glu
        515                 520                 525

Asn Leu Met Ile Val Asp Leu Met Arg Asn Asp Leu Ser Arg Val Ala
    530                 535                 540

Val Pro Gly Ser Val Thr Val Pro Lys Leu Met Asp Ile Glu Ser Tyr
```

-continued

```
545                 550                 555                 560

Lys Thr Val His Gln Met Val Ser Thr Val Glu Ala Arg Leu Arg Ala
                565                 570                 575

Asp Cys Ser Leu Val Asp Leu Leu Lys Ala Val Phe Pro Gly Gly Ser
            580                 585                 590

Ile Thr Gly Ala Pro Lys Leu Arg Ser Met Glu Ile Ile Asp Gly Leu
        595                 600                 605

Glu Asn Ala Pro Arg Gly Val Tyr Cys Gly Ser Ile Gly Tyr Leu Gly
    610                 615                 620

Tyr Asn Cys Val Ala Asp Leu Asn Ile Ala Ile Arg Ser Leu Ser Tyr
625                 630                 635                 640

Asp Gly Gln Glu Ile Arg Phe Gly Ala Gly Gly Ala Ile Thr Phe Leu
                645                 650                 655

Ser Asp Pro Gln Asp Glu Phe Asp Glu Val Leu Leu Lys Ala Glu Ala
            660                 665                 670

Ile Leu Lys Pro Ile Trp His Tyr Leu His Ala Pro Asn Thr Pro Leu
        675                 680                 685

His Tyr Glu Leu Arg Glu Asp Lys Leu Leu Leu Ala Glu His Cys Val
    690                 695                 700

Ser Glu Met Pro Ala Arg Gln Ala Phe Ile Glu Pro
705                 710                 715


<210> SEQ ID NO 43
<211> LENGTH: 137
<212> TYPE: PRT
<213> ORGANISM: Xanthomonas albilineans

<400> SEQUENCE: 43

Met Arg Pro Pro Arg Leu Arg Ala Asn Gln Asp Gly Leu Leu Met Asp
1               5                   10                  15

Thr Ala Gly Arg Val Val Glu Gly Cys Thr Ser Asn Leu Phe Leu Val
            20                  25                  30

Glu Asn Gly His Leu Val Thr Pro Asp Leu Gly Val Ala Gly Val Ser
        35                  40                  45

Gly Ile Met Arg Gly Arg Val Ile Glu Tyr Gly Arg Gln His Gly Leu
    50                  55                  60

Ala Cys Ala Val Lys His Val Tyr Pro Asp Gln Leu Val Arg Ala Gln
65                  70                  75                  80

Glu Val Phe Leu Thr Asn Ala Val Phe Gly Ile Leu Leu Val Arg Ser
                85                  90                  95

Ile Asp Ala His Ser Tyr Arg Ile Asp Pro Val Thr Leu Arg Leu Leu
            100                 105                 110

Asp Ala Leu Cys Gln Gly Val Tyr Phe Thr Glu Arg Ser Leu His Gln
        115                 120                 125

Val Ser Thr His Ala Gly Gln Asp Pro
    130                 135


<210> SEQ ID NO 44
<211> LENGTH: 200
<212> TYPE: PRT
<213> ORGANISM: Xanthomonas albilineans

<400> SEQUENCE: 44

Met Pro Ala Lys Thr Leu Glu Ser Lys Asp Tyr Cys Gly Glu Ser Phe
1               5                   10                  15

Val Ser Glu Asp Arg Ser Gly Gln Ser Leu Glu Ser Ile Arg Phe Glu
```

-continued

```
            20                  25                  30

Asp Cys Thr Phe Arg Gln Cys Asn Phe Thr Glu Ala Glu Leu Asn Arg
        35                  40                  45

Cys Lys Phe Arg Glu Cys Glu Phe Val Asp Cys Asn Leu Ser Leu Ile
    50                  55                  60

Ser Ile Pro Gln Thr Ser Phe Met Glu Val Arg Phe Val Asp Cys Lys
65                  70                  75                  80

Met Leu Gly Val Asn Trp Thr Ser Ala Gln Trp Pro Ser Val Lys Met
                85                  90                  95

Glu Gly Ala Leu Ser Phe Glu Arg Cys Ile Leu Asn Asp Ser Leu Phe
            100                 105                 110

Tyr Gly Leu Tyr Leu Ala Gly Val Lys Met Val Glu Cys Arg Ile His
        115                 120                 125

Asp Ala Asn Phe Thr Glu Ala Asp Cys Glu Asp Ala Asp Phe Thr Gln
    130                 135                 140

Ser Asp Leu Lys Gly Ser Thr Phe His Asn Thr Lys Leu Thr Gly Ala
145                 150                 155                 160

Ser Phe Ile Asp Ala Val Asn Tyr His Ile Asp Ile Phe His Asn Asp
                165                 170                 175

Ile Lys Arg Ala Arg Phe Ser Leu Pro Glu Ala Ala Ser Leu Leu Asn
            180                 185                 190

Ser Leu Asp Ile Glu Leu Ser Asp
        195                 200


<210> SEQ ID NO 45
<211> LENGTH: 202
<212> TYPE: PRT
<213> ORGANISM: Xanthomonas albilineans

<400> SEQUENCE: 45

Met His Pro Pro Ser Pro Leu Asn Thr Gln Gln Lys Asp Trp Leu Thr
1               5                   10                  15

Arg Gly Gly Ser Leu Thr Ala His Leu Arg Leu Leu Gly Gln Val Gln
            20                  25                  30

Val Gln Val Gln Arg Glu His Lys Ser Met Ala Trp Leu Asp Glu Tyr
        35                  40                  45

Arg Val Leu Gly Leu Ser Arg Cys Leu Leu Val Trp Val Arg Glu Val
    50                  55                  60

Val Leu Val Val Asp Ala Lys Pro Tyr Val Tyr Ala Arg Ser Leu Thr
65                  70                  75                  80

Pro Leu Thr Ala Ser Tyr Asn Ala Trp Gln Ala Val Arg Ser Ile Gly
                85                  90                  95

Ser Arg Pro Leu Ala Asp Leu Leu Phe Arg Asp Arg Ser Val Leu Arg
            100                 105                 110

Ser Ala Leu Ala Ser Arg Arg Ile Thr Ala Gln His Pro Leu His Arg
        115                 120                 125

Arg Ala Cys Asn Phe Val Ala Gln Ser His Ala Thr Gln Ala Leu Leu
    130                 135                 140

Ala Arg Arg Ser Val Phe Thr Arg Gln Gly Ala Pro Leu Leu Ile Thr
145                 150                 155                 160

Glu Cys Met Leu Pro Ala Leu Trp Ala Thr Leu Glu Pro Val Ala Ala
                165                 170                 175

Pro Arg Gln Ala Ser Leu Ser Ala Asp Gly Pro Cys Arg His Ser Ala
            180                 185                 190
```

-continued

```
Gln Ile Val Ser Pro Glu Ser Met Leu Glu
        195                 200


<210> SEQ ID NO 46
<211> LENGTH: 278
<212> TYPE: PRT
<213> ORGANISM: Xanthomonas albilineans

<400> SEQUENCE: 46

Met Pro Asn Ala Val Pro Met Gln Gly Ala Arg Gly Leu Pro Gln Pro
1               5                   10                  15

Gln Ala Met Asn Pro Gly Leu Pro Ser Val Gly Gly Leu Ser Ala Gly
            20                  25                  30

Gln Pro Leu Gln Leu Ser Leu Ala Pro Glu Leu Gln Ala Ala Ala Arg
        35                  40                  45

Ser Ala His Arg His Leu Leu Asp Asp Gly Thr Ala Leu Tyr Leu Leu
    50                  55                  60

Ala Phe Asp Thr Ala Gln Phe Asp Pro Gly Ala Phe Ala Ala Met Ala
65                  70                  75                  80

Ile Ala Arg Pro Asp Ser Ile Ala Arg Ser Val Arg Lys Arg Gln Ala
                85                  90                  95

Glu Phe Leu Phe Gly Arg Leu Ala Ala Arg Leu Ala Leu Gln Glu Val
            100                 105                 110

Leu Gly Pro Ala Gln Ala Gln Ala Asp Ile Ala Ile Gly Ala Thr Arg
        115                 120                 125

Ala Pro Cys Trp Pro Ala Gly Ser Leu Gly Ser Ile Ser His Cys Glu
    130                 135                 140

Asp Tyr Ala Ala Ala Ile Ala Met Ala Ala Gly Thr Arg His Gly Val
145                 150                 155                 160

Gly Ile Asp Leu Glu Arg Pro Ile Thr Pro Ala Ala Arg Ala Ala Leu
                165                 170                 175

Leu Ser Ile Ala Ile Asp Ala Asp Glu Ala Ala Arg Leu Ala Lys Ala
            180                 185                 190

Ala Asp Ala Gln Trp Pro Gln Asp Leu Leu Leu Thr Ala Leu Phe Ser
        195                 200                 205

Ala Lys Glu Ser Leu Phe Lys Ala Ala Tyr Ser Ala Val Gly Arg Tyr
    210                 215                 220

Phe Asp Phe Ser Ala Ala Arg Leu Cys Gly Ile Asp Leu Ala Arg Gln
225                 230                 235                 240

Cys Leu His Leu Arg Leu Thr Glu Thr Leu Cys Ala Gln Phe Val Ala
                245                 250                 255

Gly Gln Val Cys Glu Val Gly Phe Ala Arg Leu Pro Pro Asp Leu Val
            260                 265                 270

Leu Thr His Tyr Ala Trp
        275


<210> SEQ ID NO 47
<211> LENGTH: 634
<212> TYPE: PRT
<213> ORGANISM: Xanthomonas albilineans

<400> SEQUENCE: 47

Met Ser Val Glu Thr Gln Lys Glu Thr Leu Gly Phe Gln Thr Glu Val
1               5                   10                  15

Lys Gln Leu Leu Gln Leu Met Ile His Ser Leu Tyr Ser Asn Lys Glu
            20                  25                  30
```

-continued

```
Ile Phe Leu Arg Glu Leu Ile Ser Asn Ala Ser Asp Ala Ala Asp Lys
        35                  40                  45

Leu Arg Phe Glu Ala Leu Val Lys Pro Glu Leu Leu Asp Gly Asp Ala
    50                  55                  60

Gln Leu Arg Ile Arg Ile Gly Phe Asp Lys Asp Ala Gly Thr Val Thr
65                  70                  75                  80

Ile Asp Asp Asn Gly Ile Gly Met Ser Arg Glu Glu Ile Val Ala His
                85                  90                  95

Leu Gly Thr Ile Ala Lys Ser Gly Thr Ser Asp Phe Leu Lys His Leu
            100                 105                 110

Ser Gly Asp Gln Lys Lys Asp Ser His Leu Ile Gly Gln Phe Gly Val
        115                 120                 125

Gly Phe Tyr Ser Ala Phe Ile Val Ala Asp Gln Val Asp Val Tyr Ser
    130                 135                 140

Arg Arg Ala Gly Leu Pro Ala Ser Asp Gly Val His Trp Ser Ser Arg
145                 150                 155                 160

Gly Glu Gly Glu Phe Glu Val Ala Thr Ile Asp Lys Pro Glu Arg Gly
                165                 170                 175

Thr Arg Ile Val Leu His Leu Lys Glu Glu Glu Lys Gly Phe Ala Asp
            180                 185                 190

Gly Trp Lys Leu Arg Ser Ile Val Arg Lys Tyr Ser Asp His Ile Ala
        195                 200                 205

Leu Pro Ile Glu Leu Ile Lys Glu His Tyr Gly Glu Asp Lys Asp Lys
    210                 215                 220

Pro Glu Thr Pro Glu Trp Glu Thr Val Asn Arg Ala Ser Ala Leu Trp
225                 230                 235                 240

Thr Arg Pro Arg Thr Glu Ile Lys Asp Glu Glu Tyr Gln Glu Leu Tyr
                245                 250                 255

Lys His Ile Ala His Asp His Glu Asn Pro Val Ala Trp Ser His Asn
            260                 265                 270

Lys Val Glu Gly Lys Leu Glu Tyr Thr Ser Leu Leu Tyr Leu Pro Gly
        275                 280                 285

Arg Ala Pro Phe Asp Leu Tyr Gln Arg Asp Ala Ser Arg Gly Leu Lys
    290                 295                 300

Leu Tyr Val Gln Arg Val Phe Ile Met Asp Gln Ala Asp Gln Phe Leu
305                 310                 315                 320

Pro Leu Tyr Leu Arg Phe Ile Lys Gly Ile Val Asp Ser Ser Asp Leu
                325                 330                 335

Pro Leu Asn Val Ser Arg Glu Ile Leu Gln Ser Gly Pro Val Ile Asp
            340                 345                 350

Ser Met Lys Ser Ala Leu Thr Lys Arg Ala Leu Asp Met Leu Glu Lys
        355                 360                 365

Leu Ala Lys Asp Asp Pro Glu Arg Tyr Lys Gly Val Trp Lys Asn Phe
    370                 375                 380

Gly Gln Val Leu Lys Glu Gly Pro Ala Gln Asp Phe Gly Asn Arg Glu
385                 390                 395                 400

Lys Ile Ala Gly Leu Leu Arg Phe Ala Ser Thr His Ser Gly Asp Asp
                405                 410                 415

Ala Gln Asn Val Ser Leu Ala Asp Tyr Val Ala Arg Met Lys Asp Gly
            420                 425                 430

Gln Asp Lys Leu Tyr Tyr Leu Thr Gly Glu Ser Tyr Ala Gln Ile Lys
        435                 440                 445

Asp Ser Pro His Leu Glu Val Phe Arg Lys Lys Gly Ile Glu Val Leu
```

-continued

```
    450                 455                 460

Leu Leu Thr Asp Arg Ile Asp Glu Trp Leu Met Ser Tyr Leu Thr Glu
465                 470                 475                 480

Phe Asp Ser Lys Ser Phe Val Asp Val Ala Arg Gly Asp Leu Asp Leu
                485                 490                 495

Gly Lys Leu Asp Ser Glu Glu Glu Lys Gln Ala Gln Glu Glu Ala Ala
            500                 505                 510

Lys Ala Lys Gln Gly Leu Ala Glu Arg Ile Gln Gln Val Leu Lys Asp
        515                 520                 525

Glu Val Ala Glu Val Arg Val Ser His Arg Leu Thr Asp Ser Pro Ala
    530                 535                 540

Ile Leu Ala Ile Gly Gln Gly Asp Met Gly Leu Gln Met Arg Gln Ile
545                 550                 555                 560

Leu Glu Ala Ser Gly Gln Lys Leu Pro Glu Ser Lys Pro Val Phe Glu
                565                 570                 575

Phe Asn Pro Ala His Pro Leu Ile Glu Lys Leu Asp Ala Glu Pro Asp
            580                 585                 590

Val Asp Arg Phe Gly Asp Leu Ala Arg Val Leu Phe Asp Gln Ala Ala
        595                 600                 605

Leu Ala Ala Gly Asp Ser Leu Lys Asp Pro Ala Ala Tyr Val Arg Arg
    610                 615                 620

Leu Asn Lys Leu Leu Leu Glu Leu Ser Ala
625                 630


<210> SEQ ID NO 48
<211> LENGTH: 20
<212> TYPE: DNA
<213> ORGANISM: Xanthomonas albilineans

<400> SEQUENCE: 48

gcgtaccgtt gtccagtagg                                                   20


<210> SEQ ID NO 49
<211> LENGTH: 20
<212> TYPE: DNA
<213> ORGANISM: Xanthomonas albilineans

<400> SEQUENCE: 49

gctggaaacc gagaatctga                                                   20


<210> SEQ ID NO 50
<211> LENGTH: 20
<212> TYPE: DNA
<213> ORGANISM: Xanthomonas albilineans

<400> SEQUENCE: 50

gacacgatca gccgctagga                                                   20


<210> SEQ ID NO 51
<211> LENGTH: 20
<212> TYPE: DNA
<213> ORGANISM: Xanthomonas albilineans

<400> SEQUENCE: 51

accagcagtt gggccagcct                                                   20


<210> SEQ ID NO 52
<211> LENGTH: 19
<212> TYPE: DNA
```

-continued

```
<213> ORGANISM: Xanthomonas albilineans

<400> SEQUENCE: 52

tgcccacagg ccgtcgagt                                                   19


<210> SEQ ID NO 53
<211> LENGTH: 20
<212> TYPE: DNA
<213> ORGANISM: Xanthomonas albilineans

<400> SEQUENCE: 53

gcgagaggac aagctgctgc                                                  20


<210> SEQ ID NO 54
<211> LENGTH: 20
<212> TYPE: DNA
<213> ORGANISM: Xanthomonas albilineans

<400> SEQUENCE: 54

cgttgaggat gcagcgctcg                                                  20
```